(12) United States Patent
Allen et al.

(10) Patent No.: US 9,505,878 B2
(45) Date of Patent: *Nov. 29, 2016

(54) CATALYSTS AND METHODS FOR POLYMER SYNTHESIS

(71) Applicant: Novomer, Inc., Ithaca, NY (US)

(72) Inventors: Scott D. Allen, Ithaca, NY (US); Anna E. Cherian, Ithaca, NY (US); Chris A. Simoneau, Ithaca, NY (US); Jay J. Farmer, Ithaca, NY (US); Geoffrey W. Coates, Ithaca, NY (US); Alexei Gridnev, Ithaca, NY (US); Robert E. LaPointe, Ithaca, NY (US)

(73) Assignee: Novomer, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/615,902

(22) Filed: Feb. 6, 2015

(65) Prior Publication Data
US 2015/0252145 A1    Sep. 10, 2015

Related U.S. Application Data

(60) Continuation of application No. 13/755,112, filed on Jan. 31, 2013, now Pat. No. 8,951,930, which is a division of application No. 13/059,967, filed as application No. PCT/US2009/054773 on Aug. 24, 2009, now Pat. No. 8,633,123.

(60) Provisional application No. 61/091,013, filed on Aug. 22, 2008, provisional application No. 61/096,313, filed on Sep. 11, 2008, provisional application No. 61/098,739, filed on Sep. 19, 2008.

(51) Int. Cl.
| C08G 64/34 | (2006.01) |
| C07F 15/06 | (2006.01) |
| B01J 31/18 | (2006.01) |
| C07C 251/24 | (2006.01) |
| C07C 279/12 | (2006.01) |
| C07D 213/53 | (2006.01) |
| C07D 487/04 | (2006.01) |
| C07D 487/22 | (2006.01) |
| C07F 9/535 | (2006.01) |
| C07F 9/6561 | (2006.01) |
| C08F 4/80 | (2006.01) |
| C07F 19/00 | (2006.01) |
| B01J 31/02 | (2006.01) |
| B01J 31/22 | (2006.01) |

(52) U.S. Cl.
CPC .............. *C08G 64/34* (2013.01); *B01J 31/182* (2013.01); *C07C 251/24* (2013.01); *C07C 279/12* (2013.01); *C07D 213/53* (2013.01); *C07D 487/04* (2013.01); *C07D 487/22* (2013.01); *C07F 9/5355* (2013.01); *C07F 9/6561* (2013.01); *C07F 15/065* (2013.01); *C07F 19/005* (2013.01); *C08F 4/80* (2013.01); *B01J 31/0239* (2013.01); *B01J 31/0259* (2013.01); *B01J 31/0265* (2013.01); *B01J 31/183* (2013.01); *B01J 31/1835* (2013.01); *B01J 31/2243* (2013.01); *B01J 2531/025* (2013.01); *B01J 2531/0238* (2013.01); *B01J 2531/0252* (2013.01); *B01J 2531/0294* (2013.01); *B01J 2531/31* (2013.01); *B01J 2531/62* (2013.01); *B01J 2531/845* (2013.01); *C07C 2101/14* (2013.01)

(58) Field of Classification Search
CPC ...................................................... C08G 64/34
USPC ................ 528/371; 556/33; 548/106; 546/6; 544/64, 225
See application file for complete search history.

(56) References Cited

U.S. PATENT DOCUMENTS

| 6,133,402 | A | 10/2000 | Coates et al. |
| 6,309,997 | B1 | 10/2001 | Fujita et al. |
| 6,875,718 | B2 | 4/2005 | Fujita et al. |
| 7,304,172 | B2 | 12/2007 | Coates et al. |
| 7,371,579 | B1 | 5/2008 | Rokita et al. |
| 8,163,867 | B2 | 4/2012 | Lee et al. |
| 8,247,520 | B2 | 8/2012 | Allen et al. |
| 8,470,956 | B2 * | 6/2013 | Allen ................. C08G 64/0208 528/196 |
| 8,604,155 | B2 * | 12/2013 | Allen ................. C08G 64/0208 528/196 |

(Continued)

FOREIGN PATENT DOCUMENTS

| CN | 101020747 A | 8/2007 |
| CN | 100384909 C | 4/2008 |

(Continued)

OTHER PUBLICATIONS

Bahramian, B. et al., Manganese (III) salen immobilized on montmorillonite as biomimetic alkene epoxidation and alkane hydroxylation catalyst with sodium periodate, Catalysis Communications, 7:289-296 (2006).

(Continued)

*Primary Examiner* — Duc Troung
(74) *Attorney, Agent, or Firm* — Choate, Hall & Stewart LLP; John P. Rearick; Nicholas J. Pace

(57) ABSTRACT

The present invention provides unimolecular metal complexes having increased activity in the copolymerization of carbon dioxide and epoxides. Also provided are methods of using such metal complexes in the synthesis of polymers. According to one aspect, the present invention provides metal complexes comprising an activating species with co-catalytic activity tethered to a multidentate ligand that is coordinated to the active metal center of the complex.

27 Claims, No Drawings

(56) References Cited

U.S. PATENT DOCUMENTS

| | | | | |
|---|---|---|---|---|
| 8,633,123 B2* | 1/2014 | Allen | .................... | C07F 19/005 502/102 |
| 8,921,508 B2 | 12/2014 | Allen et al. | | |
| 8,946,109 B2* | 2/2015 | Allen | .................... | C07F 19/005 502/102 |
| 8,951,930 B2* | 2/2015 | Allen | .................... | C07F 19/005 502/102 |
| 8,956,989 B2* | 2/2015 | Allen | .................... | C07F 19/005 502/102 |
| 2004/0110722 A1 | 6/2004 | Ornberg et al. | | |
| 2005/0003135 A1 | 1/2005 | Schmidhalter et al. | | |
| 2005/0192454 A1 | 9/2005 | North et al. | | |
| 2008/0103040 A1 | 5/2008 | Rodriguez et al. | | |
| 2010/0029896 A1 | 2/2010 | Ok et al. | | |
| 2010/0324260 A1 | 12/2010 | Jeong et al. | | |
| 2011/0152497 A1 | 6/2011 | Allen et al. | | |
| 2011/0230580 A1 | 9/2011 | Allen et al. | | |
| 2013/0066044 A1 | 3/2013 | Allen et al. | | |
| 2013/0144031 A1 | 6/2013 | Allen et al. | | |
| 2013/0144032 A1 | 6/2013 | Allen et al. | | |
| 2013/0144033 A1 | 6/2013 | Allen et al. | | |
| 2013/0244864 A1 | 9/2013 | Allen et al. | | |
| 2014/0046008 A1 | 2/2014 | Allen et al. | | |
| 2014/0228538 A1 | 8/2014 | Allen et al. | | |
| 2014/0343246 A1 | 11/2014 | Allen et al. | | |
| 2015/0232496 A1 | 8/2015 | Job et al. | | |
| 2015/0299386 A1 | 10/2015 | Allen et al. | | |

FOREIGN PATENT DOCUMENTS

| | | |
|---|---|---|
| CN | 101328624 A | 12/2008 |
| CN | 101412809 A | 4/2009 |
| CN | 102212085 A | 10/2011 |
| JP | 2003-507549 A | 2/2003 |
| JP | 2005-145977 A | 6/2005 |
| JP | 2010-001443 A | 1/2010 |
| KR | 10-0853358 B1 | 8/2008 |
| WO | WO-00/72893 A2 | 12/2000 |
| WO | WO-01/14454 A1 | 3/2001 |
| WO | WO-01/19823 A2 | 3/2001 |
| WO | WO-2007091616 A1 | 8/2007 |
| WO | WO-2008/136591 A1 | 11/2008 |
| WO | WO-2008/150033 A1 | 12/2008 |
| WO | WO-2009/137540 A1 | 11/2009 |
| WO | WO-2010/022388 A2 | 2/2010 |
| WO | WO-2010/028362 A1 | 3/2010 |
| WO | WO-2013/012895 A1 | 1/2013 |
| WO | WO-2013/067460 A1 | 5/2013 |
| WO | WO-2014/031811 A1 | 2/2014 |

OTHER PUBLICATIONS

Bahramian, B. et al., Selective alkene epoxidation and alkane hydroxylation with sodium periodate cartayzed by cationic Mn(III)-salen supported on Dowex MSC1, Applied Catalysis A: General, 301:169-175 (2006).

Bahramian, B. et al., Water-soluble manganese(III) salen complex as a mild and selective catalyst for oxidation of alocohols, Applied Catalysis A: General, 315:52-57 (2006).

Barone, G. et al., Confinement effects on the interaction of native DNA with Cu(II)-5-(triethylammoniummethyl)Salicylidene ortho-phenylendiiminate in $C_{12}E_4$ liquid crystals, Dalton Transactions, 4172-4178 (2008).

Bhattacharya, S. and Mandal, S.S., Ambient Oxygen Activating Water Soluble Cobalt-Salen Complex for DNA Cleavage, Journal the Chemical Society, Chemical Communications, 24:2489-2490 (1995).

Boghaei, D.M. et al., Synthesis, characterization, spectroscopic and thermodynamic studies of charge transfer interaction of a new water-soluble cobalt(II) Schiff base complex with imidazole derivatives, Spectrochimica Acta Part A, 69:624-628 (2008).

Campbell, E.J. and Nguyen, S.T., Unsymmetrical salen-type ligands: high yield synthesis of salen-type Schiff bases containing two different benzaldehyde moieties, Tetrahedron Letters, 42:1221-1225 (2001).

Chen, S. et al., Efficient catalytic synthesis of optically active cyclic carbonates via coupling reaction of epoxides and carbon dioxide, Tetrahedron Letters, 48(2):297-300 (2006).

Cohen, C.T. and Coates, G.W., Alternating Copolymerization of Propylene Oxide and Carbon Dioxide with Highly Efficient and Selective (Salen)Co(III) Catalysts: Effect of Ligand and Cocatalyst Variation, Journal of Polymer Science, 44:5182-5191 (2006).

Cozzi, P.G., Metal-Salen Schiff base complexes in catalysi: practical aspects, Chemical Society Reviews 33:410-421 (2004).

Darensbourg, D.J. and Fitch, S.B., (Tetramethyltetraazaan-nulene)chromium Chloride: A Highly Active Catalyst for the Alternating Copolymerization of Epoxides and Carbon Dioxide, Inorganic Chemistry, 46:5474-5476 (2007).

Dessolin, J. et al., Selective targeting of synthetic antioxidants to mitochondria: towards a mitochondrial medicine for neurodegenerative diseases? European Journal of Pharmacology, 447:155-161 (2002).

Haikarainen, A. et al., Synthesis and characterization of bulky salen-type complexes of Co, Cu, Fe, Mn and Ni with amphiphilic solubility properties, Dalton Transactions, 991-995 (2001).

Haikarainen, A. et el., Salen Complexes with Bulky Substituents as Useful Tools for Biomimetic Phenol Oxidation Research, Bioorganic & Medicinal Chemistry, 9:1633-1638 (2001).

International Search Report for PCT/US2009/054773, 6 pages (May 12, 2010).

Kitaura, R. et al., Immobilization of a Metallo Schiff Base into a Microporus Coordination Plymer, Angewandte Chemie, International Edition, 43(20):2684-2687 (2004).

Kureshy, R.I. et al., Dicationic chiral Mn(III) salen complex exchanged n the interlayers of montmorillonite clay: a heterogeneous enantioselective catalyst for epoxidation of nonfunctionalied alkenes, Journal of Catalysis, 221(1):234-240 (2004).

Lin, Y. et al., A Lewis Acid-Lewis Base Bifunctional Catalyst from a New Mixed Ligand, Organic Letters, 9(4):567-570 (2007).

Lu, X. and Wang, Y., Highly Active, Binary Catalyst Systems for the Alternating Copolymerization of $CO_2$ and Epoxides under Mild Conditions, Angewandte Chemie International Edition, 43:3574-3577 (2004).

Lu, X. et al., Design of Highly Active Binary Catalyst Systems for CO/Epoxide Copolymerization: Polymer Selectivity, Enantioselectivity, and Stereochemistry Control, Journal of the American Chemical Society, 128:1664-1674 (2006).

Mandal, S.S. et al., Metal-Ion-Dependent Oxidative DNA Cleavage by Transition Metal Complexes of a New Water-Soluble Salen Derivative, Journal of Inorganic Biochemistry, 63(4):265-272 (1996).

Mandal, S.S. et al., Role of the Central Metal Ion and Ligand Charge in the DNA Binding and Modification by Metallosalen Complexes, Bioconjugate Chemistry, 8(6):798-812 (1997).

Miao, C. et al., Bifunctional Metal-Salen Complexes as Efficient Catalysts for the Fixation of $CO_2$ with Epoxides under Solvent Free Conditions, ChemSusChem, 1:236-241 (2008).

Mirkhani, V. et al., Biomimetic Alkene Epoxidation and Alkane Hydroxylation with Sodium Periodate Catalyzed by Mn(III)-*salen* Supported on Amberlite IRA-200, Monatshefte fur Chemie, 138:1303-1308 (2007).

Miyasaka, H. et al., One-dimensional arrangement of $Mn^{III}$ salen and a TCNQ radical with single-chain magnet behavior, Chemistry: A European Journal, 12(27):7028-7040 (2006).

Muller, J.G. et al., DNA Modifcation Promoted by Water-Soluble Nickel(II) Salen Complexes: A A Switch to DNA Alkylation, Journal of Inorganic Biochemistry, 54(3):199-206 (1994).

Nakano, K et al., Selective Formation of Polycarbonate over Cyclic Carbonate: Copolymerization of Epoxides with Carbon Dioxide Catalyzed by a Cobalt (III) Complex with Piperidinium End-Capping Arm, Angewandte Chemie International Edition, 45:7274-7277 (2006).

Niu, Y. et al., Alternating Copolymerization of Carbon Dioxide and Propylene Oxide Catalyzed by (R, R)-SalenCo$^{III}$—(2,4-

(56) References Cited

OTHER PUBLICATIONS dinitrophenoxy) and Lewis-Basic Cocatalyst, Journal of Polymer Science, Part A: Polymer Chemistry, 45(22):5050-5056 (2007).
Noh, E.K. et al., Two Components in a Molecule: Highly Efficient and Thermally Robust Catalytic System for CO/Epoxide Copolymerization, Journal of the American Chemical Society, 129:8082-8083 (2007).
Paddock, P.L. and Nguyen, S.T., Alternating Copolymerization of $CO_2$ and Propylene Oxide Catalzed by $Co^{III}$(salen)/ Lewis Base, Macromolecules, 38(15):6251-6253 (2005).
Pajunen, A. et al., {2,2'-[(R,R)-Cyclohexane-1,2-diylbis-(nitrilomethylidyne)]bis[6-tert-butyl-4-(triphenylphosphoniomethyl)phenolato]-O,N,N',P}copper(II) dichloride hexakis(deuterochloroform solvate, Acta Crystallographica Section C, 56:321-322 (2000).
Ren, W. et al., Mechanistic Aspects of the Copolymerization od $CO_2$ with Epoxides Using a Thermally Stable Single-Site Cobalt(III) Catalyst, Journal of the American Chemical Society, 131:11509-11518 (2009).
Sakamoto, S. et al., T-Site Selective Photocleavage of DNA by Cationic Schiff Base Complex of Manganese (III), Chemistry Letters, 11:1127-1128 (1998).
Sato, K. et al., Stereospecific Binding of Chemically Modified Salen-type Schiff Base Complexes of Copper(II) with DNA [salen = bis(salicyclidene)ethylenediamine], Journal the Chemical Society, Chemical Communications, (5):625-626 (1994).
Schoen, E. et al., Gas-Phase and Solution-Phase Polymerization of Epoxides by Cr(salen) Complexes: Evidence for a Dinuclear Cationic Mechanism, Inorganic Chemistry, 43(23):7278-7280 (2004).
Search report for Singapore Patent Application No. 201101242-4, mailed Apr. 5, 2012.
Shearer, J.M. and Rokita, S.E., Diamine Preparation for Synthesis of a Water Soluble Ni(II) Salen Complex, Bioorganic and Medicinal Chemistry Letters, 9(3):501-504 (1999).
Shimakoshi, H. et al., Syntheses of new water-soluble dicobalt complexes having two cobalt-carbon bonds and their ability for DNA cleavage, Tetrahedron Letters, 44(28):5197-5199 (2003).
Silvestri, A. et al., The interaction of native DNA with Zn(II) and Cu(II) complexes of 5-triethyl ammonium methyle salicylidene orto-phenylendiimine, Journal of Inorganic Biochemistry 101(5):841-848 (2007).
Sujith, S. et al., A Highly Active and Recyclable Catalytic System for $CO_2$/Propylene Oxide Copolymerization, Angewandte Chemie International Edition in English, 47:7306-7309 (2008).
Takahashi, K. et al., Design of Salen-Type Ni(II) Complexes for Recognition of DNA Base Sequence, Nucleic Acids Symposium Series, 51:189-190 (2007).
Tanaka, T. et al., Synthesis of New Cationic Schiff Base Complexes of Copper(II) and Their Selective Binding with DNA, Bulletin of the Chemical Society of Japan, 70(3):615-629 (1997).
Tang, N. et al., Nickel and Cobalt Reagents Promote Selective Oxidation of Z-DNA, Biochemistry, 28(50):16648-16654 (1999).
Voituriez, A. et al., Design and electropolymerization of new chiral thiophene-salen complexes, Synthetic Metals, 156(2-4):166-175 (2006).
Woodson, S.A. et al., A primer extension assay for modification of guanine by Ni(II) complexes, Nucleic Acids Research, 21(23):5524-5525 (1993).
Zhang, X. et al., Asymmetric epoxidation of chromenes catalyzed by chiral pyrrolidine SalenMn(III) complexes with an anchored functional group, Applied Organometallic Chemistry, 22:592-597 (2008).
Zhang, X. et al., Intramolecularly two-centered cooperation catalysis for the synthesis of cyclic carbonates from $CO_2$ and epoxides, Tetrahedron Letters, 49:6589-6592 (2008).
Zhou, X. et al., A Ni(Salen)-Biotin Conjugate for Rapid Isolation of Accessible DNA, Journal of the American Chemical Society, 122(37):9046-9047 (2000).

\* cited by examiner

CATALYSTS AND METHODS FOR POLYMER SYNTHESIS

PRIORITY CLAIM

This application is a continuation of U.S. patent application Ser. No. 13/755,112, filed Jan. 31, 2013 (now U.S. Pat. No. 8,951,930), which is a divisional of U.S. patent application Ser. No. 13/059,967, filed on Feb. 18, 2011 (now U.S. Pat. No. 8,633,123), which is a national phase application under 35 U.S.C. 371 of PCT International Application No. PCT/US2009/054773, filed on Aug. 24, 2009, which claims priority to U.S. Provisional Patent Application Ser. No. 61/091,013, filed Aug. 22, 2008; U.S. Provisional Patent Application Ser. No. 61/096,313, filed Sep. 11, 2008 and U.S. Provisional Patent Application Ser. No. 61/098,739, filed Sep. 19, 2008. The entire contents of each of these priority applications are incorporated herein by reference.

BACKGROUND

Catalysts capable of effecting the copolymerization of epoxides and carbon dioxide to form aliphatic polycarbonates (APCs) have been known in the art since the 1960s. The early catalysts were based on heterogeneous zinc compounds and suffered from low reactivity, a lack of selectivity for polymer formation vs. cyclic carbonate formation, and a tendency to produce polycarbonates contaminated with ether linkages.

Improved catalysts based on transition metals have been discovered over the past decade or so. These newer catalysts have increased reactivity and improved selectivity. Nevertheless, even using highly active catalysts such as those disclosed in U.S. Pat. No. 7,304,172, the reaction times required to make high molecular weight polymer are typically quite long. In addition, the best-performing catalysts disclosed in the '172 patent require the addition of a separate co-catalyst to achieve optimum activity.

Attempts to address these shortcomings have been made. Catalysts described by Nozaki and co-workers (*Angew. Chem. Int. Ed.* 2006, 45, 7274-7277) tether an amine co-catalyst to a ligand of the catalyst. These next-generation catalytic systems suffer from lengthy and complicated syntheses and undesirable induction times prior to onset of polymerization. There remains a need for catalysts that have increased activity that will further reduce the polymerization time required to produce high molecular weight APCs.

SUMMARY

The present invention provides, among other things, unimolecular catalyst systems having activity in the copolymerization of carbon dioxide and epoxides and methods of using the same. In some embodiments, the present invention provides metal complexes having an activating species with co-catalytic activity tethered to a multidentate ligand that is coordinated to an active metal center of a metal complex.

In certain embodiments, the present invention provides unimolecular metal complexes and methods for using the same in the copolymerization of carbon dioxide and epoxides. In some embodiments, provided metal complexes have the structure:

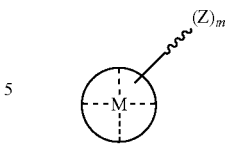

wherein:

M is a metal atom;

comprises a multidentate ligand;

$\sim\!\!\!\sim\!\!\!\sim (Z)_m$ represents one or more activating moieties attached to the multidentate ligand, where $\sim\!\!\!\sim\!\!\!\sim$ is a linker moiety covalently coupled to the ligand, each Z is an activating functional group; and m is an integer from 1 to 4 representing the number of Z groups present on an individual linker moiety.

In some embodiments, tethered activating functional groups (Z) are neutral nitrogen-containing moieties. In certain embodiments, neutral nitrogen-containing moieties are selected from the group consisting of:

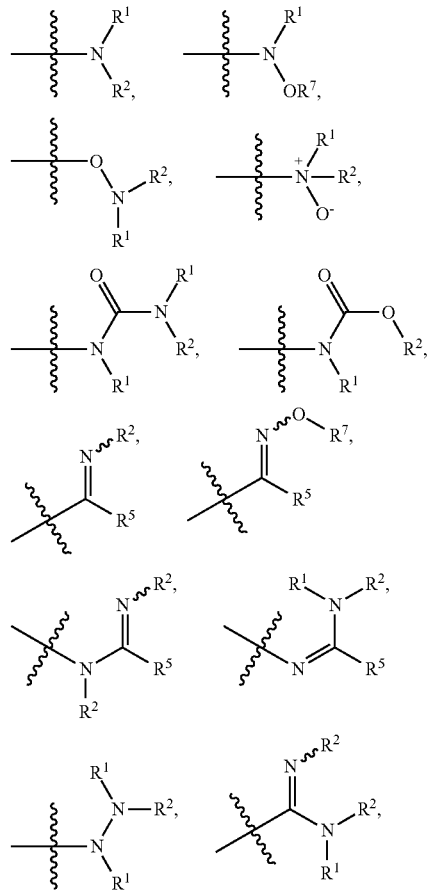

-continued

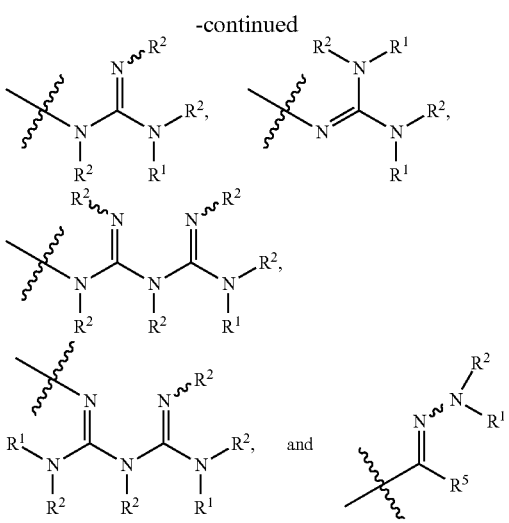

or a combination of two or more of these,
wherein:
  each occurrence of $R^1$, and $R^2$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein $R^1$ and $R^2$ groups can be taken together with intervening atoms to form one or more optionally substituted rings optionally containing one or more additional heteroatoms;
  each occurrence of $R^5$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein an $R^5$ group can be taken with an $R^1$ or $R^2$ group to form one or more optionally substituted rings; and
  each occurrence of $R^7$ is independently hydrogen, a hydroxyl protecting group, or an optionally substituted radical selected from the group consisting of $C_{1-20}$ acyl; $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In some embodiments, tethered activating functional groups (Z) are cationic moieties. In certain embodiments, cationic moieties are selected from the group consisting of:

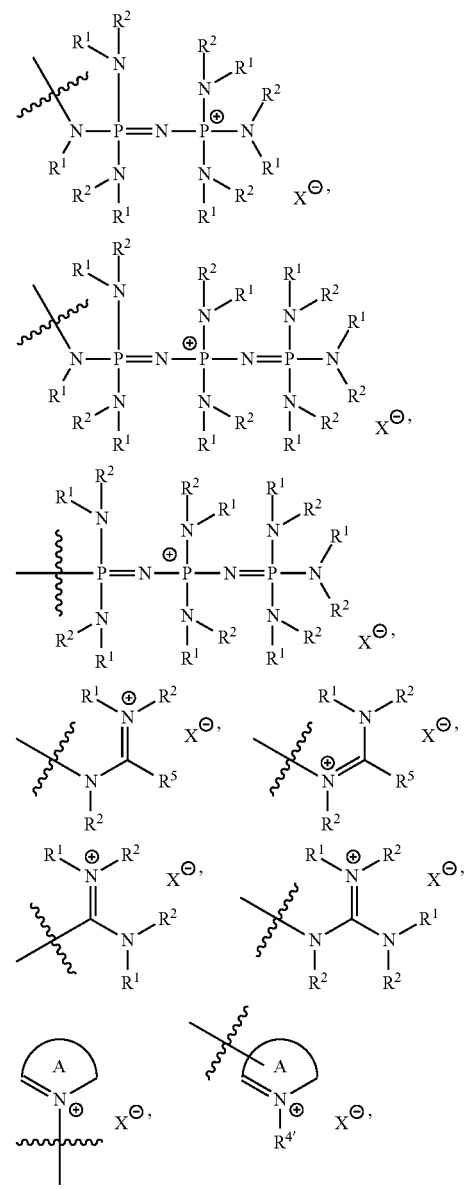

-continued

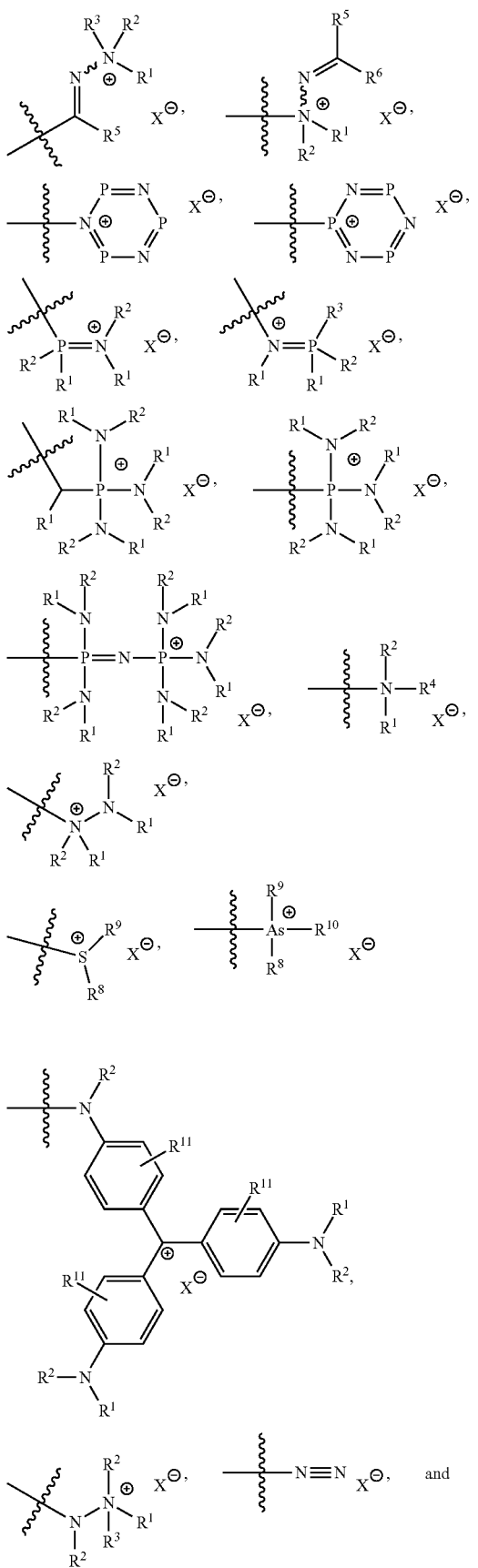

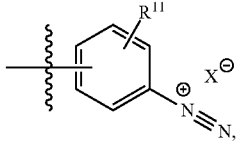

or a combination of two or more of these,
wherein:
each occurrence of $R^1$, $R^2$, and $R^3$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein any two or more $R^1$, $R^2$, and $R^3$ groups can be taken together with intervening atoms to form one or more optionally substituted rings optionally containing one or more additional heteroatoms;

$R^4$ is hydrogen or —$OR^7$;

$R^{4'}$ is hydrogen, hydroxyl, or optionally substituted $C_{1-20}$ aliphatic;

each occurrence of $R^5$ and $R^6$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein $R^5$ and $R^6$ can be taken together with intervening atoms to form one or more optionally substituted rings optionally containing one or more heteroatoms, and an $R^5$ or $R^6$ group can be taken with an $R^1$ or $R^2$ group to form one or more optionally substituted rings;

each occurrence of $R^2$ is independently hydrogen, a hydroxyl protecting group, or an optionally substituted radical selected from the group consisting of $C_{1-20}$ acyl; $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

each occurrence of $R^8$, $R^9$, and $R^{10}$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein any two or more $R^8$, $R^9$ and $R^{10}$ groups can be taken together with intervening atoms to form one or more optionally substituted rings;

each occurrence of $R^{11}$ is independently selected from the group consisting of:
halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-N_3$, $-OR^y$, $-OC(O)N(R^y)_2$, $-N(R^y)_2$, $-NR^yC(O)R^y$, $-NR^yC(O)OR^y$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where each occurrence of $R^y$ is independently $-H$, or an optionally substituted radical selected from the group consisting of $C_{1-6}$ aliphatic, 3- to 7-membered heterocyclic, phenyl, and 8- to 10-membered aryl, and where two or more adjacent $R^{11}$ groups can be taken together to form an optionally substituted saturated, partially unsaturated, or aromatic 5- to 12-membered ring containing 0 to 4 heteroatoms;

$X^-$ is any anion, and

Ring A is an optionally substituted, 5- to 10-membered heteroaryl group.

In some embodiments, an activating functional group (Z) is a phosphorous-containing functional group.

In certain embodiments, a phosphorous-containing functional group is chosen from the group consisting of: phosphines ($-PR^y_2$); Phosphine oxides $-P(O)R^y_2$; phosphinites $P(OR^7)R^y_2$; phosphonites $P(OR^7)_2R^y$; phosphites $P(OR^7)_3$; phosphinates $OP(OR^7)R^y_2$; phosphonates; $OP(OR^7)_2R^y$; phosphates $-OP(OR^7)_3$; phosphonium salts ($[-PR^y_3]^+$) where the phosphorous-containing functional group may be linked to a metal complex through any available position (e.g. direct linkage via the phosphorous atom, or in some cases via an oxygen atom).

In certain embodiments, a phosphorous-containing functional group is chosen from the group consisting of:

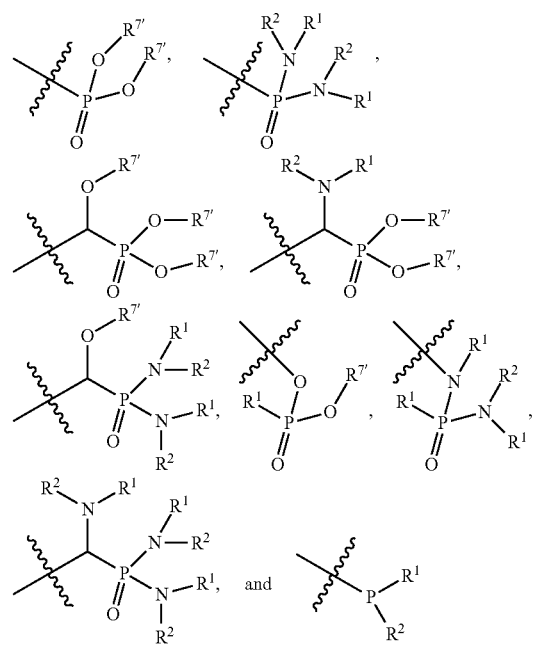

or a combination of two or more of these
wherein $R^1$ and $R^2$, are as defined above; and
each $R^{7'}$ is independently hydrogen, a hydroxyl protecting group, or an optionally substituted radical selected from the group consisting of $C_{1-20}$ acyl; $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; and where two $R^{7'}$ groups can be taken together with intervening atoms to form an optionally substituted ring optionally containing one or more heteroatoms, and an $R^{7'}$ group can be taken with an $R^1$ or $R^2$ group to an optionally substituted ring;

In some embodiments, phosphorous containing functional groups include those disclosed in *The Chemistry of Organophosphorus Compounds. Volume 4. Ter- and Quinquevalent Phosphorus Acids and their Derivatives*. The Chemistry of Functional Group Series Edited by Frank R. Hartley (Cranfield University, Cranfield, U.K.). Wiley: New York. 1996. ISBN 0-471-95706-2, the entirety of which is hereby incorporated herein by reference.

In certain embodiments, a phosphorous-containing functional group has the structure $$*\!-\!(X)_b\!-\![(R^6R^7R^8P)^+]_nQ^{n-}, \text{ wherein:}$$

X is —O—, —N=, or —NR$^z$—,
b is 1 or 0,
each of R$^6$, R$^7$ and R$^8$ are independently present or absent and, if present, are independently selected from the group consisting of optionally substituted C$_1$-C$_{20}$ aliphatic, optionally substituted C$_6$-C$_{14}$ aryl, optionally substituted 3- to 14-membered heterocyclic, optionally substituted 5- to 14-membered heteroaryl, halogen, =O, —OR$^z$, =NR$^z$, and N(R$^z$)$_2$ where R$^z$ is hydrogen, or an optionally substituted C$_1$-C$_{20}$ aliphatic, optionally substituted 6- to 14-membered aryl, optionally substituted 3- to 14-membered heterocyclic, or optionally substituted 5- to 14-membered heteroaryl,
Q is any anion, and
n is an integer between 1 and 4.

In some embodiments, the present disclosure encompasses methods for the copolymerization of epoxides and carbon dioxide, such methods comprising contacting one or more epoxides with a catalyst described above in the presence of carbon dioxide.

In some embodiments, the present disclosure encompasses methods for the formation of cyclic carbonates from epoxides and carbon dioxide, such methods comprising contacting one or more epoxides with a catalyst described above in the presence of carbon dioxide.

In some embodiments, the present disclosure encompasses methods for the formation of polyethers, such methods comprising contacting one or more epoxides with a catalyst described above.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl. In certain embodiments, the term aliphatic group encompasses aliphatic groups wherein one or more hydrogen atoms are replaced with a halogen atom. In certain embodiments, the term aliphatic group encompasses chlorinated or fluorinated aliphatic groups including perfluorinated compounds.

The term "epoxide", as used herein, refers to a substituted or unsubstituted oxirane. Such substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived by removal of a single hydrogen atom from an aliphatic moiety. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived by the removal of a single hydrogen atom from a straight- or branched-chain aliphatic moiety having at least one carbon-carbon double bond. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, allyl, 1,3-butadienyl, butenyl, 1-methyl-2-buten-1-yl, allyl, 1,3-butadienyl, allenyl, and the like.

The term "alkynyl," as used herein, refers to a monovalent group derived by the removal of a single hydrogen atom from a straight- or branched-chain aliphatic moiety having at least one carbon-carbon triple bond. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refer to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, and spiro[4.5]decane, to name but a few.

The term "aryl" used alone or as part of a larger moiety as in "aralkyl", "aralkoxy", or "aryloxyalkyl", refers to monocyclic and polycyclic ring systems having a total of six to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one to six carbon atoms are independently replaced by one or more of oxygen, sulfur, nitrogen, or phosphorus. Heteroaliphatic groups may be substituted or unsubstituted, branched or unbranched, cyclic or acyclic, and include saturated, unsaturated or partially unsaturated groups.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 it electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or polycyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is saturated, partially unsaturated, or aromatic and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "acyl" as used herein refers to a group having a formula —C(O)R where R is hydrogen or an optionally substituted aliphatic, aryl, or heterocyclic group.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chlorop-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protecting Groups in Organic Synthesis*, T. W. Greene and P. G. M. Wuts, 3$^{rd}$ edition, John Wiley & Sons, 1999, the entirety of which is incorporated herein by reference.

When substituents are described herein, the term "radical" or "optionally substituted radical" is sometimes used. In this context, "radical" means a moiety or functional group having an available position for attachment to the structure on which the substituent is bound. In general the point of attachment would bear a hydrogen atom if the substituent were an independent neutral molecule rather than a substituent. The terms "radical" or "optionally-substituted radical" in this context are thus interchangeable with "group" or "optionally-substituted group".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted group" or "optionally substituted radical" may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond that crosses a bond in a ring of the depicted molecule. This convention indicates that one or more of the substituents may be attached to the ring at any available position (usually in place of a hydrogen atom of the parent structure). In cases where an atom of a ring so substituted has two substitutable positions, two groups may be present on the same ring atom. Unless otherwise indicated, when more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)N(R$^\circ$)$_2$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ_2$; —C(S)NR$^\circ_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —(C$_{1-4}$ straight or branched)alkylene)O—N(R$^\circ$)$_2$; or —(C$_{1-4}$ straight or branched) alkylene)C(O)O—N(R$^\circ$)$_2$, wherein each R$^\circ$ may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-4}$C(O)N(R$^\circ$)$_2$; —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with intervening atom(s) form an unsubstituted 3-12-membered saturated, partially unsaturated, or aryl mono- or bicyclic ring having 0-4 heteroatoms independently selected from nitrogen, oxygen, or sulfur. A substitutable nitrogen may be substituted with three R$^†$ substituents to provide a charged ammonium moiety —N$^+$(R$^†$)$_3$, wherein the ammonium moiety is further complexed with a suitable counterion.

Suitable substituents on the aliphatic group of R$^†$ are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "catalyst" refers to a substance the presence of which increases the rate and/or extent of a chemical reaction, while not being consumed or undergoing a permanent chemical change itself.

As used herein, the term "multidentate" refers to ligands having multiple sites capable of coordinating to a single metal center.

As used herein, the term "activating moiety" refers to a moiety comprising one or more activating functional groups. In certain embodiments, an activating moiety improves the catalytic activity of a metal complex. In some embodiments, such improved catalytic activity is characterized by higher conversion of starting materials compared to a metal complex lacking an activating moiety. In some embodiments, such improved catalytic activity is characterized by higher rate of conversion of starting materials compared to a metal complex lacking an activating moiety. In some embodiments, such improved catalytic activity is characterized by higher yield of product compared to a metal complex lacking an activating moiety.

DETAILED DESCRIPTION OF CERTAIN EMBODIMENTS

The present invention provides, among other things, unimolecular metal complexes for the copolymerization of carbon dioxide and epoxides and methods of using the same. In certain embodiments, provided metal complexes contain a metal-ligand moiety tethered to one or more activating moieties. In some embodiments, an activating moiety comprises a linker and one or more activating functional groups. In some embodiments, provided metal complexes act as polymerization catalysts. In certain embodiments, at least one activating functional group present on the tethered moiety can act as a polymerization co-catalyst and thereby increase the rate of the copolymerization.

In certain embodiments, provided metal complexes include a metal atom coordinated to a multidentate ligand and at least one activating moiety tethered to the multidentate ligand. In certain embodiments, provided metal complexes have the structure:

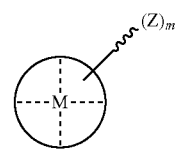

wherein:
M is a metal atom;

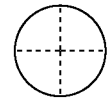

comprises a multidentate ligand;
—∿∿ (Z)$_m$ represents one or more activating moieties attached to the multidentate ligand, where —∿∿ is a linker moiety covalently coupled to the ligand, each Z is an activating functional group; and m is an integer from 1 to 4 representing the number of Z groups present on an individual linker moiety.

In certain embodiments, provided metal complexes include a metal atom coordinated to a multidentate ligand and at least one activating moiety tethered to the multidentate ligand. In some embodiments, there are 1 to 10 activating moieties —∿∿ (Z)$_m$ tethered to the multidentate ligand. In certain embodiments, there are 1 to 8 such activating moieties tethered to the multidentate ligand. In certain embodiments, there are 1 to 4 such activating moieties tethered to the multidentate ligand.

I. Activating Functional Groups

In some embodiments, an activating functional group is selected from the group consisting of neutral nitrogen-containing functional groups, cationic moieties, phosphorous-containing functional groups, and combinations of two or more of these.

Ia. Neutral Nitrogen-Containing Activating Groups

In some embodiments, one or more tethered activating functional groups on provided metal complexes are neutral nitrogen-containing moieties. In some embodiments, such moieties include one or more of the structures in Table Z-1:

TABLE Z-1

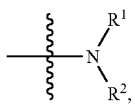

TABLE Z-1-continued

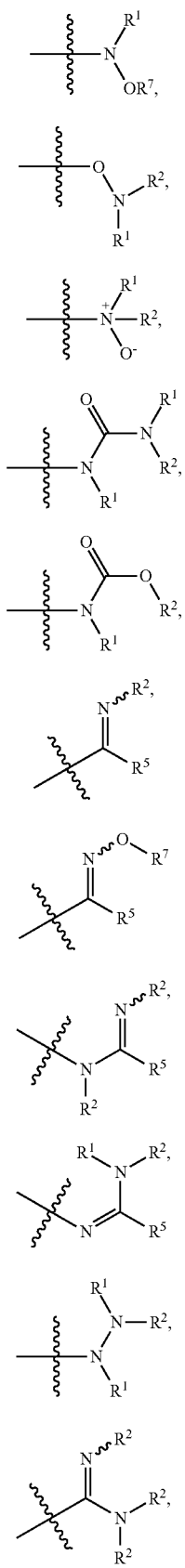

TABLE Z-1-continued

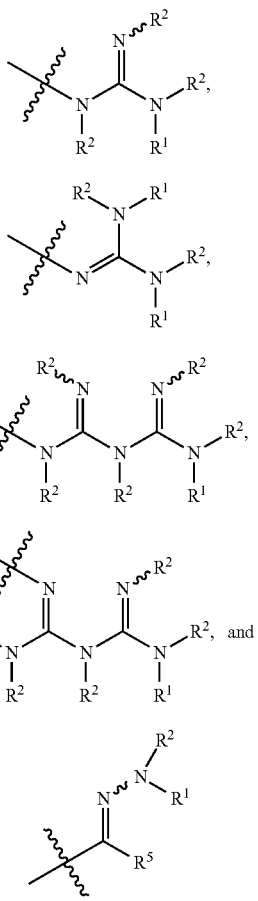

or a combination of two or more of these, wherein:
each occurrence of $R^1$, and $R^2$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein two or more $R^1$ and $R^2$ groups can be taken together with intervening atoms to form one or more optionally substituted rings optionally containing one or more additional heteroatoms;
each occurrence of $R^5$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein an $R^5$ group can be taken with an $R^1$ or $R^2$ group to form one or more optionally substituted rings;

each occurrence of $R^2$ is independently hydrogen, a hydroxyl protecting group, or an optionally substituted radical selected from the group consisting of $C_{1-20}$ acyl; $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

In some embodiments, an activating functional group is an N-linked amino group:

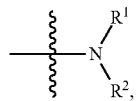

where $R^1$ and $R^2$ are as defined above.

In certain embodiments, $R^1$ and $R^2$ are both hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In certain embodiments, $R^1$ and $R^2$ are each independently an optionally substituted radical selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, $R^1$ and $R^2$ are each independently optionally substituted $C_{1-12}$ aliphatic. In some embodiments, $R^1$ and $R^2$ are each independently optionally substituted $C_{1-6}$ aliphatic. In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted phenyl. In some embodiments, each occurrence of $R^1$ and $R^2$ is independently an optionally substituted 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —$C(R^y)_2$—, —$C(R^y)_2C(R^y)_2$—, —$C(R^y)_2C(R^y)_2C(R^y)_2$—, —$C(R^y)_2OC(R^y)_2$—, and —$C(R^y)_2NR^yC(R^y)_2$—. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^yCH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In specific embodiments, an N-linked amine activating functional group is selected from the group consisting of:

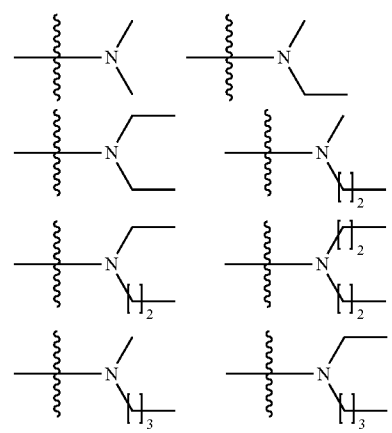

-continued

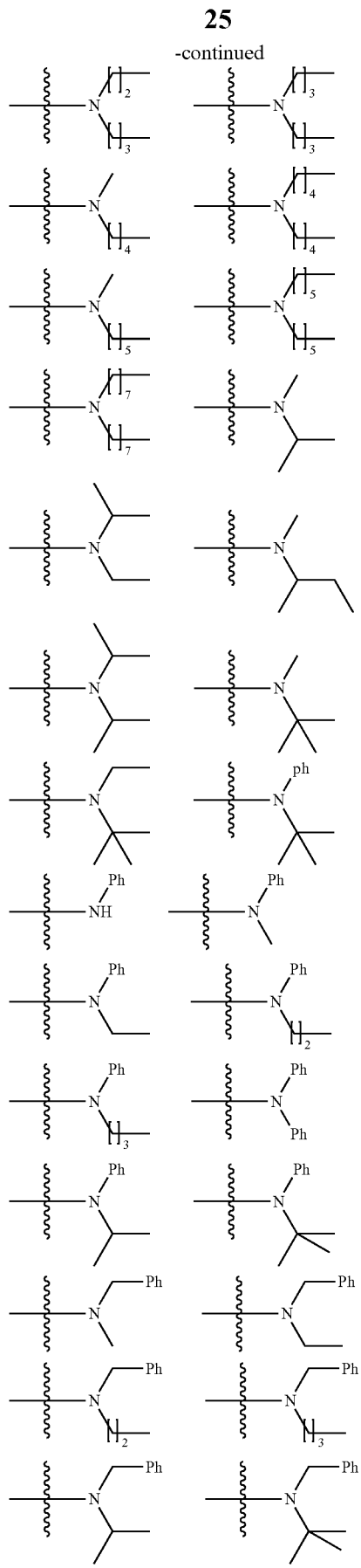
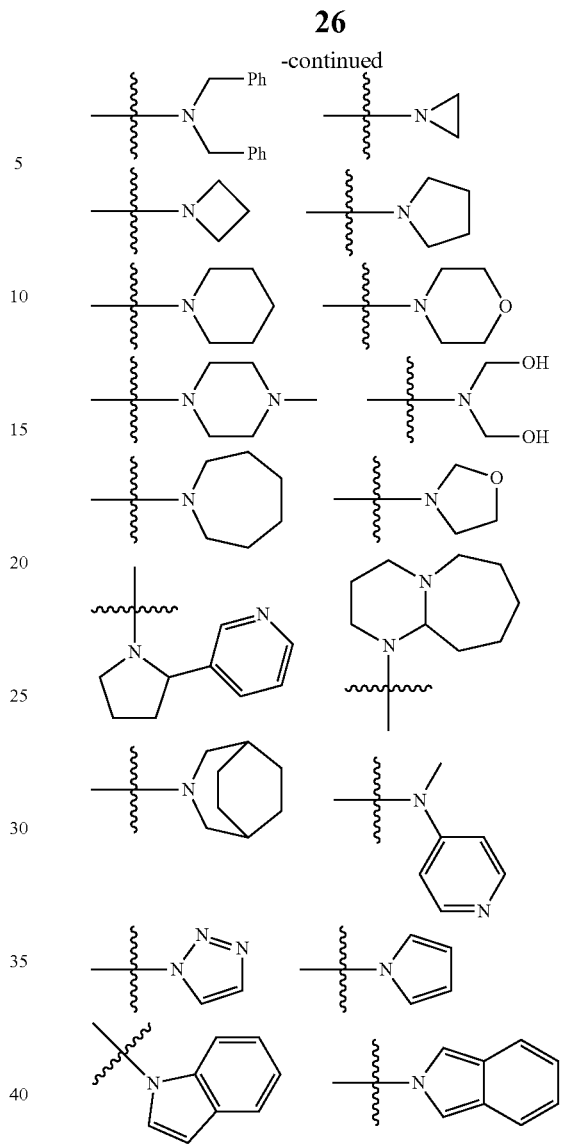

In some embodiments, one or more activating functional groups is an N-linked hydroxyl amine derivative:

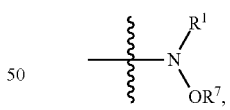

wherein $R^1$ and $R^7$ are as defined above.

In certain embodiments, $R^7$ is hydrogen. In some embodiments, $R^7$ is an optionally substituted radical selected from the group consisting of $C_{1-12}$ aliphatic, phenyl, 8- to 10-membered aryl, and 3- to 7-membered heterocyclic. In certain embodiments, $R^7$ is a $C_{1-12}$ aliphatic. In certain embodiments, $R^7$ is a $C_{1-6}$ aliphatic. In some embodiments, $R^7$ is an optionally substituted 8- to 10-membered aryl group. In certain embodiments, $R^7$ is an optionally substituted phenyl. In some embodiments, $R^7$ is methyl, ethyl, propyl, butyl, pentyl, hexyl, heptyl, octyl, phenyl or benzyl.

In certain embodiments, $R^1$ is hydrogen. In some embodiments, $R^1$ is an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In some embodiments, R¹ is an optionally substituted radical selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In some embodiments, R¹ is an optionally substituted radical selected from the group consisting of $C_{1-12}$ aliphatic and $C_{1-12}$ heteroaliphatic. In some embodiments, R¹ is an optionally substituted $C_{1-20}$ aliphatic. In certain embodiments, R¹ is an optionally substituted $C_{1-12}$ aliphatic. In some embodiments, R¹ is an optionally substituted $C_{1-6}$ aliphatic. In some embodiments, R¹ is an optionally substituted $C_{1-12}$ heteroaliphatic. In some embodiments, R¹ is an optionally substituted 8- to 10-membered aryl. In certain embodiments, R¹ is an optionally substituted phenyl. In some embodiments, R¹ is an optionally substituted 5- to 10-membered heteroaryl. In some embodiments, R¹ is an optionally substituted 3- to 7-membered heterocyclic.

In certain embodiments, R¹ is methyl, ethyl, propyl, butyl, pentyl, hexyl, heptyl, octyl, phenyl or benzyl. In some embodiments, R¹ is butyl. In some embodiments, R¹ is isopropyl. In some embodiments, R¹ is phenyl. In some embodiments, R¹ is benzyl. In some embodiments, R¹ is perfluoro. In some embodiments, R¹ is —$CF_2CF_3$.

In certain embodiments, R¹ and R⁷ are taken together with intervening atoms to form one or more optionally substituted rings optionally containing one or more additional heteroatoms.

In certain embodiments, one or more N-linked hydroxyl amine activating functional groups are selected from the group consisting of:

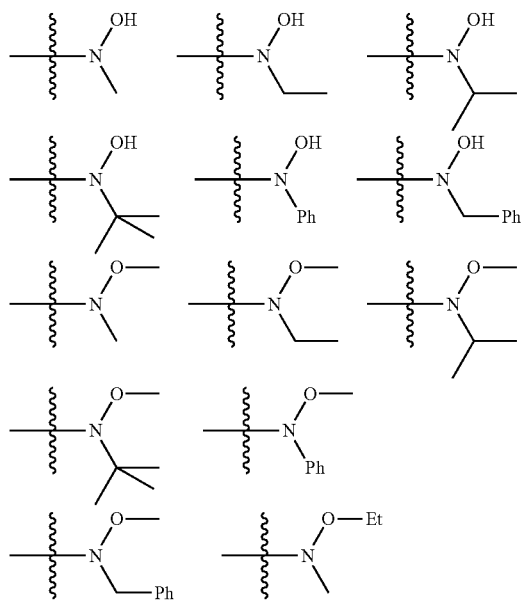

In some embodiments, an activating functional group in a provided metal complex is an amidine. In certain embodiments, such amidine activating functional groups are selected from:

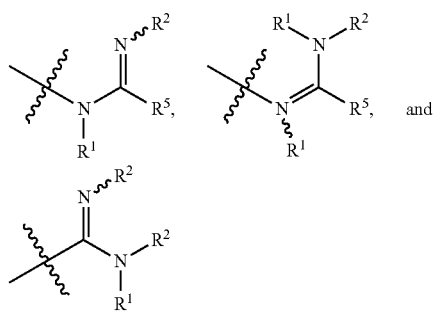

where each occurrence of R¹, R² and R⁵ are as defined above.

In certain embodiments, each R¹ and R² is hydrogen. In some embodiments, only one of R¹ and R² is hydrogen. In certain embodiments, each R¹ and R² is independently an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In some embodiments, each R¹ and R² is independently an optionally substituted radical selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, R¹ and R² are each independently an optionally substituted radical selected from the group consisting of $C_{1-12}$ aliphatic and $C_{1-12}$ heteroaliphatic. In some embodiments, each occurrence of R¹ and R² is independently an optionally substituted $C_{1-20}$ aliphatic. In some embodiments, R¹ and R² are each independently optionally substituted $C_{1-12}$ aliphatic. In some embodiments, R¹ and R² are each independently optionally substituted $C_{1-6}$ aliphatic.

In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —$C(R^y)_2$—, —$C(R^y)_2C(R^y)_2$—, —$C(R^y)_2C(R^y)_2C(R^y)_2$—, —$C(R^y)_2OC(R^y)_2$—, and —$C(R^y)_2NR^yC(R^y)_2$—. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^yCH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In certain embodiments, $R^5$ is H. In certain embodiments, $R^5$ is optionally substituted $C_{1-20}$ aliphatic. In some embodiments, $R^5$ is optionally substituted 6- to 14-membered aryl. In certain embodiments, $R^5$ is optionally substituted $C_{1-12}$ aliphatic. In some embodiments, $R^5$ is optionally substituted $C_{1-6}$ aliphatic. In certain embodiments, $R^5$ is optionally substituted phenyl.

In some embodiments, one or more $R^1$ or $R^2$ groups are taken together with $R^5$ and intervening atoms to form an optionally substituted ring. In certain embodiments, $R^1$ and $R^5$ are taken together to form an optionally substituted 5- or 6-membered ring. In some embodiments, $R^2$ and $R^5$ are taken together to form an optionally substituted 5- or 6-membered ring optionally containing one or more additional heteroatoms. In some embodiments, $R^1$, $R^2$ and $R^5$ are taken together to form an optionally substituted fused ring system. In some embodiments such rings formed by combinations of any of $R^1$, $R^2$ and $R^5$ are partially unsaturated or aromatic.

In certain embodiments, an activating functional group is an N-linked amidine:

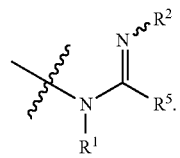

In certain embodiments, N-linked amidine groups are selected from the group consisting of:

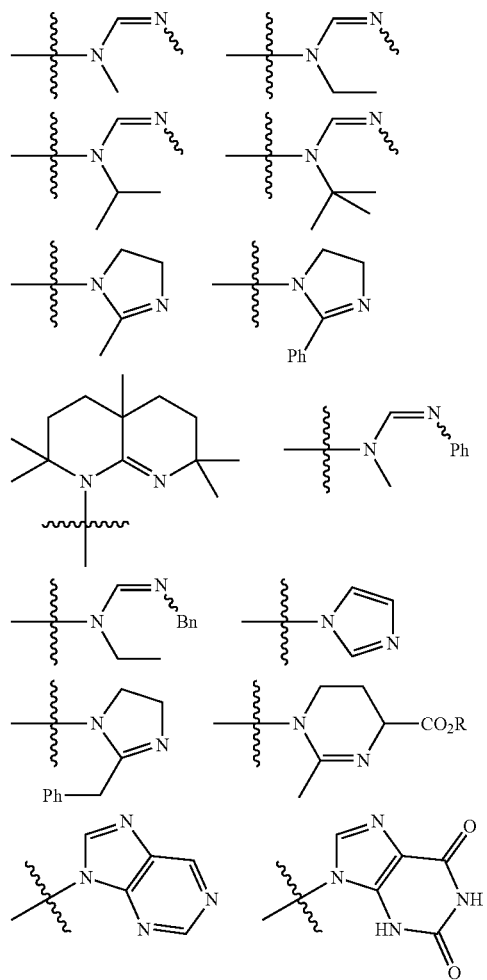

In certain embodiments, activating functional groups are amidine moieties linked through the imine nitrogen:

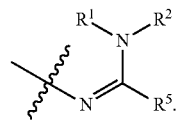

In certain embodiments, imine-linked amidine activating functional groups are selected from the group consisting of:

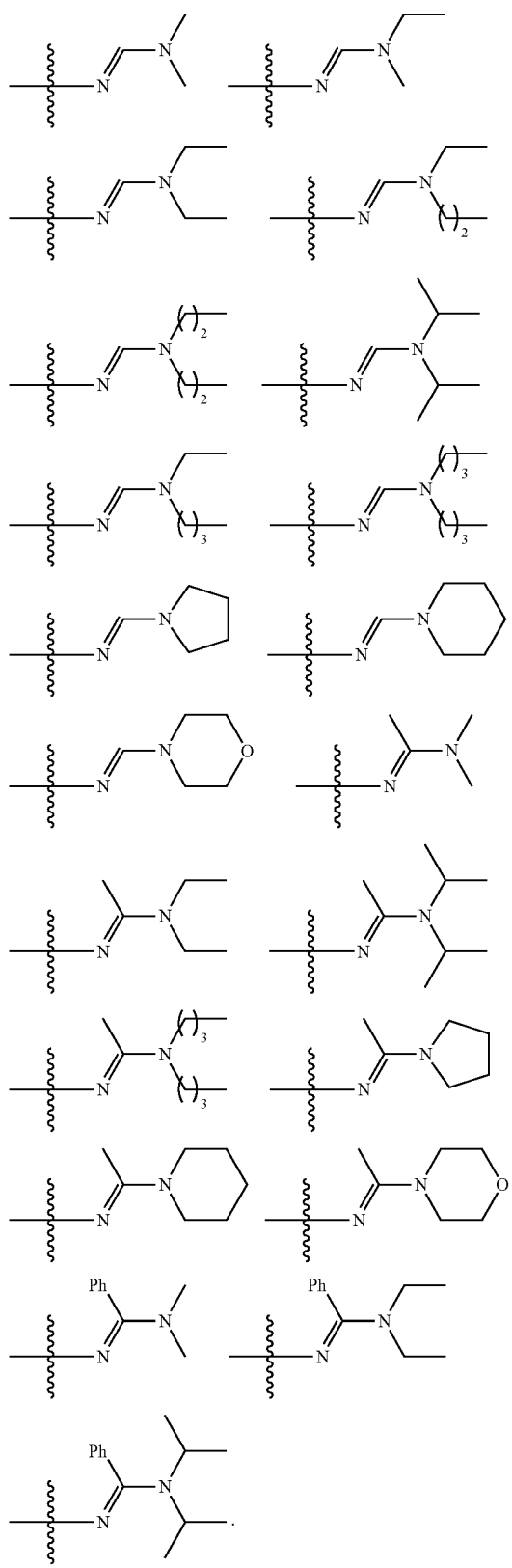
In certain embodiments, activating functional groups are amidine moieties linked through a carbon atom:
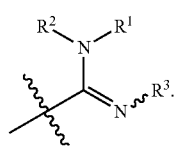
In certain embodiments, carbon-linked amidine activating groups are selected from the group consisting of:
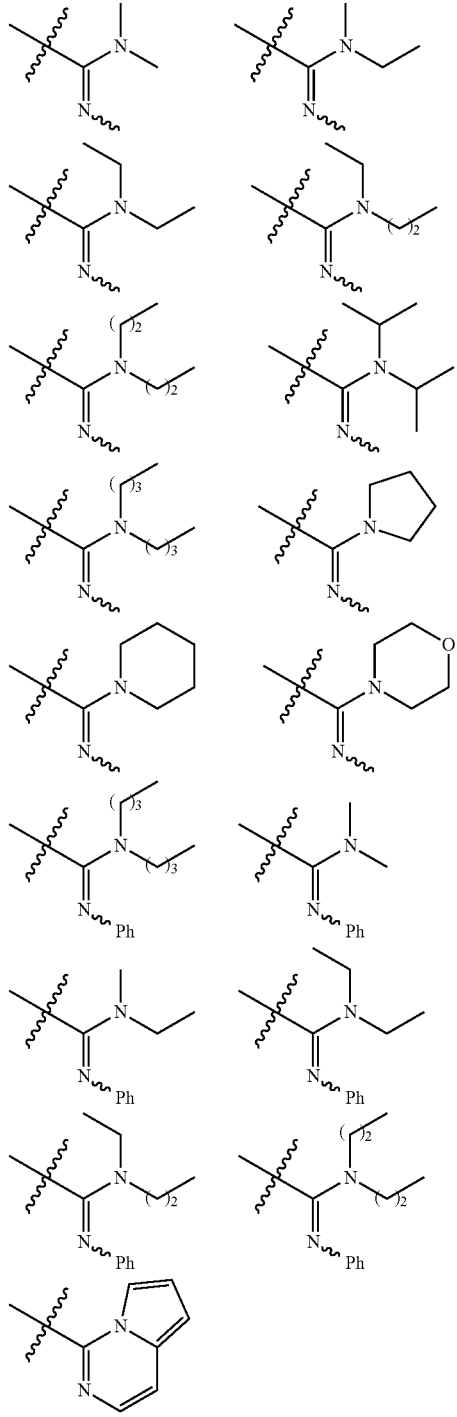

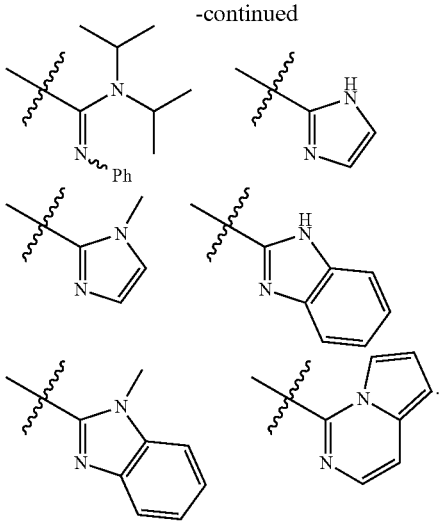

In some embodiments, one or more activating functional groups is a carbamate. In certain embodiments, a carbamate is N-linked:

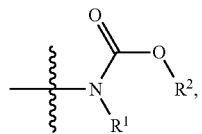

where $R^1$ and $R^2$ are as defined above. In some embodiments, a carbamate is O-linked:

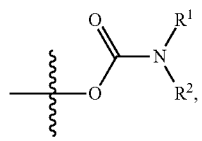

where $R^1$ and $R^2$ are as defined above.

In certain embodiments, $R^1$ and $R^2$ are both hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In some embodiments, $R^1$ and $R^2$ are each independently an optionally substituted radical selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, $R^1$ and $R^2$ are each independently optionally substituted $C_{1-12}$ aliphatic. In some embodiments, $R^1$ and $R^2$ are each independently optionally substituted $C_{1-6}$ aliphatic. In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —C($R^y$)$_2$—, —C($R^y$)$_2$C($R^y$)$_2$—, —C($R^y$)$_2$C($R^y$)$_2$C($R^y$)$_2$—, —C($R^y$)$_2$OC($R^y$)$_2$—, and —C($R^y$)$_2$NR$^y$C($R^y$)$_2$—. In certain embodiments, $R^1$ and $R^2$ are taken together to form a ring fragment selected from the group consisting of: —CH$_2$—, —CH$_2$CH$_2$—, —CH$_2$CH$_2$CH$_2$—, —CH$_2$OCH$_2$—, and —CH$_2$NR$^y$CH$_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle. In some embodiments, $R^2$ is selected from the group consisting of: methyl, t-butyl, t-amyl, benzyl, adamantyl, allyl, 4-methoxycarbonylphenyl, 2-(methylsulfonyl)ethyl, 2-(4-biphenylyl)-prop-2-yl, 2-(trimethylsilyl)ethyl, 2-bromoethyl, and 9-fluorenylmethyl.

In some embodiments, an activating functional group is a guanidine or bis-guanidine group:

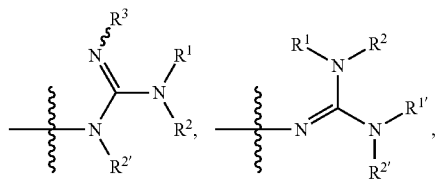

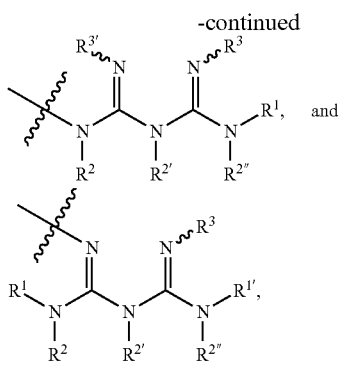

where each occurrence of $R^1$, $R^{1'}$, $R^2$, $R^{2'}$, $R^{2''}$, $R^3$, and $R^{3'}$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein any two or more $R^1$, $R^{1'}$, $R^2$, $R^{2'}$, $R^{2''}$, $R^3$, and $R^{3'}$ groups can be taken together with intervening atoms to form one or more optionally substituted rings optionally containing one or more additional heteroatoms;

In certain embodiments, each occurrence of $R^1$, $R^{1'}$, $R^2$, $R^{2'}$, $R^{2''}$, $R^3$, and $R^{3'}$ is hydrogen. In some embodiments, each occurrence of $R^1$, $R^{1'}$, $R^2$, $R^{2'}$, $R^{2''}$, $R^3$, and $R^{3'}$ is hydrogen or an optionally substituted radical selected from the group consisting of $C_{1-20}$ aliphatic; $C_{1-20}$ heteroaliphatic; 3- to 7-membered heterocyclic, phenyl, and 8- to 10-membered aryl. In some embodiments, each occurrence of $R^1$, $R^{1'}$, $R^2$, $R^{2'}$, $R^{2''}$, $R^3$, and $R^{3'}$ is hydrogen or an optionally substituted radical selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur. In certain embodiments, each occurrence of $R^1$, $R^{1'}$, $R^2$, $R^{2'}$, $R^{2''}$, $R^3$, and $R^{3'}$ is independently hydrogen or an optionally substituted radical selected from the group consisting of $C_{1-20}$ aliphatic, phenyl, and 8- to 10-membered aryl. In certain embodiments, each occurrence of $R^1$ and $R^2$ is independently an optionally hydrogen or an optionally substituted $C_{1-8}$ aliphatic, phenyl, or 8- to 10-membered aryl group. In some embodiments, each occurrence of $R^1$, $R^{1'}$, $R^2$, $R^{2'}$, $R^{2''}$, $R^3$, and $R^{3'}$ is independently hydrogen or an optionally substituted $C_{1-20}$ aliphatic. In some embodiments, each occurrence of $R^1$ and $R^2$ is independently hydrogen an optionally substituted aryl group or an optionally substituted $C_{1-8}$ aliphatic group. In some embodiments, each occurrence of $R^1$, $R^{1'}$, $R^2$, $R^{2'}$, $R^{2''}$, $R^3$, and $R^{3'}$ is independently hydrogen or an optionally substituted $C_{1-6}$ aliphatic group. In some embodiments, each occurrence of $R^1$, $R^{1'}$, $R^2$, $R^{2'}$, $R^{2''}$, $R^3$, and $R^{3'}$ is independently hydrogen or an optionally substituted $C_{1-4}$ aliphatic group. In some embodiments, each occurrence of $R^1$, $R^{1'}$, $R^2$, $R^{2'}$, $R^{2''}$, $R^3$, and $R^{3'}$ is independently an optionally substituted $C_{1-20}$ aliphatic. In some embodiments, $R^1$, $R^{1'}$, $R^2$, $R^{2'}$, $R^{2''}$, $R^3$, and $R^{3'}$ are each independently optionally substituted $C_{1-12}$ aliphatic. In some embodiments, $R^1$, $R^{1'}$, $R^2$, $R^{2'}$, $R^{2''}$, $R^3$, and $R^{3'}$ are each independently optionally substituted $C_{1-6}$ aliphatic. In some embodiments, one or more occurrence of $R^{1'}$, $R^2$, $R^{2''}$, $R^{2''}$, $R^3$, and $R^{3'}$ is independently an optionally substituted $C_{1-20}$ heteroaliphatic. In some embodiments, one or more occurrence of $R^1$, $R^{1'}$, $R^2$, $R^{2'}$, $R^{2''}$, $R^3$, and $R^{3'}$ is independently hydrogen or an optionally substituted phenyl or 8- to 10-membered aryl. In some embodiments, one or more occurrence of $R^1$, $R^{1'}$, $R^2$, $R^{2'}$, $R^{2''}$, $R^3$, and $R^{3'}$ is independently hydrogen, or an optionally substituted 5- to 10-membered heteroaryl.

In some embodiments, $R^1$ is optionally substituted $C_{1-6}$ aliphatic. In certain embodiments, $R^{1'}$ is optionally substituted $C_{1-6}$ aliphatic. In certain embodiments, $R^2$ is optionally substituted $C_{1-6}$ aliphatic. In certain embodiments, $R^{2'}$ is optionally substituted $C_{1-6}$ aliphatic. In certain embodiments, $R^{2''}$ is optionally substituted $C_{1-6}$ aliphatic. In certain embodiments, $R^3$ is optionally substituted $C_{1-6}$ aliphatic. In certain embodiments, $R^{3'}$ is optionally substituted $C_{1-6}$ aliphatic. In some embodiments, each occurrence of $R^1$, $R^{1'}$, $R^2$, $R^{2'}$, $R^{2''}$, $R^3$, and $R^{3'}$ is independently hydrogen, methyl, ethyl, propyl, butyl, pentyl, hexyl, heptyl, octyl, phenyl or benzyl. In certain embodiments, $R^1$, $R^{1'}$, $R^2$, $R^{2'}$, $R^{2''}$, $R^3$, and $R^{3'}$ are each methyl or ethyl. In some embodiments, one or more $R^1$, $R^{1'}$, $R^2$, $R^{2'}$, $R^{2''}$, $R^3$, and $R^{3'}$ is perfluoro.

In some embodiments, any two or more $R^1$, $R^{1'}$, $R^2$, $R^{2'}$, $R^{2''}$, $R^3$, and $R^{3'}$ groups are taken together with intervening atoms to form one or more optionally substituted rings.

In certain embodiments, $R^1$ and $R^2$ are taken together with intervening atoms to form an optionally substituted ring optionally containing one or more additional heteroatoms. In some embodiments, $R^2$ and $R^{2'}$ are taken together with intervening atoms to form an optionally substituted ring optionally containing one or more additional heteroatoms. In certain embodiments, $R^1$ and $R^3$ are taken together with intervening atoms to form an optionally substituted ring optionally containing one or more additional heteroatoms. In some embodiments, [$R^2$ and $R^{2'}$] and [$R^1$ and $R^3$] are taken together with intervening atoms to form an optionally substituted ring optionally containing one or more additional heteroatoms. In some embodiments, three or more $R^1$, $R^{1'}$, $R^2$, $R^{2'}$, $R^{2''}$, $R^3$, and $R^{3'}$ groups are taken together with any intervening atoms to form optionally substituted rings. In certain embodiments, $R^1$ and $R^2$ groups are taken together to form an optionally substituted 5- or 6-membered ring. In some embodiments, three or more $R^1$ and/or $R^2$ groups are taken together to form an optionally substituted fused ring system.

In certain embodiments where an activating functional group is a guanidine or bis guanidine moiety, it is chosen from the group consisting of:

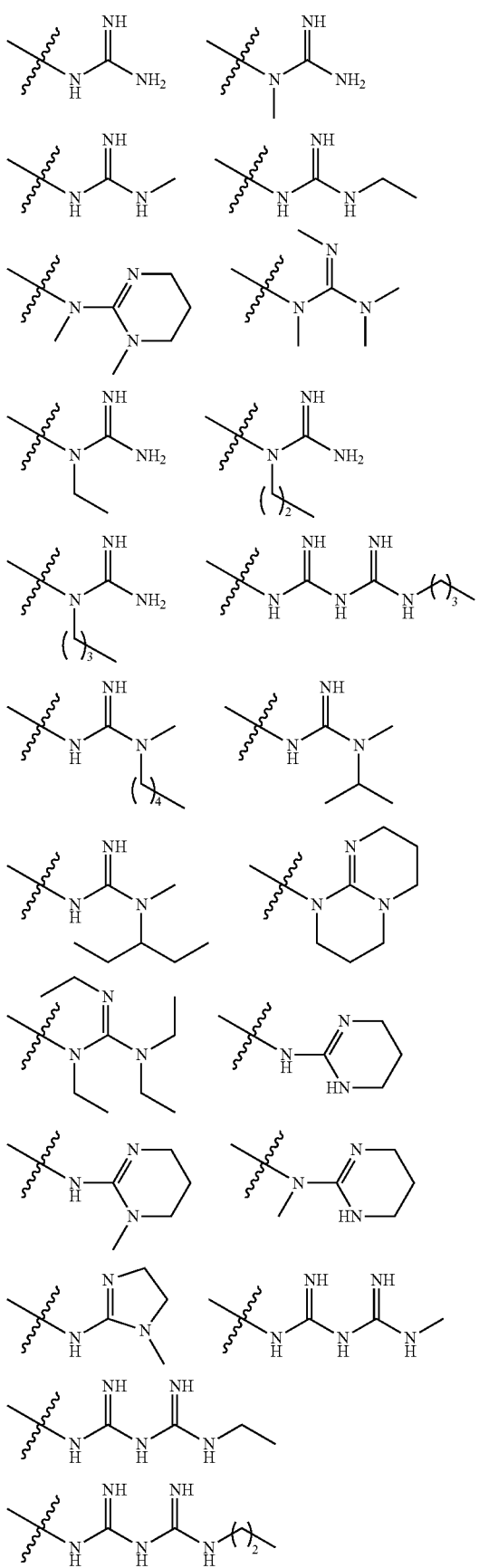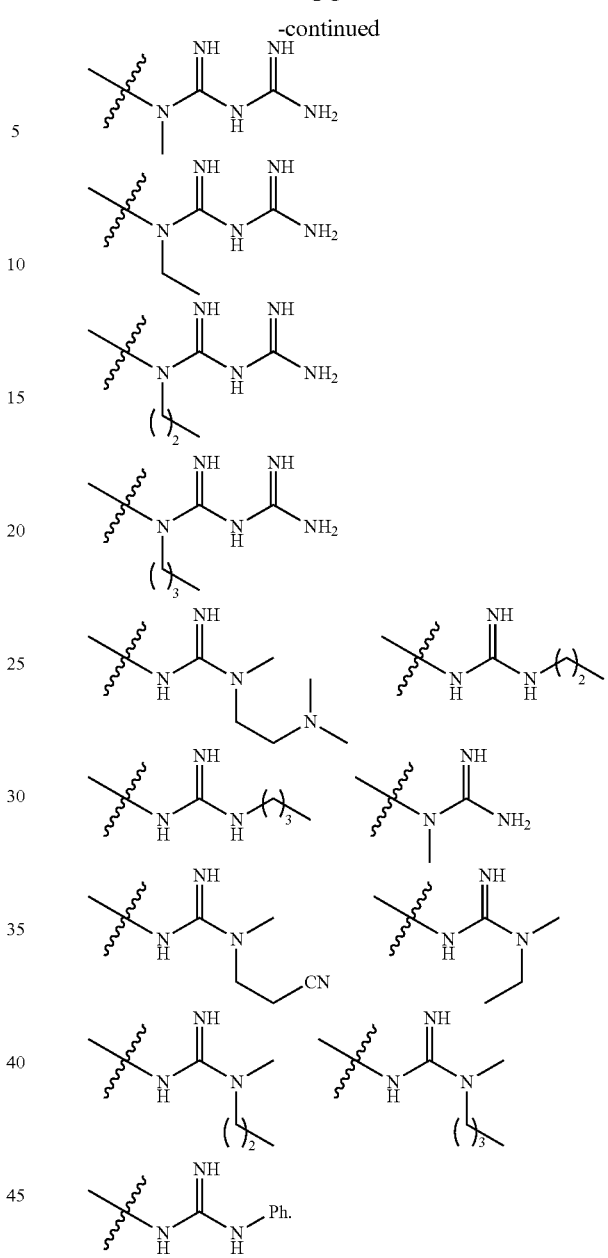

In some embodiments, an activating functional group is a urea:

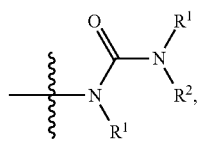

where $R^1$, and $R^2$ are as defined above.

In certain embodiments, $R^1$ and $R^2$ are each hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, $R^1$ and $R^2$ are each independently optionally substituted $C_{1-12}$ aliphatic. In some embodiments, $R^1$ and $R^2$ are each independently optionally substituted $C_{1-6}$ aliphatic. In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —C($R^{y}$)$_2$—, —C($R^{y}$)$_2$C($R^{y}$)$_2$—, —C($R^{y}$)$_2$C($R^{y}$)$_2$C($R^{y}$)$_2$—, —C($R^{y}$)$_2$OC($R^{y}$)$_2$—, and —C($R^{y}$)$_2$NR$^{y}$C($R^{y}$)$_2$—. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^{y}CH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In certain embodiments, activating functional groups are oxime or hydrazone groups:

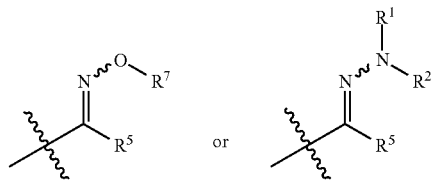

where $R^1$, $R^2$, $R^5$, and $R^7$ are as defined above.

In certain embodiments, $R^1$ and $R^2$ are both hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, 5- to 14-membered heteroaryl, 8- to 10-membered aryl and 3- to 7-membered heterocyclic. In certain embodiments, $R^1$ and $R^2$ are each independently an optionally substituted radical selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, $R^1$ and $R^2$ are each independently optionally substituted $C_{1-12}$ aliphatic. In some embodiments, $R^1$ and $R^2$ are each independently optionally substituted $C_{1-6}$ aliphatic. In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —C(R$^y$)$_2$—, —C(R$^y$)$_2$C(R$^y$)$_2$—, —C(R$^y$)$_2$C(R$^y$)$_2$C(R$^y$)$_2$—, —C(R$^y$)$_2$OC(R$^y$)$_2$—, and —C(R$^y$)$_2$NR$^y$C(R$^y$)$_2$—. In certain embodiments, $R^1$ and $R^2$ are taken together to form a ring fragment selected from the group consisting of: —CH$_2$—, —CH$_2$CH$_2$—, —CH$_2$CH$_2$CH$_2$—, —CH$_2$OCH$_2$—, and —CH$_2$NR$^y$CH$_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In certain embodiments, $R^5$ is H. In certain embodiments, $R^5$ is optionally substituted $C_{1-20}$ aliphatic, and in some embodiments $R^5$ is optionally substituted 6- to 14-membered aryl. In certain embodiments, $R^5$ is optionally substituted $C_{1-12}$ aliphatic and in some embodiments, optionally substituted $C_{1-6}$ aliphatic. In certain embodiments, $R^5$ is optionally substituted phenyl.

In some embodiments, one or more $R^1$ or $R^2$ groups are taken together with $R^5$ and intervening atoms to form an optionally substituted ring. In certain embodiments, $R^1$ and $R^5$ are taken together to form an optionally substituted 5- or 6-membered ring. In some embodiments, $R^2$ and $R^5$ are taken together to form an optionally substituted 5- or 6-membered ring optionally containing one or more additional heteroatoms. In some embodiments, $R^1$, $R^2$ and $R^5$ are taken together to form an optionally substituted fused ring system. In some embodiments such rings formed by combinations of any of $R^1$, $R^2$ and $R^5$ are partially unsaturated or aromatic.

In certain embodiments, $R^7$ is —H. In certain embodiments, $R^7$ is optionally substituted $C_{1-20}$ aliphatic, while in some embodiments $R^5$ is optionally substituted 6- to 14-membered aryl. In certain embodiments, $R^7$ is optionally substituted $C_{1-12}$ aliphatic or in some embodiments, optionally substituted $C_{1-6}$ aliphatic. In certain embodiments, $R^7$ is optionally substituted $C_{1-12}$ acyl or in some embodiments, optionally substituted $C_{1-6}$ acyl. In certain embodiments, $R^7$ is optionally substituted phenyl. In some embodiments, $R^7$ is a hydroxyl protecting group. In some embodiments, $R^7$ is a silyl protecting group.

In some embodiments, an activating functional group is an N-oxide derivative:

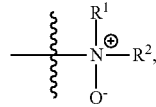

where $R^1$ and $R^2$ are as defined above.

In certain embodiments, $R^1$ and $R^2$ are both hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, 5- to 14-membered heteroaryl, phenyl, or 8- to 10-membered aryl and 3- to 7-membered heterocyclic.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, $R^1$ and $R^2$ are each independently optionally substituted $C_{1-12}$ aliphatic. In some embodiments, $R^1$ and $R^2$ are each independently optionally substituted $C_{1-6}$ aliphatic. In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —CF$_2$CF$_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —C(R$^y$)$_2$—, —C(R$^y$)$_2$C(R$^y$)$_2$—, —C(R$^y$)$_2$C(R$^y$)$_2$C(R$^y$)$_2$—, —C(R$^y$)$_2$OC(R$^y$)$_2$—, and —C(R$^y$)$_2$NR$^y$C(R$^y$)$_2$—. In certain embodiments, $R^1$ and $R^2$ are taken together to form a ring fragment selected from the group consisting of: —CH$_2$—, —CH$_2$CH$_2$—, —CH$_2$CH$_2$CH$_2$—, —CH$_2$OCH$_2$—, and —CH$_2$NR$^y$CH$_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In specific embodiments, an N-oxide activating functional group is selected from the group consisting of:

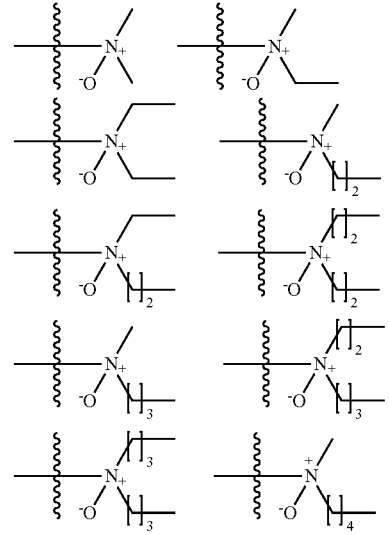

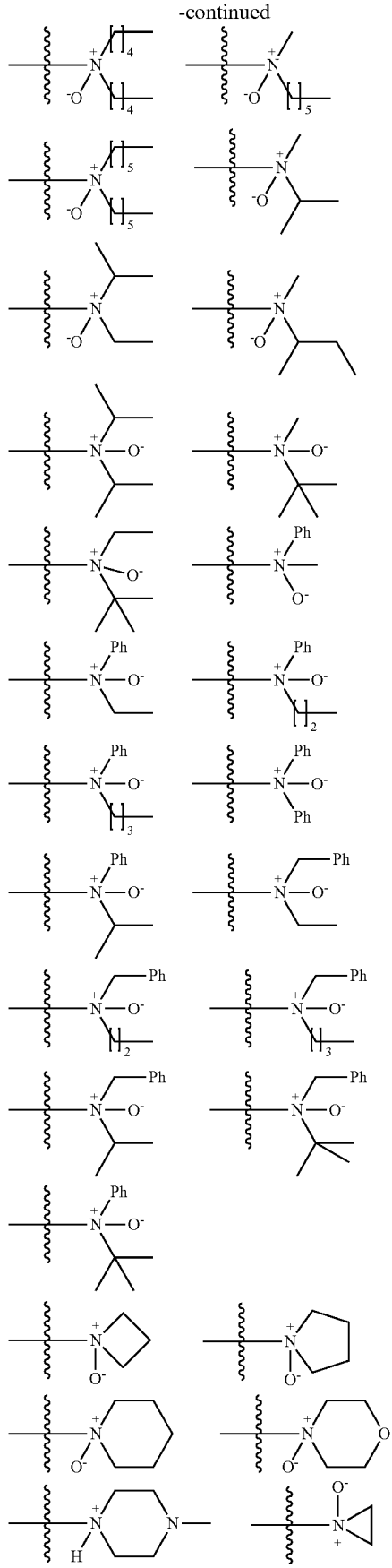
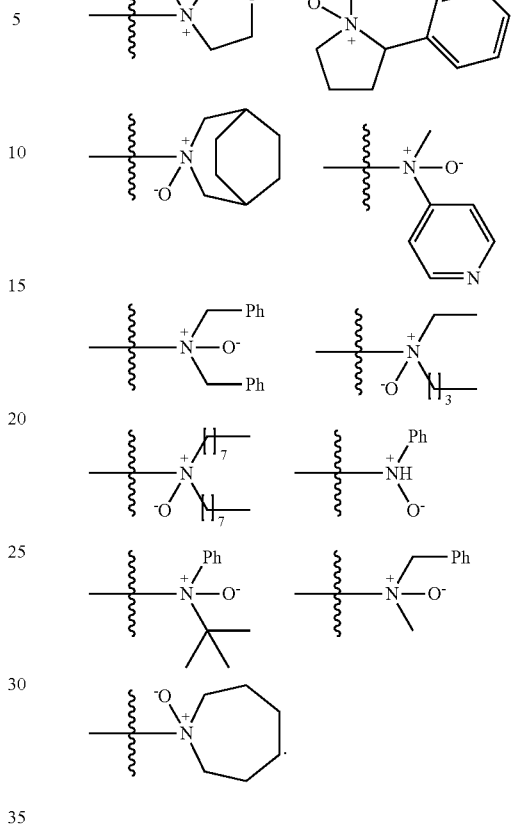
I.b. Cationic Activating Groups
In some embodiments, one or more tethered activating functional groups on provided metal complexes are cationic moieties include cationic moieties. In some embodiments, such moieties include one or more of the structures in Table Z-2:
TABLE Z-2
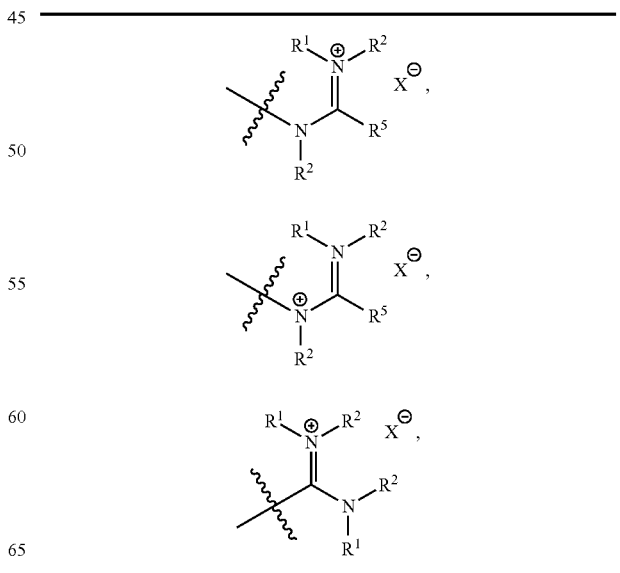

TABLE Z-2-continued
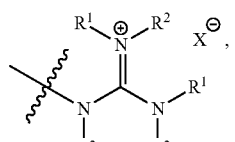
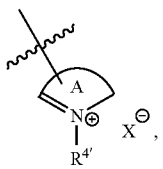
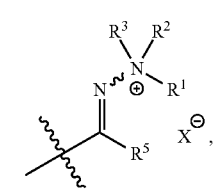
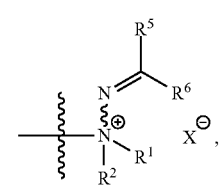
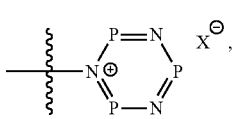
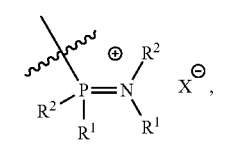
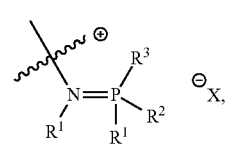
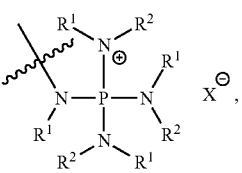
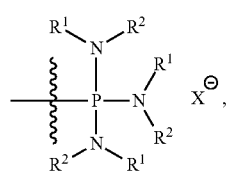
TABLE Z-2-continued
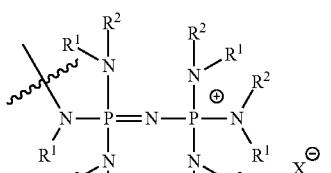
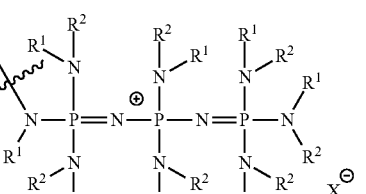
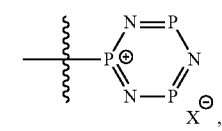
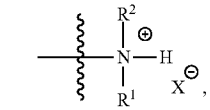
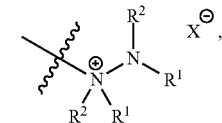
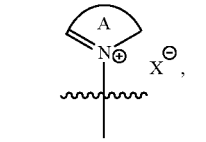
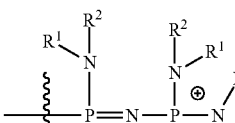
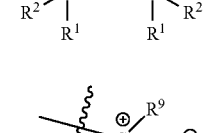
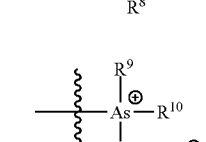

TABLE Z-2-continued

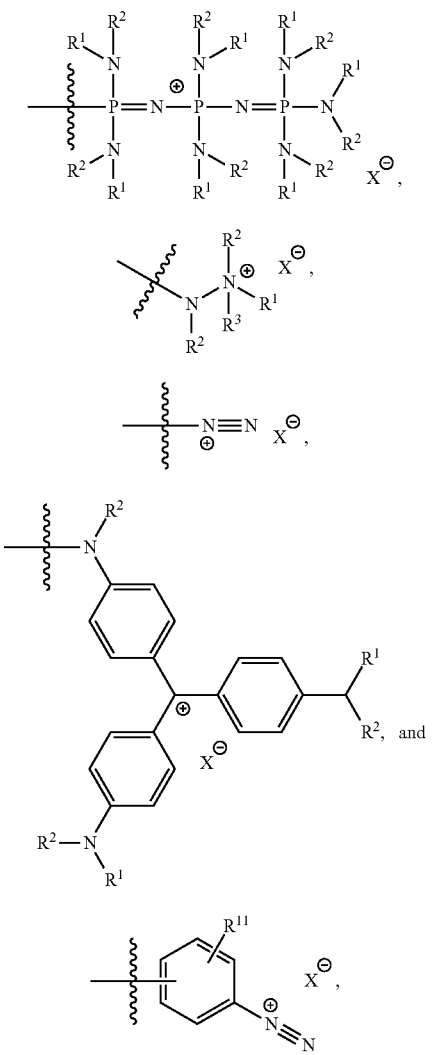

or a combination of two or more of these, wherein:
each occurrence of $R^1$, $R^2$, and $R^3$ is as previously defined;
$R^{4'}$ is hydrogen, hydroxyl, optionally substituted $C_{1-20}$ aliphatic;
each occurrence of $R^5$ and $R^6$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein $R^5$ and $R^6$ can be taken together with intervening atoms to form one or more optionally substituted rings optionally containing one or more heteroatoms, and an $R^5$ or $R^6$ group can be taken with an $R^1$ or $R^2$ group to form one or more optionally substituted rings;
each occurrence of $R^8$, $R^9$, and $R^{10}$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; wherein any two or more $R^8$, $R^9$ and $R^{10}$ groups can be taken together with intervening atoms to form one or more optionally substituted rings;
each occurrence of $R^{11}$ is independently selected from the group consisting of:
halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-N_3$, $-OR^7$, $-OC(O)N(R^y)_2$, $-N(R^y)_2$, $-NR^yC(O)R^y$, $-NR^yC(O)OR^y$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where each occurrence of $R^y$ is independently hydrogen or an optionally substituted $C_{1-6}$ aliphatic group, and where two or more adjacent $R^{11}$ groups can be taken together to form an optionally substituted saturated, partially unsaturated, or aromatic 5- to 12-membered ring containing 0 to 4 heteroatoms;
$X^-$ is any anion, and
Ring A is an optionally substituted, 5- to 10-membered heteroaryl group. In certain embodiments, a cationic activating functional group is a protonated amine:

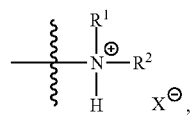

where $R^1$ and $R^2$ are as defined above.
In certain embodiments, $R^1$ and $R^2$ are both hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, 5- to 14-membered heteroaryl, phenyl, or 8- to 10-membered aryl and 3- to 7-membered heterocyclic. In certain embodiments, $R^1$ and $R^2$ are each independently an optionally substituted radical selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, $R^1$ and $R^2$ are each independently optionally substituted $C_{1-12}$ aliphatic. In some embodiments, $R^1$ and $R^2$ are each independently optionally substituted $C_{1-6}$ aliphatic. In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —$C(R^y)_2$—, —$C(R^y)_2C(R^y)_2$—, —$C(R^y)_2C(R^y)_2C(R^y)_2$—, —$C(R^y)_2OC(R^y)_2$—, and —$C(R^y)_2NR^yC(R^y)_2$—. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^yCH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In specific embodiments, a protonated amine activating functional group is selected from the group consisting of:

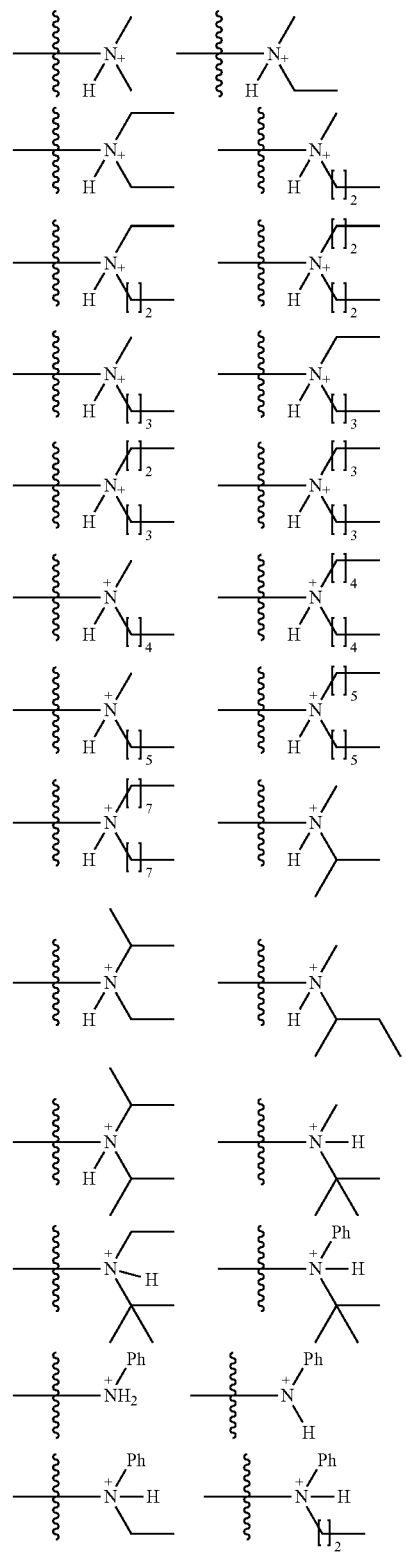

-continued

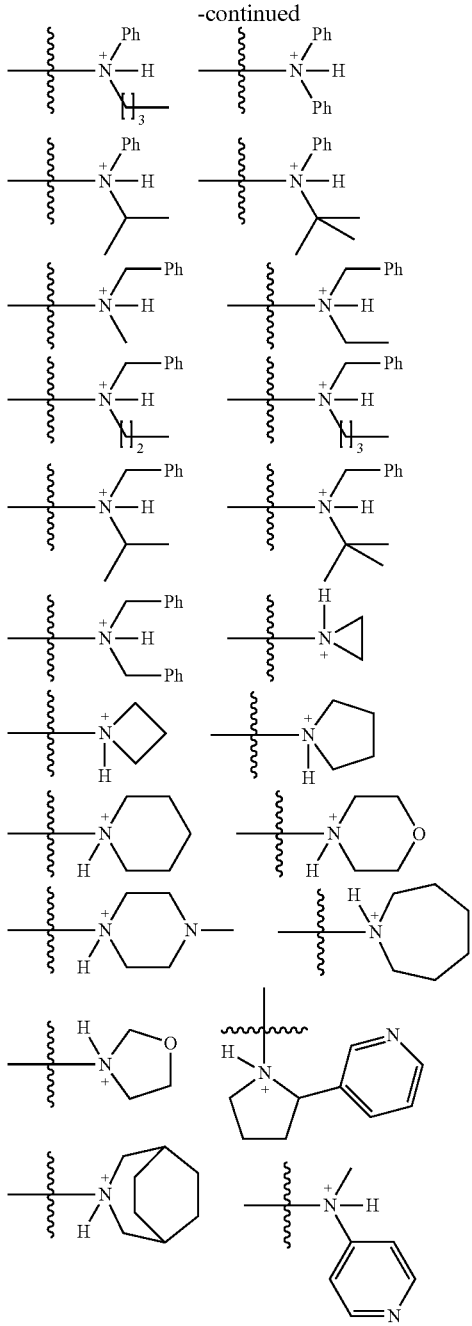

In certain embodiments, an activating functional group is a guanidinium group:

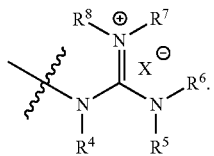

In some embodiments, each of $R^4$, $R^5$, $R^6$, $R^7$, and $R^8$ is hydrogen.

In some embodiments, each occurrence of $R^4$, $R^5$, $R^6$, $R^7$, and $R^8$ is independently hydrogen or $C_{1-20}$ aliphatic. In some embodiments, each occurrence of $R^4$, $R^5$, $R^6$, $R^7$, and $R^8$ is independently hydrogen or $C_{1-12}$ aliphatic. In some embodiments, each occurrence of $R^4$, $R^5$, $R^6$, $R^7$, and $R^8$ is independently hydrogen or $C_{1-20}$ heteroaliphatic. In some embodiments, each occurrence of $R^4$, $R^5$, $R^6$, $R^7$, and $R^8$ is independently hydrogen or phenyl. In some embodiments, each occurrence of $R^4$, $R^5$, $R^6$, $R^7$, and $R^8$ is independently hydrogen or 8- to 10-membered aryl. In some embodiments, each occurrence of $R^4$, $R^5$, $R^6$, $R^7$, and $R^8$ is independently hydrogen or 5- to 10-membered heteroaryl. In some embodiments, each occurrence of $R^4$, $R^5$, $R^6$, $R^7$, and $R^8$ is independently hydrogen or 3- to 7-membered heterocyclic. In some embodiments, one or more of $R^4$, $R^5$, $R^6$, and $R^7$ is optionally substituted $C_{1-12}$ aliphatic. In certain embodiments, any of ($R^4$ and $R^5$), ($R^5$ and $R^6$), ($R^6$ and $R^7$), ($R^7$ and $R^8$), and ($R^4$ and $R^7$) can be taken together with intervening atoms to form one or more optionally substituted rings. In some embodiments, ($R^4$ and $R^5$) and ($R^6$ and $R^7$) are taken together to form rings.

It will be appreciated that when a guanidinium cation is depicted as

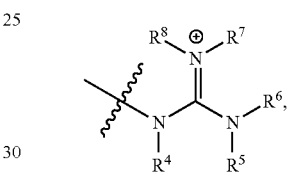

all such resonance forms are contemplated and encompassed by the present disclosure. For example, such groups can also be depicted as

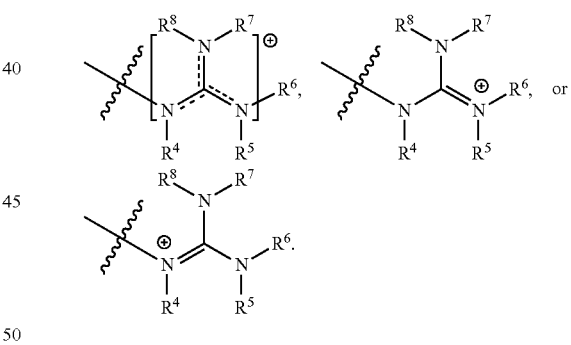

In specific embodiments, a guanidinium activating functional group is selected from the group consisting of:

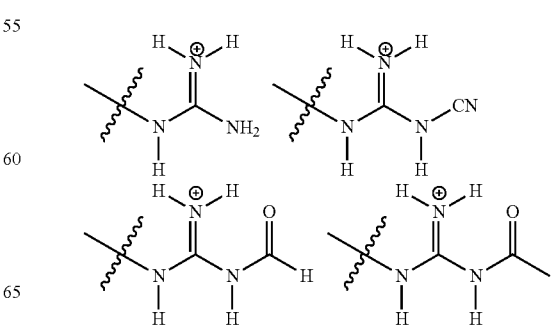

-continued

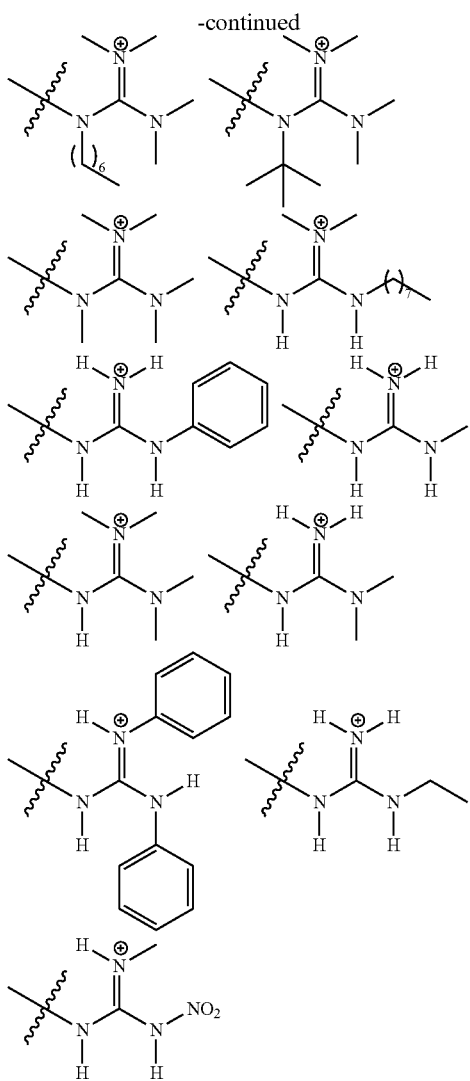

In some embodiments, an activating functional group is a sulfonium group or an arsonium group:

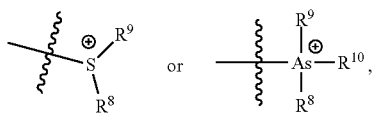

where $R^8$, $R^9$, and $R^{10}$ are as defined above.

In certain embodiments, each occurrence of $R^8$, $R^9$, and $R^{10}$ is independently optionally substituted $C_{1-20}$ aliphatic. In some embodiments, each occurrence of $R^8$, $R^9$, and $R^{10}$ is independently hydrogen or optionally substituted $C_{1-20}$ heteroaliphatic. In some embodiments, each occurrence of $R^9$, $R^{10}$, and $R^{11}$ is independently hydrogen or optionally substituted phenyl. In some embodiments, each occurrence of $R^9$, $R^{10}$, and $R^{11}$ is independently hydrogen or optionally substituted 8- to 10-membered aryl. In some embodiments, each occurrence of $R^8$, $R^9$, and $R^{10}$ is independently hydrogen or optionally substituted 5- to 10-membered heteroaryl. In some embodiments, each occurrence of $R^9$, $R^{10}$, and $R^{11}$ is independently hydrogen or optionally substituted 3- to 7-membered heterocyclic. In some embodiments, $R^8$ and $R^9$ are taken together with intervening atoms to form one or more rings selected from the group consisting of: optionally substituted $C_3$-$C_{14}$ carbocycle, optionally substituted 3- to 14-membered heterocycle, optionally substituted $C_6$-$C_{10}$ aryl, and optionally substituted 5- to 10-membered heteroaryl.

In certain embodiments, $R^8$, $R^9$ and $R^{10}$ are each methyl. In certain embodiments, $R^8$, $R^9$ and $R^{10}$ are each phenyl.

In specific embodiments, an arsonium activating functional group is selected from the group consisting of:

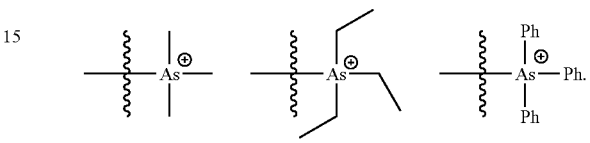

In some embodiments, an activating functional group is an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In some embodiments, a nitrogen-containing heterocycle includes a quaternarized nitrogen atom. In certain embodiments, a nitrogen-containing heterocycle includes an iminium moiety such as

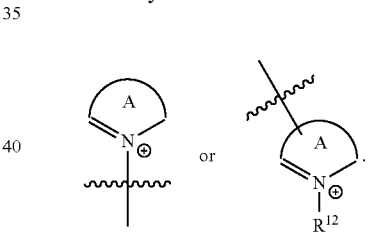

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In some embodiments, a ring nitrogen to which the attachment is made is thereby quaternized, and in some embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In some embodiments, an activating functional group is

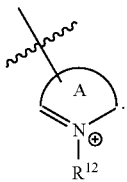

In certain embodiments, ring A is an optionally substituted, 5- to 10-membered heteroaryl group.

In some embodiments, Ring A is an optionally substituted, 6-membered heteroaryl group. In some embodiments, Ring A is a ring of a fused heterocycle. In some embodiments, Ring A is an optionally substituted pyridyl group.

In some embodiments, $R^{12}$ is hydrogen. In some embodiments, $R^{12}$ is an optionally substituted $C_{1-20}$ aliphatic group. In some embodiments, $R^{12}$ is $C_{1-20}$ heteroaliphatic. In some embodiments, $R^{12}$ is optionally substituted phenyl, 8- to 10-membered aryl; 5- to 10-membered heteroaryl. In some embodiments, $R^{12}$ is 3- to 7-membered heterocyclic. In some embodiments, $R^{12}$ is an optionally substituted $C_{1-12}$ aliphatic group. In some embodiments, $R^{12}$ is neopentyl. In some embodiments, $R^{12}$ is oxide or hydroxyl.

In some embodiments, when Z is

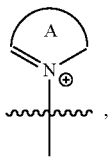

ring A is other than an imidazole, an oxazole, or a thiazole.

In specific embodiments, a nitrogen-containing heterocycle activating functional group is selected from the group consisting of:

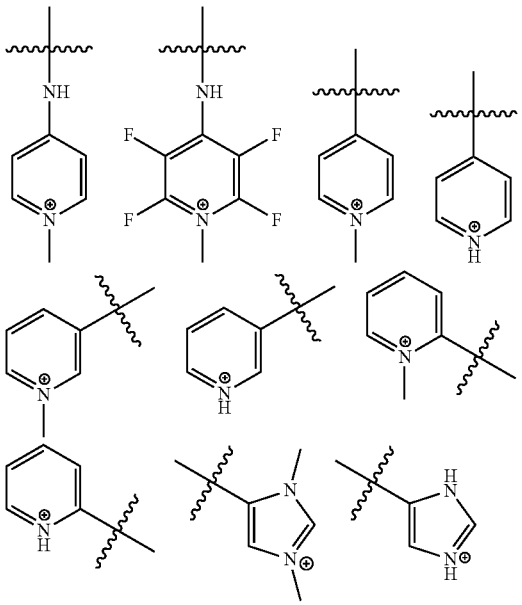

-continued

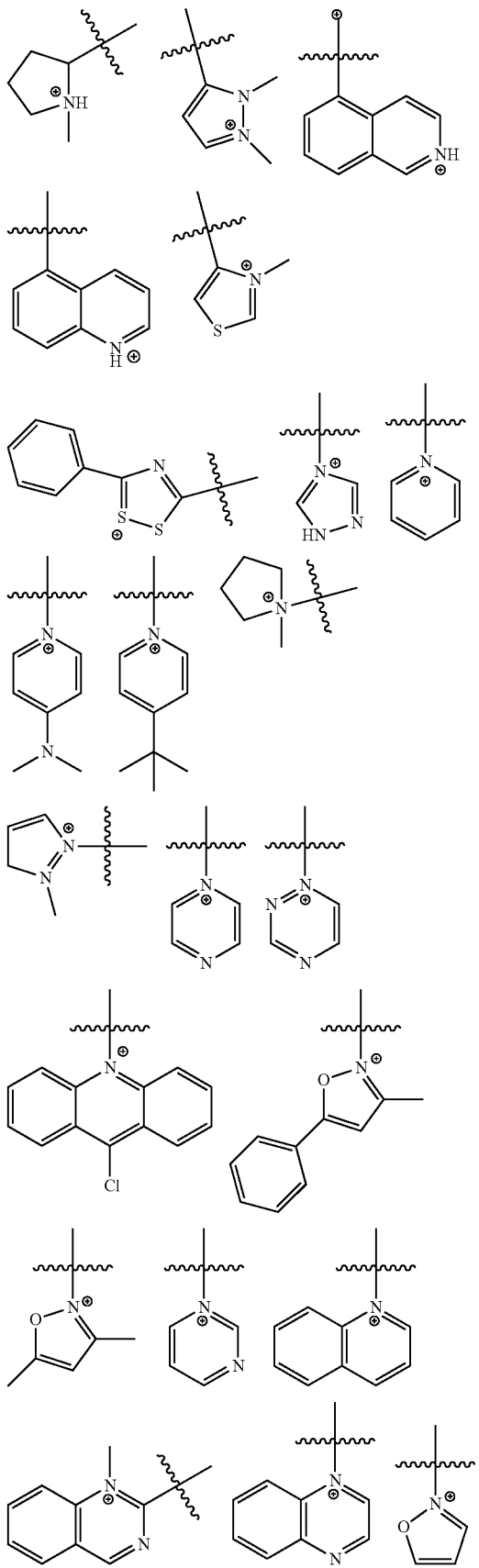

-continued

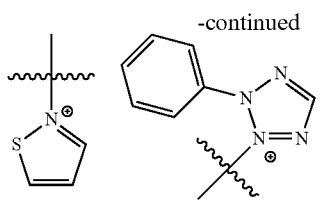

In some embodiments, an activating functional group is

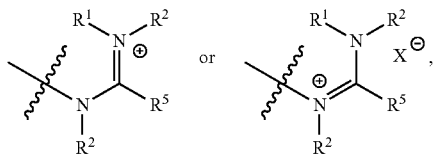

where $R^1$, $R^2$ and $R^5$ are as defined above.

In certain embodiments, $R^1$ and $R^2$ are each hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In certain embodiments, $R^1$ and $R^2$ are each independently an optionally substituted radical selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, $R^1$ and $R^2$ are each independently optionally substituted $C_{1-12}$ aliphatic. In some embodiments, $R^1$ and $R^2$ are each independently optionally substituted $C_{1-6}$ aliphatic. In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —$C(R^y)_2$—, —$C(R^y)_2C(R^y)_2$—, —$C(R^y)_2C(R^y)_2C(R^y)_2$—, —$C(R^y)_2OC(R^y)_2$—, and —$C(R^y)_2NR^yC(R^y)_2$—. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^yCH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In certain embodiments, $R^5$ is H. In certain embodiments, $R^5$ is optionally substituted $C_{1-20}$ aliphatic, and in some embodiments $R^5$ is optionally substituted 6- to 14-membered aryl. In certain embodiments, $R^5$ is optionally substituted $C_{1-12}$ aliphatic and in some embodiments, optionally substituted $C_{1-6}$ aliphatic. In certain embodiments, $R^5$ is methyl, ethyl, propyl, butyl, pentyl, hexyl, heptyl, octyl, phenyl or benzyl. In some embodiments, $R^5$ is perfluoro. In some embodiments, $R^5$ is —$CF_2CF_3$. In certain embodiments, $R^5$ is optionally substituted phenyl.

In some embodiments, one or more $R^1$ or $R^2$ groups are taken together with $R^5$ and intervening atoms to form an optionally substituted ring. In certain embodiments, $R^1$ and $R^5$ are taken together to form an optionally substituted 5- or 6-membered ring. In some embodiments, $R^2$ and $R^5$ are taken together to form an optionally substituted 5- or 6-membered ring optionally containing one or more additional heteroatoms. In some embodiments, $R^1$, $R^2$ and $R^5$ are taken together to form an optionally substituted fused ring system. In some embodiments such rings formed by combinations of any of $R^1$, $R^2$ and $R^5$ are partially unsaturated or aromatic.

In some embodiments, an activating functional group is

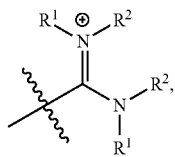

where $R^1$ and $R^2$ are as defined above.

In certain embodiments, $R^1$ and $R^2$ are each independently an optionally substituted group selected from the group consisting of $C_{1-20}$ aliphatic; $C_{1-20}$ heteroaliphatic; phenyl; and 8-10-membered aryl. In some embodiments, $R^1$ and $R^2$ are each independently an optionally substituted 4-7-membered heterocyclic. In some embodiments, $R^1$ and $R^2$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, $R^1$ and $R^2$ are each independently selected from the group consisting of methyl, ethyl, propyl, butyl, pentyl, hexyl, heptyl, octyl, or benzyl. In some embodiments, each occurrence of $R^1$ and $R^2$ is independently perfluoro. In some embodiments, each occurrence of $R^1$ and $R^2$ is independently —$CF_2CF_3$.

In some embodiments, an activating functional group is

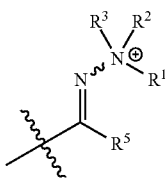

where $R^1$, $R^2$, $R^3$, and $R^5$ are as defined above.

In certain embodiments, $R^1$, $R^2$, and $R^3$ are each independently an optionally substituted group selected from the group consisting of $C_{1-20}$ aliphatic; $C_{1-20}$ heteroaliphatic; phenyl; and 8-10-membered aryl. In certain embodiments, $R^1$, $R^2$, and $R^3$ are each independently an optionally substituted 4-7-membered heterocyclic. In some embodiments, $R^1$ and $R^2$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In certain embodiments, $R^1$, $R^2$, and $R^3$ are each independently an optionally substituted $C_{1-6}$ aliphatic. In certain embodiments, $R^1$, $R^2$, and $R^3$ are each independently selected from the group consisting of methyl, ethyl, propyl, butyl, pentyl, hexyl, heptyl, octyl, or benzyl. In certain embodiments, $R^1$, $R^2$, and $R^3$ are each independently perfluoro. In some embodiments, $R^1$, $R^2$, and $R^3$ are each independently —$CF_2CF_3$.

In certain embodiments, $R^5$ is hydrogen. In certain embodiments $R^5$ is an optionally substituted group selected from the group consisting of $C_{1-12}$ aliphatic and $C_{1-12}$ heteroaliphatic. In some embodiments, $R^5$ is an optionally substituted $C_{1-12}$ aliphatic. In some embodiments, $R^5$ is optionally substituted $C_{1-6}$ aliphatic.

In some embodiments, an activating functional group is

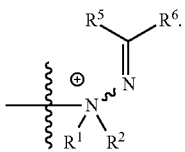

In certain embodiments, $R^1$ and $R^2$ are each independently an optionally substituted group selected from the group consisting of $C_{1-20}$ aliphatic; $C_{1-20}$ heteroaliphatic; phenyl; and 8-10-membered aryl. In some embodiments, $R^1$ and $R^2$ are each independently an optionally substituted 4-7-membered heterocyclic. In some embodiments, $R^1$ and $R^2$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, $R^1$ and $R^2$ are each independently selected from the group consisting of methyl, ethyl, propyl, butyl, pentyl, hexyl, heptyl, octyl, or benzyl. In some embodiments, each occurrence of $R^1$ and $R^2$ is independently perfluoro. In some embodiments, each occurrence of $R^1$ and $R^2$ is independently —$CF_2CF_3$.

In certain embodiments, $R^5$ and $R^6$ are each independently an optionally substituted group selected from the group consisting of $C_{1-20}$ aliphatic; $C_{1-20}$ heteroaliphatic; phenyl, and 8-10-membered aryl. In some embodiments, $R^5$ and $R^6$ are each independently an optionally substituted $C_{1-20}$ aliphatic. In some embodiments, $R^5$ and $R^6$ are each independently an optionally substituted $C_{1-20}$ heteroaliphatic having. In some embodiments, $R^5$ and $R^6$ are each independently an optionally substituted phenyl or 8-10-membered aryl. In some embodiments, $R^5$ and $R^6$ are each independently an optionally substituted 5- to 10-membered heteroaryl. In some embodiments, $R^3$ and $R^4$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, $R^5$ and $R^6$ are each independently an optionally substituted $C_{1-6}$ aliphatic. In some embodiments, each occurrence of $R^5$ and $R^6$ is independently methyl, ethyl, propyl, butyl, pentyl, hexyl, heptyl, octyl, or benzyl. In some embodiments, each occurrence of $R^5$ and $R^6$ is independently perfluoro. In some embodiments, each occurrence of $R^5$ and $R^6$ is independently —$CF_2CF_3$.

In some embodiments, an activating functional group is

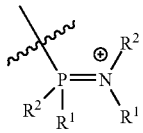

where $R^1$ and $R^2$ are as defined above.

In certain embodiments, $R^1$ and $R^2$ are each hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, $R^1$ and $R^2$ are each independently optionally substituted $C_{1-12}$ aliphatic. In some embodiments, $R^1$ and $R^2$ are each independently optionally substituted $C_{1-6}$ aliphatic. In some embodiments, each occurrence of $R^1$ and $R^2$ is independently an optionally substituted $C_{1-20}$ heteroaliphatic. In some embodiments, each occurrence of $R^1$ and $R^2$ is independently an optionally substituted $C_{1-12}$ heteroaliphatic. In some embodiments, each occurrence of $R^1$ and $R^2$ is independently an optionally substituted phenyl or 8- to 10-membered aryl. In some embodiments, each occurrence of $R^1$ and $R^2$ is independently an optionally substituted phenyl group. In some embodiments, each occurrence of $R^1$ and $R^2$ is independently an optionally substituted 5- to 10-membered heteroaryl group. In some embodiments, each occurrence of $R^1$ and $R^2$ is independently an optionally substituted 3- to 7-membered heterocyclic.

In certain embodiments, $R^1$ and $R^2$ are each independently hydrogen, methyl, ethyl, propyl, butyl, pentyl, hexyl, heptyl, octyl, optionally substituted phenyl, or optionally substituted benzyl. In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted rings. In certain embodiments, $R^1$ and $R^2$ are taken together to form a ring fragment selected from the group consisting of: —$C(R^y)_2$—, —$C(R^y)_2C(R^y)_2$—, —$C(R^y)_2C(R^y)_2C(R^y)_2$—, —$C(R^y)_2OC(R^y)_2$—, and —$C(R^y)_2NR^yC(R^y)_2$—. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^yCH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In some embodiments, an activating functional group is

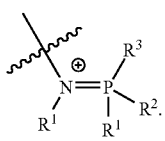

In certain embodiments, $R^1$, $R^2$, and $R^3$ are each independently an optionally substituted group selected from the group consisting of $C_{1-20}$ aliphatic; $C_{1-20}$ heteroaliphatic; phenyl; and 8-10-membered aryl. In certain embodiments, $R^1$, $R^2$, and $R^3$ are each independently an optionally substituted 4-7-membered heterocyclic. In some embodiments, $R^1$ and $R^2$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In certain embodiments, $R^1$, $R^2$, and $R^3$ are each independently an optionally substituted $C_{1-6}$ aliphatic. In certain embodiments, $R^1$, $R^2$, and $R^3$ are each independently selected from the group consisting of methyl, ethyl, propyl, butyl, pentyl, hexyl, heptyl, octyl, or benzyl. In certain embodiments, $R^1$, $R^2$, and $R^3$ are each independently perfluoro. In some embodiments, $R^1$, $R^2$, and $R^3$ are each independently —$CF_2CF_3$.

In some embodiments, an activating functional group is

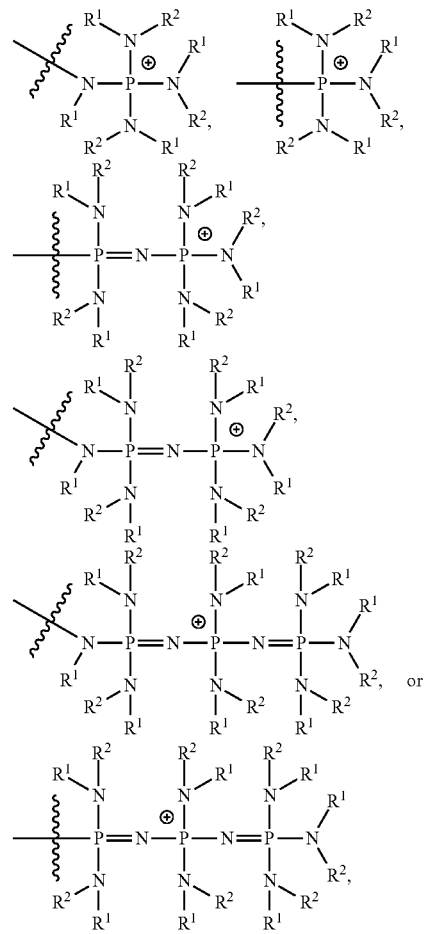

where $R^1$ and $R^2$ are as defined above.

In certain embodiments, $R^1$ and $R^2$ are each hydrogen. In some embodiments, only one of $R^1$ and $R^2$ is hydrogen. In certain embodiments, $R^1$ and $R^2$ are each independently an optionally substituted radical selected from the group consisting of $C_{1-20}$ aliphatic; $C_{1-20}$ heteroaliphatic, phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur.

In certain embodiments, $R^1$ and $R^2$ are each independently an optionally substituted radical selected from the group consisting of $C_{1-12}$ aliphatic and $C_{1-12}$ heteroaliphatic. In some embodiments, each occurrence of $R^1$ and $R^2$ is independently an optionally substituted $C_{1-20}$ aliphatic. In some embodiments, R¹ and R² are each independently optionally substituted $C_{1-12}$ aliphatic. In some embodiments, R¹ and R² are each independently optionally substituted $C_{1-6}$ aliphatic. In some embodiments, each occurrence of R¹ and R² is independently an optionally substituted $C_{1-20}$ heteroaliphatic. In some embodiments, each occurrence of R¹ and R² is independently an optionally substituted $C_{1-12}$ heteroaliphatic. In some embodiments, each occurrence of R¹ and R² is independently an optionally substituted 8- to 10-membered aryl. In some embodiments, each occurrence of R¹ and R² is independently an optionally substituted phenyl group. In some embodiments, each occurrence of R¹ and R² is independently an optionally substituted 5- to 10-membered heteroaryl group. In some embodiments, each occurrence of R¹ and R² is independently an optionally substituted 3- to 7-membered heterocyclic.

In certain embodiments, R¹ and R² are each independently hydrogen, methyl, ethyl, propyl, butyl, pentyl, hexyl, heptyl, octyl, optionally substituted phenyl, or optionally substituted benzyl. In certain embodiments, R¹ and R² are both methyl, ethyl, propyl, butyl, pentyl, hexyl, heptyl, octyl, phenyl or benzyl. In some embodiments, R¹ and R² are each butyl. In some embodiments, R¹ and R² are each isopropyl. In some embodiments, R¹ and R² are perfluoro. In some embodiments, R¹ and R² are —CF₂CF₃. In some embodiments, R¹ and R² are each phenyl. In some embodiments, R¹ and R² are each benzyl.

In some embodiments, R¹ and R² are taken together with intervening atoms to form one or more optionally substituted rings. In certain embodiments, R¹ and R² are taken together to form a ring fragment selected from the group consisting of: —C(R^y)₂—, —C(R^y)₂C(R^y)₂—, —C(R^y)₂C(R^y)₂C(R^y)₂—, —C(R^y)₂OC(R^y)₂—, and —C(R^y)₂NR^yC(R^y)₂—. In certain embodiments, R¹ and R² are taken together to form a ring fragment selected from the group consisting of: —CH₂—, —CH₂CH₂—, —CH₂CH₂CH₂—, —CH₂OCH₂—, and —CH₂NR^yCH₂—. In some embodiments, R¹ and R² are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In some embodiments, an activating functional group is

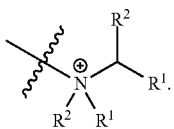

In certain embodiments, R¹ and R² are each independently an optionally substituted group selected from the group consisting of $C_{1-20}$ aliphatic; $C_{1-20}$ heteroaliphatic; phenyl; and 8-10-membered aryl. In some embodiments, R¹ and R² are each independently an optionally substituted 4-7-membered heterocyclic. In some embodiments, R¹ and R² can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, R¹ and R² are each independently selected from the group consisting of methyl, ethyl, propyl, butyl, pentyl, hexyl, heptyl, octyl, or benzyl. In some embodiments, each occurrence of R¹ and R² is independently perfluoro. In some embodiments, each occurrence of R¹ and R² is independently —CF₂CF₃.

In some embodiments, an activating functional group is

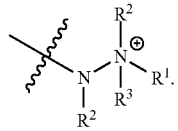

In certain embodiments, R¹, R², and R³ are each independently an optionally substituted group selected from the group consisting of $C_{1-20}$ aliphatic; $C_{1-20}$ heteroaliphatic; phenyl; and 8-10-membered aryl. In certain embodiments, R¹, R², and R³ are each independently an optionally substituted 4-7-membered heterocyclic. In some embodiments, R¹ and R² can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In certain embodiments, R¹, R², and R³ are each independently an optionally substituted $C_{1-6}$ aliphatic. In certain embodiments, R¹, R², and R³ are each independently selected from the group consisting of methyl, ethyl, propyl, butyl, pentyl, hexyl, heptyl, octyl, or benzyl. In certain embodiments, R¹, R², and R³ are each independently perfluoro. In some embodiments, R¹, R², and R³ are each independently —CF₂CF₃.

In some embodiments, an activating functional group is

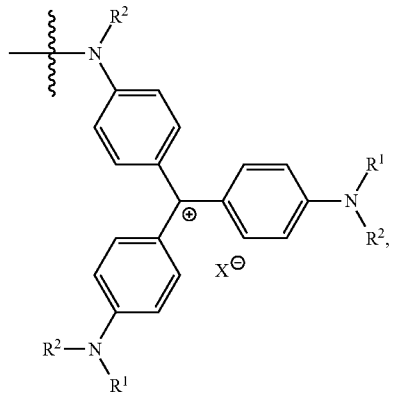

where R¹ and R² are as defined above.

In certain embodiments, R¹ and R² are each independently an optionally substituted group selected from the group consisting of $C_{1-20}$ aliphatic; $C_{1-20}$ heteroaliphatic; phenyl; and 8-10-membered aryl. In some embodiments, R¹ and R² are each independently an optionally substituted 4-7-membered heterocyclic. In some embodiments, R¹ and R² can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, R¹ and R² are each independently selected from the group consisting of methyl, ethyl, propyl, butyl, pentyl, hexyl, heptyl, octyl, or benzyl. In some embodiments, each occurrence of $R^1$ and $R^2$ is independently perfluoro. In some embodiments, each occurrence of $R^1$ and $R^2$ is independently —$CF_2CF_3$.

In certain embodiments, X is any anion. In certain embodiments, X is a nucleophile. In some embodiments, X is a nucleophile capable of ring opening an epoxide. In certain embodiments, X is absent. In certain embodiments, X is a nucleophilic ligand. Exemplary nucleophilic ligands include, but are not limited to, —$OR^x$, —$SR^x$, —$O(C=O)R^x$, —$O(C=O)OR^x$, —$O(C=O)N(R^x)_2$, —$N(R^x)(C=O)R^x$, —NC, —CN, halo (e.g., —Br, —I, —Cl), —$N_3$, —$O(SO_2)R^x$ and —$OPR^x_3$, wherein each $R^x$ is, independently, selected from hydrogen, optionally substituted aliphatic, optionally substituted heteroaliphatic, optionally substituted aryl and optionally substituted heteroaryl.

In certain embodiments, X is —$O(C=O)R^x$, wherein $R^x$ is selected from optionally substituted aliphatic, fluorinated aliphatic, optionally substituted heteroaliphatic, optionally substituted aryl, fluorinated aryl, and optionally substituted heteroaryl.

For example, in certain embodiments, X is —$O(C=O)R^x$, wherein $R^x$ is optionally substituted aliphatic. In certain embodiments, X is —$O(C=O)R^x$, wherein $R^x$ is optionally substituted alkyl and fluoroalkyl. In certain embodiments, X is —$O(C=O)CH_3$ or —$O(C=O)CF_3$.

Furthermore, in certain embodiments, X is —$O(C=O)R^x$, wherein $R^x$ is optionally substituted aryl, fluoroaryl, or heteroaryl. In certain embodiments, X is —$O(C=O)R^x$, wherein $R^x$ is optionally substituted aryl. In certain embodiments, X is —$O(C=O)R^x$, wherein $R^x$ is optionally substituted phenyl. In certain embodiments, X is —$O(C=O)C_6H_5$ or —$O(C=O)C_6F_5$.

In certain embodiments, X is —$OR^x$, wherein $R^x$ is selected from optionally substituted aliphatic, optionally substituted heteroaliphatic, optionally substituted aryl, and optionally substituted heteroaryl.

For example, in certain embodiments, X is —$OR^x$, wherein $R^x$ is optionally substituted aryl. In certain embodiments, X is —$OR^x$, wherein $R^x$ is optionally substituted phenyl. In certain embodiments, X is —$OC_6H_5$ or —$OC_6H_2(2,4-NO_2)$.

In certain embodiments, X is halo. In certain embodiments, X is —Br. In certain embodiments, X is —Cl. In certain embodiments, X is —I.

In certain embodiments, X is —$O(SO_2)R^x$. In certain embodiments X is —OTs. In certain embodiments X is —$OSO_2Me$. In certain embodiments X is —$OSO_2CF_3$. In some embodiments, X is a 2,4-dinitrophenolate anion.

I.c. Phosphorous-Containing Activating Groups

In some embodiments, activating functional groups Z are phosphorous containing groups.

In certain embodiments, a phosphorous-containing functional group is chosen from the group consisting of: phosphines (—$PR^y_2$); Phosphine oxides —$P(O)R^y_2$; phosphinites $P(OR^7)R^y_2$; phosphonites $P(OR^7)_2R^y$; phosphites $P(OR^7)_3$; phosphinates $OP(OR^7)R^y_2$; phosphonates; $OP(OR^7)_2R^y$; phosphates —$OP(OR^7)_3$; phosphonium salts ([—$PR^y_3$]$^+$) where a phosphorous-containing functional group may be linked to a metal complex through any available position (e.g. direct linkage via the phosphorous atom, or in some cases via an oxygen atom).

In certain embodiments, a phosphorous-containing functional group is chosen from the group consisting of:

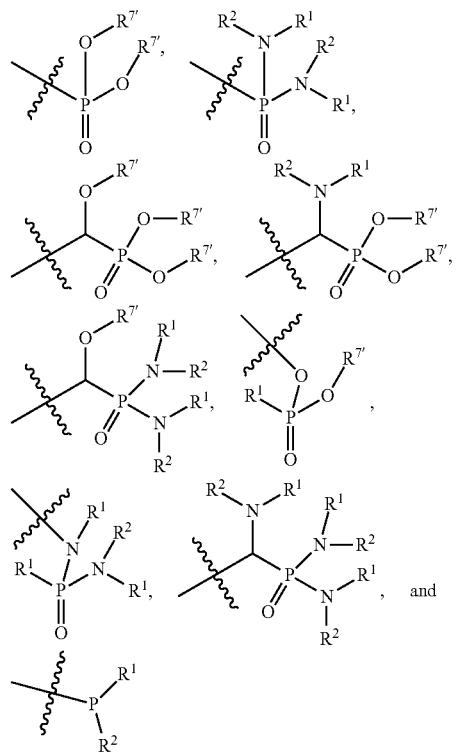

or a combination of two or more of these
wherein $R^1$ and $R^2$, are as defined above; and
each $R^{7'}$, is independently hydrogen, a hydroxyl protecting group, or an optionally substituted radical selected from the group consisting of $C_{1-20}$ acyl; $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; and where two $R^{7'}$ groups can be taken together with intervening atoms to form an optionally substituted ring optionally containing one or more heteroatoms, and an $R^7$ group can be taken with an $R^1$ or $R^2$ group to an optionally substituted ring;

In some embodiments, phosphorous containing functional groups include those disclosed in *The Chemistry of Organophosphorus Compounds. Volume 4. Ter- and Quinquevalent Phosphorus Acids and their Derivatives. The Chemistry of Functional Group Series* Edited by Frank R. Hartley (Cranfield University, Cranfield, U.K.). Wiley: New York. 1996. ISBN 0-471-95706-2, the entirety of which is hereby incorporated herein by reference.

*—$(X)_b$—[($R^6R^7R^8P$)$^+$]$_n Q^{n-}$,wherein:
X is —O—, —N=, or —$NR^z$—,
b is 1 or 0, each of R⁶, R⁷ and R⁸ are independently present or absent and, if present, are independently selected from the group consisting of optionally substituted $C_1$-$C_{20}$ aliphatic, optionally substituted phenyl, optionally substituted $C_8$-$C_{14}$ aryl, optionally substituted 3- to 14-membered heterocyclic, optionally substituted 5- to 14-membered heteroaryl, halogen, =O, —OR$^z$, =NR$^z$, and N(R$^z$)₂ where R$^z$ is hydrogen, or an optionally substituted $C_1$-$C_{20}$ aliphatic, optionally substituted phenyl, optionally substituted 8- to 14-membered aryl, optionally substituted 3- to 14-membered heterocyclic, or optionally substituted 5- to 14-membered heteroaryl, Q is any anion, and n is an integer between 1 and 4.

In some embodiments, an activating functional group is a phosphonate group:

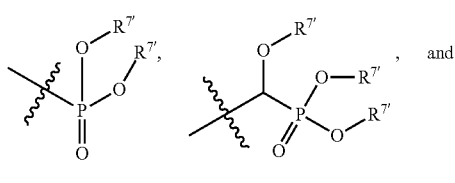

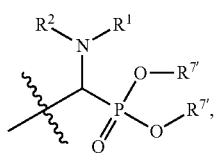

wherein R¹, R², and R⁷' is as defined above.

In specific embodiments, a phosphonate activating functional group is selected from the group consisting of:

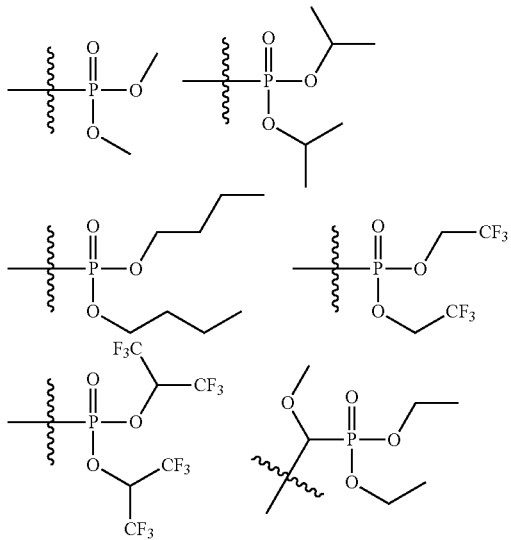

In some embodiments, an activating functional group is a phosphonic diamide group:

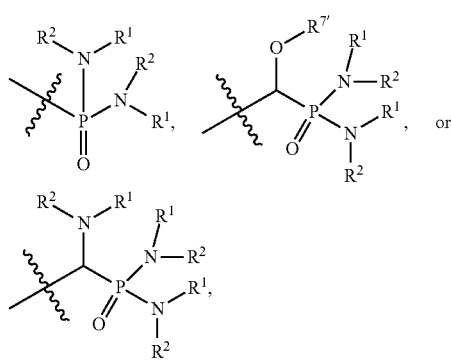

wherein R¹, R², and R⁷', are as defined above. In certain embodiments, each R¹ and R² group in a phosphonic diamide is methyl.

In some embodiments an activating functional group is a phosphine group:

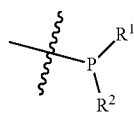

wherein R¹, and R² are as defined above.

In specific embodiments, a phosphine activating functional group is selected from the group consisting of:

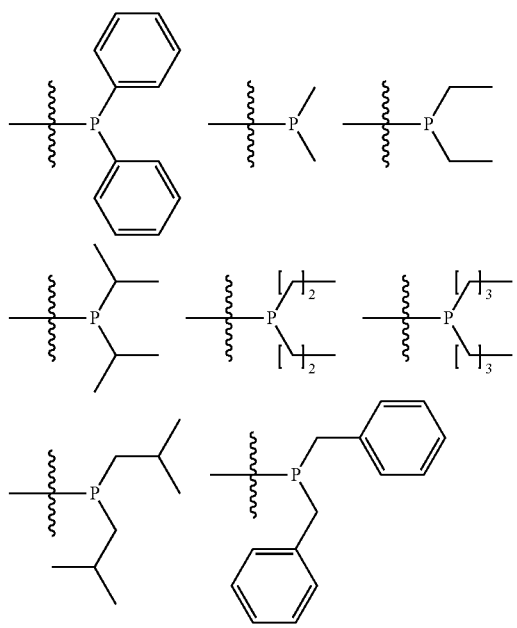

II. Linker Moieties

As described above, each activating moiety ∼∼∼(Z)$_m$ comprises a linker ∼∼∼ coupled to at least one activating functional group Z as described above, with m denoting the number of activating functional groups present on a single linker moiety.

As noted above there may be one or more activating moiety ∼∼∼(Z)$_m$ tethered to a given metal complex, similarly, each activating moiety itself may contain more than one activating functional group Z. In certain embodiments, each activating moiety contains only one activating functional group (i.e. m=1). In some embodiments, each activating moiety contains more than one activating functional groups (i.e. m>1). In certain embodiments, an activating moiety contains two activating functional groups (i.e. m=2). In certain embodiments, an activating moiety contains three activating functional groups (i.e. m=3). In certain embodiments, an activating moiety contains four activating functional groups (i.e. m=4). In certain embodiments where more than one activating functional group is present on an activating moiety, they are all the same functional group. In some embodiments where more than one activating functional group is present on an activating moiety, two or more of the activating functional groups are different.

In certain embodiments, each linker moiety —⁓⁓— contains 1-30 atoms including at least one carbon atom, and optionally one or more atoms selected from the group consisting of N, O, S, Si, B, and P.

In certain embodiments, the linker is an optionally substituted $C_{2-30}$ aliphatic group wherein one or more methylene units are optionally and independently replaced by —$NR^y$—, —$N(R^y)C(O)$—, —$C(O)N(R^y)$—, —O—, —C(O)—, —OC(O)—, —C(O)O—, —S—, —SO—, —$SO_2$—, —C(=S)—, —C(=$NR^y$)—, or —N=N—, where each occurrence of $R^y$ is independently —H, or an optionally substituted radical selected from the group consisting of $C_{1-6}$ aliphatic 3- to 7-membered heterocyclic, phenyl, and 8- to 10-membered aryl. In certain embodiments, a linker moiety is a $C_4$-$C_{12}$ aliphatic group substituted with one or more moieties selected from the group consisting of halogen, —$NO_2$, —CN, —$SR^y$, —S(O)$R^y$, —S(O)$_2R^y$, —$NR^yC(O)R^y$, —OC(O)$R^y$, —$CO_2R^y$, —NCO, —$N_3$, —$OR^7$, —OC(O)N($R^y$)$_2$, —N($R^y$)$_2$, —$NR^yC(O)R^y$, and —$NR^yC(O)OR^y$, where $R^y$ is —H, or an optionally substituted radical selected from the group consisting of $C_{1-6}$ aliphatic 3- to 7-membered heterocyclic, phenyl, and 8- to 10-membered aryl.

In certain embodiments, a linker moiety is an optionally substituted $C_3$-$C_{30}$ aliphatic group. In certain embodiments, a linker is an optionally substituted $C_{4-24}$ aliphatic group. In certain embodiments, a linker moiety is an optionally substituted $C_4$-$C_{20}$ aliphatic group. In certain embodiments, a linker moiety is an optionally substituted $C_4$-$C_{12}$ aliphatic group. In certain embodiments, a linker is an optionally substituted $C_{4-10}$ aliphatic group. In certain embodiments, a linker is an optionally substituted $C_{4-8}$ aliphatic group. In certain embodiments, a linker moiety is an optionally substituted $C_4$-$C_6$ aliphatic group. In certain embodiments, a linker moiety is an optionally substituted $C_6$-$C_{12}$ aliphatic group. In certain embodiments, a linker moiety is an optionally substituted $C_8$ aliphatic group. In certain embodiments, a linker moiety is an optionally substituted $C_7$ aliphatic group. In certain embodiments, a linker moiety is an optionally substituted $C_6$ aliphatic group. In certain embodiments, a linker moiety is an optionally substituted $C_5$ aliphatic group. In certain embodiments, a linker moiety is an optionally substituted $C_4$ aliphatic group. In certain embodiments, a linker moiety is an optionally substituted $C_3$ aliphatic group. In certain embodiments, a aliphatic group in the linker moiety is an optionally substituted straight alkyl chain. In certain embodiments, the aliphatic group is an optionally substituted branched alkyl chain. In some embodiments, a linker moiety is a $C_4$ to $C_{20}$ alkyl group having one or more methylene groups replaced by —C($R^aR^b$)— where $R^a$ and $R^b$ are each, independently $C_1$-$C_4$ alkyl groups. In certain embodiments, a linker moiety consists of an aliphatic group having 4 to 30 carbons including one or more gem-dimethyl substituted carbon atoms.

In certain embodiments, a linker moiety includes one or more optionally substituted cyclic elements selected from the group consisting of saturated or partially unsaturated carbocyclic, aryl, heterocyclic, or heteroaryl. In certain embodiments, a linker moiety consists of the substituted cyclic element, in some embodiments the cyclic element is part of a linker with one or more non-ring heteroatoms or optionally substituted aliphatic groups comprising other parts of the linker moiety.

In some embodiments, a linker moiety is of sufficient length to allow one or more activating functional groups to be positioned near a metal atom of a metal complex. In certain embodiments, structural constraints are built into a linker moiety to control the disposition and orientation of one or more activating functional groups near a metal center of a metal complex. In certain embodiments such structural constraints are selected from the group consisting of cyclic moieties, bicyclic moieties, bridged cyclic moieties and tricyclic moieties. In some embodiments, such structural constraints are the result of acyclic steric interactions. In certain embodiments such structural constraints are selected from the group consisting of cis double bonds, trans double bonds, cis allenes, trans allenes, and triple bonds. In some embodiments, such structural constraints are selected from the group consisting of substituted carbons including geminally disubstituted groups such as sprirocyclic rings, gem dimethyl groups, gem diethyl groups and gem diphenyl groups. In certain embodiments such structural constraints are selected from the group consisting of heteratom-containing functional groups such as sulfoxides, amides, and oximes.

In certain embodiments, linker moieties are selected from the group consisting of:

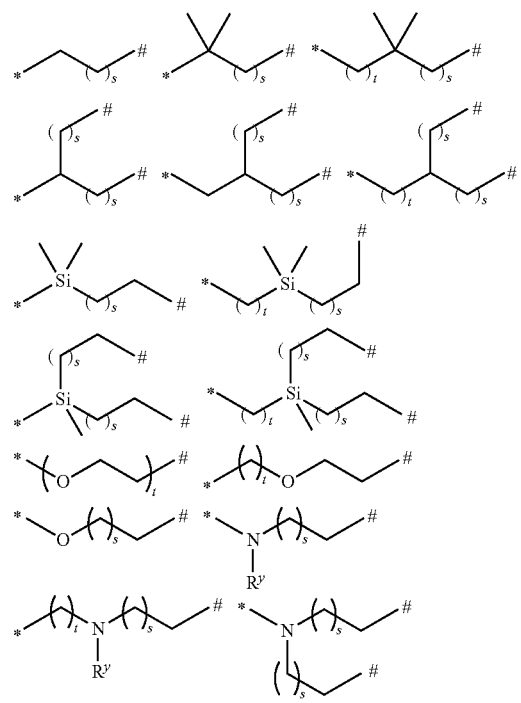

-continued

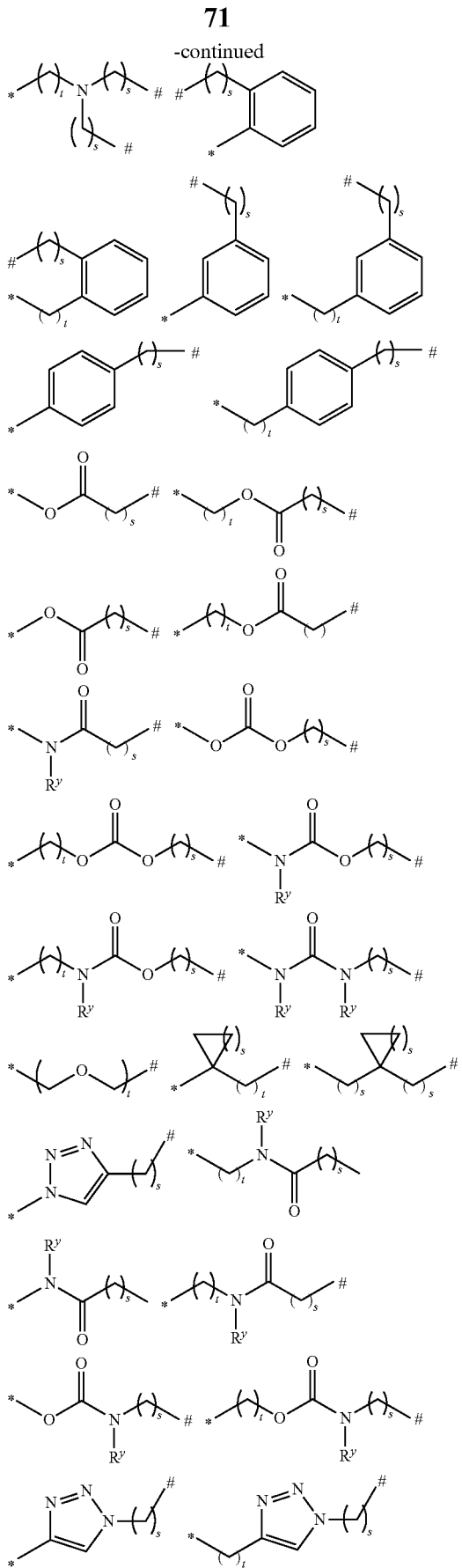

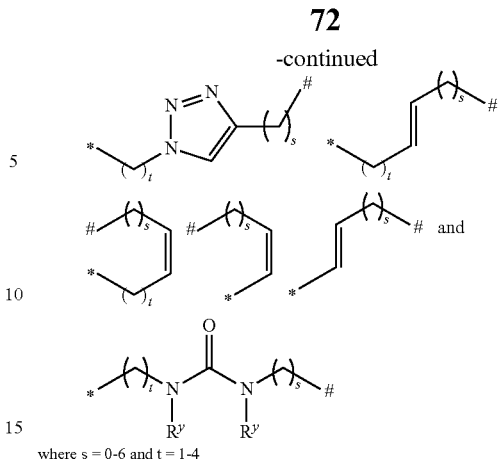

where s = 0-6 and t = 1-4 where * represents the site of attachment to a ligand, and each # represents a site of attachment of an activating functional group.

In some embodiments, s is 0. In some embodiments, s is 1. In some embodiments, s is 2. In some embodiments, s is 3. In some embodiments, s is 4. In some embodiments, s is 5. In some embodiments, s is 6.

In some embodiments, t is 1. In some embodiments, t is 2. In some embodiments, t is 3. In some embodiments, t is 4.

III. Metal Complexes

As noted above, the present invention encompasses metal complexes that include a metal atom coordinated to a multidentate ligand and at least one activating moiety tethered to a multidentate ligand. In certain embodiments, provided metal complexes have the structure:

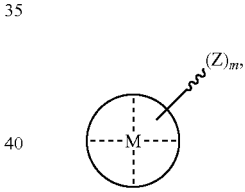

where

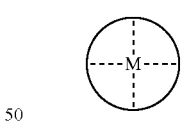

represents a metal atom coordinated to a multidentate ligand.

IIa. Metal Atoms

In certain embodiments, M is a metal atom selected from periodic table groups 3-13, inclusive. In certain embodiments, M is a transition metal selected from periodic table groups 5-12, inclusive. In certain embodiments, M is a transition metal selected from periodic table groups 4-11, inclusive. In certain embodiments, M is a transition metal selected from periodic table groups 5-10, inclusive. In certain embodiments, M is a transition metal selected from periodic table groups 7-9, inclusive. In some embodiments, M is selected from the group consisting of Cr, Mn, V, Fe, Co, Mo, W, Ru, Al, and Ni. In some embodiments, M is a metal atom selected from the group consisting of: cobalt; chromium; aluminum; titanium; ruthenium, and manganese. In some embodiments, M is cobalt. In some embodiments, M is chromium. In some embodiments, M is aluminum.

In certain embodiments, a metal complex is a zinc, cobalt, chromium, aluminum, titanium, ruthenium, or manganese complex. In certain embodiments, a metal complex is an aluminum complex. In some embodiments, a metal complex is a chromium complex.

In some embodiments, a metal complex is a zinc complex. In certain some embodiments, a metal complex is a titanium complex. In some embodiments, a metal complex is a ruthenium complex. In certain embodiments, a metal complex is a manganese complex. In certain embodiments, a metal complex is cobalt complex. In certain embodiments where the metal complex is a cobalt complex, the cobalt metal has an oxidation state of 3+ (i.e., Co(III)). In some embodiments, the cobalt metal has an oxidation state of 2+.

IIIb. Ligands

In some embodiments, a metal complex

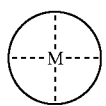

comprises a metal atom coordinated to a single tetradentate ligand and in some embodiments, the metal complex comprises a chelate containing a plurality of individual ligands. In certain embodiments, a metal complex contains two bidentate ligands. In some embodiments, a metal complex contains a tridentate ligand.

In various embodiments, tetradentate ligands suitable for metal complexes of the present invention may include, but are not limited to: salen derivatives 1, derivatives of salan ligands 2, bis-2-hydroxybenzamido derivatives 3, derivatives of the Trost ligand 4, porphyrin derivatives 5, derivatives of tetrabenzoporphyrin ligands 6, derivatives of corrole ligands 7, phthalocyaninate derivatives 8, and dibenzotetramethyltetraaza[14]annulene (tmtaa) derivatives 9 or 9'.

1

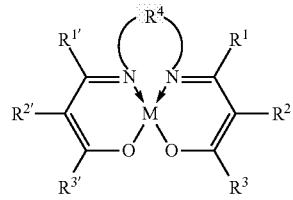

2

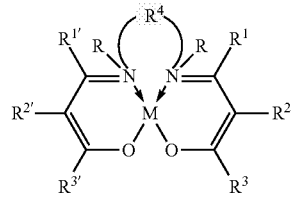

3

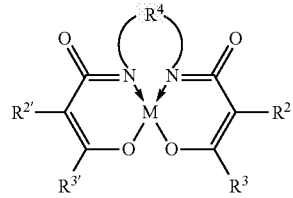

4

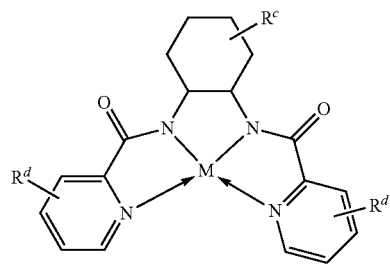

5

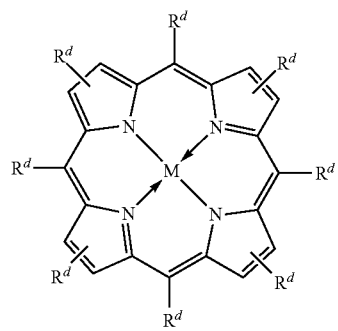

6

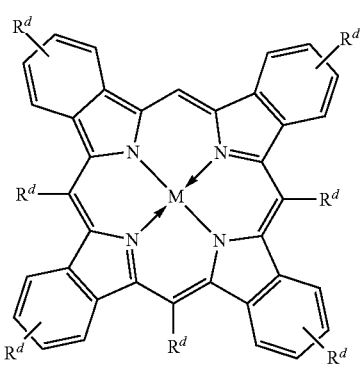

7

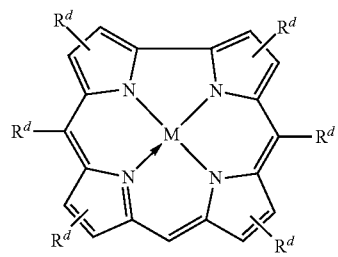

8

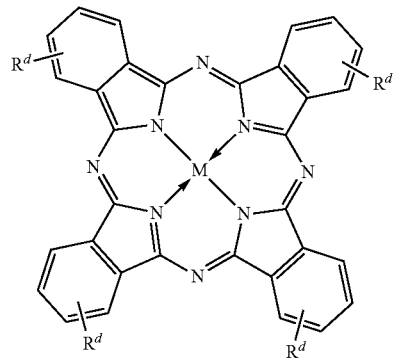

-continued

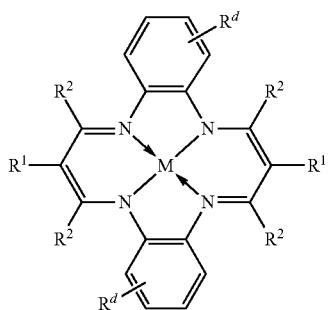

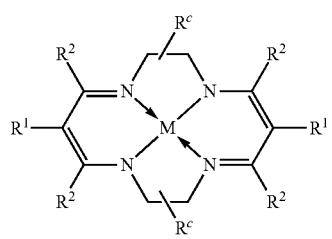

In some embodiments, a metal multidentate ligand coordinated with a metal complex may comprise a plurality of discrete ligands. In some embodiments, metal complexes include two bidentate ligands. In certain embodiments, such bidentate ligands may have the structure

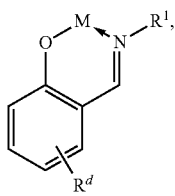

where $R^d$ and $R^1$ are as defined above. Metal complexes having two such ligands may adopt one of several geometries, and the present disclosure encompasses such variations.

In certain embodiments, metal complexes including two bidentate ligands may have structures selected from the group consisting of:

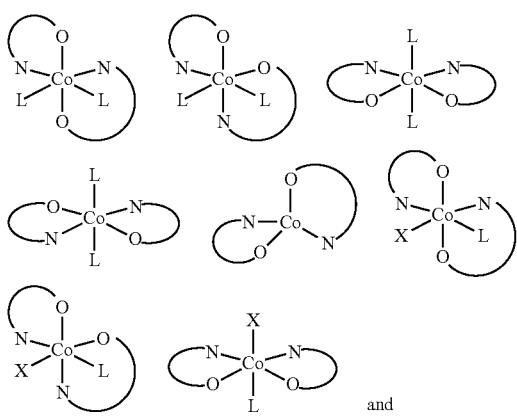

and

-continued

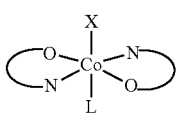

where each

represents a ligand:

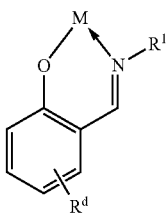

In certain embodiments, a tetradentate ligand is a salen ligand. In certain embodiments, a metal complex is a metallosalenate. In certain embodiments, a metal complex is a cobalt salen complex. In certain embodiments, a metal complex is a chromium salen complex. In some embodiments, a metal complex is an aluminum salen complex.

In certain embodiments, at least one activating moiety is tethered to a carbon atom of a phenyl ring of the salicylaldehyde-derived portions of a salen ligand. In certain embodiments, at least one activating moiety is tethered to a carbon atom of a porphyrin ligand. In certain embodiments, at least one activating moiety is tethered to a pyrrole-carbon atom of a porphyrin ligand. In certain embodiments, at least one activating moiety is tethered to a carbon atom forming the bridge between the pyrrole rings of a porphyrin ligand.

In certain embodiments, at least one activating moiety is tethered to one or more carbon atoms of only one phenyl ring of the salicylaldehyde-derived portions of a salen ligand, as shown in formula I:

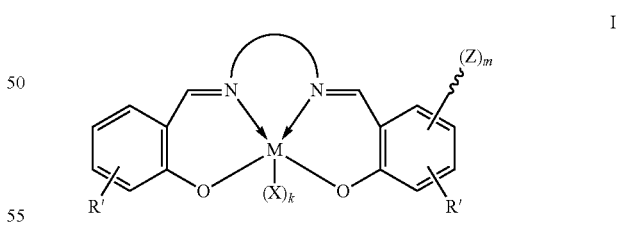

I wherein:
  M is a metal atom;
  X is a nucleophile capable of ring opening an epoxide;
  k is an integer from 0-2 inclusive;
  R' represents one or more substituents optionally present on the phenyl rings and each R' is independently selected from the group consisting of: halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-N_3$, $-OR^7$, $-OC(O)N(R^y)_2$, $-N(R^y)_2$, $-NR^yC(O)R^y$, $-NR^yC(O)OR^y$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where two or more adjacent R' groups can be taken together to form an optionally substituted saturated, partially unsaturated, or aromatic 5- to 12-membered ring containing 0 to 4 heteroatoms; $R^y$ is —H, or an optionally substituted radical selected from the group consisting of $C_{1-6}$ aliphatic, 3- to 7-membered heterocyclic, phenyl, and 8- to 10-membered aryl;

represents is an optionally substituted moiety linking the two nitrogen atoms of the diamine portion of the salen ligand, where

is selected from the group consisting of phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; or an optionally substituted $C_{2-20}$ aliphatic group, wherein one or more methylene units are optionally and independently replaced by —$NR^y$—, —$N(R^y)C(O)$—, —$C(O)N(R^y)$—, —$OC(O)N(R^y)$—, —$N(R^y)C(O)O$—, —$OC(O)O$—, —$O$—, —$C(O)$—, —$OC(O)$—, —$C(O)O$—, —$S$—, —$SO$—, —$SO_2$—, —$C(=S)$—, —$C(=NR^y)$—, —$C(=NOR^y)$— or —$N=N$—;

$\sim\!\!\sim\!\!(Z)_m$ represents one or more activating moieties, where "$\sim\!\!\sim$" is a covalent linker containing one or more atoms selected from the group consisting of C, O, N, S, and Si; Z is an activating functional group and m is an integer from 1 to 4 indicating the number of individual activating functional groups present in each activating moiety.

In certain embodiments, both salicylaldehyde-derived portions of a salen ligand bear one or more activating moieties:

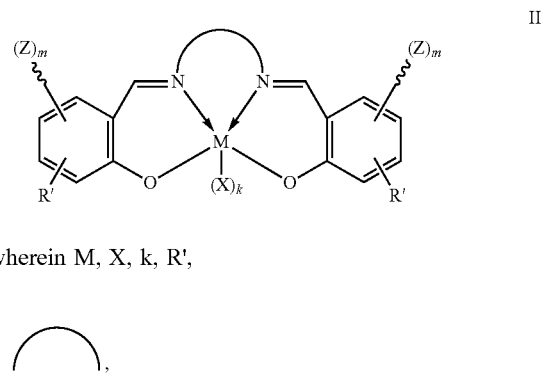

wherein M, X, k, R',

and $\sim\!\!\sim\!\!(Z)_m$ are as defined above.

In some embodiments, provided metal complexes comprise a

moiety that has the structure:

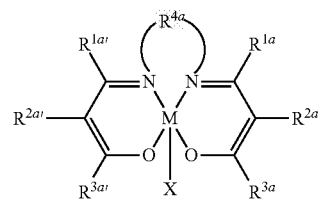

wherein:
M is a metal atom,
$R^{1a}$, $R^{1a'}$, $R^{2a}$, $R^{2a'}$, $R^{3a}$, and $R^{3a'}$ are independently a $\sim\!\!\sim\!\!(Z)_m$ group, hydrogen, halogen, —OR, —$NR_2$, —SR, —CN, —$NO_2$, —$SO_2R$, —SOR, —$SO_2NR_2$; —CNO, —$NRSO_2R$, —NCO, —$N_3$, —$SiR_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

each R is independently hydrogen, an optionally substituted radical selected the group consisting of acyl; carbamoyl; arylalkyl; phenyl, 8- to 10-membered aryl; $C_{1-12}$ aliphatic; $C_{1-12}$ heteroaliphatic; 5- to 10-membered heteroaryl; 4- to 7-membered heterocyclyl; an oxygen protecting group; and a nitrogen protecting group; or:

two R on the same nitrogen atom are taken with the nitrogen to form a 3- to 7-membered heterocyclic ring;

wherein any of [$R^{2a'}$ and $R^{3a'}$], [$R^{2a}$ and $R^{3a}$], [$R^{1a}$ and $R^{2a}$], and [$R^{1a'}$ and $R^{2a'}$] may optionally be taken together with the carbon atoms to which they are attached to form one or more rings which may in turn be substituted with one or more $R^{20a}$ groups; and $R^{4a}$ is selected from the group consisting of:

a)

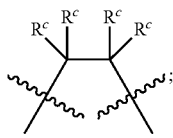

b)

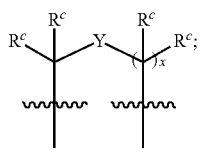

c)

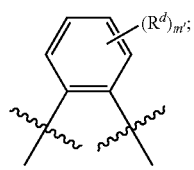

and d)

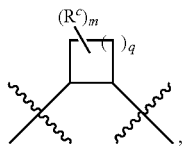, where $R^c$ at each occurrence is independently a ⎯⎯$\sim\sim$Z group, hydrogen, halogen, —OR, —$NR_2$, —SR, —CN, —$NO_2$, —$SO_2R$, —SOR, —$SO_2NR_2$; —CNO, —$NRSO_2R$, —NCO, —$N_3$, —$SiR_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

where:

two or more $R^c$ groups may be taken together with the carbon atoms to which they are attached and any intervening atoms to form one or more rings;

when two $R^c$ groups are attached to the same carbon atom, they may be taken together along with the carbon atom to which they are attached to form a moiety selected from the group consisting of: a 3- to 8-memberedspirocyclic ring, a carbonyl, an oxime, a hydrazone, an imine;

X is a nucleophile capable of ring opening an epoxide;

Y is a divalent linker selected from the group consisting of: —NR—, —N(R)C(O)—, —C(O)NR—, —O—, —C(O)—, —OC(O)—, —C(O)O—, —S—, —SO—, —$SO_2$—, —C(=S)—, —C(=NR)—, or —N=N—; a polyether; a $C_3$ to $C_8$ substituted or unsubstituted carbocycle; and a $C_1$ to $C_8$ substituted or unsubstituted heterocycle;

m' is 0 or an integer from 1 to 4, inclusive;

q is 0 or an integer from 1 to 4, inclusive; and x is 0, 1, or 2.

In some embodiments, at least one of [$R^{2a}$ and $R^{3a}$] and [$R^{2a'}$ and $R^{3a'}$] are taken together to form a ring. In some embodiments, both [$R^{2a}$ and $R^{3a}$] and [$R^{2a'}$ and $R^{3a'}$] are taken together to form rings. In some embodiments, the rings formed by [$R^{2a}$ and $R^{3a}$] and [$R^{2a'}$ and $R^{3a'}$] are substituted phenyl rings.

In certain embodiments, one or more of $R^{1a}$, $R^{1a'}$, $R^{2a}$, $R^{2a'}$, $R^{3a}$, and $R^{3a'}$ are independently a ⎯⎯$\sim\sim$Z group.

In certain embodiments of provided metal complexes, a

moiety has a structure selected from the group consisting of:

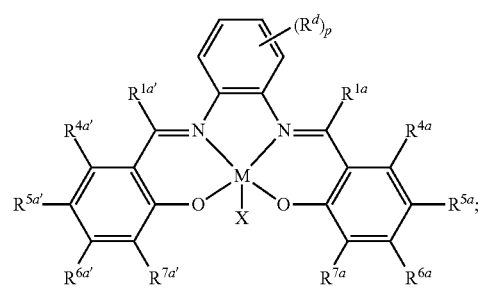

-continued

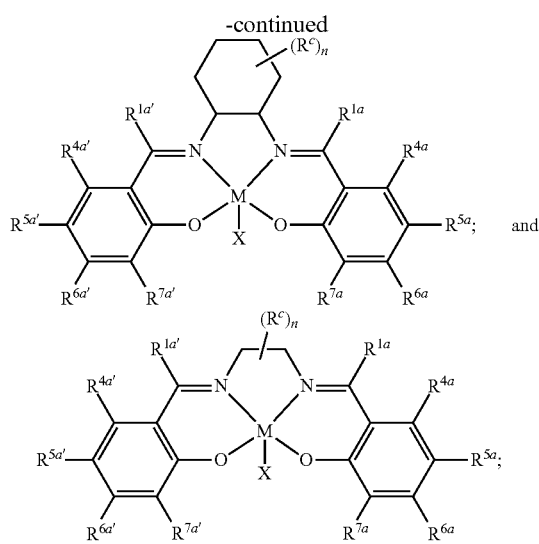

wherein:
M is a metal atom;
$R^{4a}$, $R^{4a'}$, $R^{5a}$, $R^{5a'}$, $R^{6a}$, $R^{6a'}$, $R^{7a}$, and $R^{7a'}$ are each independently a ⟶$\sim\sim$ Z group, hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;
wherein [$R^{1a}$ and $R^{4a}$], [$R^{1a'}$ and $R^{4a'}$] and any two adjacent $R^{4a}$, $R^{4a'}$, $R^{5a}$, $R^{5a'}$, $R^{6a}$, $R^{6a'}$, $R^{7a}$, and $R^{7a'}$ groups can be taken together with intervening atoms to form one or more optionally substituted rings;
n is 0 or an integer from 1 to 8, inclusive; and
p is 0 or an integer from 1 to 4, inclusive.
In some embodiments, M is Co.
In some embodiments, $R^{1a}$, $R^{1a'}$, $R^{4a}$, $R^{4a'}$, $R^{6a}$, and $R^{6a'}$ are each —H. In some embodiments, $R^{5a}$, $R^{5a'}$, $R^{7a}$ and $R^{7a'}$ are each optionally substituted C$_1$-C$_{12}$ aliphatic. In some embodiments, $R^{4a}$, $R^{4a'}$, $R^{5a}$, $R^{5a'}$, $R^{6a}$, $R^{6a'}$, $R^{7a}$, and $R^{7a'}$ are each independently selected from the group consisting of: —H, —SiR$_3$; methyl, ethyl, n-propyl, i-propyl, n-butyl, sec-butyl, t-butyl, isoamyl, t-amyl, thexyl, and trityl. In some embodiments, $R^{1a}$, $R^{1a'}$, $R^{4a}$, $R^{4a'}$, $R^{6a}$, and $R^{6a'}$ are each —H. In some embodiments, $R^{7a}$ is selected from the group consisting of —H; methyl; ethyl; n-propyl; i-propyl; n-butyl; sec-butyl; t-butyl; isoamyl; t-amyl; thexyl; and trityl. In some embodiments, $R^{5a}$ and $R^{7a}$ are independently selected from the group consisting of —H; methyl; ethyl; n-propyl; i-propyl; n-butyl; sec-butyl; t-butyl; isoamyl; t-amyl; thexyl; and trityl. In certain embodiments, one or more of $R^{5a}$, $R^{5a'}$, $R^{7a}$ and $R^{7a'}$ is a ⟶$\sim\sim$ Z group. In some embodiments, $R^{5a}$ and $R^{5a'}$ are a ⟶$\sim\sim$ Z group.

In certain embodiments of provided metal complexes, a

moiety has a structure selected from the group consisting of:

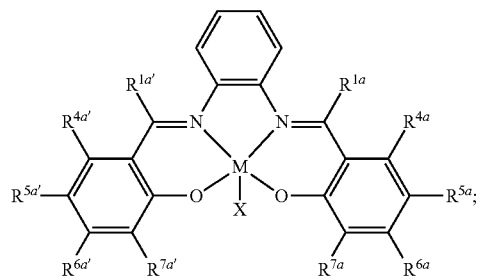

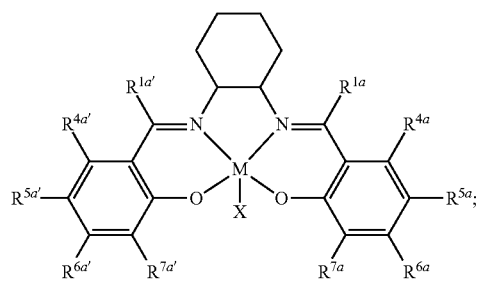

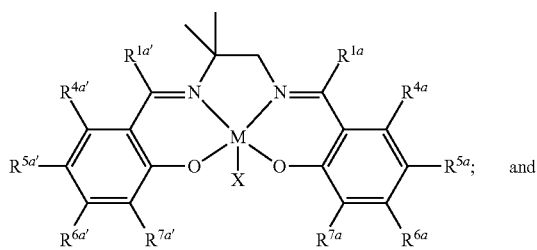

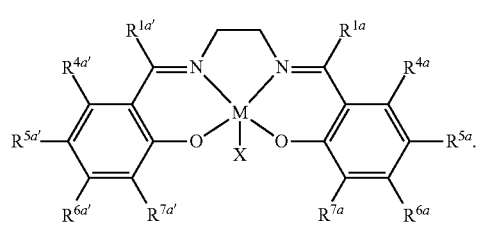

In certain embodiments of complexes having formulae described above, at least one of the phenyl rings comprising a salicylaldehyde-derived portion of a catalyst is independently selected from the group consisting of:

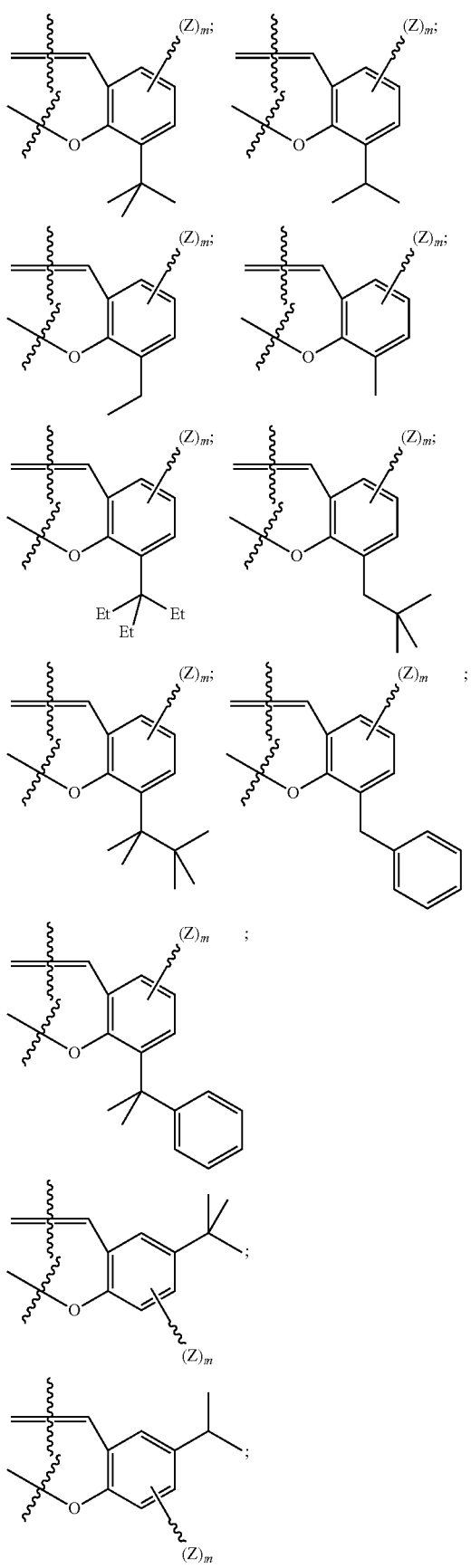
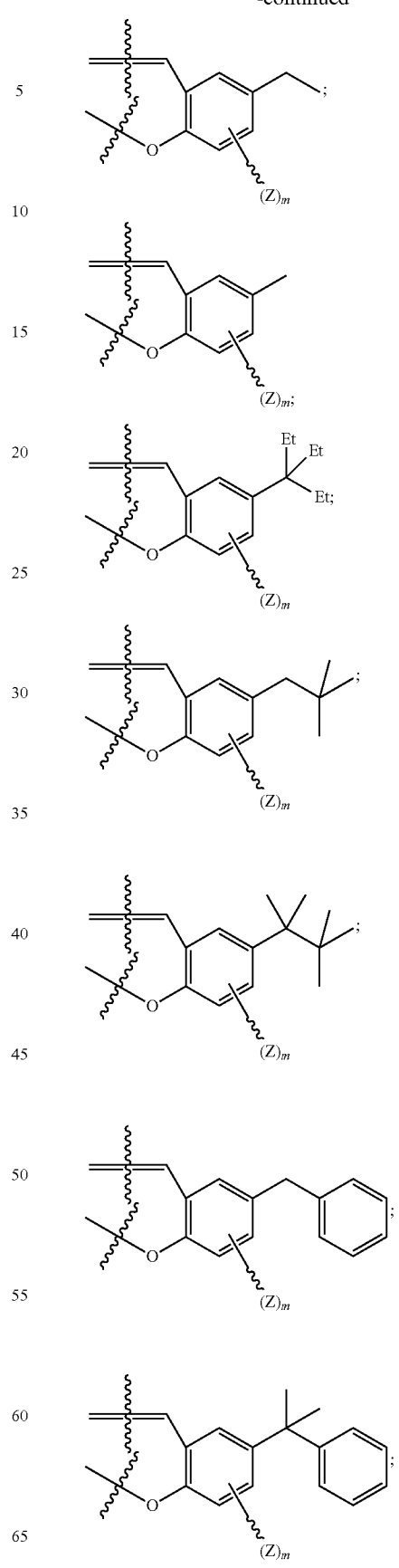

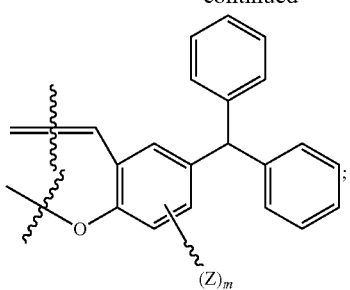
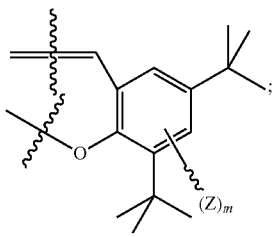
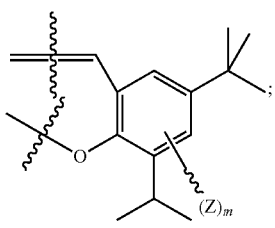
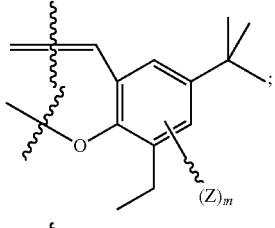
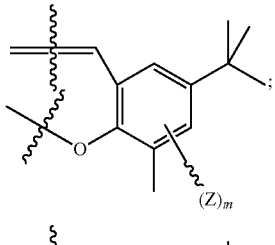
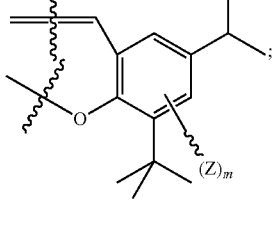
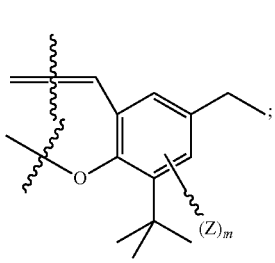
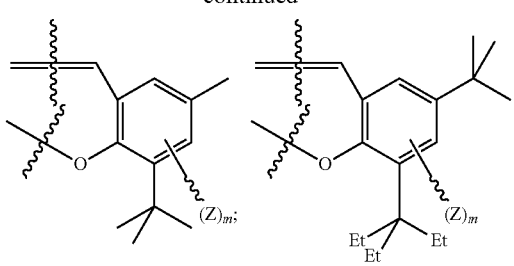
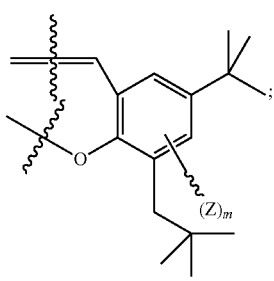
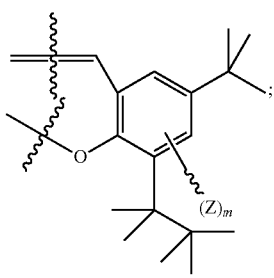
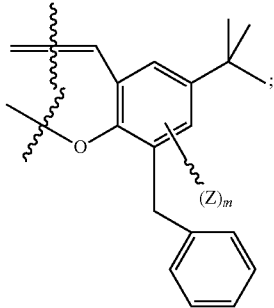
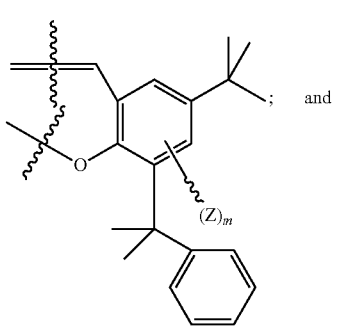

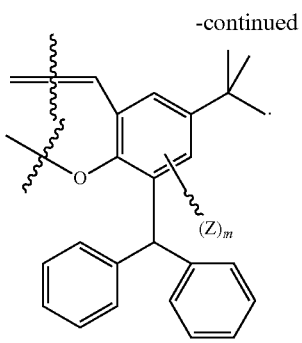

where ⌇⌇(Z)$_m$ represents one or more independently-defined activating moieties which may be bonded to any one or more unsubstituted positions of a salicylaldehyde-derived phenyl ring.

In certain embodiments, there is an activating moiety tethered to the position ortho to a metal-bound oxygen substituent of one or both of the salicylaldehyde-derived phenyl rings of a salen ligand as in formulae IIIa and IIIb:

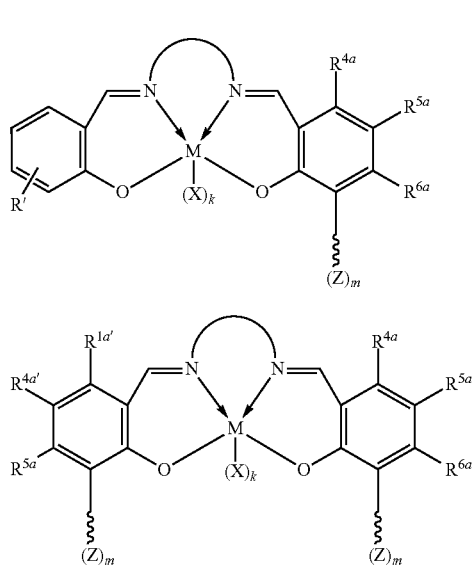

wherein:

M, X, k, R',

and ⌇⌇(Z)$_m$ are as defined above, and $R^{4a}$, $R^{4a'}$, $R^{5a}$, $R^{5a'}$, $R^{6a}$, and $R^{6a'}$ are each independently a ⌇⌇Z group, hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

wherein any two adjacent $R^{4a}$, $R^{4a'}$, $R^{5a}$, $R^{5a'}$, $R^{6a}$, and $R^{6a'}$ groups can be taken together with intervening atoms to form one or more optionally substituted rings.

In certain embodiments of compounds having formulae IIIa or IIIb, $R^{4a}$, $R^{4a'}$, $R^{6a}$, and $R^{6a'}$ are each hydrogen, and $R^{5a}$, $R^{5a'}$ are, independently, optionally substituted C$_1$-C$_{20}$ aliphatic.

In certain embodiments of complexes IIIa and IIIb, at least one of the phenyl rings comprising a salicylaldehyde-derived portion of a catalyst is independently selected from the group consisting of:

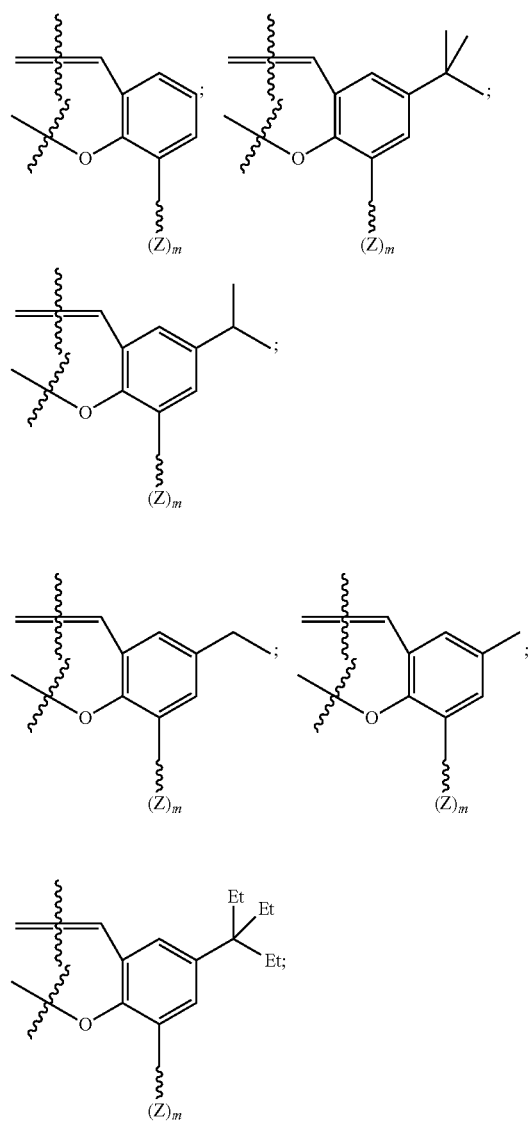

-continued

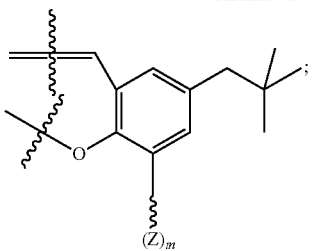

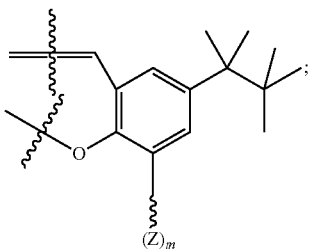

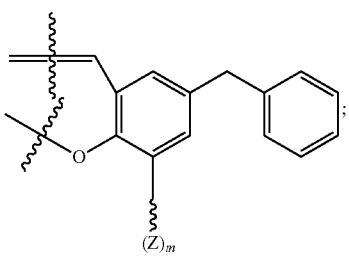

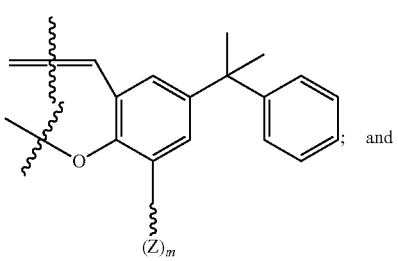

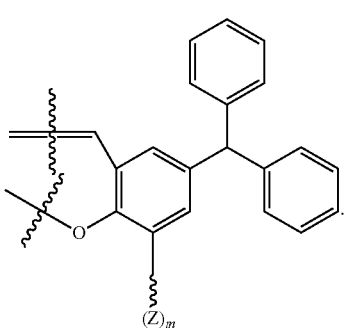

In certain embodiments, there is an activating moiety tethered to the position para to the phenolic oxygen of one or both of a salicylaldehyde-derived phenyl rings of the salen ligand as in structures IVa and IVb:

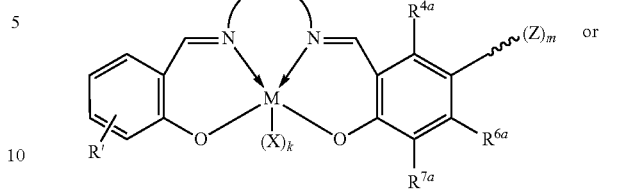

IVa

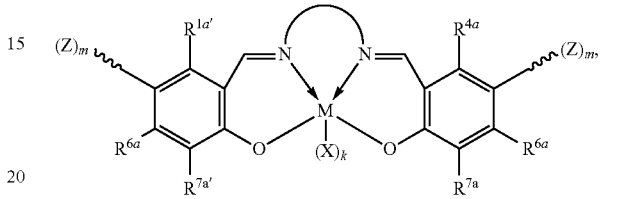

IVb where M, X, k, R', $R^{4a}$, $R^{4a'}$, $R^{6a}$, $R^{6a'}$, $R^{7a}$, $R^{7a'}$,

and $\sim\!\!\sim (Z)_m$ are as defined above.

In certain embodiments of compounds having formulae IVa or IVb, $R^{4a}$, $R^{4a'}$, $R^{6a}$, and $R^{6a'}$ are hydrogen, and each $R^{7a}$, $R^{7a'}$ is, independently, optionally substituted $C_1$-$C_{20}$ aliphatic.

In certain embodiments of catalysts IVa and IVb, at least one of the phenyl rings comprising a salicylaldehyde-derived portion of a catalyst is independently selected from the group consisting of:

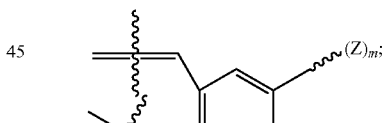

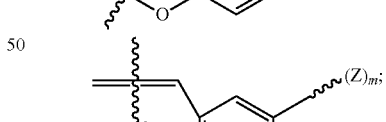

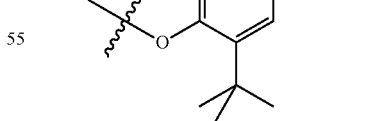

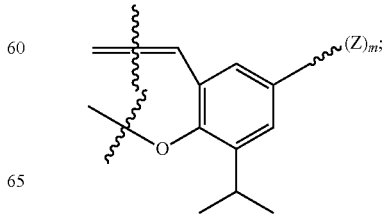

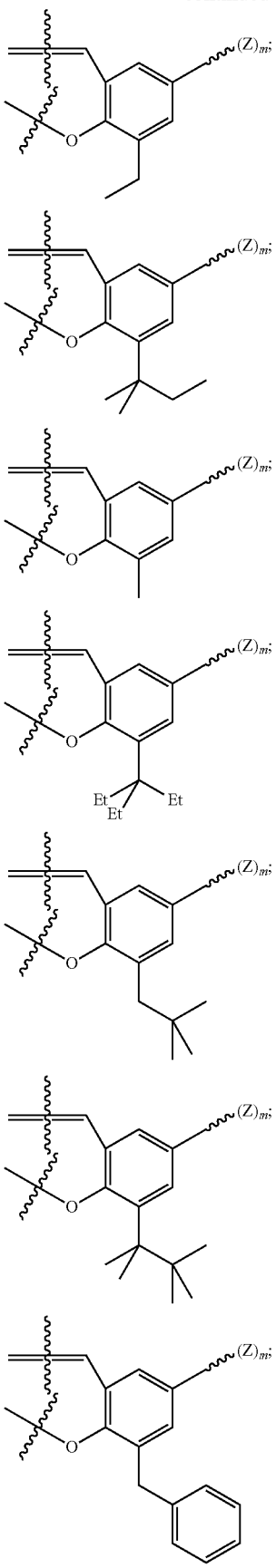

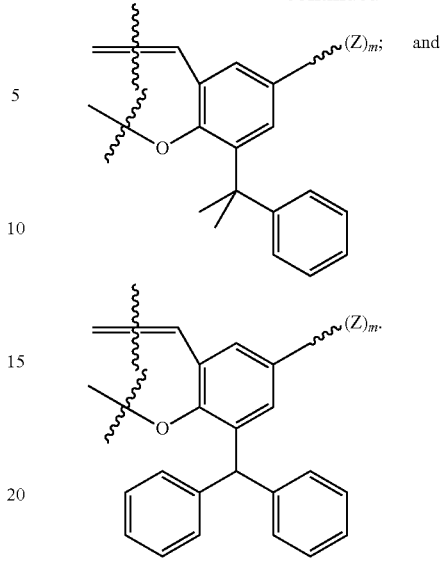

In some embodiments, there is an activating moiety tethered to the position para to the imine substituent of one or both of the salicylaldehyde-derived phenyl rings of a salen ligand as in formulae Va or Vb:

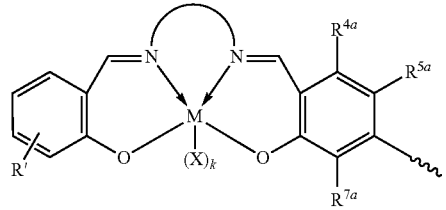

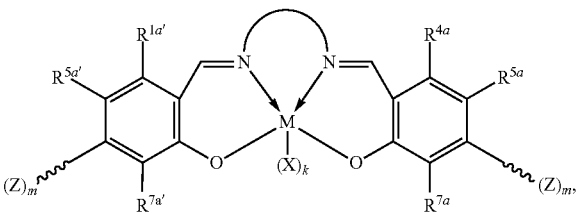

where M, X, k, R', $R^{4a}$, $R^{4a'}$, $R^{5a}$, $R^{5a'}$, $R^{7a}$, $R^{7a'}$,

and $\sim\!\!\sim\!\!\sim (Z)_m$ are as defined above.

In certain embodiments of compounds having formulae Va or Vb, each $R^4$ and $R^{4a}$ is hydrogen, and each $R^{5a}$, $R^{5a'}$, $R^{7a}$, $R^{7a'}$ is, independently, hydrogen or optionally substituted $C_1$-$C_{20}$ aliphatic.

In certain embodiments of catalysts Va and Vb, at least one of the phenyl rings comprising a salicylaldehyde-derived portion of a catalyst is independently selected from the group consisting of:

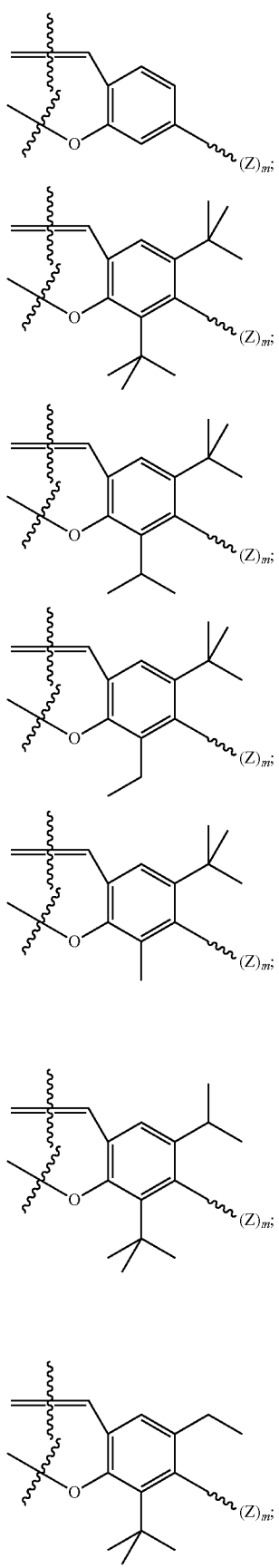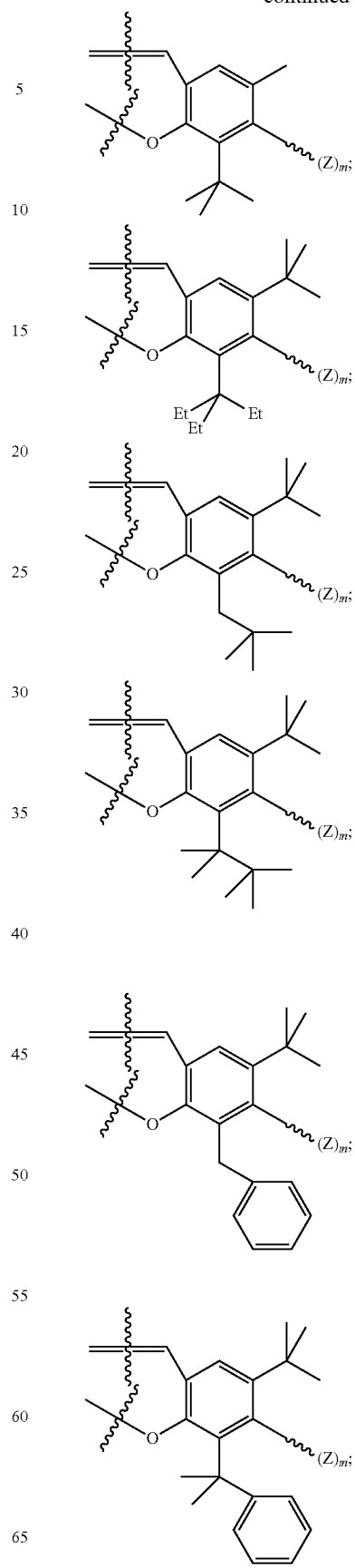

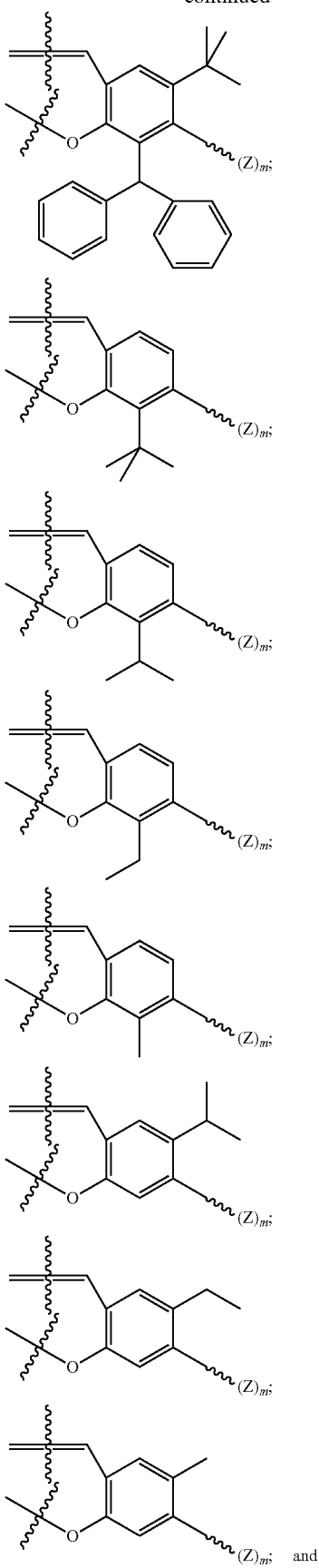

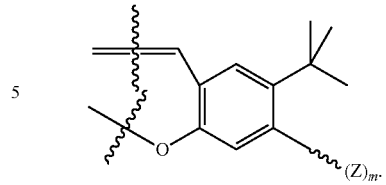

In some embodiments, there is an activating moiety tethered to the position ortho to the imine substituent of one or both of the salicylaldehyde-derived phenyl rings of a salen ligand as in formulae VIa and VIb:

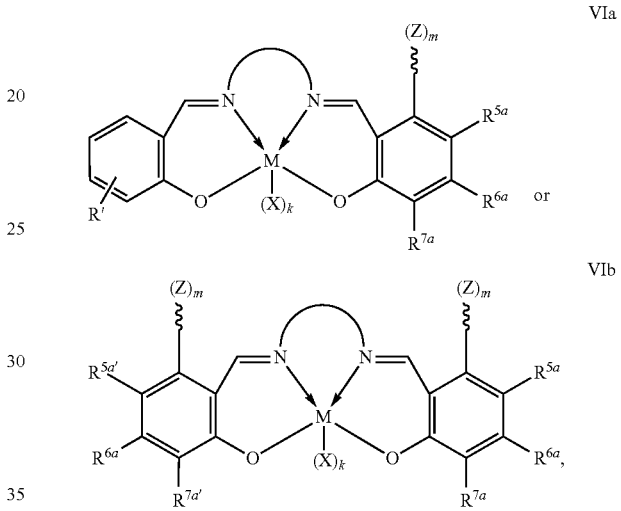

where X, k, M, R', $R^{5a}$, $R^{5a'}$, $R^{6a}$, $R^{6a'}$, $R^{7a}$, $R^{7a'}$,

and ⌇⌇$(Z)_m$ are as defined above.

In certain embodiments of compounds having formulae VIa or VIb, each $R^{6a}$ and $R^{6a'}$ is hydrogen, and each $R^{5a}$, $R^{5a'}$, $R^{7a}$, and $R^{7a'}$ is, independently, hydrogen or optionally substituted $C_1$-$C_{20}$ aliphatic.

In certain embodiments of catalysts VIa and VIb, at least one of the phenyl rings comprising a salicylaldehyde-derived portion of a catalyst is independently selected from the group consisting of:

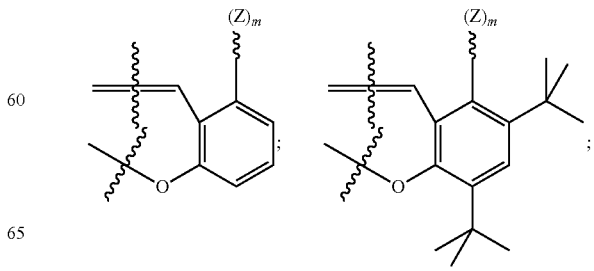

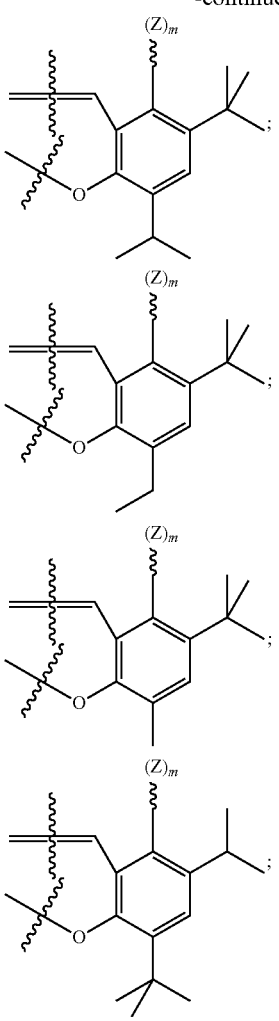
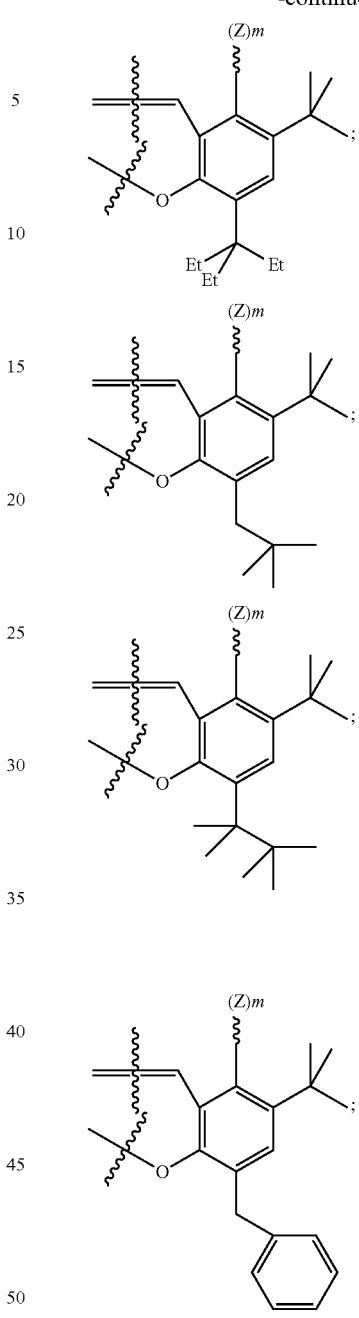
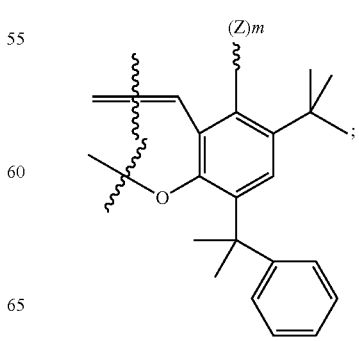

-continued

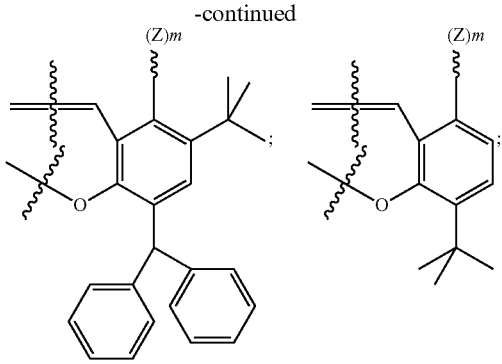

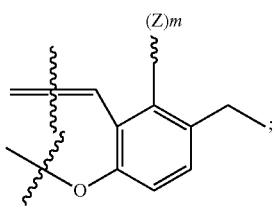

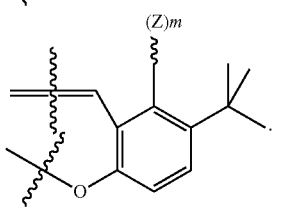

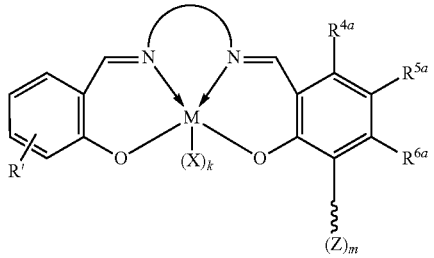

VIIa

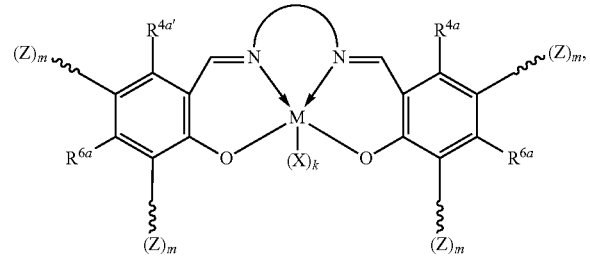

VIIb where M, X, k, R', $R^{4a}$, $R^{4a'}$, $R^{6a}$, $R^{6a'}$,

, and ⁓(Z)$_m$ are as defined above.

In certain embodiments of compounds having formulae VIa or VIb, each $R^{6a}$, $R^{6a'}$, $R^{4a}$, and $R^{4a'}$ is, independently, hydrogen or optionally substituted $C_1$-$C_{20}$ aliphatic.

In certain embodiments of compounds having formulae VIIa or VIIb, each $R^{6a}$, $R^{6a'}$, $R^{4a}$, and $R^{4a'}$ is hydrogen.

In some embodiments, there are activating moieties tethered to the positions ortho and para to the imine substituent of one or both of the salicylaldehyde-derived phenyl rings of a salen ligand as in formulae VIIIa and VIIIb:

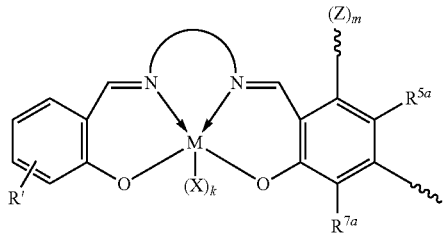

VIIIa

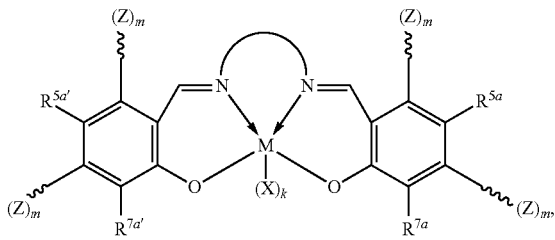

VIIIb

In some embodiments, there are activating moieties tethered to the positions ortho and para to the phenolic oxygen of one or both of the salicylaldehyde-derived phenyl rings of a salen ligand as in formulae VIIa and VIIb:

where X, k, M, R', $R^{5a}$, $R^{5a'}$, $R^{7a}$, $R^{7a'}$,

and  are as defined above.

In certain embodiments of compounds having formulae VIIIa or VIIIb, each $R^{5a}$, $R^{5a'}$, $R^{7a}$, and $R^{7a'}$ is, independently, optionally, hydrogen or substituted $C_1$-$C_{20}$ aliphatic.

In certain embodiments of the present invention, catalysts of structures VIIIa or VIIIb above, at least one of the phenyl rings comprising the salicylaldehyde-derived portion of a catalyst is independently selected from the group consisting of:

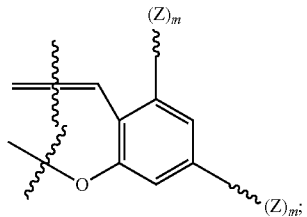

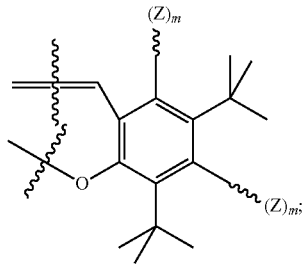

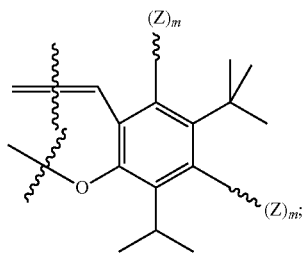

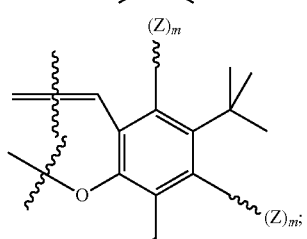

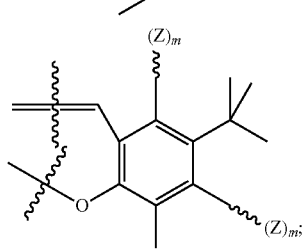

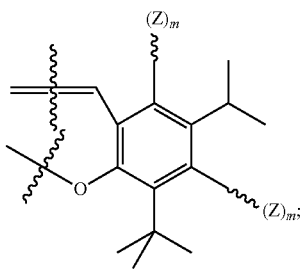

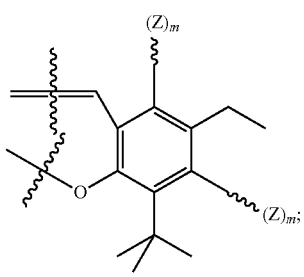

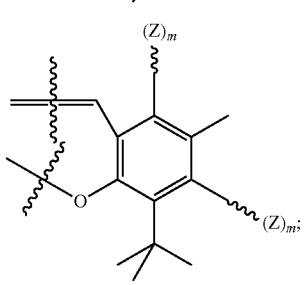

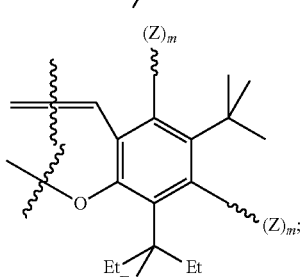

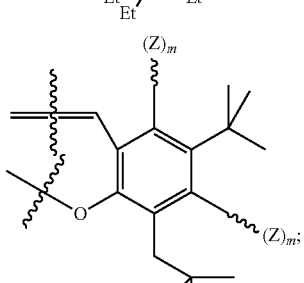

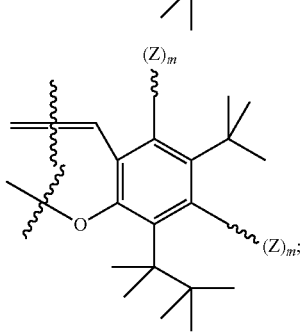

-continued
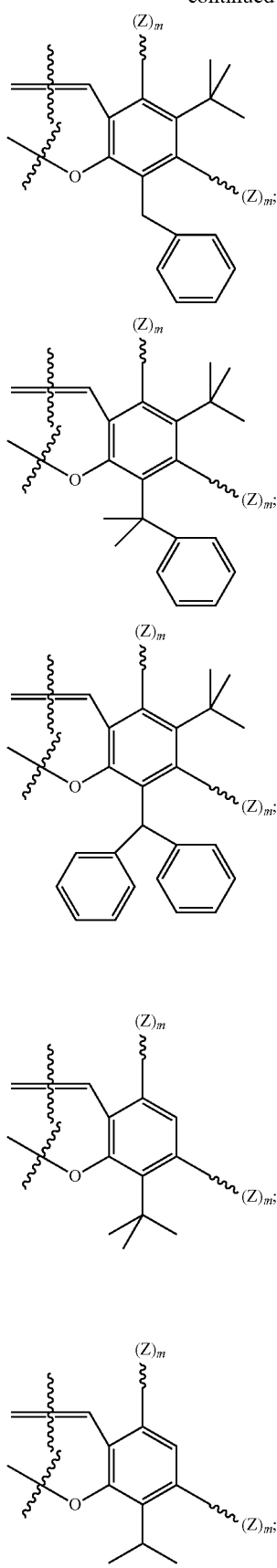
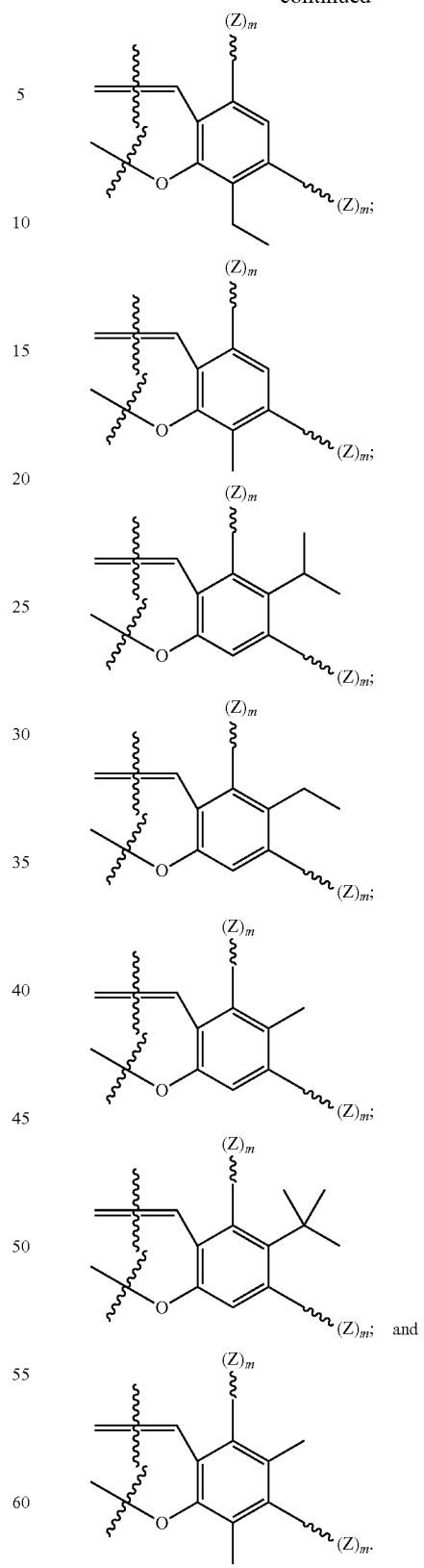
In some embodiments, there is an activating moiety tethered to the imine carbon of a salen ligand as in formulae IXa and IXb:

IXa

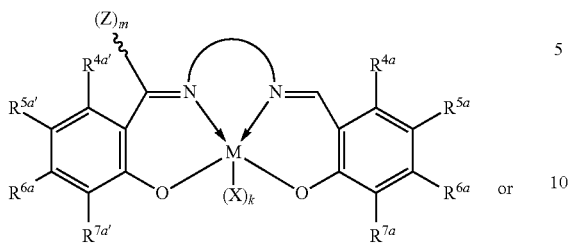

or

IXb

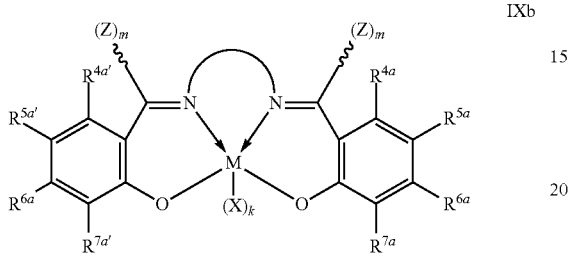

where M, X, k, $R^{4a}$, $R^{4a'}$, $R^{5a}$, $R^{5a'}$, $R^{6a}$, $R^{6a'}$, $R^{7a}$, $R^{7a'}$,

, and ⁓⁓⁓ $(Z)_m$ are as defined above with the proviso that the atom of the activating moiety attached to the salen ligand is a carbon atom.

In certain embodiments of compounds having formulae IXa or IXb, each $R^{4a}$, $R^{4a'}$, $R^{6a}$, and $R^{6a'}$ is hydrogen, and each $R^{5a}$, $R^{5a'}$, $R^{7a}$, and $R^{7a'}$ is, independently, hydrogen or optionally substituted $C_1$-$C_{20}$ aliphatic.

In certain embodiments of the present invention, metal complexes of structures IXa or IXb above, at least one of the phenyl rings comprising a salicylaldehyde-derived portion of a catalyst is independently selected from the group consisting of:

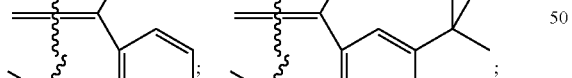

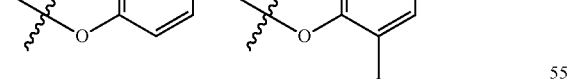

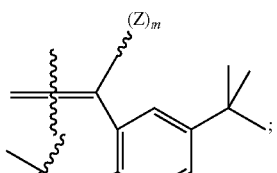

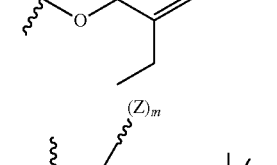

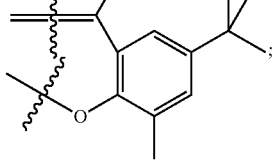

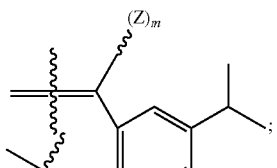

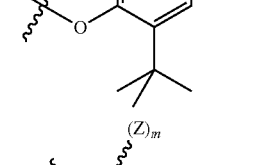

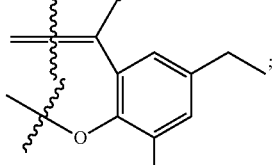

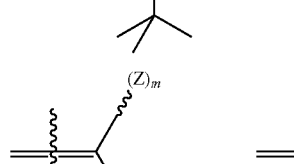

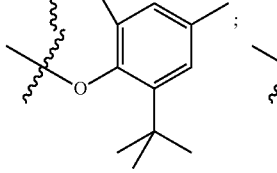

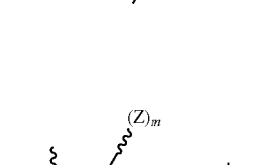

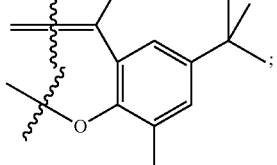

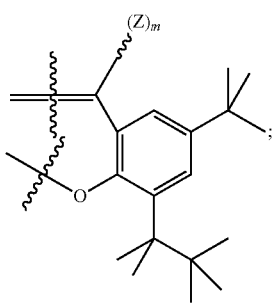
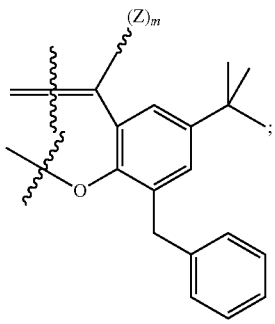
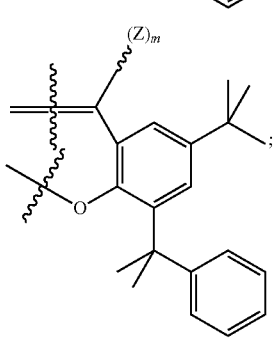
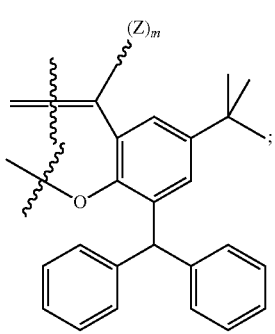
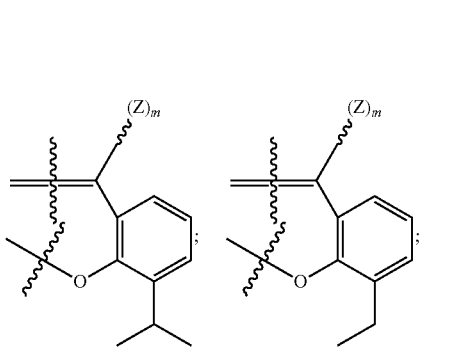

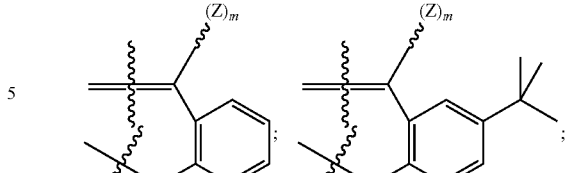
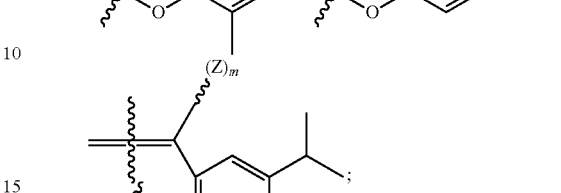
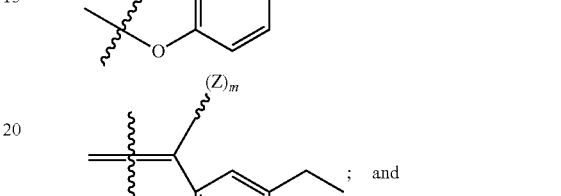
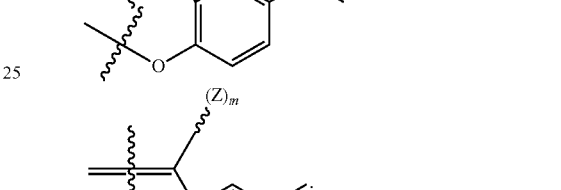
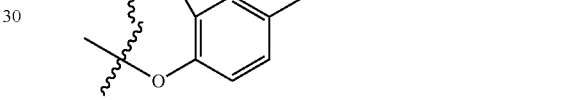; and
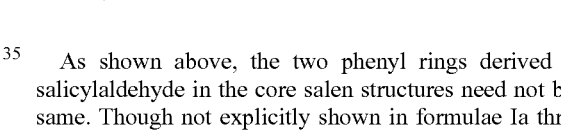.

As shown above, the two phenyl rings derived from salicylaldehyde in the core salen structures need not be the same. Though not explicitly shown in formulae Ia through IXb above, it is to be understood that a catalyst may have an activating moiety attached to different positions on each of the two rings, and such compounds are specifically encompassed within the scope of the present invention. Furthermore, activating moieties can be present on multiple parts of the ligand, for instance activating moieties can be present on the diamine bridge and on one or both phenyl rings in the same catalyst.

In certain embodiments, the salen ligand cores of catalysts Ia through IXb above are selected from the group shown below wherein any available position may be independently substituted with one or more R-groups or one or more activating moieties as described above.

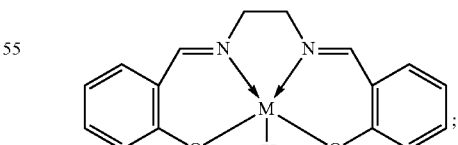;

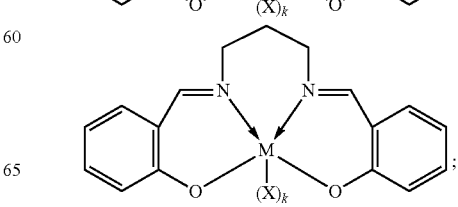;

-continued

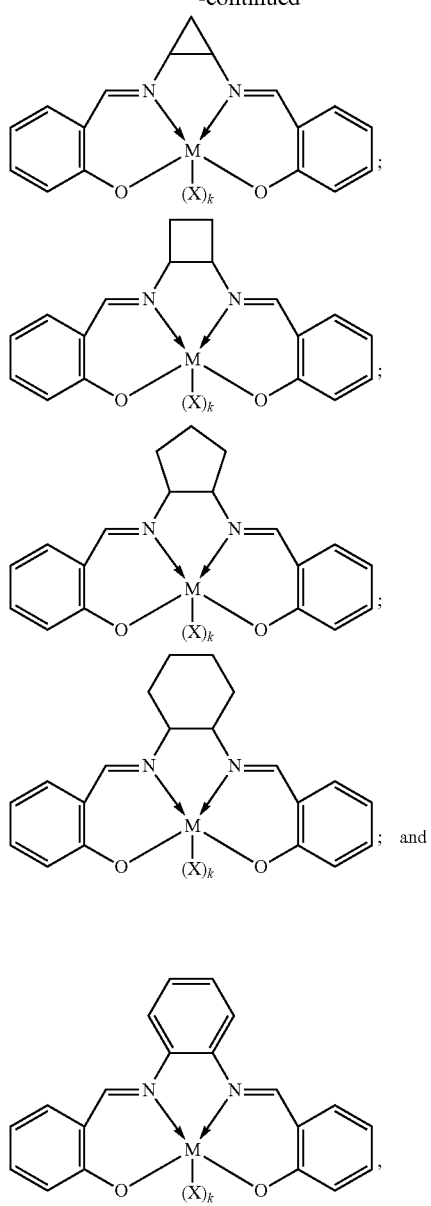

where M, X, and k, are as defined above.

In some embodiments, at least one activating moiety is tethered to the diamine-derived portion of the salen ligand, as shown in formula X:

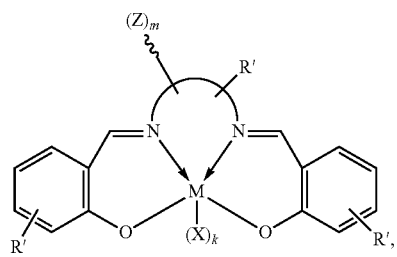

X where M, X, k, R',

and $\text{---}\!\!\!\sim\!\!\!(Z)_m$ are as defined above.

In certain embodiments, salen ligands of formula X are selected from an optionally substituted moiety consisting of:

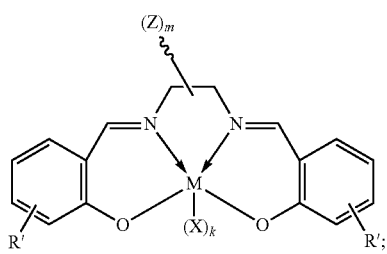

Xa

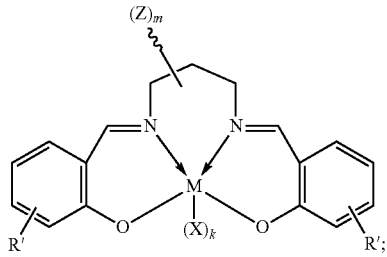

Xb

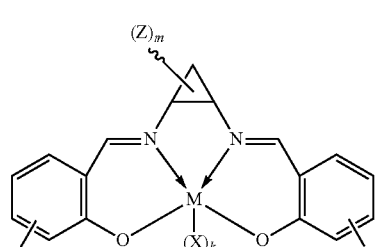

Xc

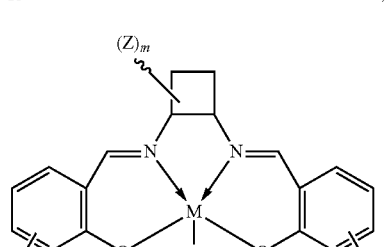

Xd

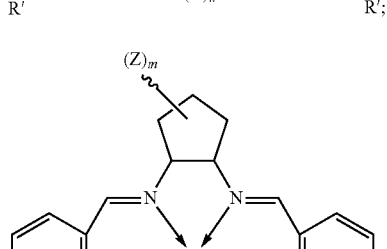

Xe

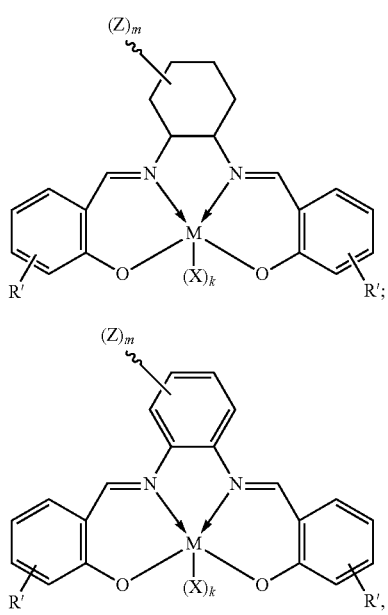
where M, X, k, R', and ⁓(Z)$_m$ are as defined above.
In certain embodiments, the diamine bridge of catalysts of formula Xa an optionally substituted moiety selected from the group consisting of:
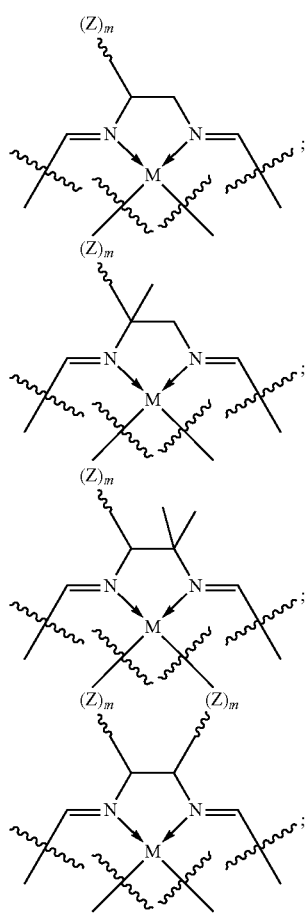
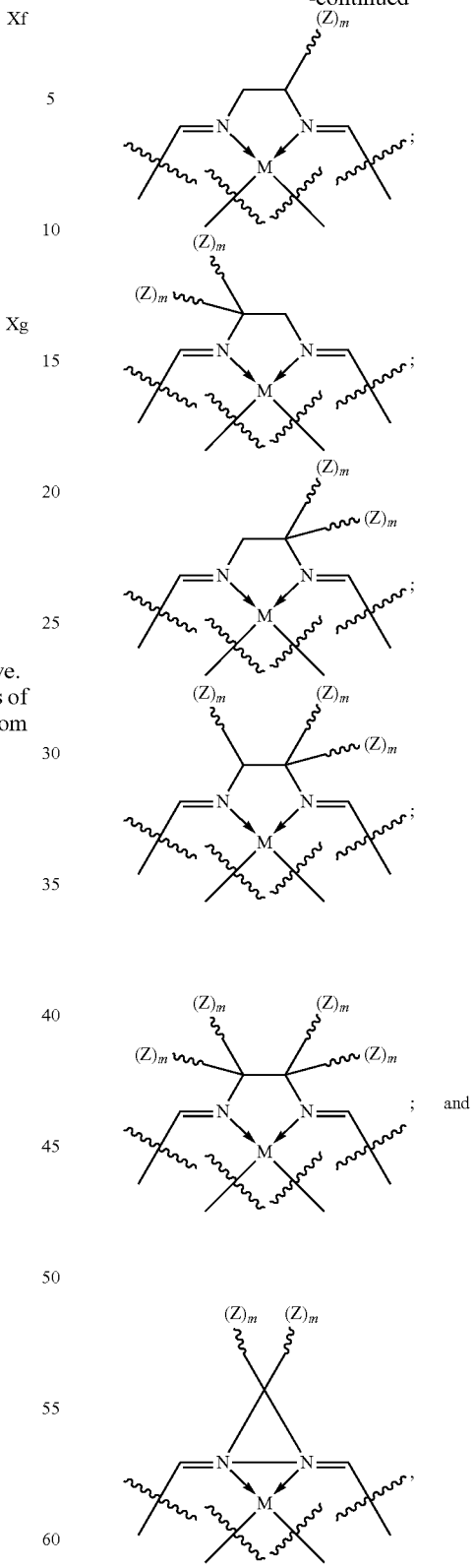
where M and ⁓(Z)$_m$ is as defined above.
In certain embodiments, metallosalenate complexes of the present invention include, but are not limited to those in Table 1 below:

TABLE 1
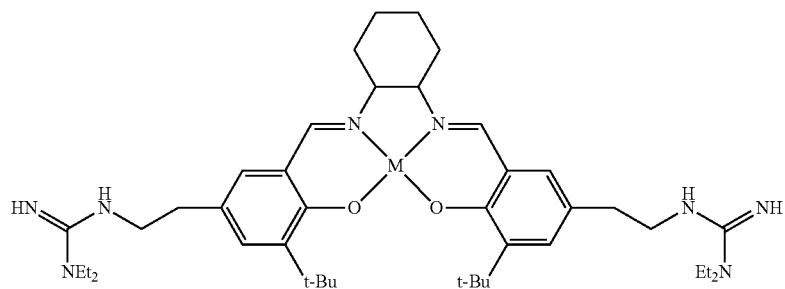
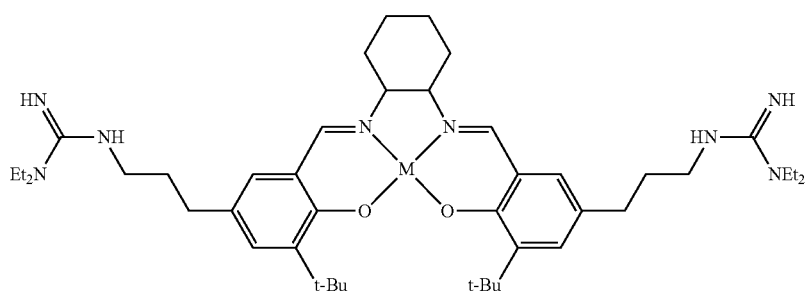
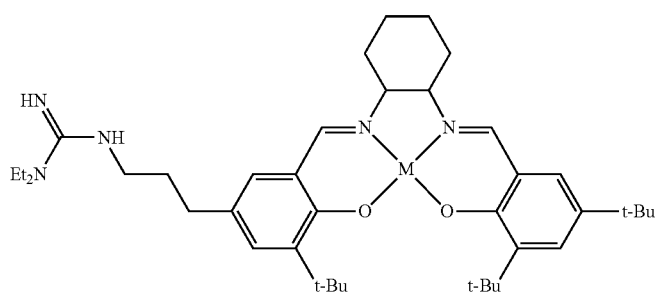
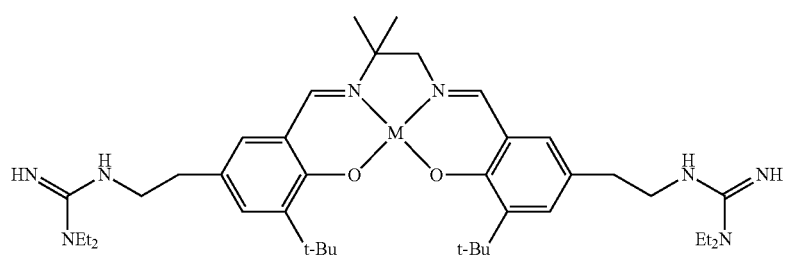
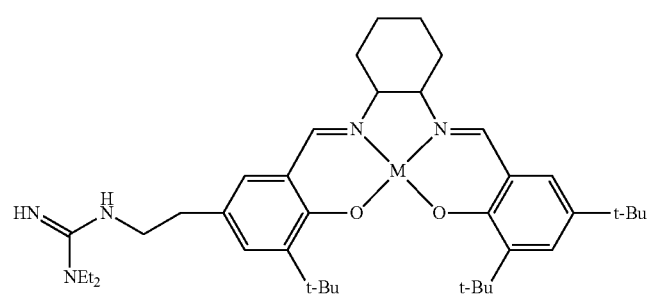

TABLE 1-continued
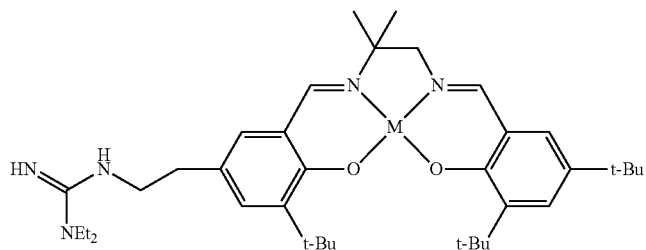
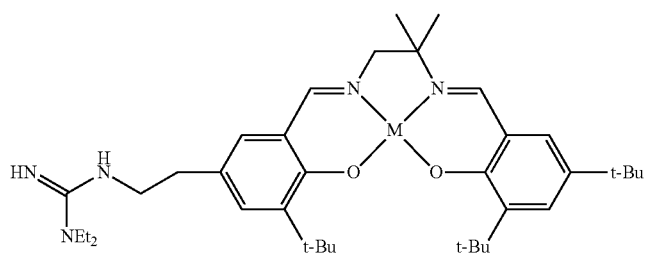
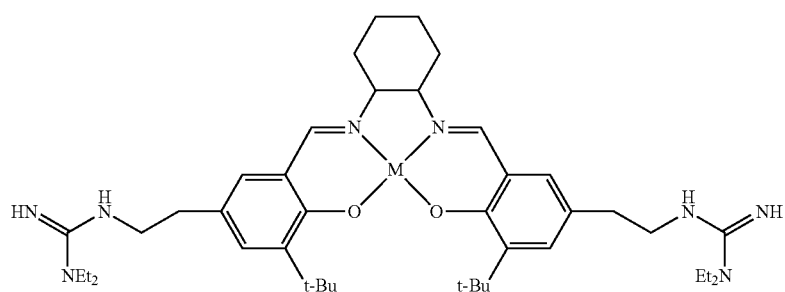
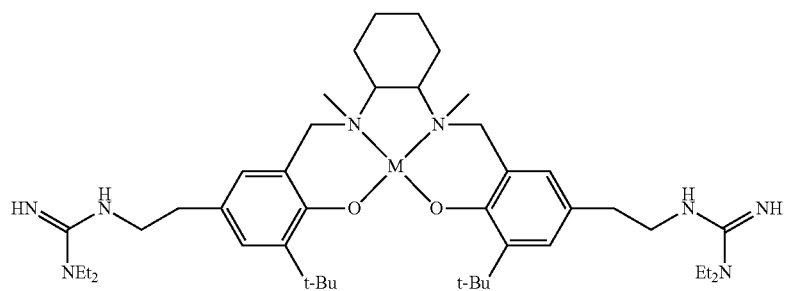
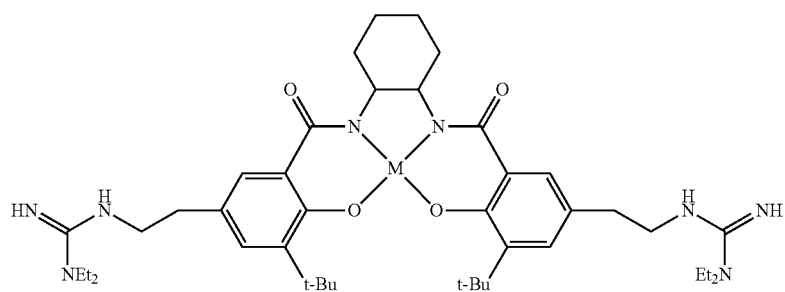

TABLE 1-continued
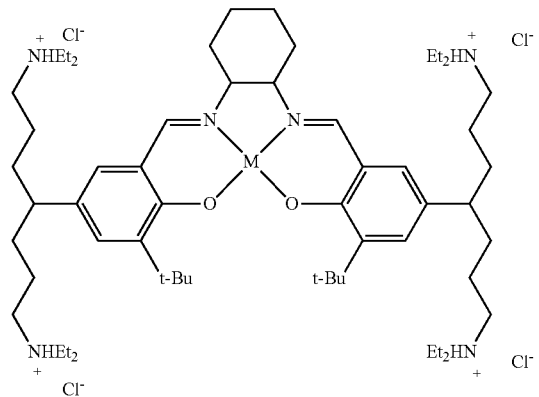
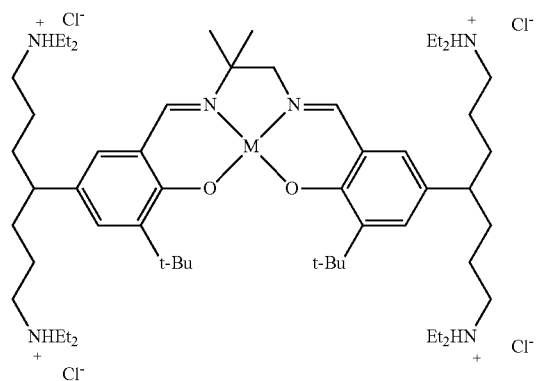
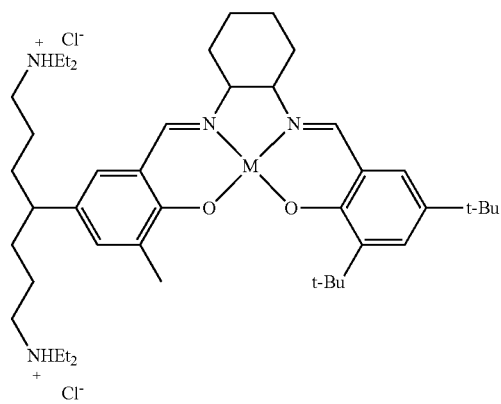
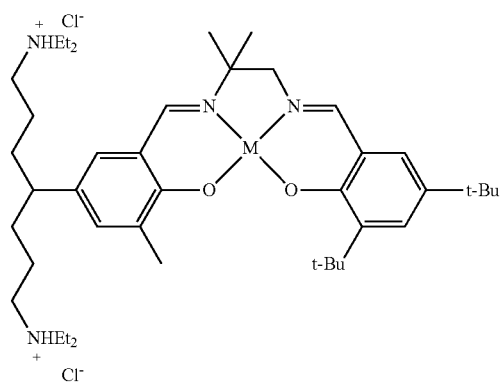

TABLE 1-continued
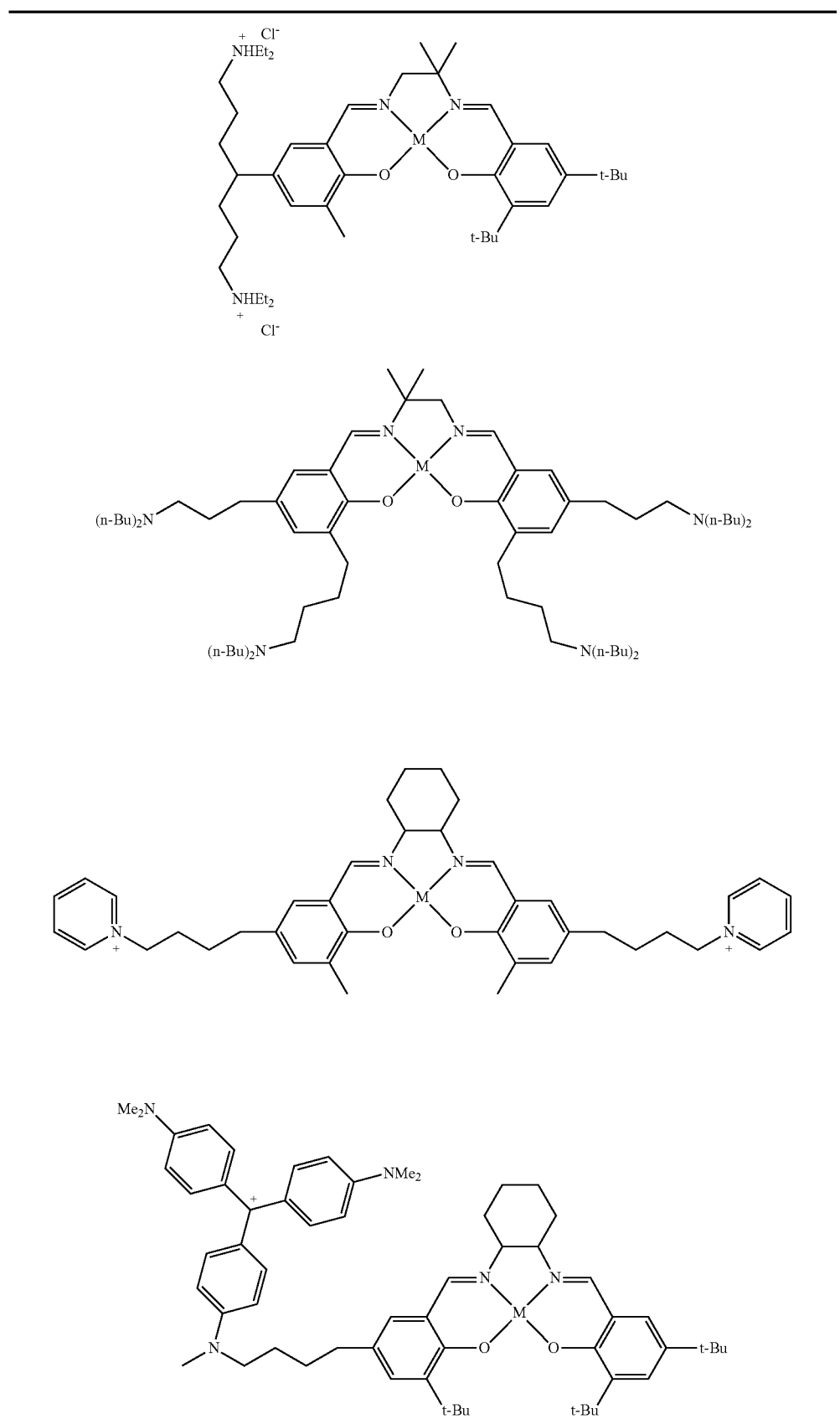

TABLE 1-continued
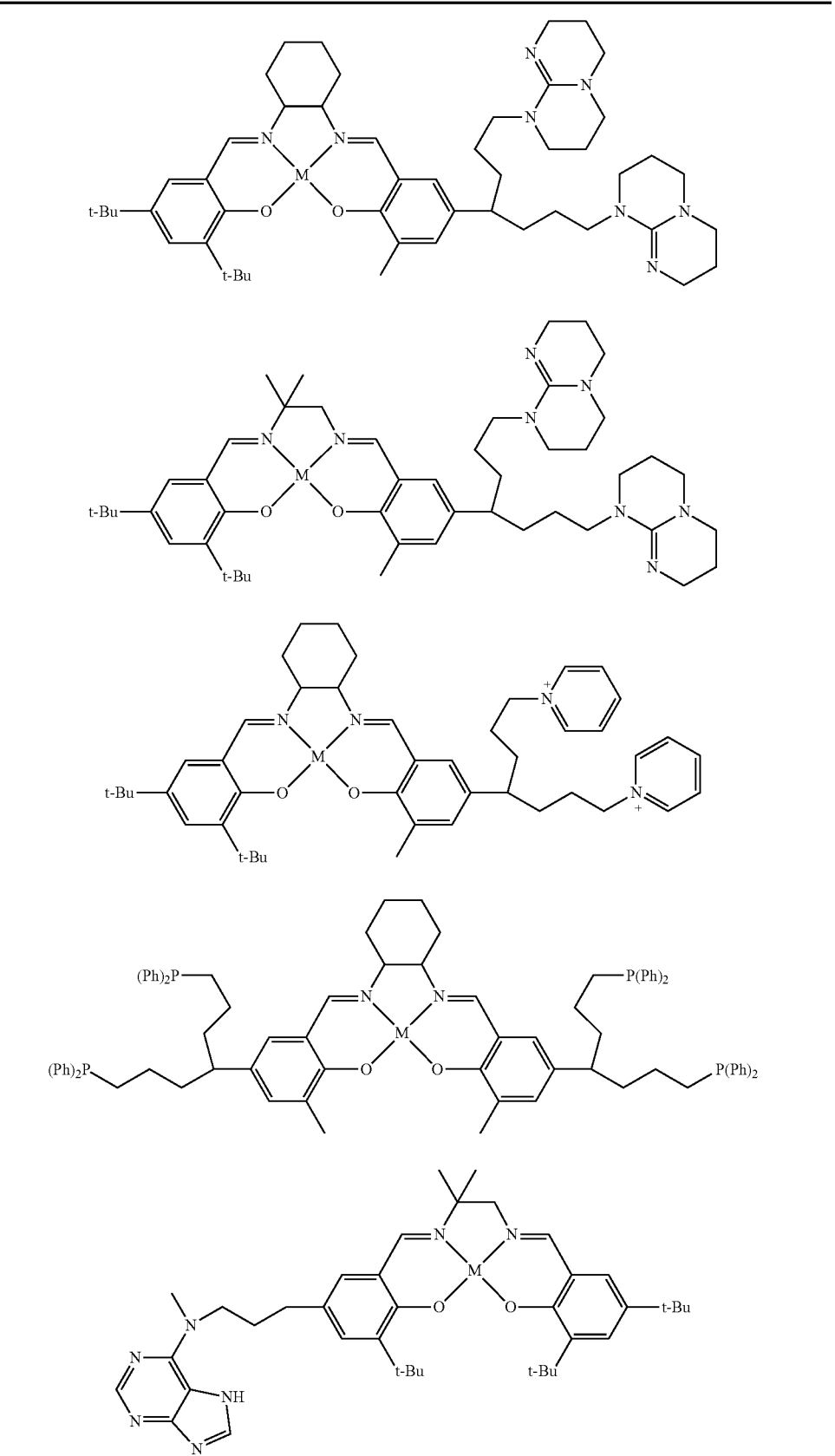

TABLE 1-continued
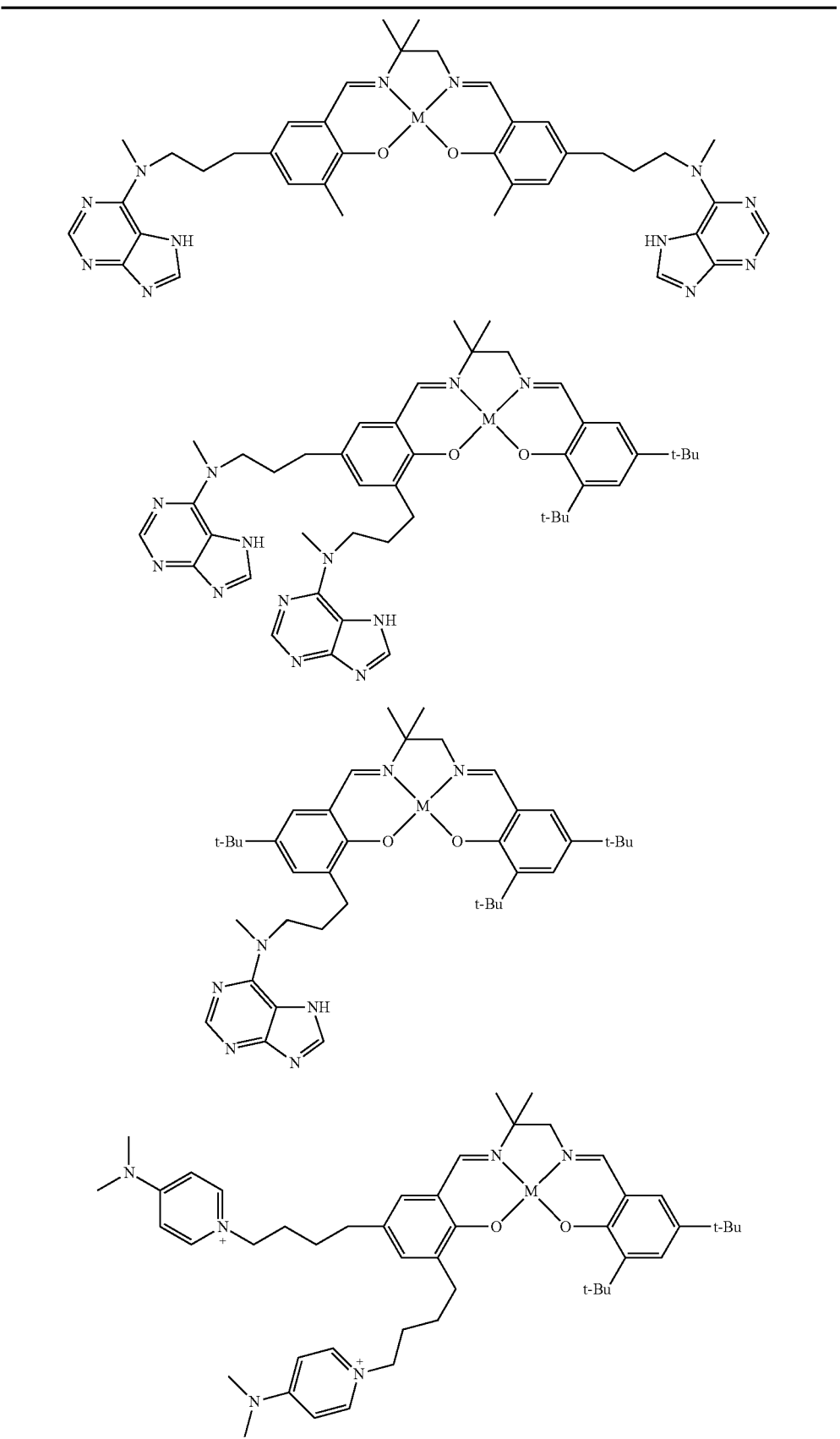

TABLE 1-continued
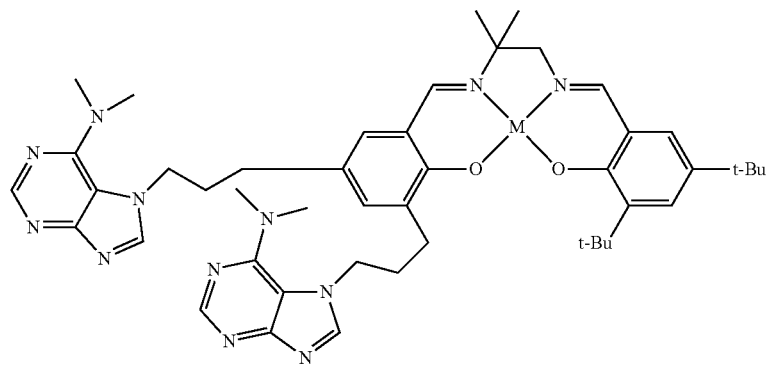
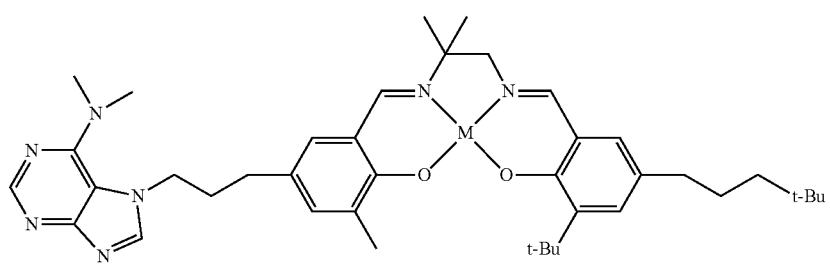
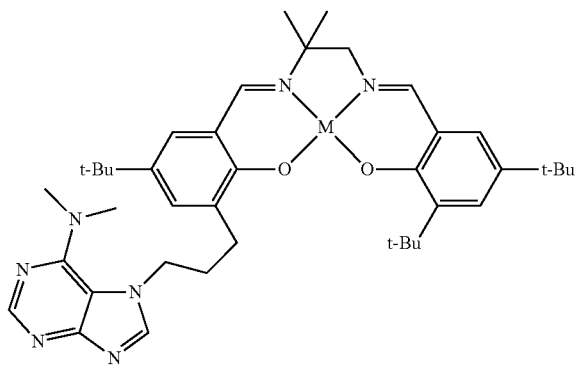
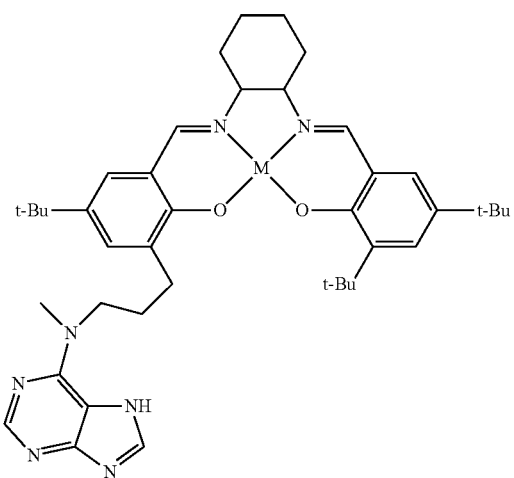

TABLE 1-continued
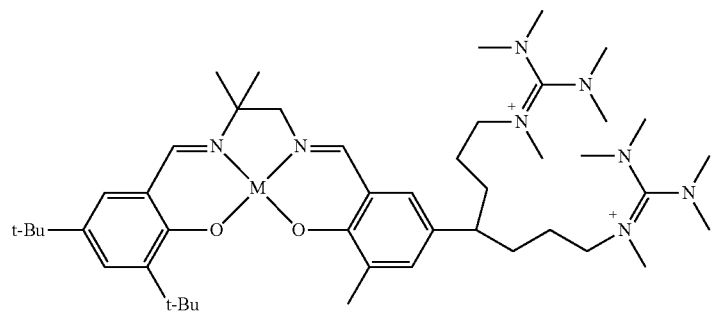
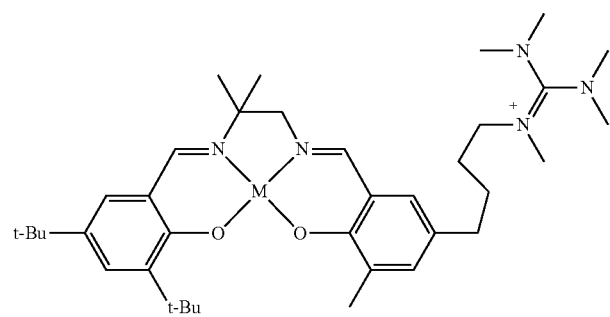
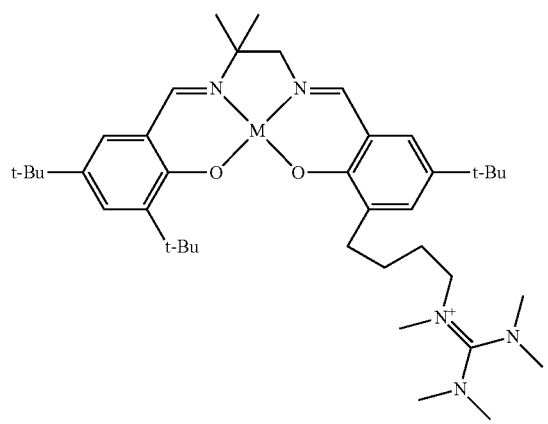
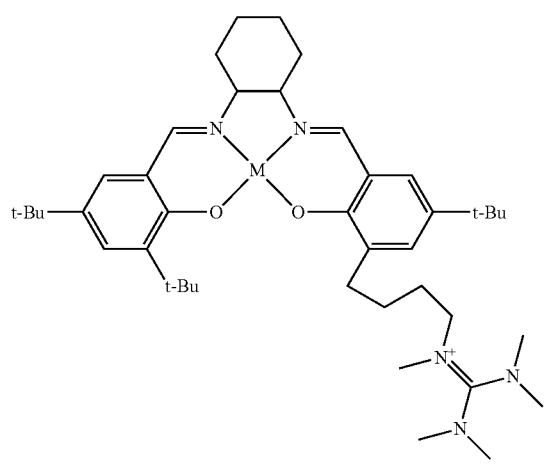

TABLE 1-continued
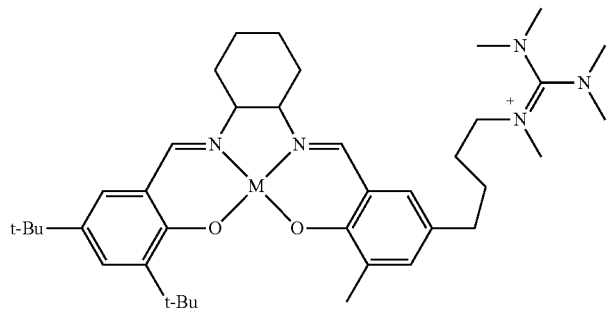
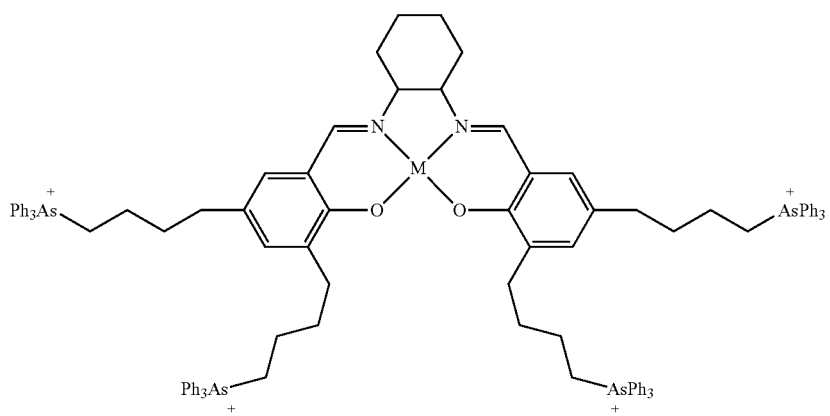
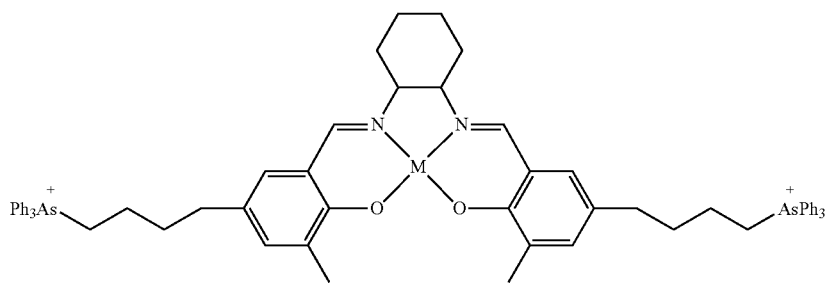
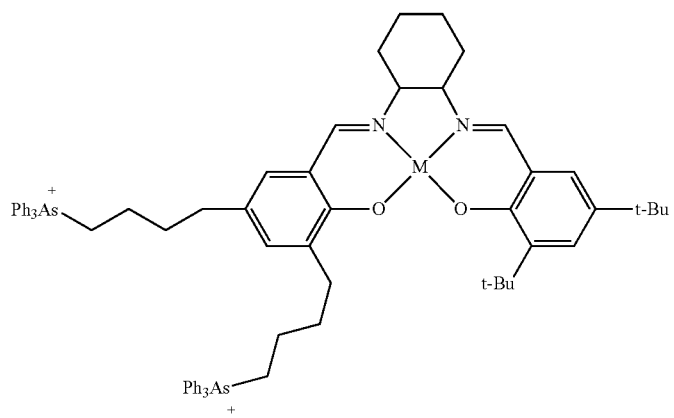

TABLE 1-continued
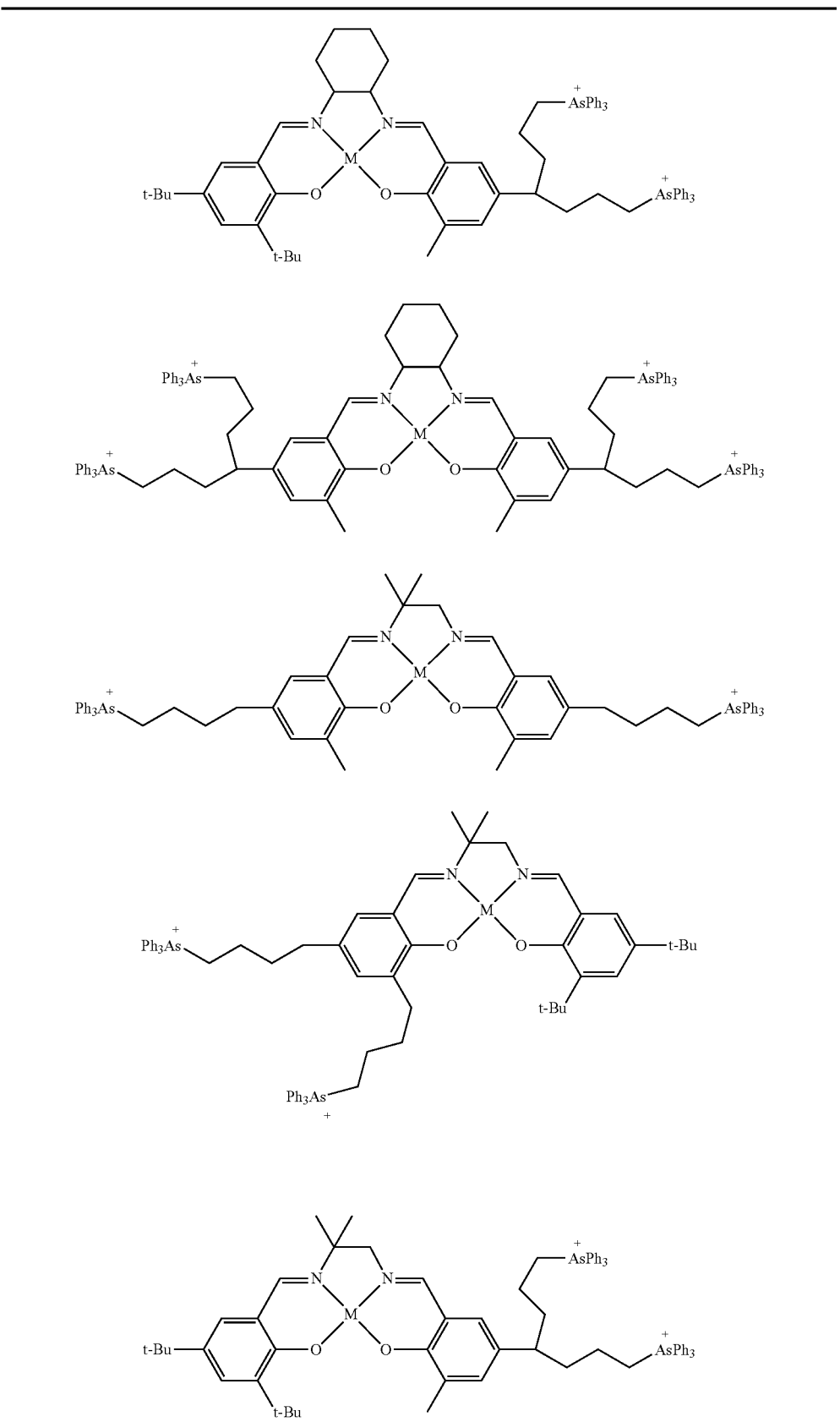

TABLE 1-continued
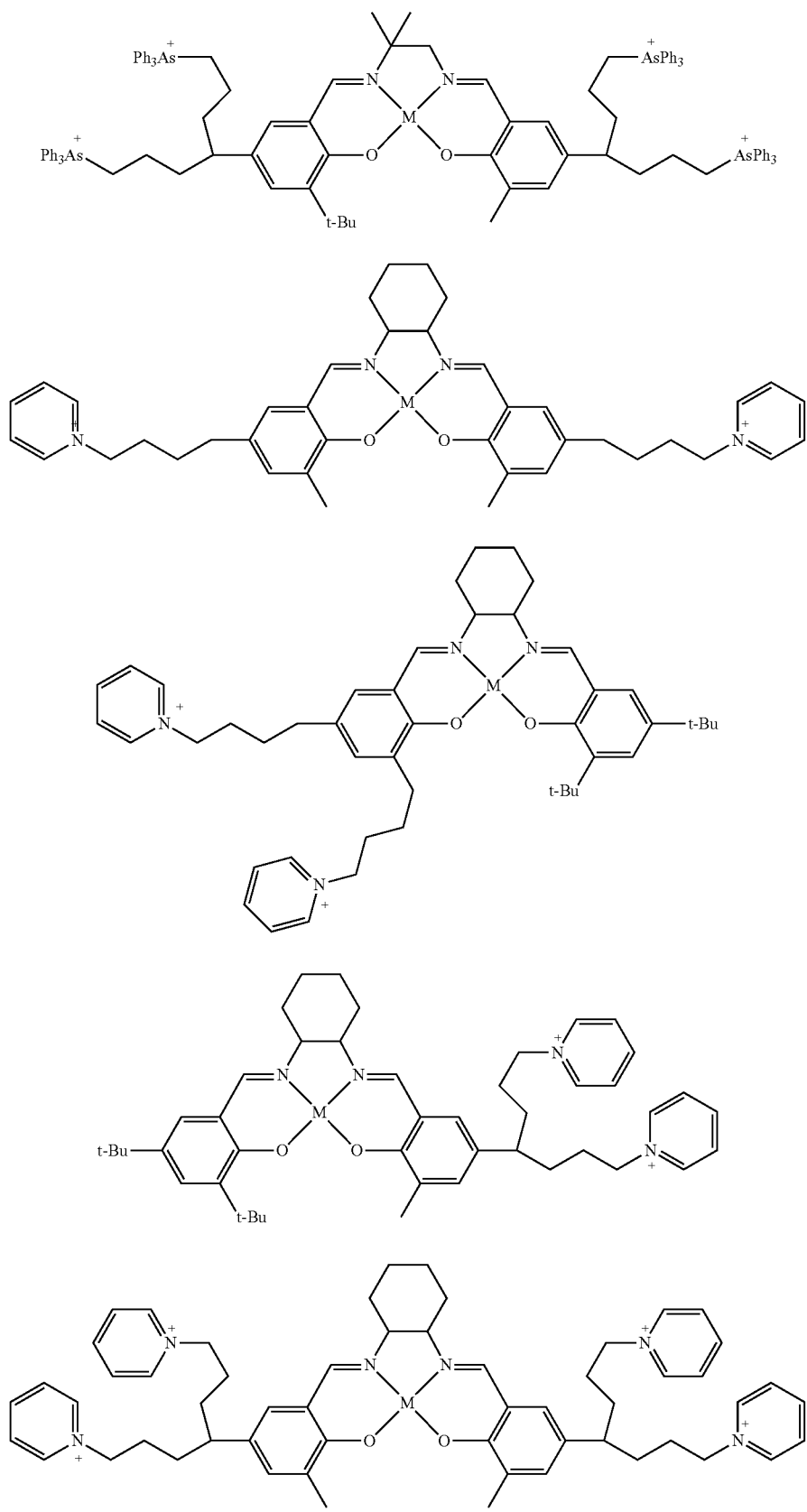

TABLE 1-continued
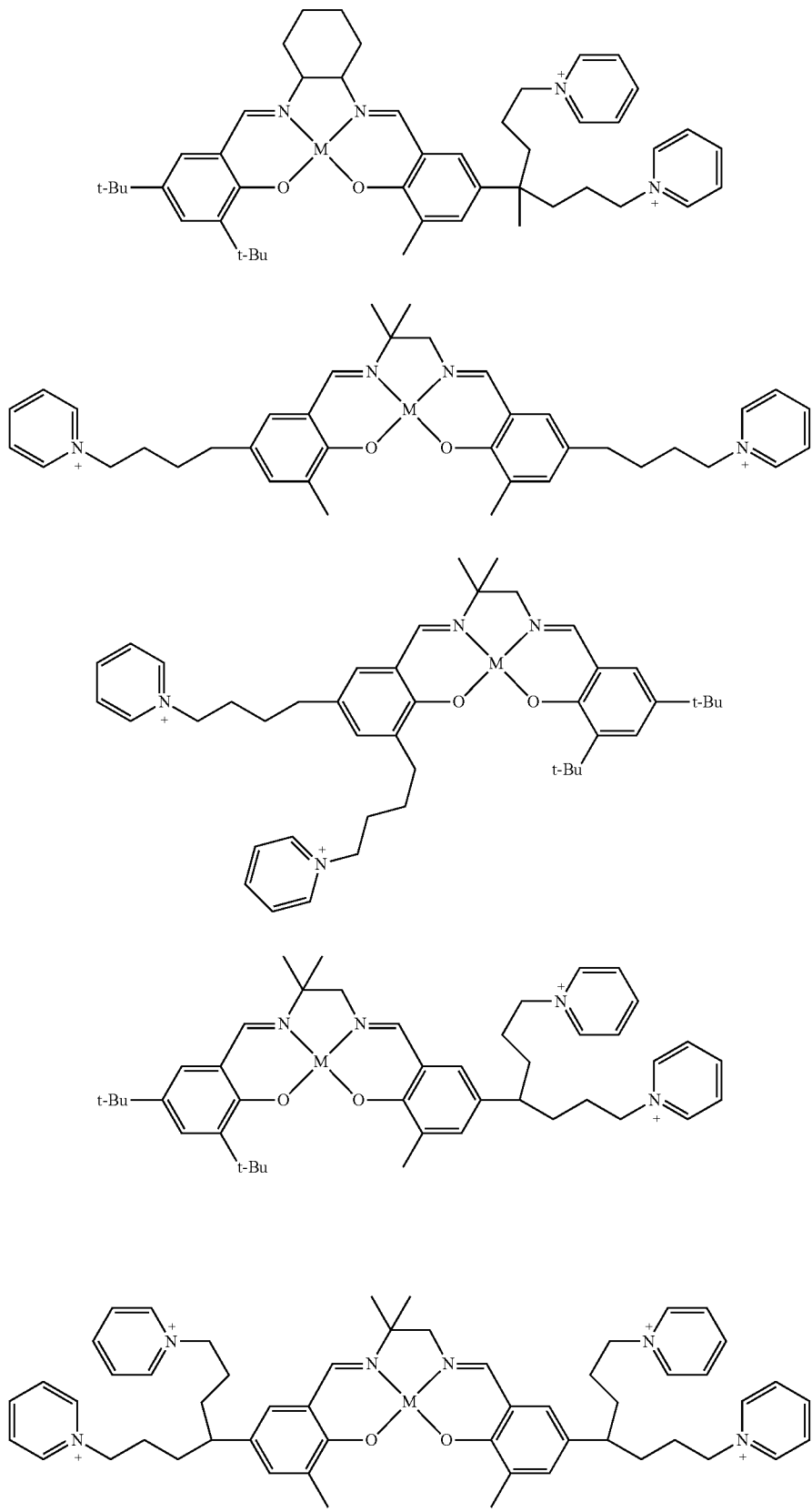

TABLE 1-continued
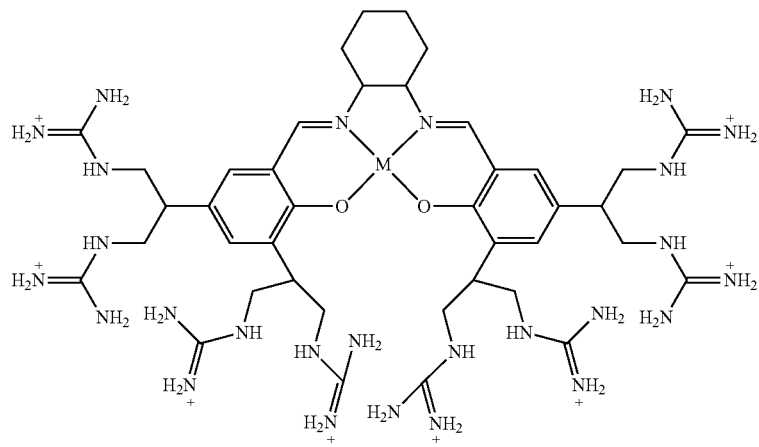
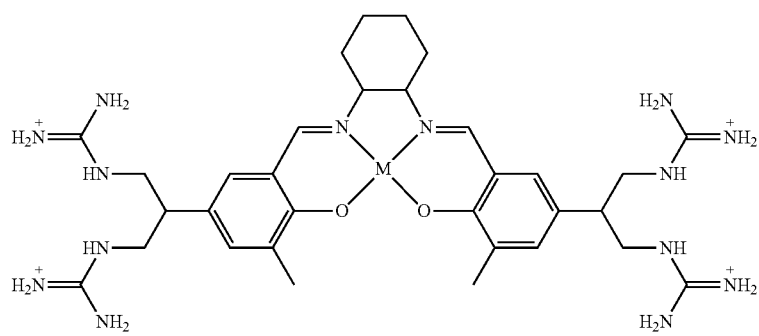
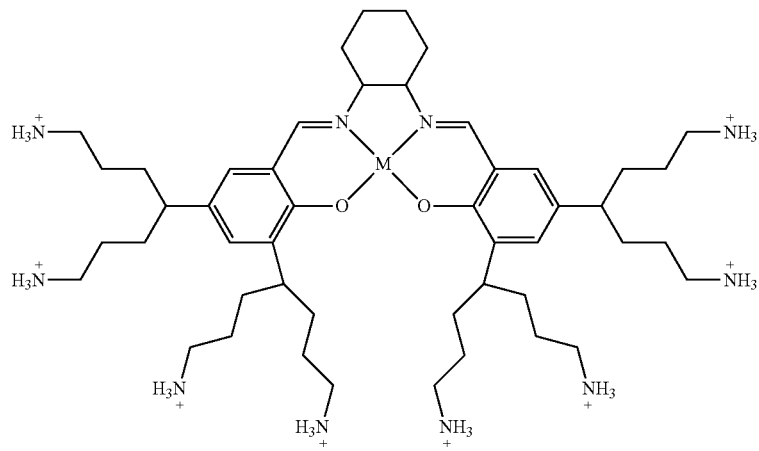
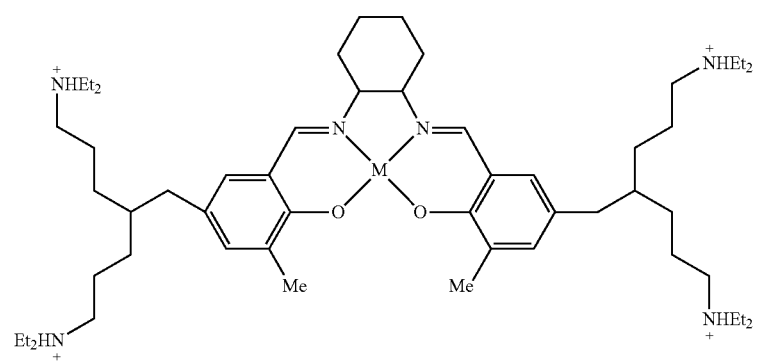

TABLE 1-continued
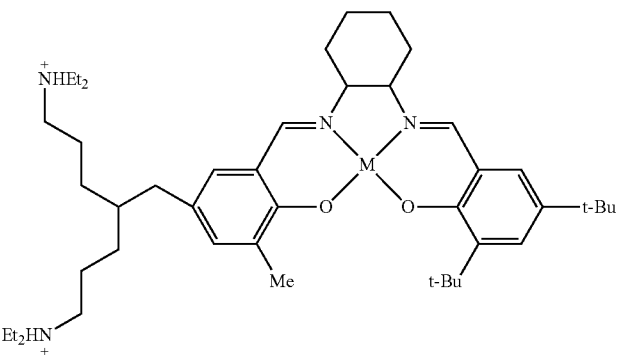
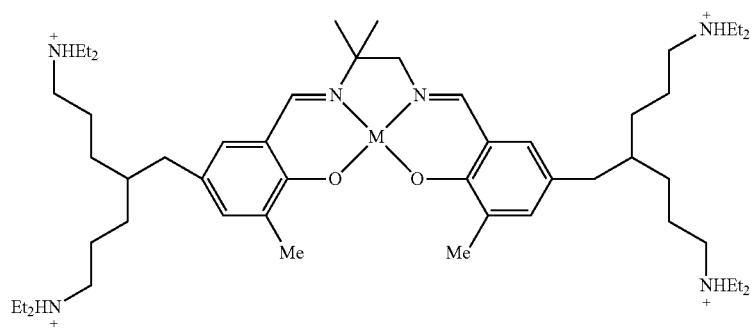
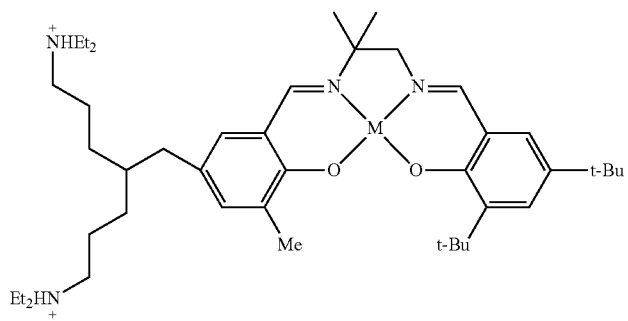
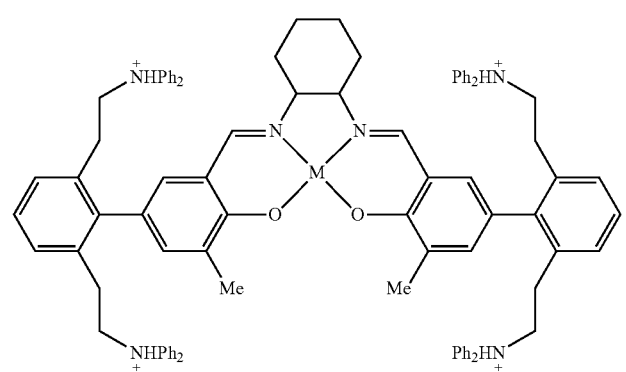

TABLE 1-continued
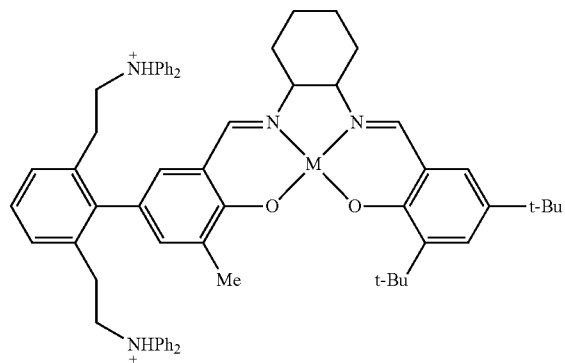
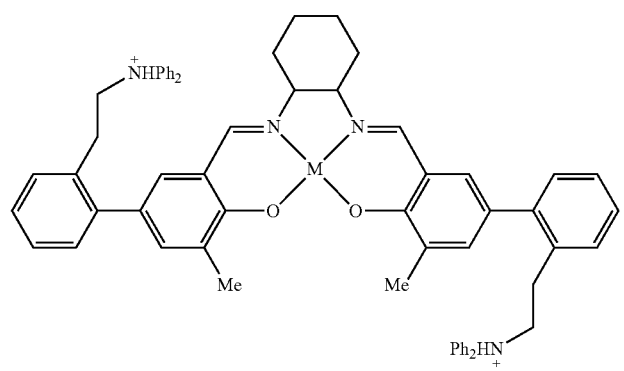
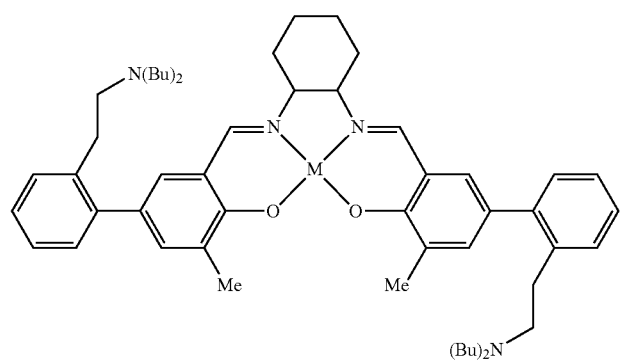
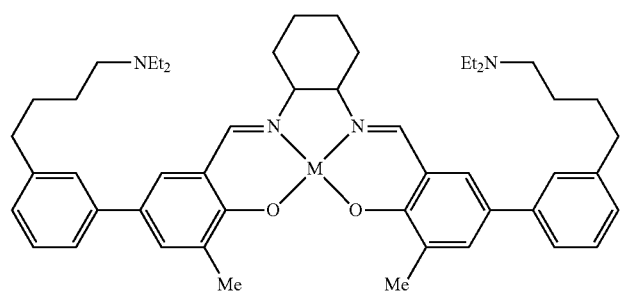

TABLE 1-continued
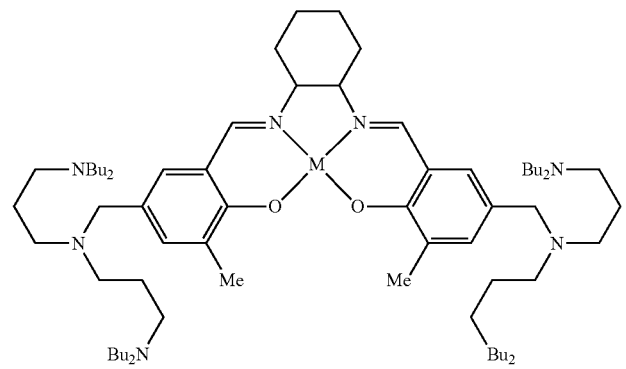
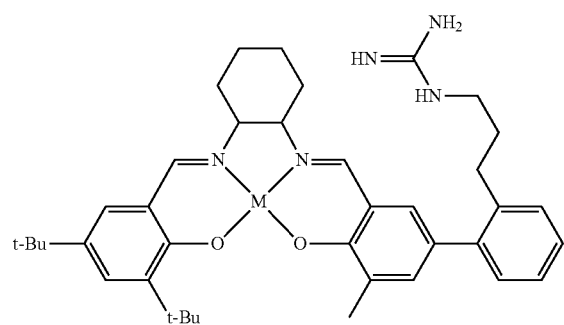
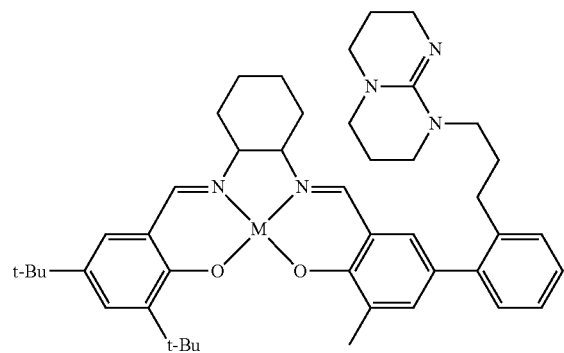
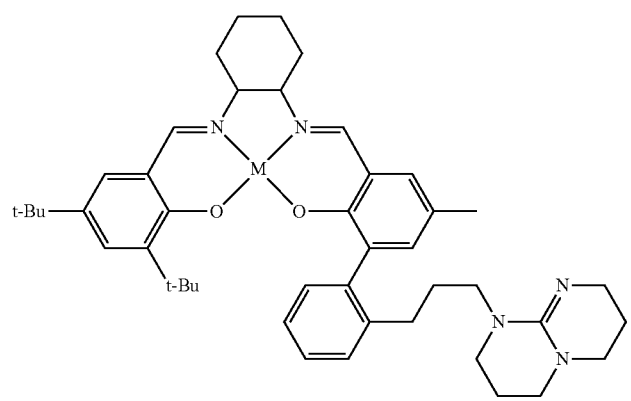

TABLE 1-continued
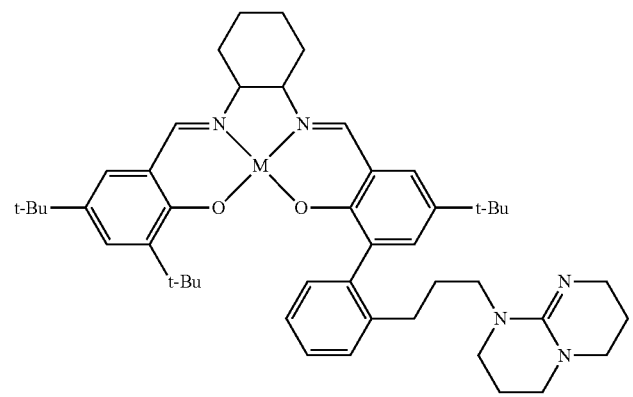
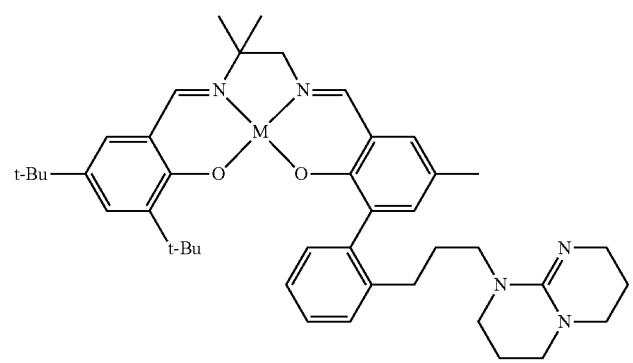
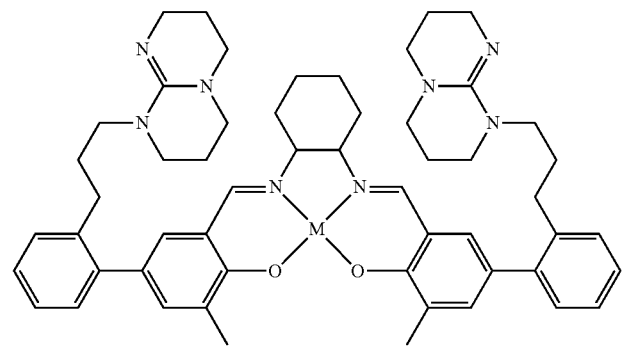
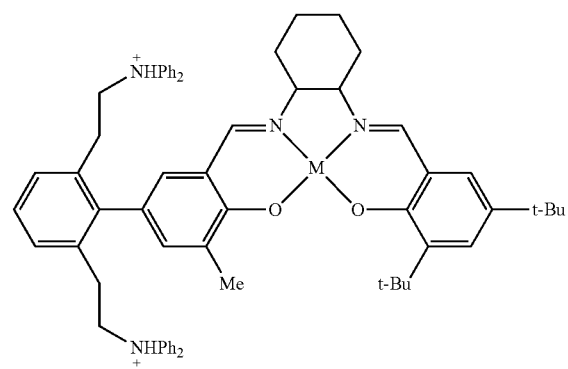

TABLE 1-continued
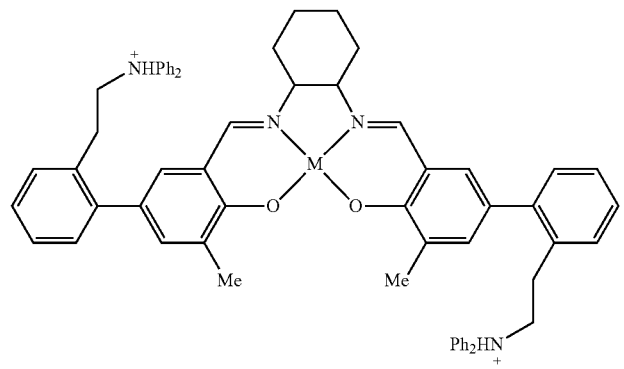
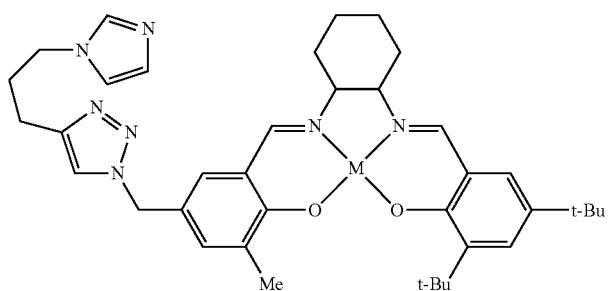
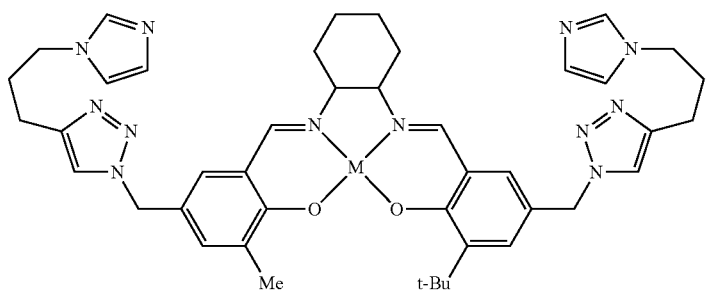
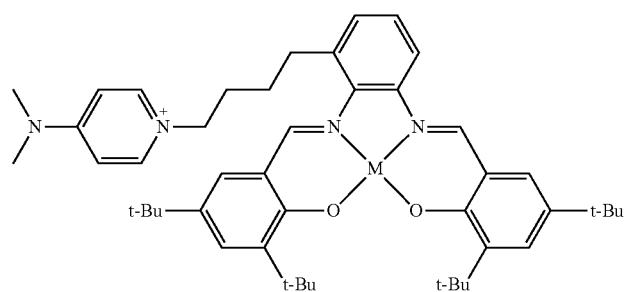
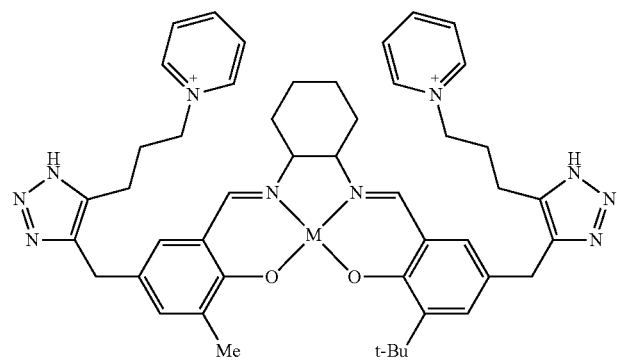

TABLE 1-continued
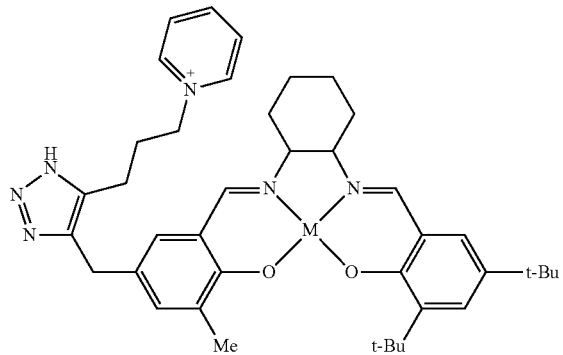
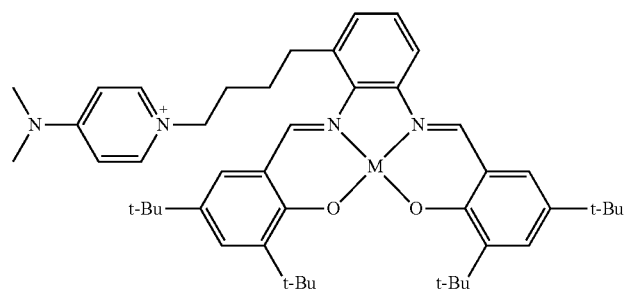
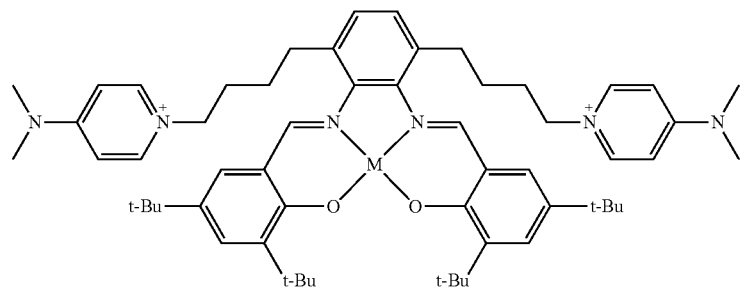
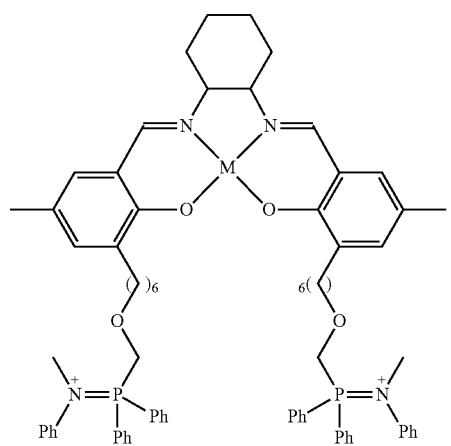

TABLE 1-continued
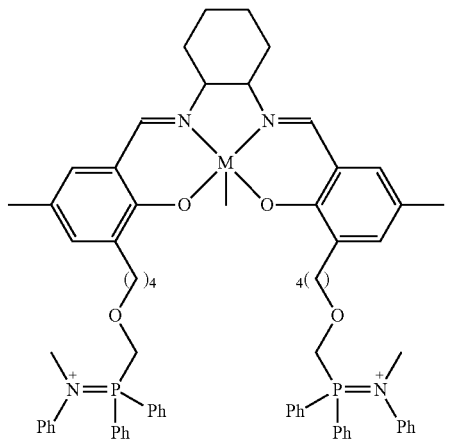
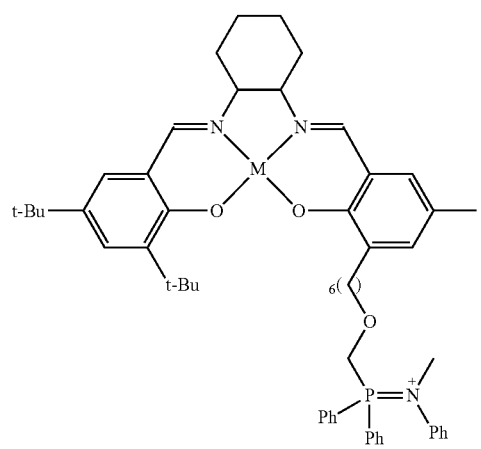
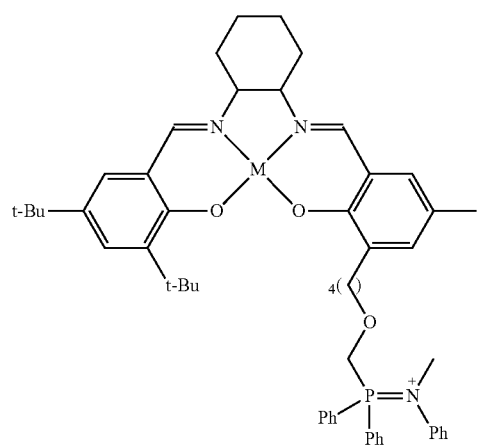

TABLE 1-continued
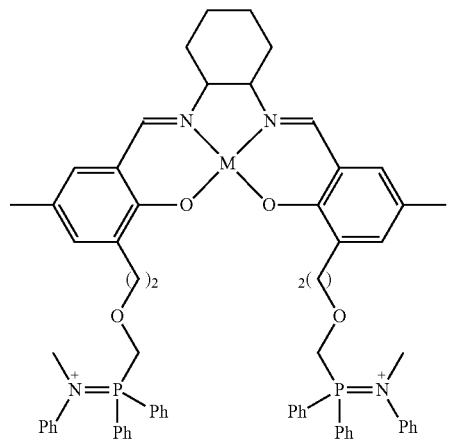
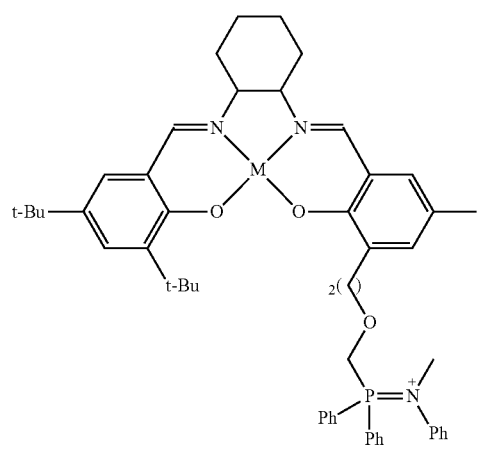
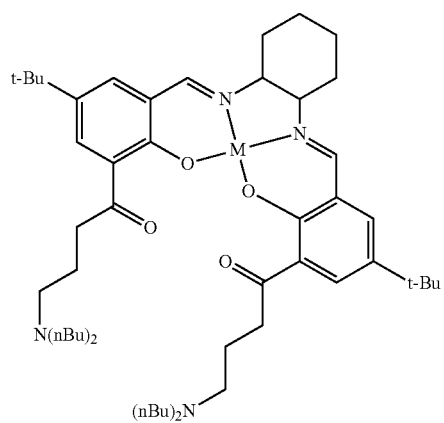

TABLE 1-continued
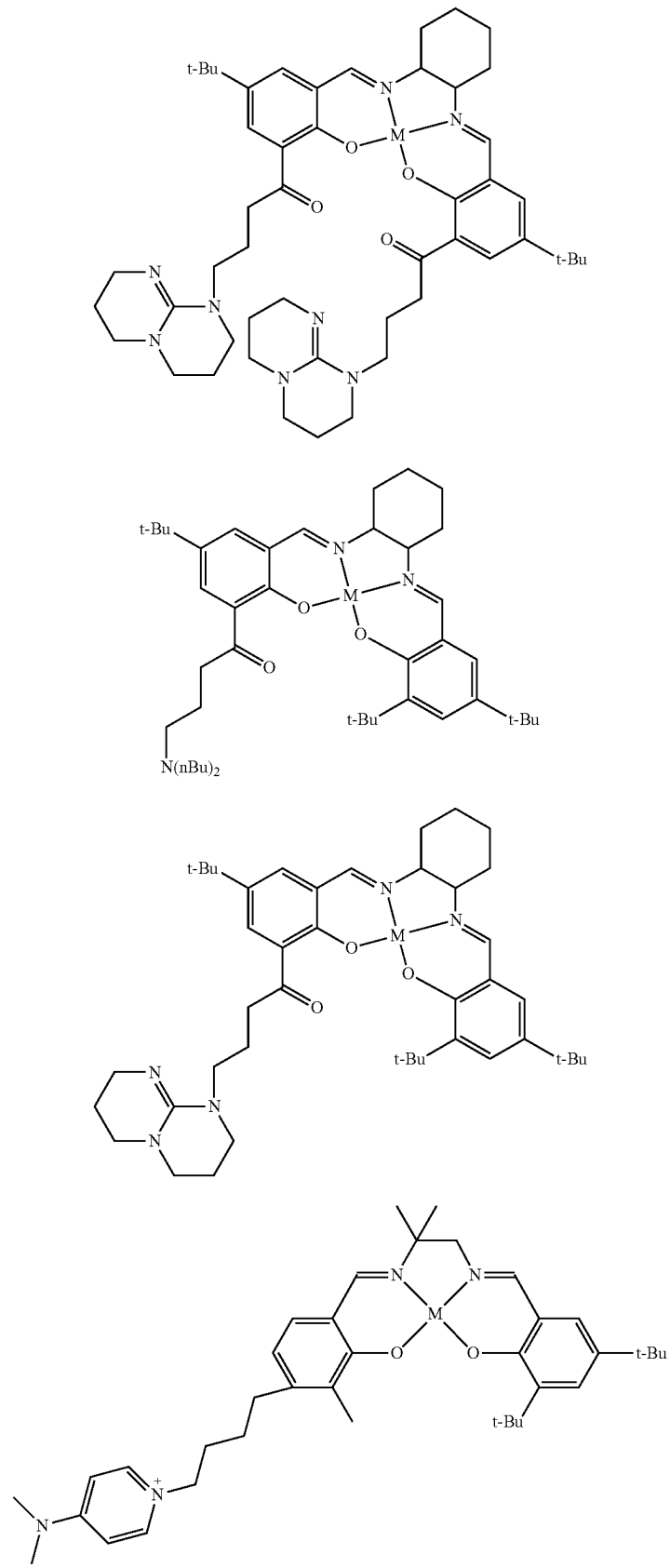

TABLE 1-continued
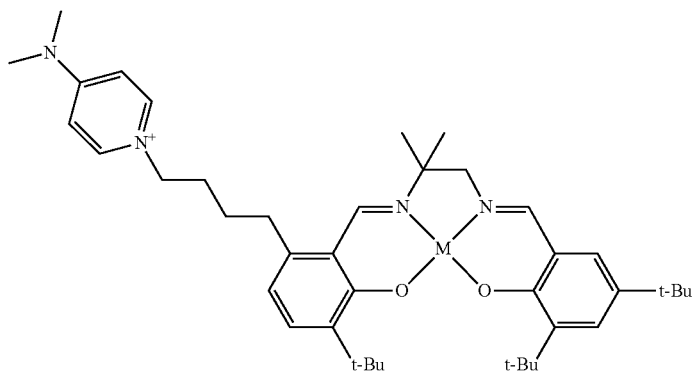
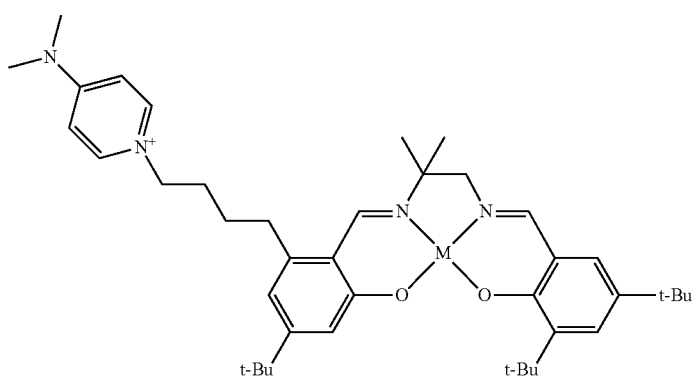
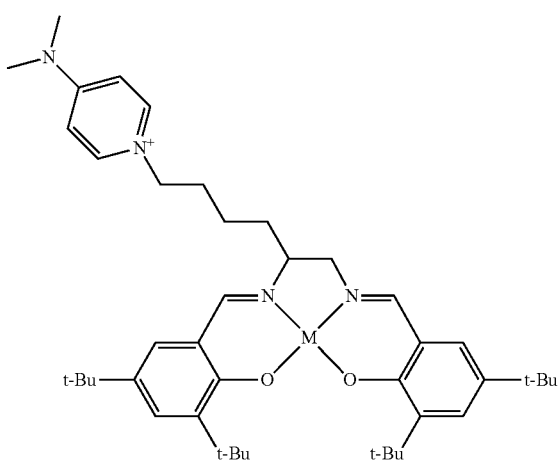
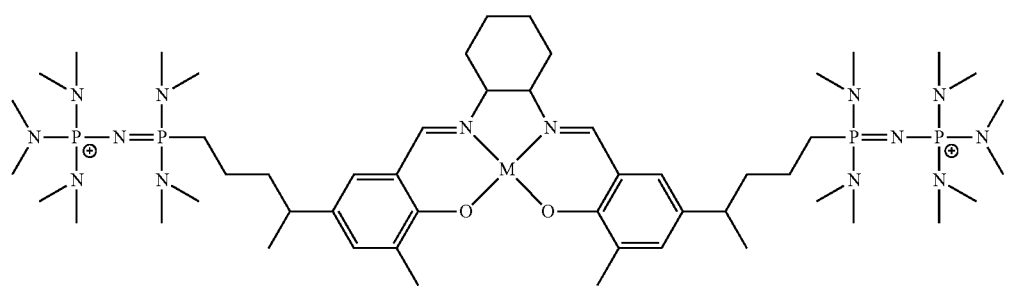

TABLE 1-continued
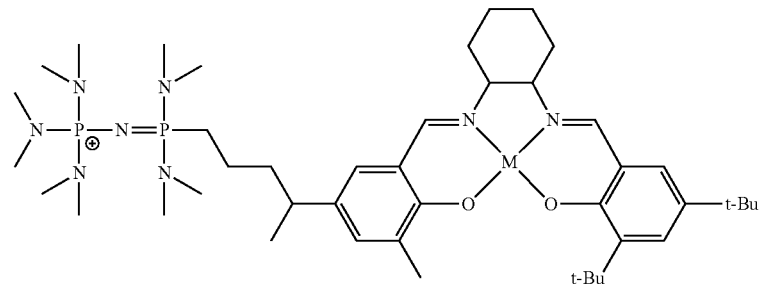
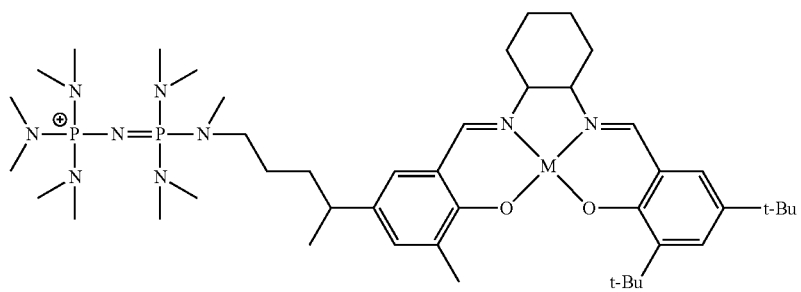
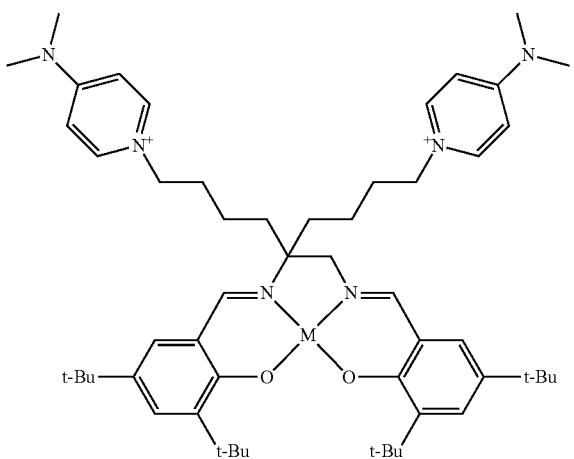
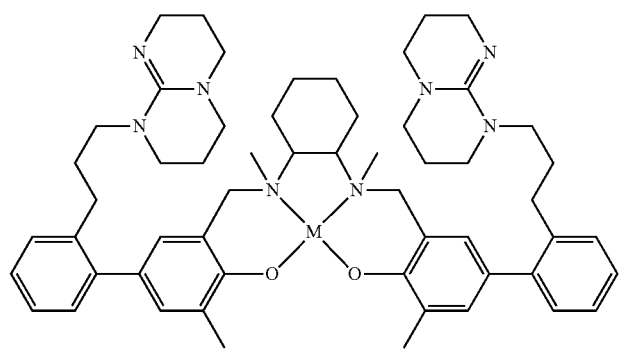

TABLE 1-continued

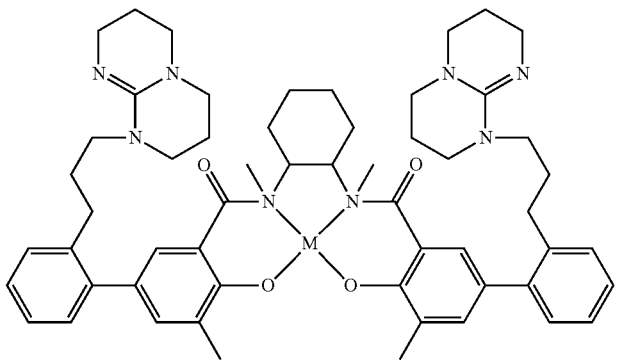

In certain embodiments, for complexes of Table 1, M is Co—X, where X is as defined above. In certain embodiments, for complexes of Table 1, M is Co—OC(O)CF$_3$. In certain embodiments, for complexes of Table 1, M is Co—OAc. In certain embodiments, for complexes of Table 1, M is Co—OC(O)C$_6$F$_5$. In certain embodiments, for complexes of Table 1, M is Co—N$_3$. In certain embodiments, for complexes of Table 1, M is Co—Cl. In certain embodiments, for complexes of Table 1, M is Co-nitrophenoxy. In certain embodiments, for complexes of Table 1, M is Co-dinitrophenoxy.

In some embodiments, for complexes of Table 1, M is Cr—X, where X is as defined above.

In certain embodiments, a tetradentate ligand is a porphyrin ligand. In some embodiments, a metal complex is a cobalt porphyrin complex. In certain embodiments, a metal complex is a chromium porphyrin complex. In some embodiments, a metal complex is an aluminum porphyrin complex.

Examples of porphyrin containing metal complexes of the present invention include, but are not limited to:

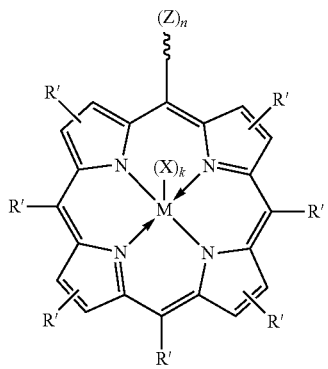

-continued

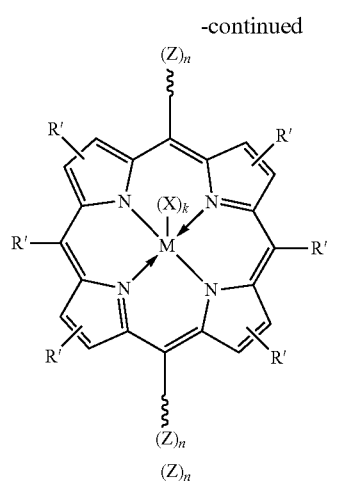

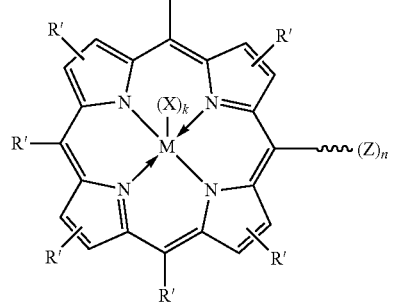

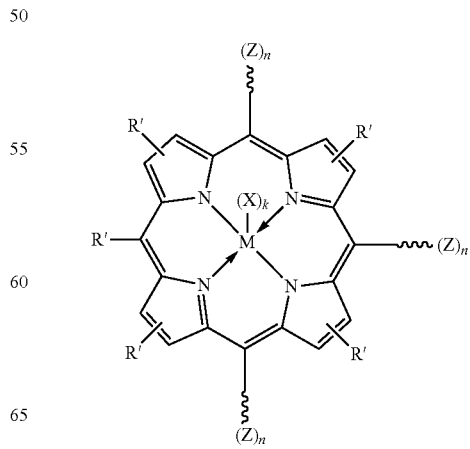

-continued
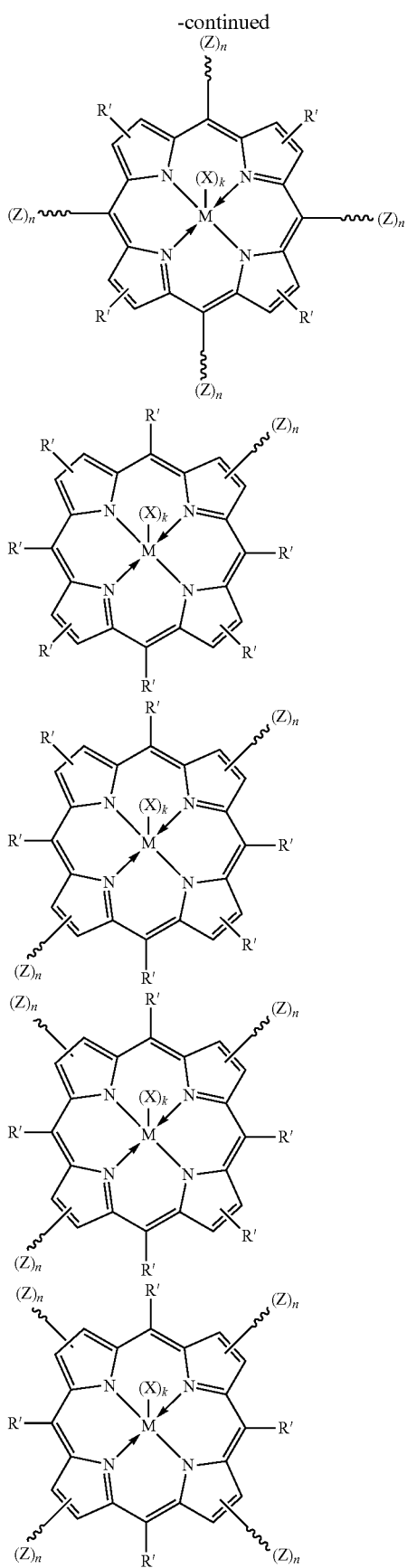
wherein each of M, X, k, R', and ⎯⎯$(Z)_m$ is as defined above.
In certain embodiments, a multidentate ligand is an optionally substituted tetrabenzoporphyrin. Suitable examples include, but are not limited to:
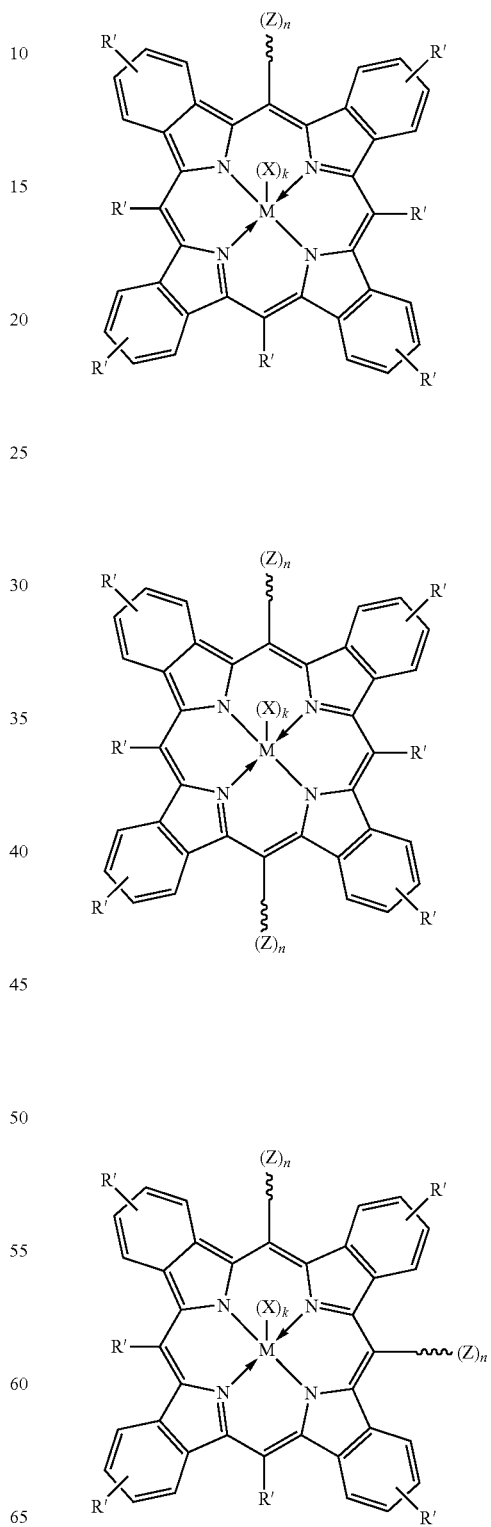

165

-continued

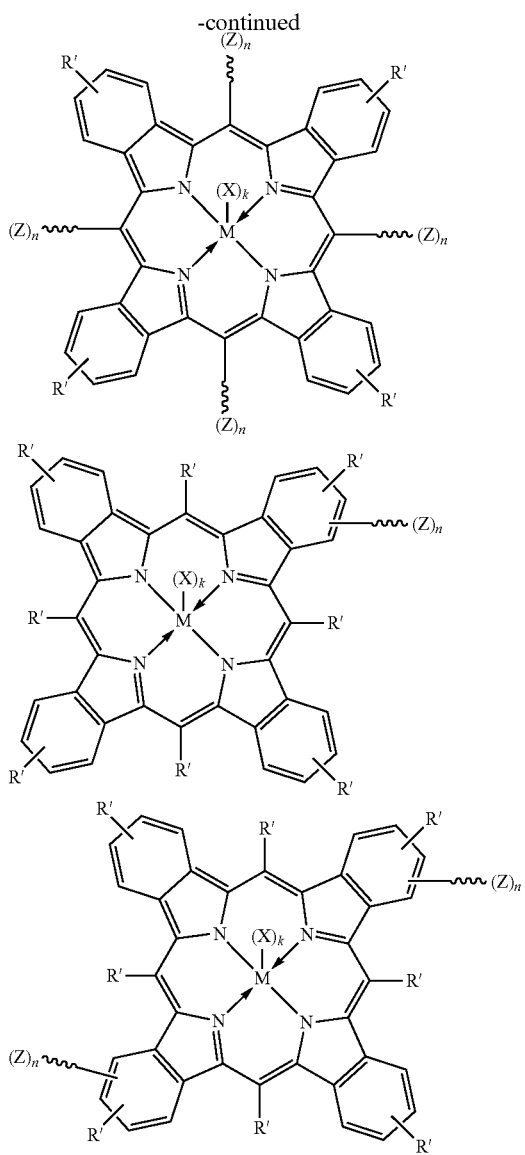

166

-continued

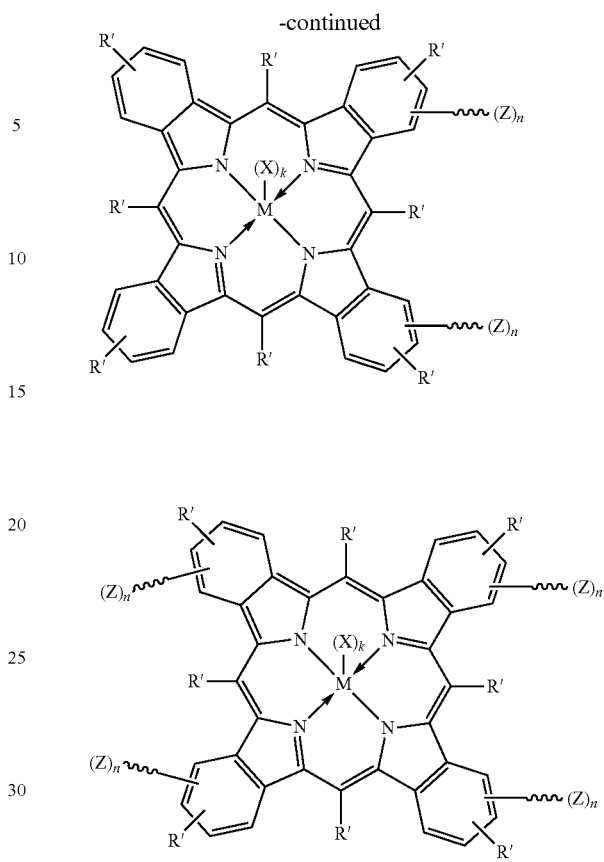

wherein M, R', and ⎯⎯⎯$(Z)_n$ are as previously defined.

In certain embodiments of porphyrin and phthalocyanine-based complexes described herein, M is aluminum. In certain embodiments of porphyrin and phthalocyanine-based complexes described herein, M is cobalt. In certain embodiments of porphyrin and phthalocyanine-based complexes described herein, M is manganese.

In certain embodiments, porphyrin complexes of the present invention include, but are not limited to those in Table 2 below:

TABLE 2

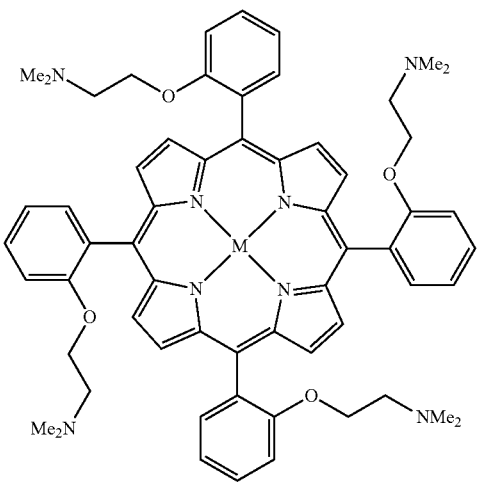

TABLE 2-continued
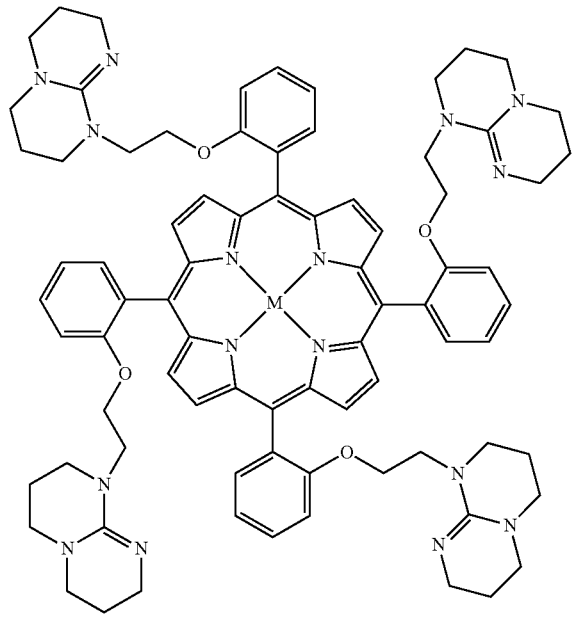
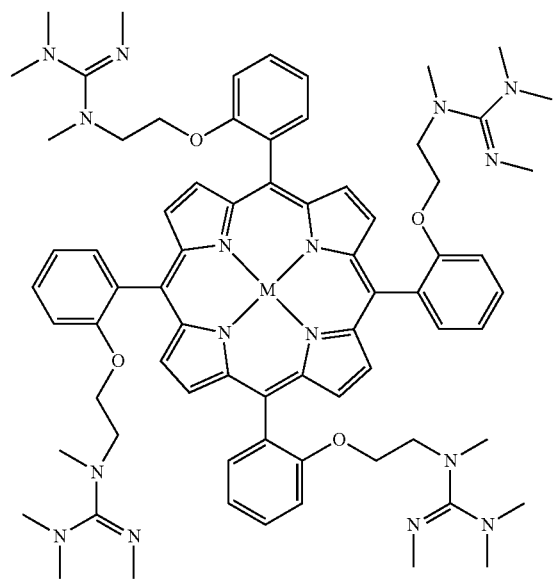

TABLE 2-continued
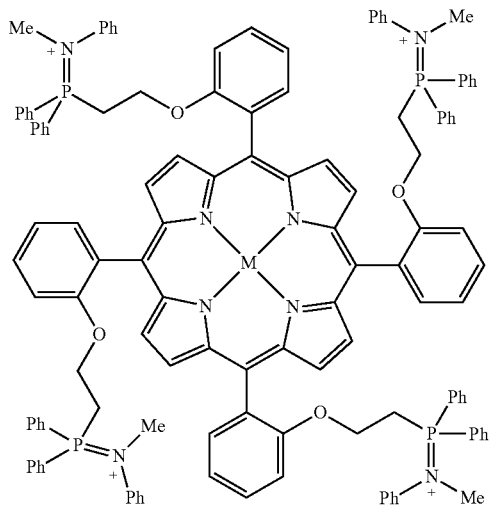
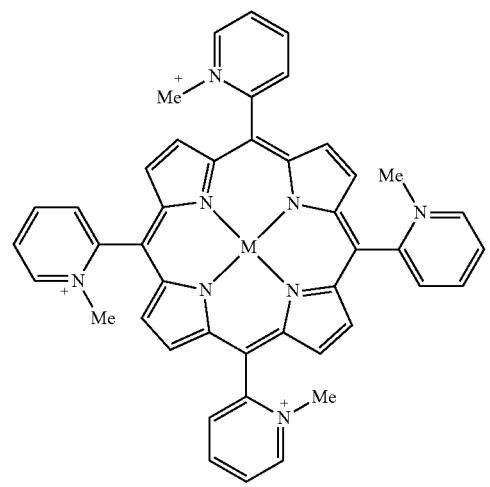
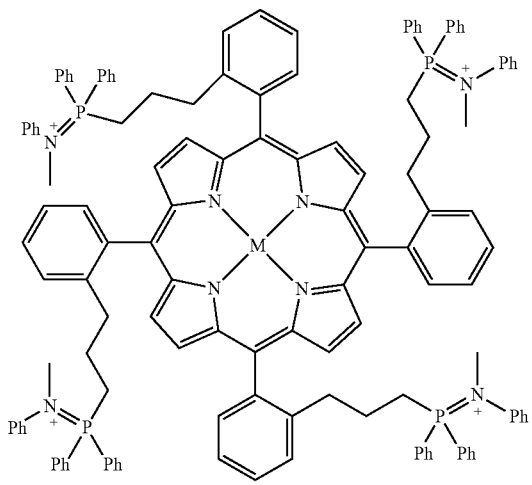

TABLE 2-continued
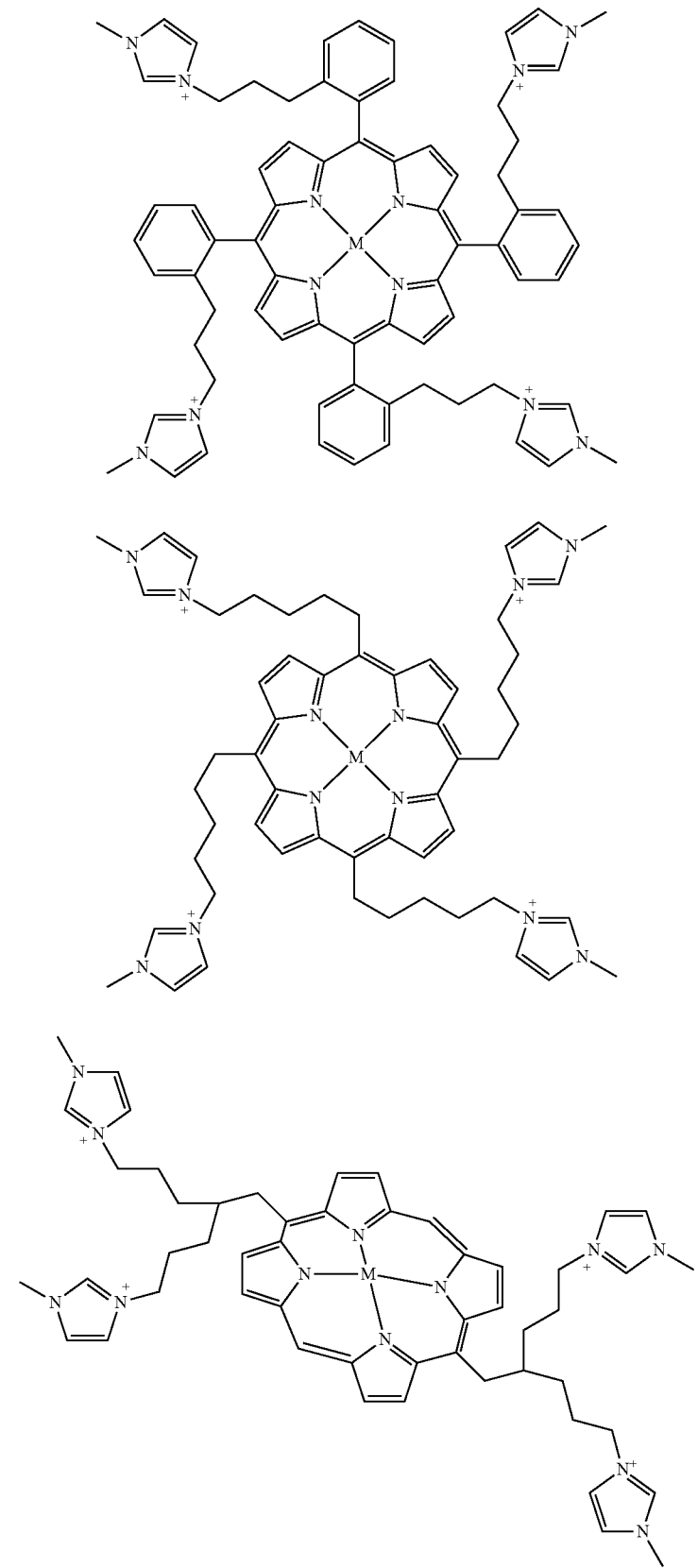

TABLE 2-continued
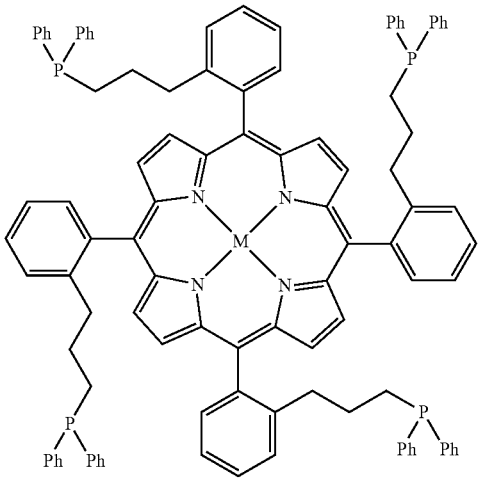
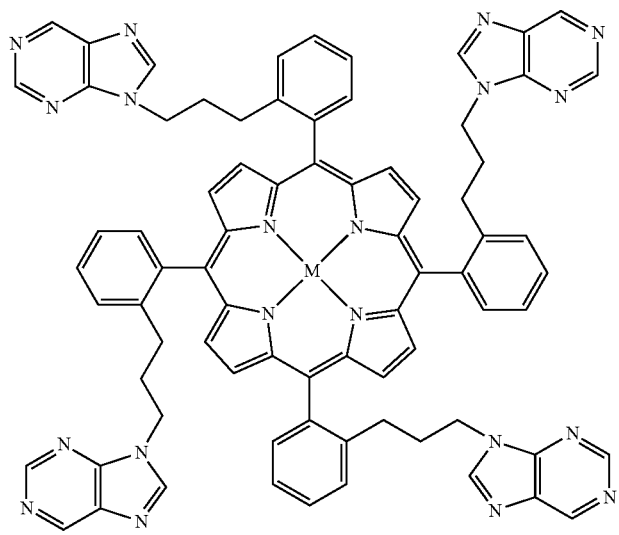
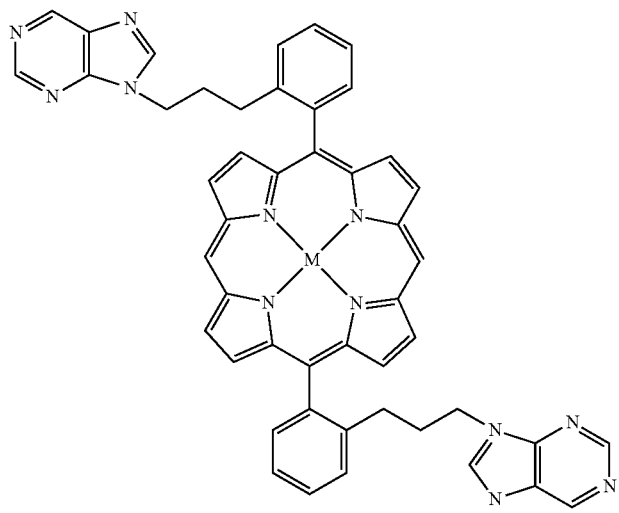

TABLE 2-continued
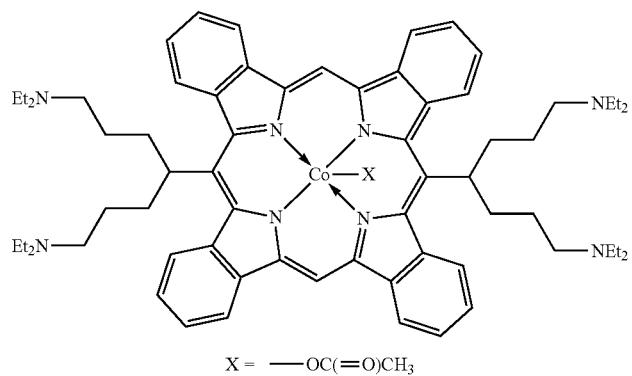
X = —OC(=O)CH₃
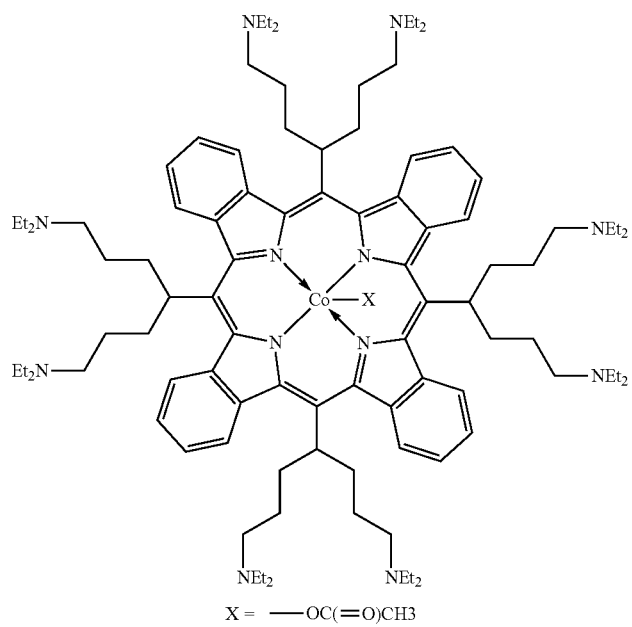
X = —OC(=O)CH3
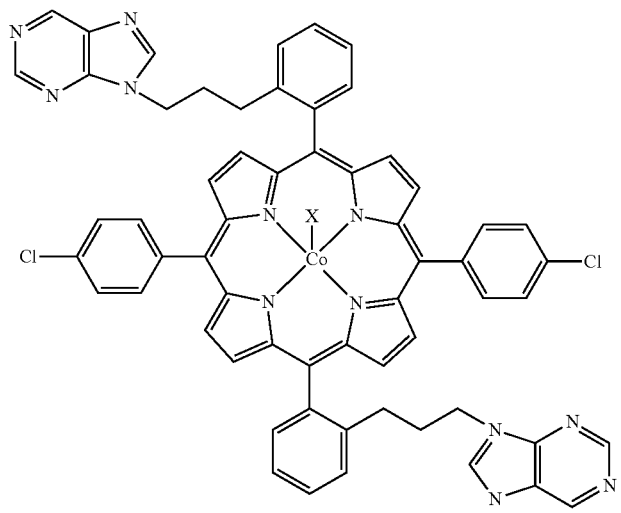

TABLE 2-continued

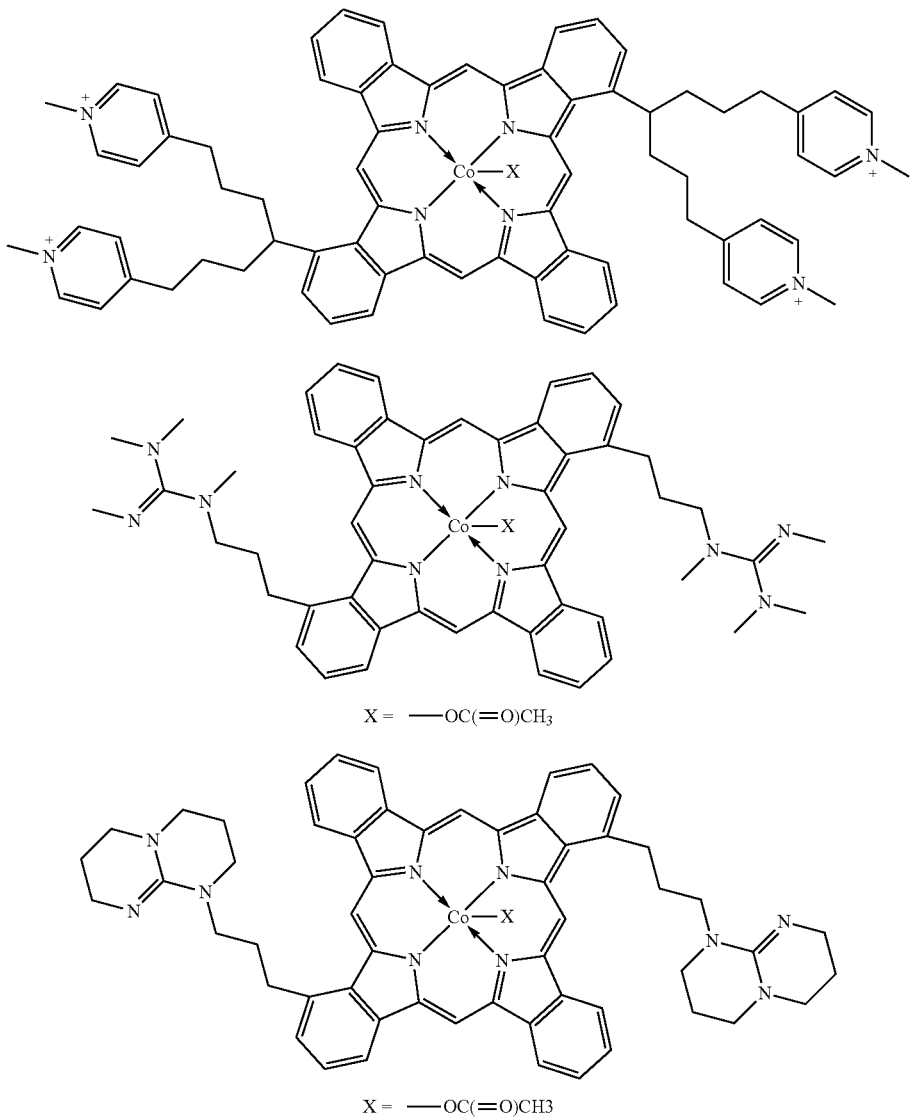

In certain embodiments, for complexes of Table 2, M is Co—X, where X is as defined above. In certain embodiments, for complexes of Table 2, M is Co—OC(O)CF$_3$. In certain embodiments, for complexes of Table 2, M is Co—OAc. In certain embodiments, for complexes of Table 1, M is Co—OC(O)C$_6$F$_5$. In certain embodiments, for complexes of Table 2, M is Co—N$_3$. In certain embodiments, for complexes of Table 2, M is Co—Cl. In certain embodiments, for complexes of Table 2, M is Co-nitrophenoxy. In certain embodiments, for complexes of Table 2, M is Co-dinitrophenoxy.

In certain embodiments, for complexes of Table 2, M is Al—X, where X is as defined above. In certain embodiments, for complexes of Table 2, M is Cr—X, where X is as defined above.

In certain embodiments, porphyrin complexes of the present invention are synthesized as shown in the following schemes:

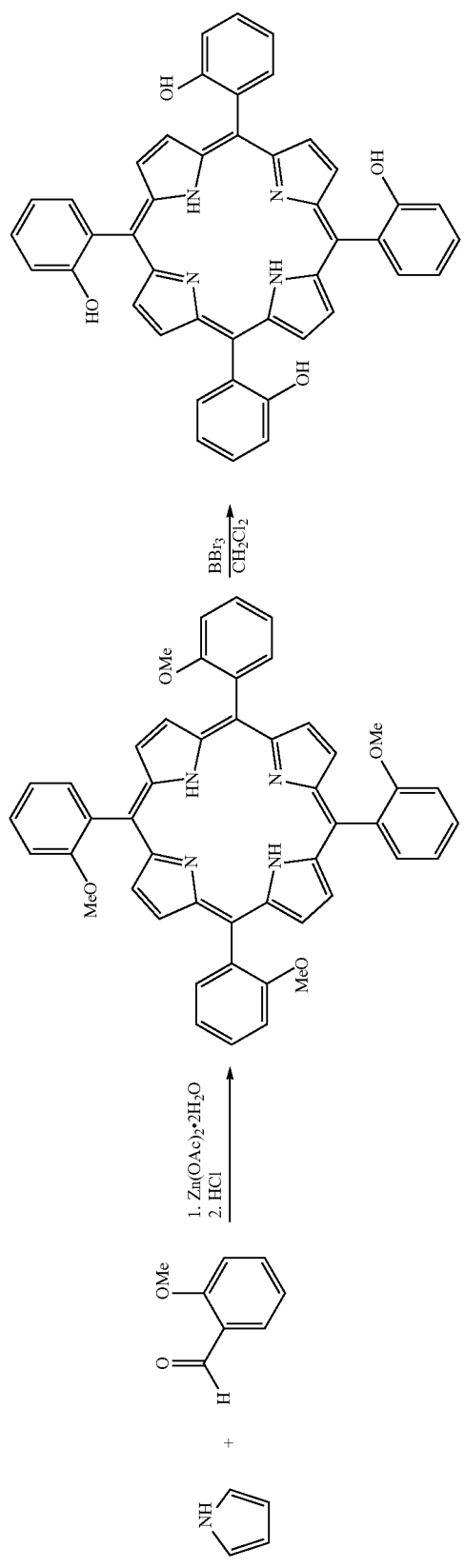
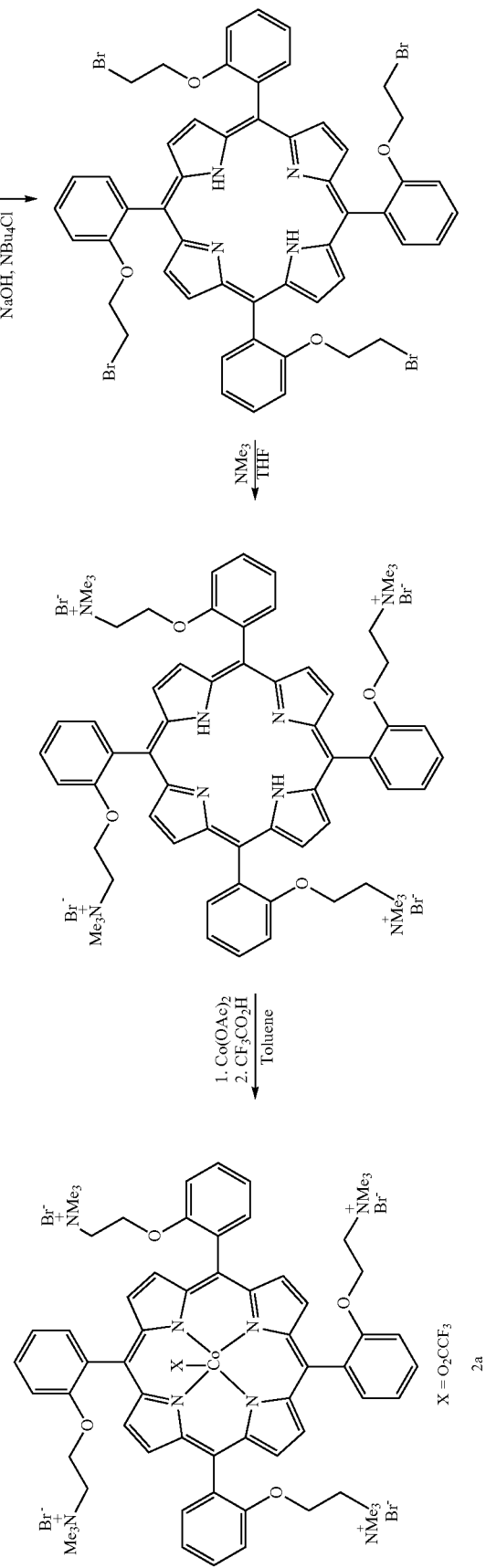

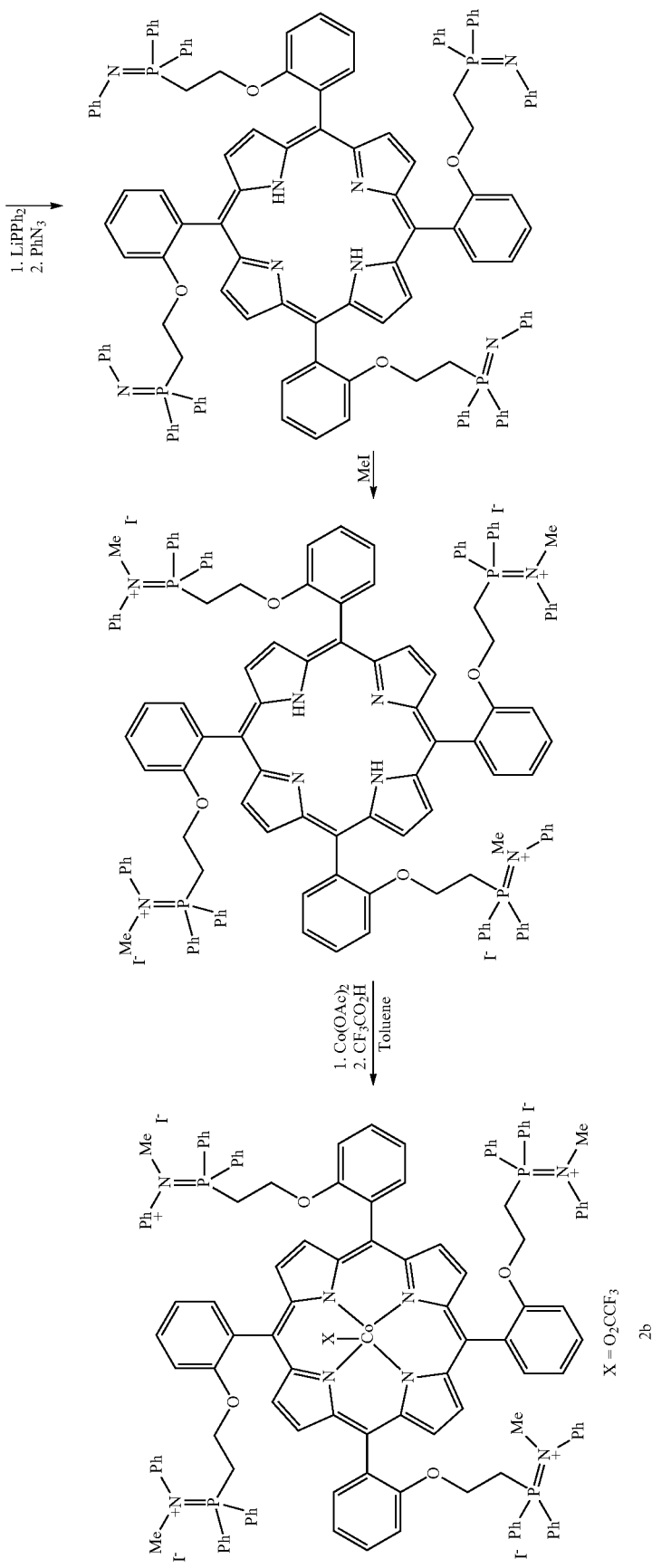

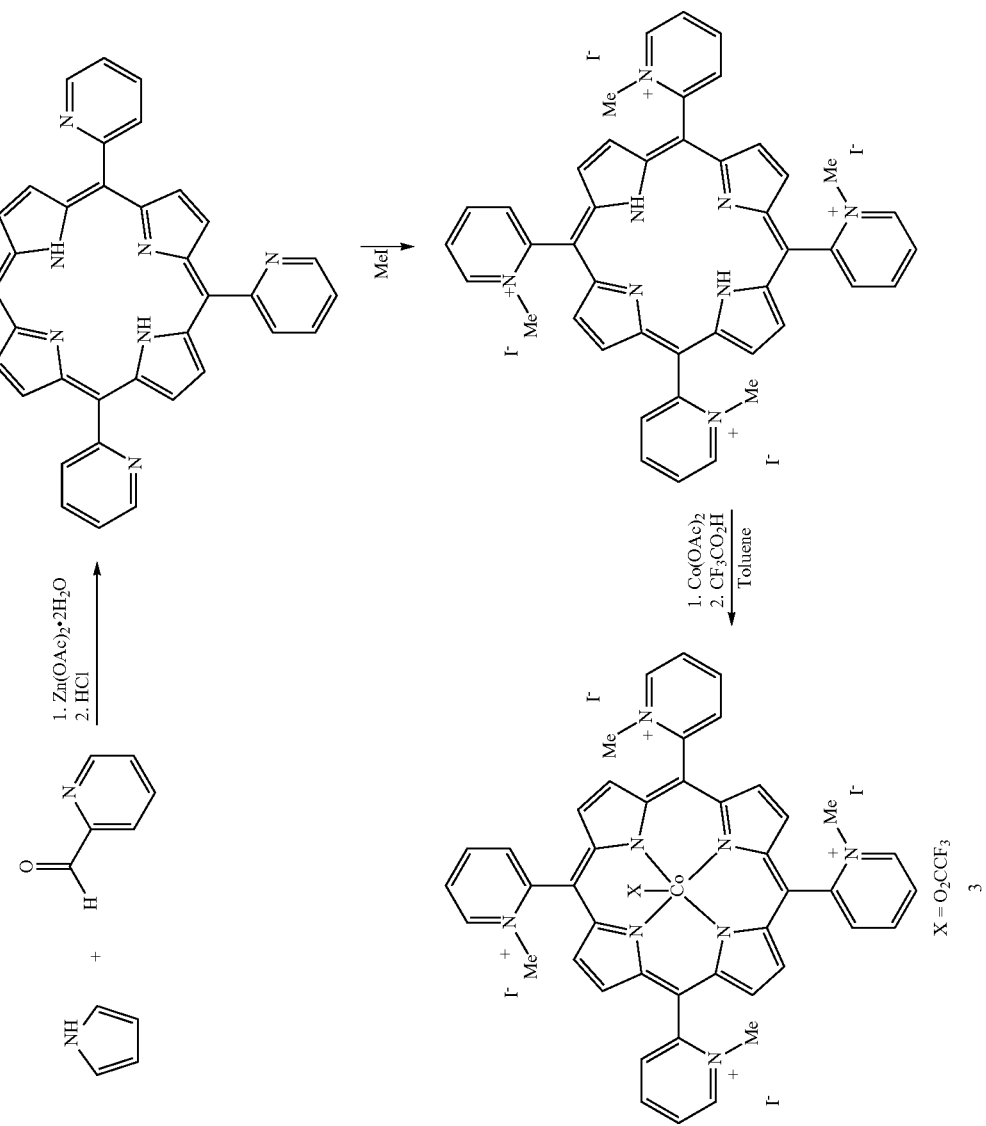

In some embodiments, the present disclosure provides methods of polymerization comprising contacting an epoxide with carbon dioxide in the presence of a provided metal complex to form a polycarbonate. In some embodiments, the present invention provides a method of polymerization, the method comprising:

a) providing an epoxide of formula:

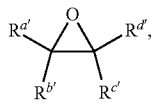

wherein:

$R^{a'}$ is hydrogen or an optionally substituted radical selected from the group consisting of $C_{1-30}$ aliphatic; $C_{1-30}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; and each of $R^{b'}$, $R^{c'}$, and $R^{d'}$ is independently hydrogen or an optionally substituted radical selected from the group consisting of $C_{1-12}$ aliphatic; $C_{1-12}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

wherein any of ($R^{a'}$ and $R^{c'}$), ($R^{c'}$ and $R^{d'}$), and ($R^{a'}$ and $R^{b'}$) can be taken together with intervening atoms to form one or more optionally substituted rings;

b) contacting the epoxide and carbon dioxide in the presence of a metal complex as described herein to provide a polymer having a formula selected from the group consisting of:

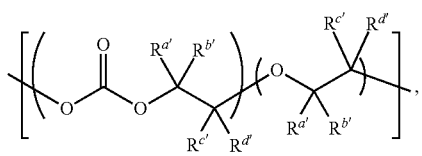

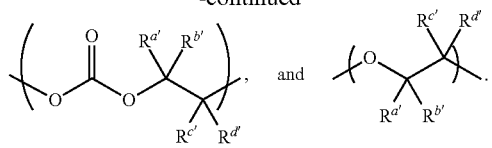

In some embodiments, a provided polymer has a formula:

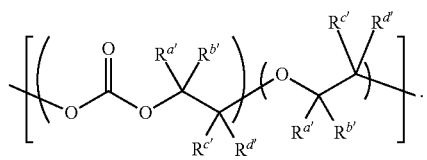

In some embodiments, a provided polymer has a formula:

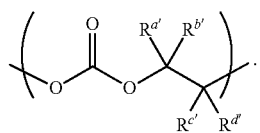

In some embodiments, carbon dioxide is optional and a provided polymer has a formula:

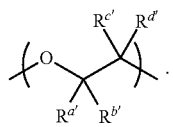

In certain embodiments, $R^{b'}$, $R^{c'}$, and $R^{d'}$ are each hydrogen. In some embodiments, $R^{a'}$ is optionally substituted $C_{1-12}$ aliphatic. In some embodiments, $R^{a'}$ is optionally substituted $C_{1-12}$ heteroaliphatic. In some embodiments, the epoxide is ethylene oxide, propylene oxide, or cyclohexene oxide.

In certain embodiments, one of $R^{a'}$, $R^{b'}$, $R^{c'}$, and $R^{d'}$ is hydrogen. In certain embodiments, two of $R^{a'}$, $R^{b'}$, $R^{c'}$, and $R^{d'}$ are hydrogen. In certain embodiments, three of $R^{a'}$, $R^{b'}$, $R^{c'}$, and $R^{d'}$ are hydrogen.

In certain embodiments, $R^{a'}$ is hydrogen. In certain embodiments, $R^{b'}$ is hydrogen. In certain embodiments, $R^{c'}$ is hydrogen. In certain embodiments, $R^{d'}$ is hydrogen.

In certain embodiments, $R^{a'}$, $R^{b'}$, $R^{c'}$, and $R^{d'}$ are each independently an optionally substituted $C_{1-30}$ aliphatic group. In certain embodiments, $R^{a'}$, $R^{b'}$, $R^{c'}$, and $R^{d'}$ are each independently an optionally substituted $C_{1-20}$ aliphatic group. In certain embodiments, $R^{a'}$, $R^{b'}$, $R^{c'}$, and $R^{d'}$ are each independently an optionally substituted $C_{1-12}$ aliphatic group. In certain embodiments, $R^{a'}$, $R^{b'}$, $R^{c'}$, and $R^{d'}$ are each independently an optionally substituted $C_{1-8}$ aliphatic group. In certain embodiments, $R^{a'}$, $R^{b'}$, $R^{c'}$, and $R^{d'}$ are each independently an optionally substituted $C_{3-8}$ aliphatic group. In certain embodiments, $R^{a'}$, $R^{b'}$, $R^{c'}$, and $R^{d'}$ are each independently an optionally substituted $C_{3-12}$ aliphatic group.

In certain embodiments, $R^{a'}$ is an optionally substituted $C_{1-30}$ aliphatic group. In certain embodiments, $R^{b'}$ is an optionally substituted $C_{1-30}$ aliphatic group. In certain embodiments, $R^{c'}$ is an optionally substituted $C_{1-30}$ aliphatic group. In certain embodiments, $R^{d'}$ is an optionally substituted $C_{1-30}$ aliphatic group.

In some embodiments, an $R^{a'}$ and an $R^{b'}$ attached to the same carbon are taken together to form one or more optionally substituted 3-12-membered carbocyclic rings. In some embodiments, an $R^{a'}$ and an $R^{b'}$ attached to the same carbon are taken together to form a polycyclic carbocycle comprising two or more optionally substituted 3-8-membered carbocyclic rings. In some embodiments, an $R^{a'}$ and an $R^{b'}$ attached to the same carbon are taken together to form a polycyclic carbocycle comprising two or more optionally substituted 5-7-membered carbocyclic rings.

In some embodiments, an $R^{a'}$ and an $R^{b'}$ attached to the same carbon are taken together to form a bicyclic carbocycle comprising two optionally substituted 3-12-membered carbocyclic rings. In some embodiments, an $R^{a'}$ and an $R^{b'}$ attached to the same carbon are taken together to form a bicyclic carbocycle comprising two optionally substituted 3-8-membered carbocyclic rings. In some embodiments, an $R^{a'}$ and an $R^{b'}$ attached to the same carbon are taken together to form a bicyclic carbocycle comprising two optionally substituted 5-7-membered carbocyclic rings.

In certain embodiments, an $R^{a'}$ and an $R^{b'}$ attached to the same carbon are taken together to form an optionally substituted 3-12-membered carbocyclic ring. In certain embodiments, an $R^{a'}$ and an $R^{b'}$ attached to the same carbon are taken together to form an optionally substituted 3-8-membered carbocyclic ring. In certain embodiments, an $R^{a'}$ and an $R^{b'}$ attached to the same carbon are taken together to form an optionally substituted 5-7-membered carbocyclic ring.

In some embodiments, an $R^{b'}$ and an $R^{c'}$ attached to adjacent carbons are taken together to form one or more optionally substituted 3-12-membered carbocyclic rings. In some embodiments, an $R^{b'}$ and an $R^{c'}$ attached to adjacent carbons are taken together to form a polycyclic carbocycle comprising two or more optionally substituted 3-8-membered carbocyclic rings. In some embodiments, an $R^{b'}$ and an $R^{c'}$ attached to adjacent carbons are taken together to form a polycyclic carbocycle comprising two or more optionally substituted 5-7-membered carbocyclic rings.

In some embodiments, an $R^{b'}$ and an $R^{c'}$ attached to adjacent carbons are taken together to form a bicyclic carbocycle comprising two optionally substituted 3-12-membered carbocyclic rings. In some embodiments, an $R^{b'}$ and an $R^{c'}$ attached to adjacent carbons are taken together to form a bicyclic carbocycle comprising two optionally substituted 3-8-membered carbocyclic rings. In some embodiments, an $R^{b'}$ and an $R^{c'}$ attached to adjacent carbons are taken together to form a bicyclic carbocycle comprising two optionally substituted 5-7-membered carbocyclic rings.

In certain embodiments, an $R^{b'}$ and an $R^{c'}$ attached to adjacent carbons are taken together to form an optionally substituted 3-12-membered carbocyclic ring. In certain embodiments, an $R^{b'}$ and an $R^{c'}$ attached to adjacent carbons are taken together to form an optionally substituted 3-8-membered carbocyclic ring. In certain embodiments, an $R^{b'}$ and an $R^{c'}$ attached to adjacent carbons are taken together to form an optionally substituted 5-7-membered carbocyclic ring.

In certain embodiments, the polymer comprises a copolymer of two different repeating units where $R^{a'}$, $R^{b'}$, and $R^{c'}$ of the two different repeating units are not all the same. In some embodiments, a polymer comprises a copolymer of three or more different repeating units wherein $R^{a'}$, $R^{b'}$, and $R^{c'}$ of each of the different repeating units are not all the same as $R^{a'}$, $R^{b'}$, and $R^{c'}$ of any of the other different repeating units. In some embodiments, a polymer is a random copolymer. In some embodiments, a polymer is a tapered copolymer.

In some embodiments, a polymer contains a metal complex as described herein. In some embodiments, a polymer comprises residue of a metal complex as described herein. In some embodiments, a polymer comprises a salt of an organic cation and X, wherein X is a nucleophile or counterion. In some embodiments, X is 2,4-dinitrophenolate anion.

In some embodiments, $R^{a'}$ is optionally substituted $C_{1-12}$ aliphatic. In some embodiments, $R^{a'}$ is optionally substituted $C_{1-12}$ heteroaliphatic. In some embodiments, $R^{a'}$ is optionally substituted phenyl. In some embodiments, $R^{a'}$ is optionally substituted 8- to 10-membered aryl. In some embodiments, $R^{a'}$ is optionally substituted 5- to 10-membered heteroaryl. In some embodiments, $R^{a'}$ is optionally substituted 3- to 7-membered heterocyclic.

In certain embodiments, $R^{a'}$ is selected from methyl, ethyl, propyl, butyl, vinyl, allyl, phenyl, trifluoromethyl,

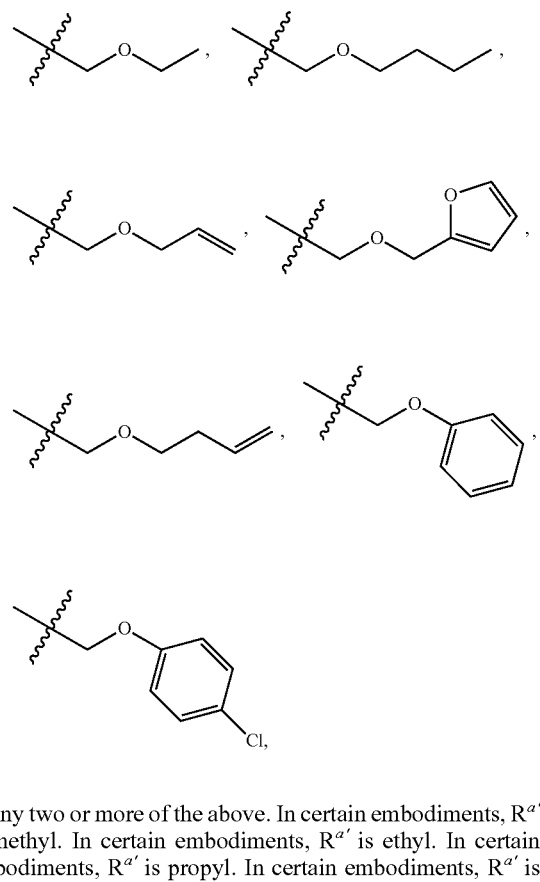

or any two or more of the above. In certain embodiments, $R^{a'}$ is methyl. In certain embodiments, $R^{a'}$ is ethyl. In certain embodiments, $R^{a'}$ is propyl. In certain embodiments, $R^{a'}$ is butyl. In certain embodiments, $R^{a'}$ is vinyl. In certain embodiments, $R^{a'}$ is allyl. In certain embodiments, $R^{a'}$ is phenyl. In certain embodiments, $R^{a'}$ is trifluoromethyl. In certain embodiments, $R^{a'}$ is

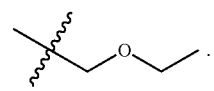 [SMILES: *COCC]

In certain embodiments, $R^{a'}$ is

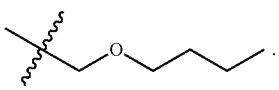 [SMILES: *COCCCC]

In certain embodiments, $R^{a'}$ is

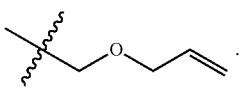 [SMILES: *COCC=C]

In certain embodiments, $R^{a'}$ is

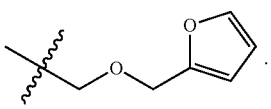 [SMILES: *COCc1ccco1]

In certain embodiments, $R^{a'}$ is

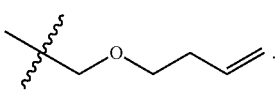 [SMILES: *COCCC=C]

In certain embodiments, $R^{a'}$ is

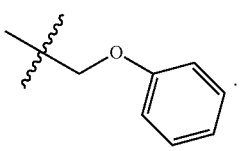 [SMILES: *COc1ccccc1]

In certain embodiments, $R^{a'}$ is

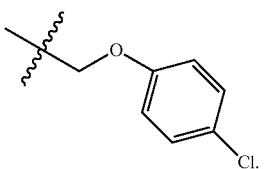 [SMILES: *COc1ccc(Cl)cc1]

In some embodiments, $R^{b'}$ is hydrogen. In some embodiments, $R^{b'}$ is optionally substituted $C_{1-12}$ aliphatic. In some embodiments, $R^{b'}$ is optionally substituted $C_{1-12}$ heteroaliphatic. In some embodiments, $R^{b'}$ is optionally substituted phenyl. In some embodiments, $R^{b'}$ is optionally substituted 8- to 10-membered aryl. In some embodiments, $R^{b'}$ is optionally substituted 5- to 10-membered heteroaryl. In some embodiments, $R^{b'}$ is optionally substituted 3- to 7-membered heterocyclic.

In some embodiments, $R^{c'}$ is hydrogen. In some embodiments, $R^{c'}$ is optionally substituted $C_{1-12}$ aliphatic. In some embodiments, $R^{c'}$ is optionally substituted $C_{1-12}$ heteroaliphatic. In some embodiments, $R^{c'}$ is optionally substituted phenyl. In some embodiments, $R^{c'}$ is optionally substituted 8- to 10-membered aryl. In some embodiments, $R^{c'}$ is optionally substituted 5- to 10-membered heteroaryl. In some embodiments, $R^{c'}$ is optionally substituted 3- to 7-membered heterocyclic.

In some embodiments, $R^{a'}$ and $R^{c'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, $R^{b'}$ and $R^{c'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, $R^{a'}$ and $R^{b'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, the invention includes methods for synthesizing polyethers from epoxides. Suitable methods of performing these reactions are disclosed in U.S. Pat. No. 7,399,822, the entire contents of which are hereby incorporated herein by reference.

In some embodiments, the invention includes methods for synthesizing cyclic carbonates from carbon dioxide and epoxides using catalysts described above, suitable methods of performing this reaction are disclosed in U.S. Pat. No. 6,870,004 which is incorporated herein by reference.

EXAMPLES

Example 1

A general route to a symmetric cobalt (III) salen ligand of the present invention is shown in Schemes E1 and E2, below:

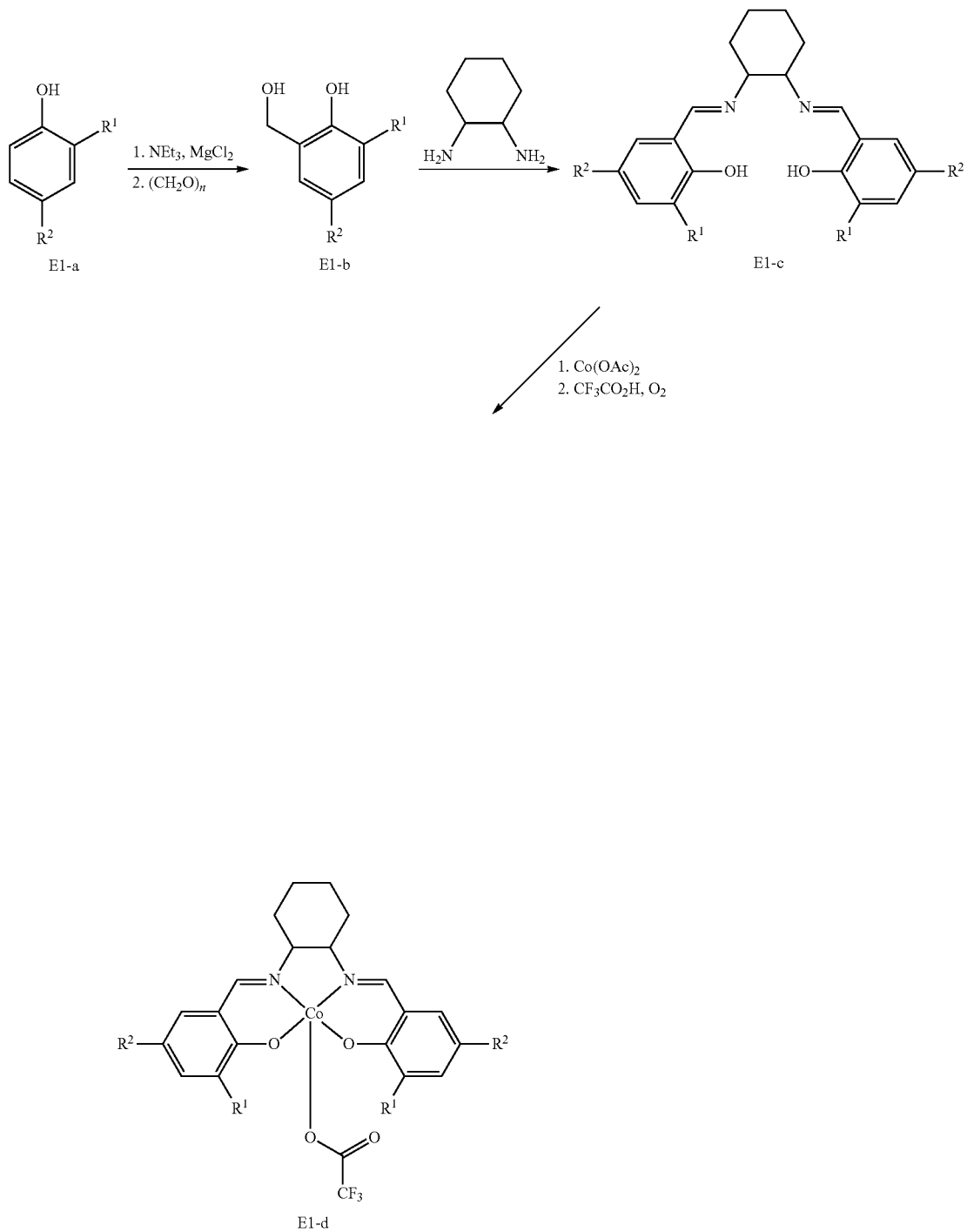

As shown in Scheme E1, disubstituted phenol E1-a is formylated to provide salicylaldehyde derivative E1-b. Two equivalents of this aldehyde are then reacted with a diamine (in this case 1,2-diamino cyclohexane) to afford Schiff base E1-c. This compound is then reacted with cobalt (II) acetate to give the Co(II)-salen complex (not shown) which is oxidized by air in the presence of trifluoroacetic acid to afford the active cobalt (III) catalyst. Similar chemistries can be applied to synthesis of the catalysts described hereinabove. One skilled in the art of organic synthesis can adapt this chemistry as needed to provide the specific catalysts described herein.

Example 2

A typical route to an asymmetric cobalt (III) salen ligand is shown in Scheme E2:

Scheme E2

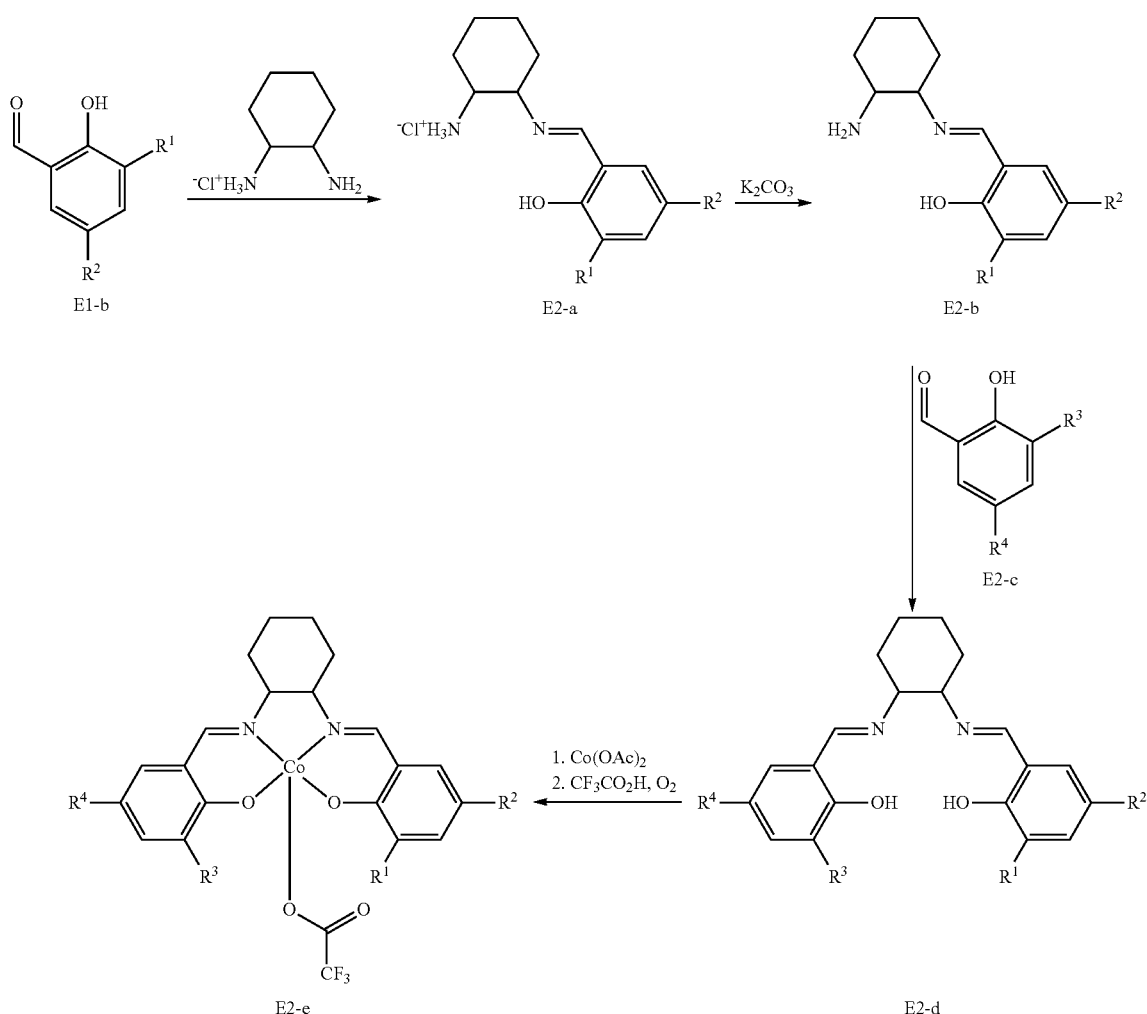

As shown in Scheme E2, disubstituted salicylaldehyde derivative E1-b is treated with one equivalent of a monohydrochloride salt of 1,2 cyclohexanediamine the resulting Schiff base E2-a is then neutralized and a second different salicylaldehyde derivative is added. This compound is then reacted with cobalt (II) acetate to give the Co(II)-salen complex which is oxidized by air in the presence of trifluoroacetic acid to afford the active cobalt (III) catalyst. Similar chemistries can be applied to synthesis of the catalysts described hereinabove. One skilled in the art of organic synthesis can adapt this chemistry as needed to provide the specific catalysts described herein.

Example 3

Example 3 describes the synthesis of a catalyst

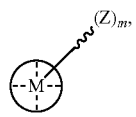

where M is Co(III),

is salcy, ⁓⁓⁓ is

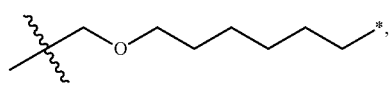

Z is a P-linked phosphorimine moiety

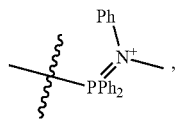

and m is 1, wherein there are one or two ⁓⁓⁓(Z)$_m$ groups present (Scheme E4 and E3, respectively).

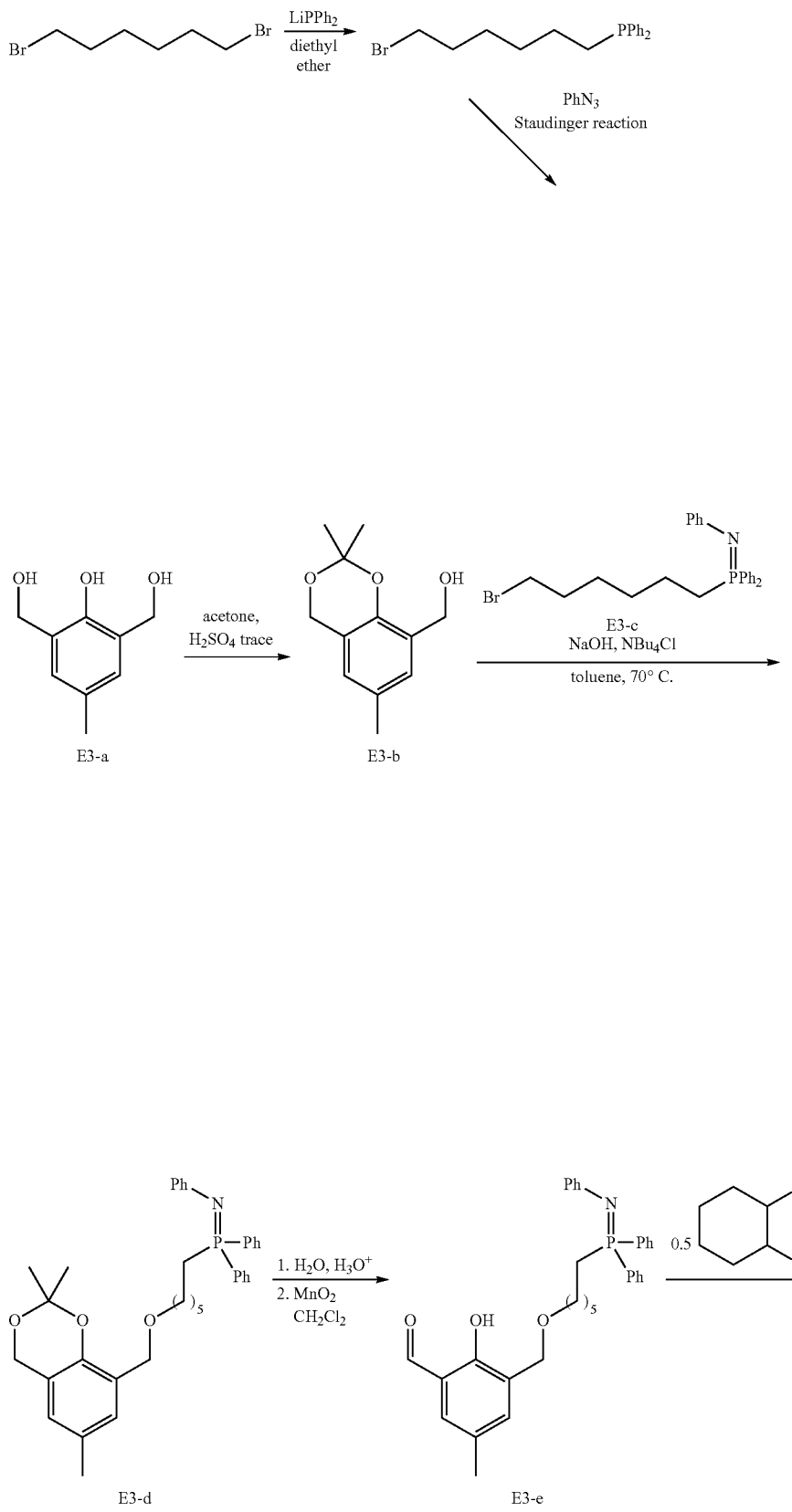

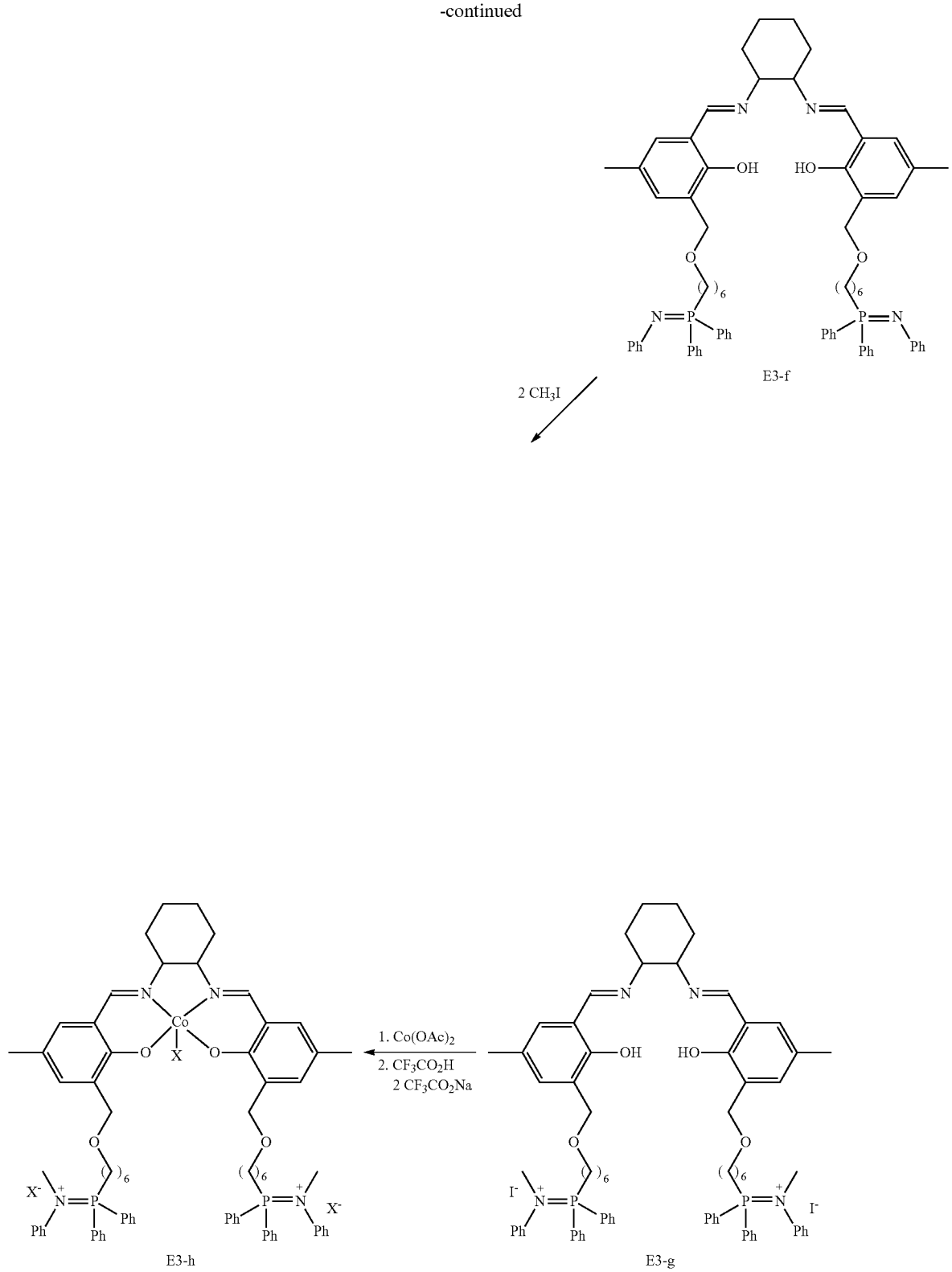

As shown in Scheme E3, triol E3-a is protected as a ketal to afford monohydric alcohol E3-b, this compound is then alkylated with bromide E3-c to afford benzyl ether E3-d. Deprotection and oxidation of the other benzylic alcohol affords salicylaldehyde E3-e which is condensed with cyclo-hexanediamine as described above to give ligand E3-f. The phosphorimine nitrogen is then quaternized and the metal complex formed as before to provide catalyst E3-h. In an alternative route not shown here the metal is first inserted and then quarternization is performed.

Scheme E3b

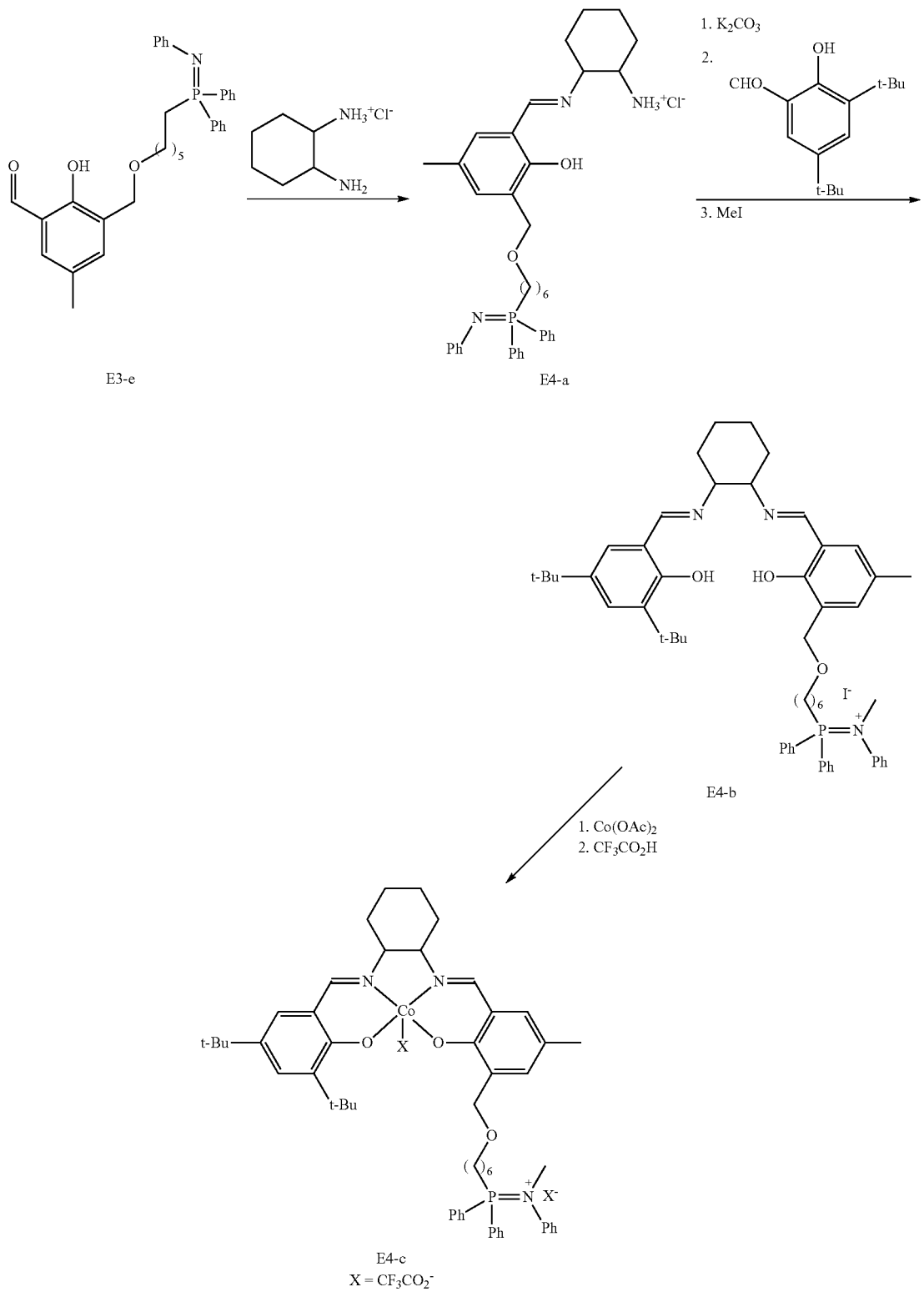

As shown in Scheme E3b, salicyladedyde E3-e (described above) is condensed with cyclohexanediamine monohydrochloride to afford the mono-Schiff base hydrochloride E4a. This salt is then neutralized, condensed with di-t-butyl salicaldehyde, and methylated to give E4-b. The resulting ligand is metallated and oxidized as described above for Scheme E3 to give catalyst E4-c.

Example 4

Example 4 describes the synthesis of catalysts where M is Co(III),

is salcy, ——ᴡᴡ is

Z is a 1-[4-dimethylamino-pyridinium]

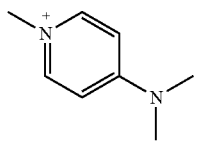

or 1-[N-methylimidazolium],

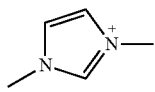

and m is 1, wherein there are one or two ——ᴡᴡ (Z)$_m$ groups present (Scheme E5 and E6, respectively).

Scheme E4

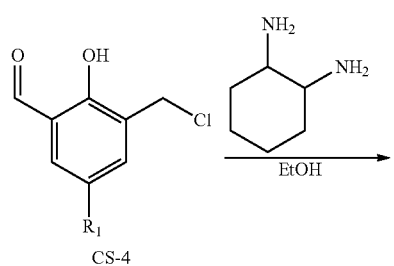

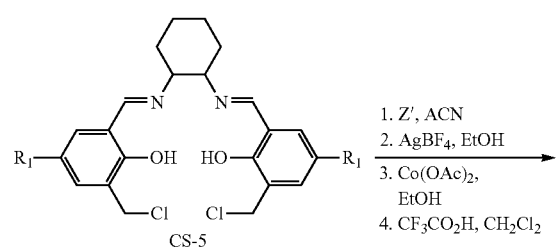

-continued

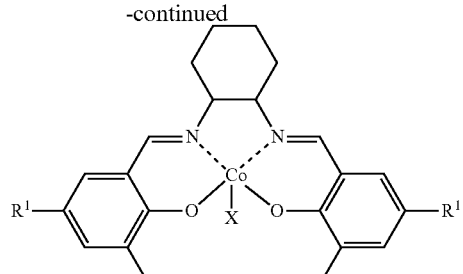

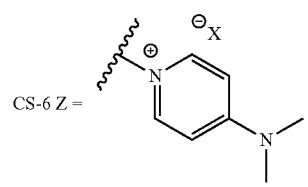

CS-6 Z =

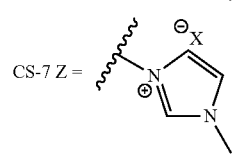

CS-7 Z =

$R_1$ = Me or t-Bu
$X = O_2CCF_3$

Z' = N,N-dimethylamino pyridine or N-methyl imidazole

Scheme E4 shows the synthesis of compounds CS-6 and CS-7. For each compound trans-1,2-Diaminocyclohexane (2.0 mol) is slowly added to an anhydrous ethanol solution of benzyl chloride CS-4 (1.0 mol). The reaction is stirred and heated to reflux for 3 h, then cooled to rt and diluted with water. This mixture is cooled overnight in the freezer and solids are collected by filtration to afford dichloride CS-5. The dichloride CS-5 (1.0 mol) is reacted with N,N-Dimethylamino pyridine (2.0 mol) or N-methyl imidazole in acetonitrile. The reactions are heated at 80° C. for 18 h and then the solvent is removed in vacuo to provide the respective ammonium salts. These salts are metallated and oxidized as described previously to provide catalysts CS-6 and CS-7.

Example 5

Example 5 describes the synthesis of catalysts where M is Co(III),

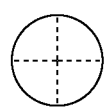

is salcy, ——ᴡᴡ is

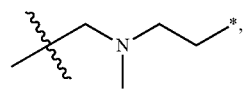

Z is a 1-[N-methylimidazolium] (CS-8), or dimethylamino (CS-9) and m is 1, wherein there are two ——ᴡᴡ (Z)$_m$ groups present (Scheme E5 and E6, respectively).

Scheme E5

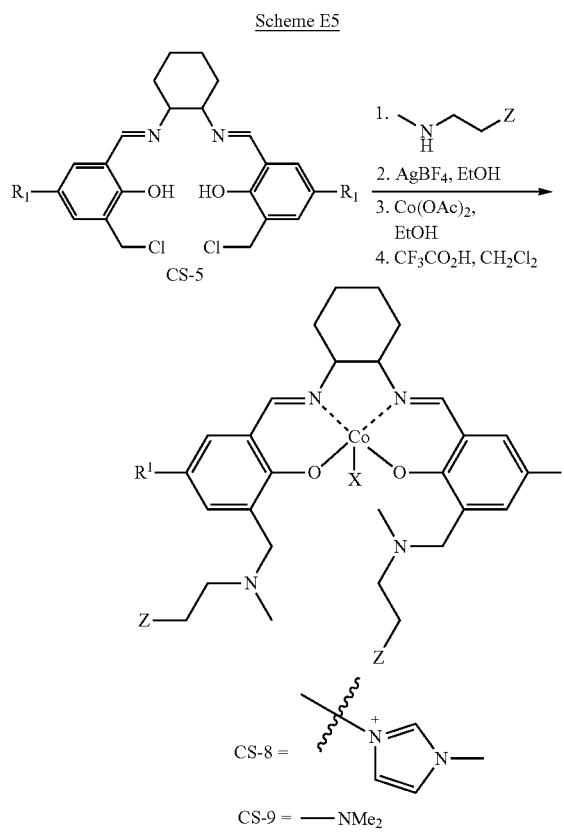

is salcy, ⁓⁓⁓ is

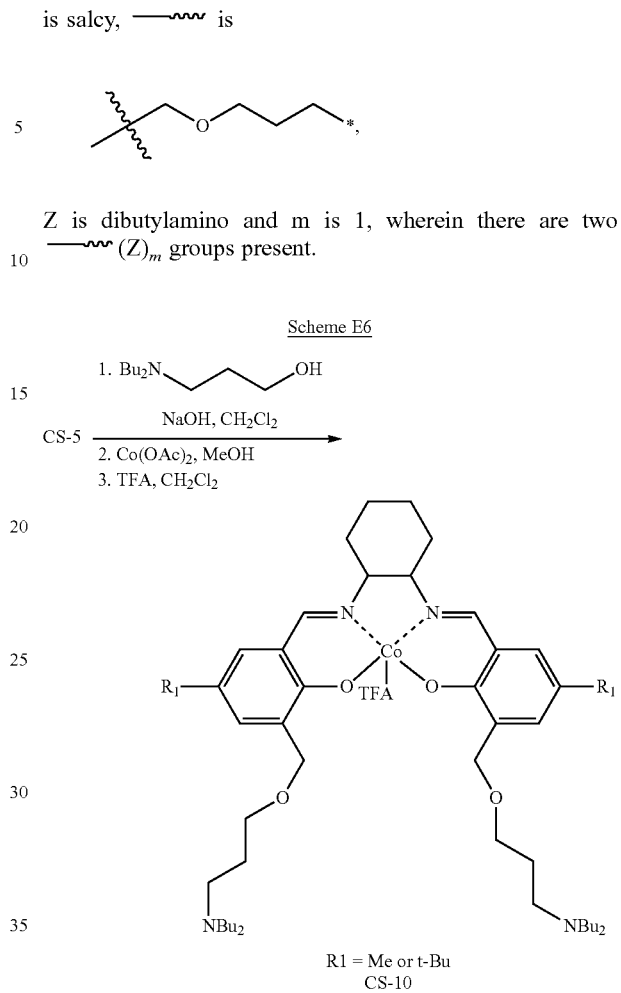

Z is dibutylamino and m is 1, wherein there are two ⁓⁓⁓(Z)$_m$ groups present.

Scheme E6

Scheme E5 shows the synthesis of compounds CS-8 and CS-9 using conditions similar to those described above. Synthesis of CS-8: The known compound 1-(2-methylaminoethyl)-3-methylimidazole (2.0 mol) is combined with CS-5 (1.0 mol) in acetonitrile. The reaction is heated to 80° C. for 18 h and then the solvent is removed in vacuo, metallation with Co(OAc)$_2$ and oxidation in TFA are then performed as described above to afford catalyst CS-8. Synthesis of CS-9: N,N,N'-Trimethyl-1,2-ethanediamine (4.0 mol) is combined with CS-5 (1.0 mol) in acetonitrile. The reaction is heated to 80° C. for 18 h, cooled, and the solvent is removed in vacuo. The crude product is diluted with ether, filtered to remove amine salts, and concentrated in vacuo. The residue is dissolved in degassed methanol and combined with Co(OAc)$_2$ (1.0 mol). After stirring for 3 h the residue is filtered and washed with methanol. Trifluoroacetic acid (1.0 mol) is added slowly to a stirring solution of the solid residue in dichloromethane. After stirring open to air for 3 h, the solids are filtered and dried in vacuo to produce CS-9.

Example 6

Example 6 and Scheme E6 describe the synthesis of catalysts where M is Co(III),

Synthesis of CS-10:

Ligand CS-5 (1.0 mol), 3-(dibutylamino)-1-propanol (2.0 mol), a 50% NaOH solution (10 mol), tetrabutylammonium bisulphate (4 mol %), and dichloromethane are combined and heated at 65° C. overnight. The reaction mixture is concentrated in vacuo to remove the bulk of the solvent and the aqueous layer is extracted with ethyl acetate. The organic layer is separated, dried with magnesium sulfate, filtered, and concentrated in vacuo. After purification using silica gel the product is dissolved in degassed methanol and combined with Co(OAc)$_2$ (1.0 mol). After stirring for 3 h, the residue is filtered and washed with methanol. Trifluoroacetic acid (1.0 mol) is added slowly to a dichloromethane solution of the solid residue. After stirring open to air for 3 h, the solids are filtered and dried in vacuo to produce CS-10.

Example 7

Example 7 and Scheme E7 describe the synthesis of catalysts where M is Co(III), is salcy, ⎯⎯⁓⁓⎯ includes two

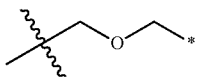 [SMILES: *COC*]

groups taken together to form a ring including the Z group, Z is 3-[N-methylpyridinium] and m is 1, wherein there is one ⎯⁓⁓⎯ $(Z)_m$ group present.

Scheme E7

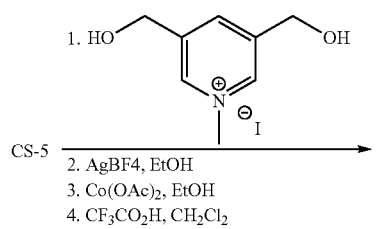

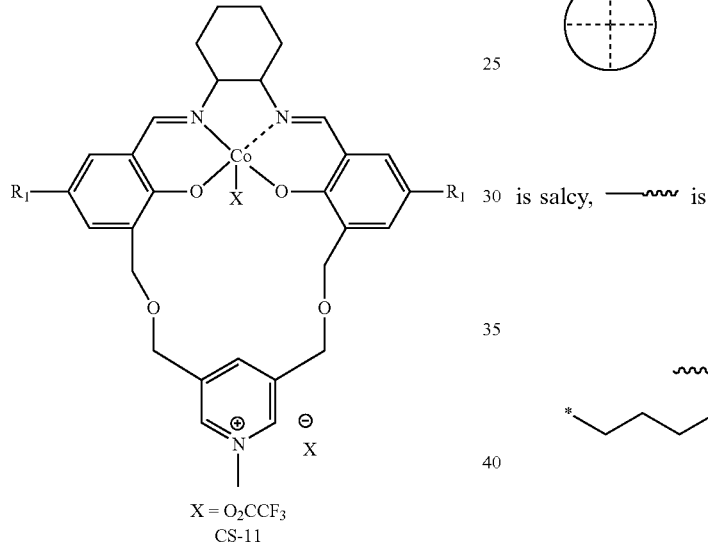

X = O$_2$CCF$_3$
CS-11

Synthesis of CS-11.

Ligand CS-5 (1.0 mol), 3,5-bis(hydroxymethyl)-N-methylpyridinium iodide (2.0 mol), a 50% NaOH solution (10 mol), tetrabutylammonium bisulphate (4 mol %), and dichloromethane are combined and heated at 65° C. overnight. The reaction mixture is concentrated in vacuo to remove the bulk of the solvent and the aqueous layer is extracted with ethyl acetate. The organic layer is separated, dried with magnesium sulfate, filtered, and concentrated in vacuo. The procedure detailed above for the metallation and oxidation is followed to produce CS-11.

Example 8

Example 8 and Scheme E8 describe the synthesis of catalysts where M is Co(III),

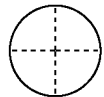

is salcy, ⎯⁓⁓⎯ is

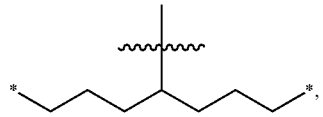

Z is 1-[4-t-butylpyridinium], and m is 2, wherein there are two ⎯⁓⁓⎯ $(Z)_m$ groups present.

Scheme E8

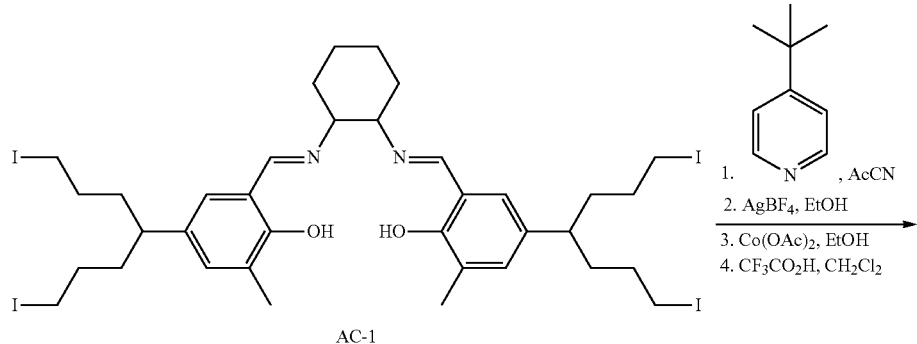

AC-1

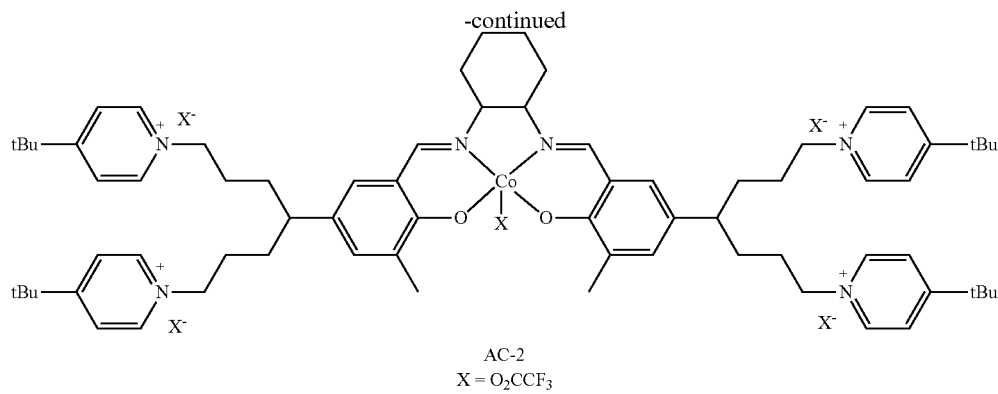

AC-2
X = O₂CCF₃

Synthesis of AC-2.

Intermediate AC-1 (0.37 g, 0.35 mmol), 4-tbutylpyridine (0.21 mL, 1.41 mmol), and AcCN (4 mL) were combined in a sealed vial and heated to 80° C. with stirring for 18 h. The solvent was removed in vacuo, leaving a yellow residue (0.61 g, 110% yield, AcCN present). $^1$H NMR (400 MHz, CDCl$_3$, δ): 9.53 (t, 8H), 8.21 (s, 2H), 7.94 (t, 8H), 7.08 (s, 2H), 6.83 (s, 2H), 4.81 (m, 8H), 3.29 (m, 2H), 2.78 (m, 2H), 2.15 (s, 6H), 1.5-2.0 (m, 24H), 1.36 (s, 36H); IR (ATR, film cast from AcCN): $v_{C=N}$=1637 cm$^{-1}$. A solution of the residue (0.30 g, 0.19 mmol) in dry EtOH (5 mL) was added to AgBF$_4$ (0.19 g, 0.85 mmol) in a schlenk tube and stirred overnight shielded from the light. The solution was filtered through Celite and the solvent was removed in vacuo, giving a solid residue. This residue was flashed over a small plug of silica gel with 5:1 CH$_2$Cl$_2$:EtOH as eluant. The solvent was removed to give a solid residue (0.18 g, 67% yield). $^1$H NMR (400 MHz, CDCl$_3$, δ): 8.75 (t, 8H), 7.98 (d, 2H), 7.92 (t, 8H), 7.1-7.3 (m, 4H), 4.52 (m, 8H), 3.6 (m, 2H), 2.7 (m, 2H), 2.19 (s, 6H), 1.5-2.0 (m, 24H), 1.38 (s, 36H); IR (ATR, film cast from CH$_2$Cl$_2$): $v_{C=N}$=1641 cm$^{-1}$, $v_{BF4}$=1050 cm$^{-1}$. A solution of the residue (0.18 g, 0.12 mmol) in dry EtOH (4 mL) was added to Co(OAc)$_2$ (0.022 g, 0.12 mmol) in a schlenk tube under N$_2$. The solution was stirred for 3 h at room temperature, and the solvent was removed in vacuo. The residue was triturated with ether, dried in vacuo, and redissolved in CH$_2$Cl$_2$. A solution of CF$_3$CO$_2$H (9 µL, 0.12 mmol) in CH$_2$Cl$_2$ (80 µL) was added and the solution stirred for 3 h open to air. Solid NaO$_2$CCF$_3$ (0.067 g, 0.49 mmol) was added, and the solution was stirred under N$_2$ for 2 days. The solution was filtered through Celite and the solvent was removed in vacuo to leave a brown residue (0.071 g, 37% yield). $^1$H NMR (400 MHz, DMSO-d$_6$, δ): 8.86 (t, 8H), 8.08 (t, 8H), 8.07 (s, 2H), 7.30 (m, 4H), 4.44 (m, 8H), 3.54 (m, 2H), 2.9 (m, 2H), 2.47 (s, 6H), 1.5-2.0 (m, 24H), 1.29 (s, 36H); IR (ATR): $v_{C=O}$=1682 cm$^{-1}$, $v_{C=N}$=1641 cm$^{-1}$.

Additional ligands AC-6 through AC-11 were synthesized using the conditions described for compound AC-2 and are summarized in Scheme E8b and Table E8:

Scheme E8b

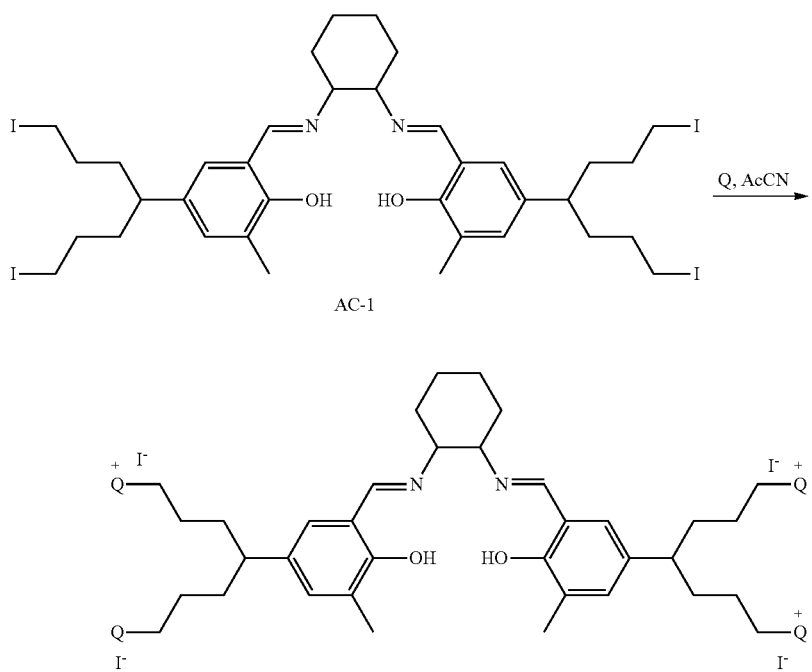

TABLE E8

| Compound | Q (Scheme E8b) | $^1$H NMR spectra$^a$ (δ, ppm) | IR$^b$ (cm$^{-1}$) |
|---|---|---|---|
| AC-6$^c$ |  | 9.0 (d, 8H), 8.6 (t, 4H), 8.5 (s, 2H), 8.1 (t, 8H), 6.9 (s, 2H), 6.8 (s, 2H), 4.5 (t, 8H), 3.4 (m, 2H), 2.1 (s, 6H), 1.4-2.9 (m, 24H). | $v_{C=N}$ = 1629 |
| AC-7 | 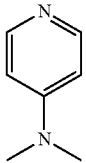 | 8.61 (d, 8H), 8.29 (s, 2H), 6.99 (s, 2H), 6.92 (d, 8H), 6.85 (s, 2H), 4.30 (t, 8H), 3.34 (m, 2H), 3.23 (s, 24H), 2.65 (m, 2H), 2.18 (s, 6H), 1.4-2.9 (m, 16H). | $v_{C=N}$ = 1649 |
| AC-8 | 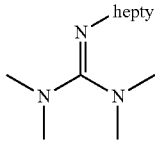 | | $v_{C=N}$ = 1627 |
| AC-9 | 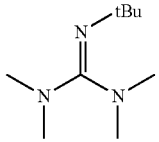 | | $v_{C=N}$ = 1610 |
| AC-10 | 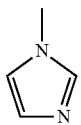 | | $v_{C=N}$ = 1627 |
| AC-11 | 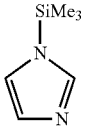 | | $v_{C=N}$ = 1628 |

$^a$400 MHz, CDCl$_3$.
$^b$All compounds exhibited the loss of a peak at 1213 cm$^{-1}$ attributed to the CH$_2$I group in AC-1.
$^c$NMR spectrum is in DMSO-d$_6$.

Example 9

Example 9 and Scheme E9 describe the synthesis of catalysts where M is Co(III),

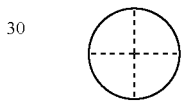

is salcy, ⁓⁓⁓ is

Z is N,N-bis-(3-dimethylaminopropyl)amino (AC-4), tetramethyl guanidino (AC-5), N-linked morpholino (AC-6), or N-linked piperidino (AC-14), and m is 2, wherein there are two ⁓⁓⁓(Z)$_m$ groups present.

Scheme E9

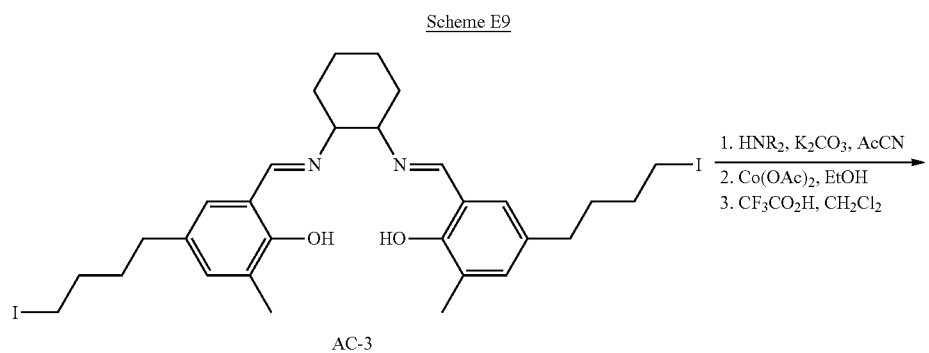

AC-3

-continued

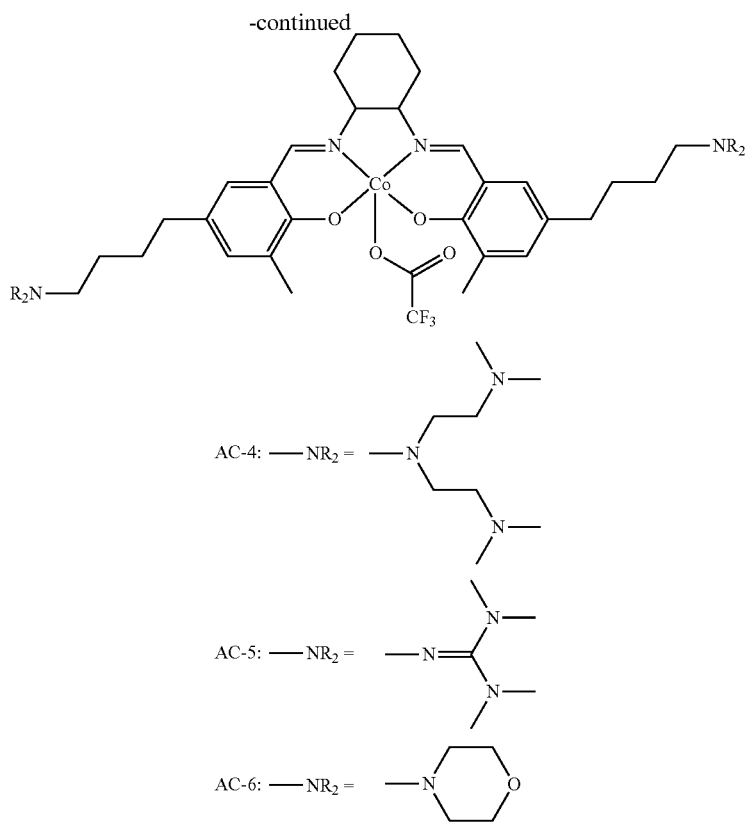

AC-4: —NR₂ =

AC-5: —NR₂ =

AC-6: —NR₂ =

Synthesis of AC-4.

Intermediate AC-3 (0.45 g, 0.63 mmol), 3,3'-iminobis(N, N'-dimethylpropylamine) (0.28 mL, 1.26 mmol), $K_2CO_3$ (0.35 g, 2.52 mmol) and AcCN (5 mL) were combined in a sealed vial and heated to 80° C. with stirring for 18 h. The solution was filtered and the solvent was removed in vacuo, triturated with ether, and dried in vacuo to leave a yellow residue (0.48 g, 91% yield). $^1$H NMR (400 MHz, $CDCl_3$, δ): 8.21 (m, 2H), 6.8-7.2 (m, 4H), 3.75 (m, 2H), 3.0-3.4 (m, 20H), 2.0-2.8 (m, 28H), 2.18 (s, 6H), 1.4-2.0 (m, 24H); IR (ATR): $v_{C=N}$=1600 cm$^{-1}$. A solution of the residue (0.21 g, 0.25 mmol) in dry EtOH (10 mL) was added to $Co(OAc)_2$ (0.045 g, 0.25 mmol) in a schlenk tube under $N_2$. $CH_2Cl_2$ (3 mL) was added to completely dissolve the solution. The solution was stirred for 18 h at room temperature, and the solvent was removed in vacuo. The residue was triturated with ether, dried in vacuo, and redissolved in $CH_2Cl_2$ (10 mL). $CF_3CO_2H$ (20 μL, 0.25 mmol) was added and the solution stirred for 3.5 h open to air. The solvent was removed in vacuo, triturated with ether, and dried in vacuo to leave a brown residue (0.28 g, 108% yield, residual $CH_2Cl_2$). $^1$H NMR (400 MHz, DMSO-$d_6$, δ): 7.92 (m, 2H), 7.1-7.4 (m, 4H), 3.58 (m, 2H), 3.0-3.4 (m, 20H), 2.0-2.8 (m, 28H), 2.3 (s, 6H), 1.4-2.0 (m, 24H); IR (ATR): $v_{C=O}$=1688 cm$^{-1}$, $v_{C=N}$=1616 cm$^{-1}$.

Synthesis of AC-5.

Intermediate AC-3 (0.20 g, 0.29 mmol), 1,1,3,3-tetramethylguanidine (0.21 mL, 1.71 mmol), $K_2CO_3$ (0.39 g, 2.85 mmol) and AcCN (2 mL) were combined in a sealed vial and reacted as in AC-4, except that the residue was also washed with hexanes. $^1$H NMR (400 MHz, $CDCl_3$, δ): 8.23 (d, 2H), 6.95 (s, 2H), 6.80 (s, 2H), 3.35 (m, 2H), 3.1 (m, 4H), 2.7-2.8 (m, 24H), 2.48 (m, 4H), 2.20 (s, 6H), 1.4-2.0 (m, 16H); IR (ATR): $v_{C=N}$=1594 cm$^{-1}$. The residue was reacted as in AC-4. IR (ATR): $v_{C=O}$=1690 cm$^{-1}$, $v_{C=N}$=1610 cm$^{-1}$.

Synthesis of AC-6.

Intermediate AC-3 (0.32 g, 0.44 mmol), morpholine (0.16 mL, 1.77 mmol), $K_2CO_3$ (0.61 g, 4.4 mmol) and AcCN (4 mL) were combined in a sealed vial and reacted as in AC-4, except that the residue was also washed with a NaOAc buffer (pH=4) solution to remove residual morpholine. $^1$H NMR (400 MHz, $CDCl_3$, δ): 8.22 (s, 2H), 6.92 (s, 2H), 6.79 (s, 2H), 3.69 (m, 8H), 3.28 (m, 2H), 2.2-2.5 (m, 16H), 2.19 (s, 6H), 1.4-2.0 (m, 16H). The residue was reacted as in AC-4. $^1$H NMR (400 MHz, DMSO-$d_6$, δ): 7.91 (s, 2H), 7.23 (s, 2H), 7.14 (s, 2H), 3.6 (m, 2H), 3.52 (m, 8H), 2.99 (m, 2H), 2.57 (s, 6H), 2.47 (m, 4H), 2.2-2.5 (m, 12H), 1.4-2.0 (m, 16H); IR (ATR): $v_{C=O}$=1671 cm$^{-1}$, $v_{C=N}$=1630 cm$^{-1}$.

Additional ligands AC-13 and AC-14 were synthesized using the conditions described for compounds AC-4 through AC-6 and are summarized in Scheme E9b and Table E9:

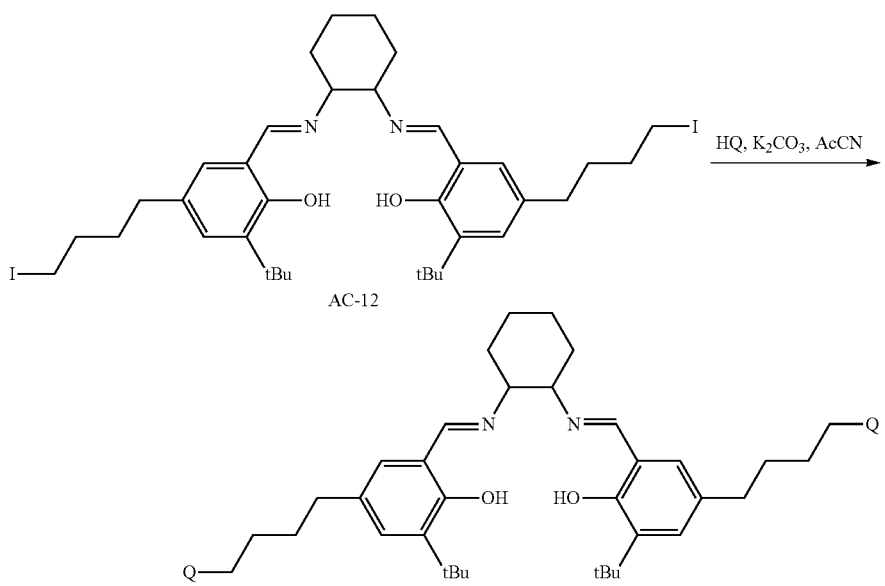

TABLE E9

| Compound | Q (Scheme E9b) | $^1$H NMR spectra[a] (δ, ppm) | IR[b] (cm$^{-1}$) |
|---|---|---|---|
| AC-13 | —N(morpholine) | 8.25 (s, 2H), 7.02 (d, 2H), 6.77 (d, 2H), 3.7 (m, 8H), 3.3 (m, 2H), 2.2-2.6 (m, 12H), 1.3-2.0 (m, 20H), 1.37 (s, 18H) | $v_{C=N}$ = 1628 |
| AC-14 | —N(piperidine) | | $v_{C=N}$ = 1629 |

[a]400 MHz, CDCl$_3$.
[b]All compounds exhibited the loss of a peak at 1213 cm$^{-1}$ attributed to the CH$_2$I group in AC-1.

Example 10

Confirmation of inventive concepts, processes, methods, and compositions described herein has been provided, among other ways, through publication by others after the priority date of the present case. For example, Examples 10-27 describe working Examples presented in Chinese Patent Application No. 200810229276.1, published as CN 101412809A. Additional experimental and characterization data are described by Lu and co-workers, *J. Am. Chem. Soc.*, 2009, 131, 11509-11518, and supporting information available at www.pubs.acs.org, the entirety each of which is hereby incorporated by reference.

In certain embodiments, provided catalysts and/or methods for the preparation of polycarbonate are characterized by one or more of the following: retaining high catalytic activity at low catalyst concentration; reaction conditions that are relatively mild; high catalytic activity with high selectivity for polymer product; alternate structure in the polycarbonate product higher than 97% with relatively narrow distribution of molecular weight; retaining high catalytic activity for copolymerization of carbon dioxide and epoxides at higher reaction temperatures (e.g., above 50° C., above 75° C., or above 100° C.); and catalysts that can be used to catalyze the polymerization of carbon dioxide with two or more alkylene oxides for the synthesis of polycarbonate polymer.

The following materials were added sequentially into a stainless steel high pressure reactor of effective volume of 200 mL at ambient temperature: 0.1 mmole of cobalt complex I-a ($R_1$ is cyclohexyl diamine, X is $NO_3^{-1}$ anion; $R_2$=H; $R_3$, $R_4$ and $R_5$ are tertiary butyl; group containing organic base group is at position 3 of the benzene ring in the ligand, n is 2) and one mole of propylene oxide. The reactor was then filled with carbon dioxide and the pressure is maintained constant at 2.0 MPa. The temperature was controlled at 25° C. The content was stirred with a magnetic stirring bar for 6 hours and the remaining carbon dioxide was slowly released. The remaining alkylene oxide was collected in −20° C. cold trap and a certain amount of mixture of methanol/chloroform was added to dissolve the high polymer. Then a large amount of diethyl ether was added to precipitate the polycarbonate. The precipitate was filtered and washed several times with diethyl ether and dried in vacuum to constant weight to afford 27 grams of polycarbonate as a white solid. The average molecular weight of the polymer was determined by gel permeation chromatography to be 101,000 g/mol with a molecular weight distribution of 1.24. A Varian INOVA-400 MHz Nuclear Magnetic Resonance spectrometer was used to determine its $^1$H-NMR and the result showed that the alternate structure is over 99%.

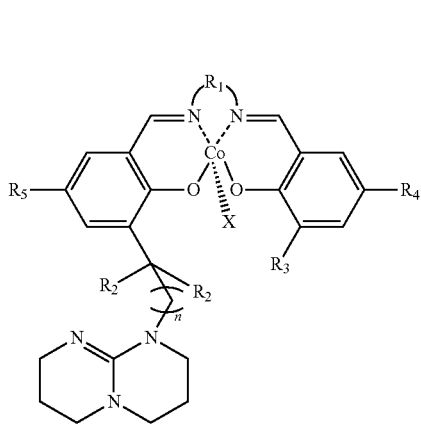

I-a

Example 11

The same equipment and reaction conditions were employed as in Example 10 with the same catalyst and the same conditions except that the molar ratio of catalyst to propylene oxide was changed from 1:10000 to 1:50000 (0.02 mmole of catalyst and 1 mole of propylene oxide were used). The reaction was carried out at 25° C. for 24 hours to afford 21 grams of poly(propylene carbonate) with a molecular weight of 223,000 g/mol and a molecular weight distribution of 1.29. The polymer formed contained more than 99% carbonate linkages.

Example 12

The same equipment and reaction conditions were employed as in Example 10 with the same catalyst and the same conditions except that the molar ratio of catalyst to propylene oxide was changed from 1:10000 to 1:200000 (0.008 mmole of catalyst and 1.6 mole of propylene oxide were used). The reaction was carried out at 50° C. for 10 hours to afford 19 grams of poly(propylene carbonate) with a molecular weight of 318,000 g/mol and a molecular weight distribution of 1.37. The polymer formed contained more than 99% carbonate linkages.

Example 13

The same equipment and reaction conditions were employed as in Example 10 with the same catalyst and the same conditions except that the molar ratio of catalyst to propylene oxide was changed from 1:10000 to 1:2000 (0.5 mmole of catalyst and 1 mole of propylene oxide were used). The reaction was carried out at 25° C. for 3 hours to afford 48 grams of poly(propylene carbonate) with a molecular weight of 52,800 g/mol and a molecular weight distribution of 1.30. The polymer formed contained more than 99% carbonate linkages.

Example 14

The same equipment and reaction conditions were employed as in Example 10 with the same catalyst and the same conditions except that the reaction temperature was changed from 25° C. to 100° C. and the reaction was carried out for 0.5 hours to afford 34 grams of poly(propylene carbonate) with a molecular weight of 112,400 g/mol and a molecular weight distribution of 1.38. The polymer formed contained more than 99% carbonate linkages.

Example 15

The same equipment and reaction conditions were employed as in Example 10 with the same catalyst and the same conditions except that the reaction temperature was changed from 25° C. to 10° C. and the reaction was carried out for 10 hours to afford 18 grams of poly(propylene carbonate) with a molecular weight of 914,000 g/mol and a molecular weight distribution of 1.38. The polymer formed contained more than 99% carbonate linkages.

Example 16

The same equipment and reaction conditions were employed as in Example 10 with the same catalyst and the same conditions except that the propylene oxide was replaced with 1,2-butylene oxide. The reaction was carried out at 25° C. for 6 hours to afford 31 grams of poly(butylene carbonate) with a molecular weight of 127,000 g/mol and a molecular weight distribution of 1.21. The polymer formed contained more than 99% carbonate linkages.

Example 17

The same equipment and reaction conditions were employed as in Example 10 with the same catalyst and the same conditions except that the propylene oxide was replaced with 1,2-octylene oxide. The reaction was carried out at 25° C. for 10 hours to afford 34 grams of poly (octylene carbonate) with a molecular weight of 109,000 g/mol and a molecular weight distribution of 1.38. The polymer formed contained more than 99% carbonate linkages.

Example 18

The same equipment and reaction conditions were employed as in Example 10 with the same catalyst and the same conditions except that the propylene oxide was replaced with a mixture of propylene oxide and cyclohexylene oxide (the molar ratio of the catalyst to propylene oxide and cyclohexylene oxide was 1:5000:5000). The reaction was carried out at 50° C. for 6 hours to afford 59 grams of poly(propylene-co-cyclohexene carbonate) with a molecular weight of 187,000 g/mol and a molecular weight distribution of 1.29. The polymer formed contained more than 99% carbonate linkages.

Example 19

The same equipment and reaction conditions were employed as in Example 10 with the same catalyst and the same conditions except that the axial anion in the cobalt complex I-a was changed from nitrate radical to acetate moiety. The reaction was carried out at 25° C. for 6 hours to afford 34 grams of poly(propylene carbonate) with a molecular weight of 95,000 g/mol and a molecular weight distribution of 1.28. The polymer formed contained more than 99% carbonate linkages.

Example 20

The same equipment and reaction conditions were employed as in Example 10 with the same catalyst and the same conditions except that the diamine skeleton in the cobalt complex I-a was changed from cyclohexane diamine to ethylene diamine. The reaction was carried out at 25° C.

for 6 hours to afford 29 grams of poly(propylene carbonate) with a molecular weight of 112,000 g/mol and a molecular weight distribution of 1.20. The polymer formed contained more than 99% carbonate linkages.

Example 21

The same equipment and reaction conditions were employed as in Example 10 with the same catalyst and the same conditions except that the diamine skeleton in the cobalt complex I-a was changed from cyclohexane diamine to o-phenylene diamine. The reaction was carried out at 25° C. for 6 hours to afford 25 grams of poly (propylene carbonate) with a molecular weight of 92,000 g/mol and a molecular weight distribution of 1.15. The polymer formed contained more than 99% carbonate linkages.

Example 22

The following materials were added sequentially into a stainless steel high pressure reactor of volume of 200 mL at ambient temperature: 0.1 mmole of cobalt complex I-b ($R_1$ is 1,2-propylene diamine, X is dinitrophenyl anion; $R_2$=H; $R_1$ is tertiary butyl; there are organic base groups at position 5 of the two benzene rings in the ligand, n is 0) and 1 mole of propylene oxide. The reactor was then filled with carbon dioxide and the pressure was maintained constant at 2.0 MPa. The reaction was carried out at 25° C. for 6 hours to afford 23 grams of polycarbonate as a white solid. The average molecular weight of the polymer was determined by gel permeation chromatography to be 81,000 g/mol with a molecular weight distribution of 1.34. The polymer formed contained more than 99% carbonate linkages.

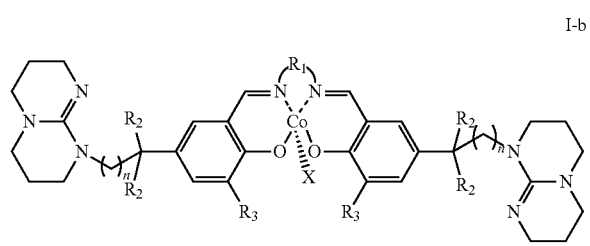

I-b

Example 23

The following materials were added sequentially into a stainless steel high pressure reactor of volume of 200 mL at ambient temperature: 0.1 mmole of cobalt complex I-c ($R_1$ is ethylene diamine, X is dinitrophenyl anion; $R_2$=H; $R_3$ is tertiary butyl; there are organic base groups at position 3 and position 5 of one of the benzene rings in the ligand, n is 0) and 1 mole of propylene oxide. The reactor was then filled with carbon dioxide and the pressure was maintained constant at 2.0 MPa. The reaction was carried out at 25° C. for 6 hours to afford 23 grams of polycarbonate as a white solid. The average molecular weight of the polymer was determined by gel permeation chromatography to be 81,000 g/mol with a molecular weight distribution of 1.34. The polymer formed contained more than 99% carbonate linkages.

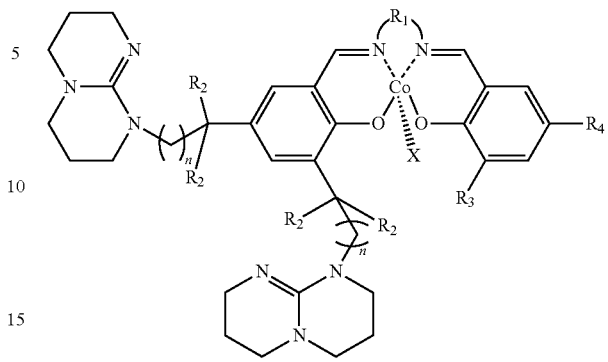

I-c

Example 24

The following materials are added sequentially into a stainless steel high pressure reactor of volume of 200 mL at ambient temperature: 0.1 mmole of cobalt complex I-b ($R_1$ is ethylene diamine, X is dinitrophenyl anion; $R_2$=H; $R_3$ and $R_4$ are tertiary butyl; there are organic base groups at position 5 of the two benzene rings in the ligand, n is 0) and 1 mole of propylene oxide. The reactor was then filled with carbon dioxide and the pressure was maintained constant at 2.0 MPa. The reaction was carried out at 25° C. for 6 hours to afford 26 grams of polycarbonate as a white solid. The average molecular weight of the polymer was determined by gel permeation chromatography to be 83,000 g/mol with a molecular weight distribution of 1.19. The polymer formed contained more than 99% carbonate linkages. The polymer formed contained more than 99% carbonate linkages.

Example 25

The following materials are added sequentially onto a stainless steel high pressure reactor of volume of 200 mL at ambient temperature: 0.1 mmole of cobalt complex I-a ($R_1$ is 2,3-butylene diamine, X is nitrate anion; $R_2$=H; $R_3$ and $R_4$ are methoxyl group; $R_1$ is tertiary butyl; there is an organic base group at position 3 of one of the benzene rings in the ligand, n is 2) and 1 mole of propylene oxide. The reactor was then filled with carbon dioxide and the pressure is maintained constant at 2.0 MPa. The reaction was carried out at 25° C. for 6 hours to afford 22 grams of polycarbonate as a white solid. The average molecular weight of the polymer was determined by gel permeation chromatography to be 73,000 g/mol with a molecular weight distribution of 1.14. The polymer formed contained more than 99% carbonate linkages.

Example 26

The same equipment and reaction conditions were employed as in Example 10 with the same catalyst and the same conditions except that the pressure was changed from 2.0 MPa to 0.1 MPa. The reaction was carried out at 25° C. for 10 hours to afford 25 grams of poly(propylene carbonate) with a molecular weight of 100,400 g/mol and a molecular weight distribution of 1.17. The polymer formed contained more than 99% carbonate linkages.

Example 27

The same equipment and reaction conditions were employed as in Example 10 with the same catalyst and the same conditions except that the pressure was changed from 2.0 MPa to 6.0 MPa. The reaction was carried out at 25° C. for 6 hours to afford 29 grams of poly(propylene carbonate) with a molecular weight of 125,000 g/mol and a molecular weight distribution of 1.25. The polymer formed contained more than 99% carbonate linkages.

TABLE E10

Summary of Examples 10-27.

| | Catalyst | | | | | | | | Reaction Conditions | | | | | | |
|---|---|---|---|---|---|---|---|---|---|---|---|---|---|---|---|
| | | | | | | | | | Cat. | | Epoxide | P | | T | t |
| Ex | Cat | R1 | R2 | R3 | R4 | R5 | X | n | | (mmol) | (mg) | (mmol) | MPa | psi | (deg C.) | (h) |
| 10 | I-a | Cy | H | tBu | tBu | tBu | NO$_3$ | 2 | PO | 0.1 | 70.5 | 1000 | 2 | 290 | 25 | 6 |
| 11 | | | | | | | | | | 0.02 | 14.1 | 1000 | 2 | 290 | 25 | 24 |
| 12 | | | | | | | | | | 0.008 | 5.64 | 1600 | 2 | 290 | 50 | 10 |
| 13 | | | | | | | | | | 0.5 | 353 | 1000 | 2 | 290 | 25 | 3 |
| 14 | | | | | | | | | | 0.1 | 70.5 | 1000 | 2 | 290 | 100 | 0.5 |
| 15 | | | | | | | | | | 0.1 | 70.5 | 1000 | 2 | 290 | 10 | 10 |
| 26 | | | | | | | | | | 0.1 | 70.5 | 1000 | 0.1 | 15 | 25 | 10 |
| 27 | | | | | | | | | | 0.1 | 70.5 | 1000 | 6 | 370 | 25 | 6 |
| 16 | | | | | | | | | BO | 0.1 | 70.5 | 1000 | 2 | 290 | 25 | 6 |
| 17 | | | | | | | | | OO | 0.1 | 70.5 | 1000 | 2 | 290 | 25 | 10 |
| 18 | | | | | | | | | PO/CHO | 0.1 | 70.5 | 1000 | 2 | 290 | 50 | 6 |
| 19 | | Cy | H | tBu | tBu | tBu | OAc | 2 | PO | 0.1 | 70.2 | 1000 | 2 | 290 | 25 | 6 |
| 20 | | En | H | tBu | tBu | tBu | NO$_3$ | 2 | PO | 0.1 | 65.1 | 1000 | 2 | 290 | 25 | 6 |
| 21 | | Ph | H | tBu | tBu | tBu | NO$_3$ | 2 | PO | 0.1 | 69.9 | 1000 | 2 | 290 | 25 | 6 |
| 25 | | Bu | H | OMe | OMe | tBu | NO$_3$ | 2 | PO | 0.1 | 62.7 | 1000 | 2 | 290 | 25 | 6 |
| 22 | I-b | Pr | | tBu | | | DNP | 0 | PO | 0.1 | 89 | 1000 | 2 | 290 | 25 | 6 |
| 24 | I-b | En | H | tBu | | | DNP | 0 | PO | 0.1 | 87.7 | 1000 | 2 | 290 | 25 | 6 |
| 23 | I-c | En | H | tBu | tBu | | DNP | 0 | PO | 0.1 | 88.2 | 1000 | 2 | 290 | 25 | 6 |

| | | Results | | | | | | |
|---|---|---|---|---|---|---|---|---|
| | | PPC | | | TOF | MW | | g PC/ | kg PC/ |
| | Ex | yield (g) | conv. (%) | TON | (h$^{-1}$) | (kDa) | PDI | g Cat | mol Cat. |
| | 10 | 27 | 26.4 | 2644 | 441 | 101 | 1.2 | 383 | 270 |
| | 11 | 21 | 20.6 | 10284 | 429 | 233 | 1.3 | 1489 | 1050 |
| | 12 | 19 | 11.6 | 23262 | 2326 | 318 | 1.4 | 3369 | 2375 |
| | 13 | 48 | 47.0 | 940 | 313 | 53 | 1.3 | 136 | 96 |
| | 14 | 34 | 33 | 3330 | 6660 | 112 | 1.4 | 482 | 340 |
| | 15 | 18 | 17.6 | 1763 | 176 | 914 | 1.4 | 255 | 180 |
| | 26 | 25 | 24.5 | 2449 | 244.9 | 100 | 1.2 | 355 | 250 |
| | 27 | 29 | 28.4 | 2840 | 473.4 | 125 | 1.3 | 411 | 290 |
| | 16 | 31 | 26.7 | 2669 | 444.9 | 127 | 1.2 | 440 | 310 |
| | 17 | 34 | 19.7 | 1974 | 197.4 | 109 | 1.4 | 482 | 340 |
| | 18 | 59 | | | | | | 837 | 590 |
| | 19 | 34 | 33.3 | 3330 | 555 | 95 | 1.3 | 484 | 340 |
| | 20 | 29 | 28.4 | 2840 | 473 | 112 | 1.2 | 446 | 290 |
| | 21 | 25 | 24.5 | 2449 | 408 | 92 | 1.2 | 358 | 250 |
| | 25 | 22 | 21.5 | 2155 | 359.1 | 73 | 1.1 | 351 | 220 |
| | 22 | 23 | 22.5 | 2253 | 375 | 81 | 1.3 | 258 | 230 |
| | 24 | 26 | 25.5 | 2547 | 424.4 | 33 | 1.2 | 296 | 260 |
| | 23 | 23 | 22.5 | 2253 | 375.4 | 81 | 1.3 | 261 | 230 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been presented by way of example.

What is claimed:

1. A metal complex having the structure:

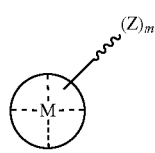

wherein:

comprises a tetradentate porphyrin ligand;

M is a metal atom optionally coordinated to up to two nucleophiles capable of ring opening an epoxide; and —⁓ (Z)$_m$ represents one or more activating moieties tethered to the multidentate ligand, where —⁓ represents a linker moiety; m represents the number of Z groups present on a linker moiety and is an integer between 1 and 4 inclusive; and each (Z) represents an activating moiety.

2. The metal complex of claim 1, wherein M is selected from the group consisting of Cr, Co, and Al.

3. The metal complex of claim 1, wherein M is Cr.

4. The metal complex of claim 1, wherein M is Co.

5. The metal complex of claim 1, wherein the metal complex is:

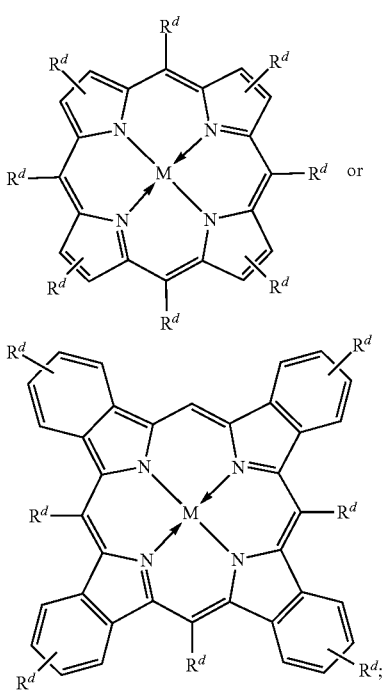

wherein
R$^d$ at each occurrence is independently a —⋀⋀— (Z)$_m$ group hydrogen halogen —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur; where two or more R$^d$ groups may be taken together with intervening atoms to form one or more optionally substituted rings optionally containing one or more heteroatoms; and R at each occurrence is independently hydrogen, an optionally substituted radical selected the group consisting of acyl; C$_{1-6}$ aliphatic; C$_{1-6}$ heteroaliphatic; carbamoyl; arylalkyl; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring.

6. The metal complex of claim 1, wherein the —⋀⋀— moiety contains 1-30 atoms including at least one carbon atom, and optionally one or more atoms selected from the group consisting of N, O, S, Si, B, and P.

7. The metal complex of claim 1, wherein the —⋀⋀— moiety is a C$_{2-30}$ aliphatic group wherein one or more methylene units are optionally and independently replaced by —NR$^y$—, —N(R$^y$)C(O)—, —C(O)N(R$^y$)—, —O—, —C(O)—, —OC(O)—, —C(O)O—, —S—, —Si(R$^y$)$_2$—, —SO—, —SO$_2$—, —C(=S)—, —C(=NR$^y$)—, or —N=N—, where each occurrence of R$^y$ is independently —H, or an optionally substituted radical selected from the group consisting of C$_{1-6}$ aliphatic, 3- to 7-membered heterocyclic, phenyl, and 8- to 10-membered aryl.

8. The metal complex of claim 1, wherein the —⋀⋀— moiety is selected from the group consisting of:

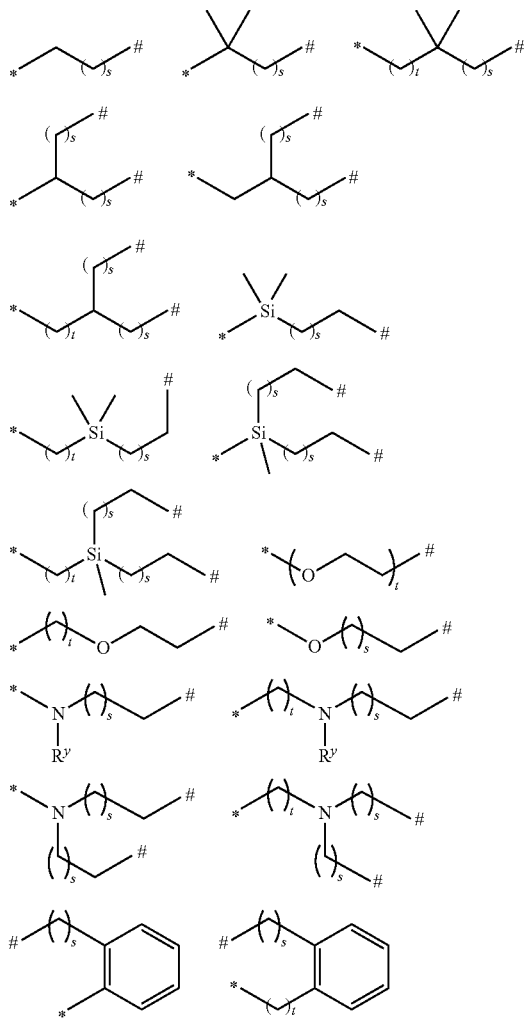

223
-continued

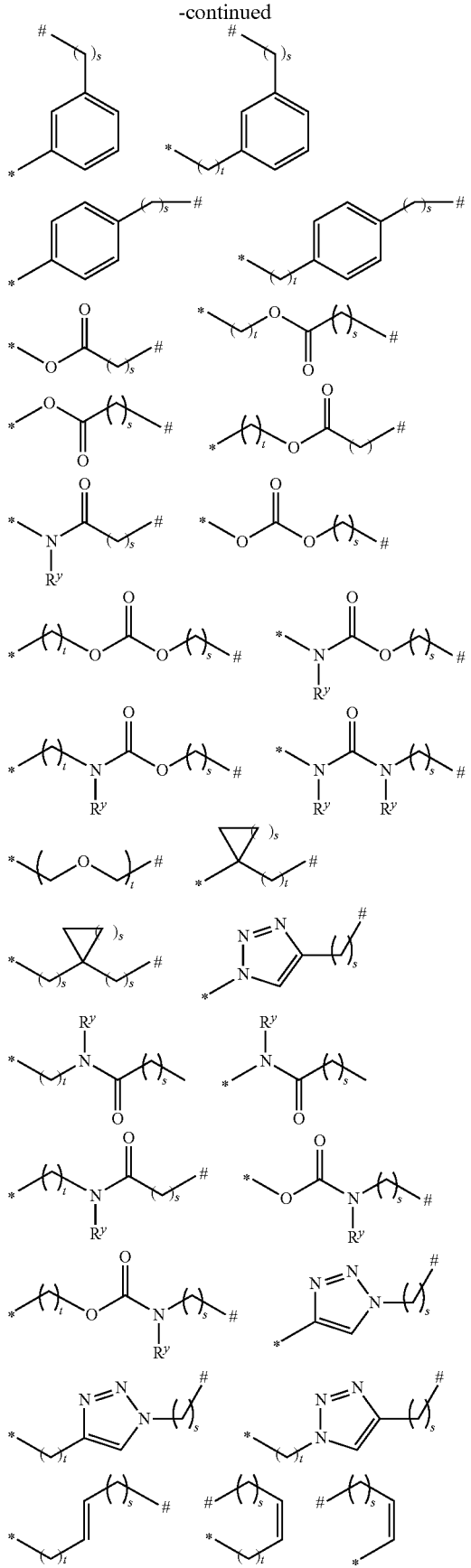

224
-continued

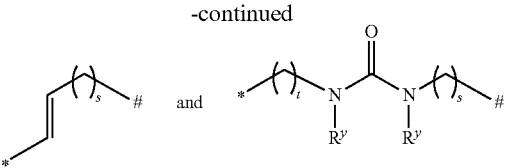

where s = 0-6 and t = 1-4 where * represents the site of attachment to the ligand, and each # represents a site of attachment of an activating functional group; and each occurrence of $R^y$ is independently —H, or an optionally substituted radical selected from the group consisting of $C_{1-6}$ aliphatic, 3- to 7-membered heterocyclic, phenyl, and 8- to 10-membered aryl.

9. The metal complex of claim 1, wherein each Z group is independently selected from the group consisting of:

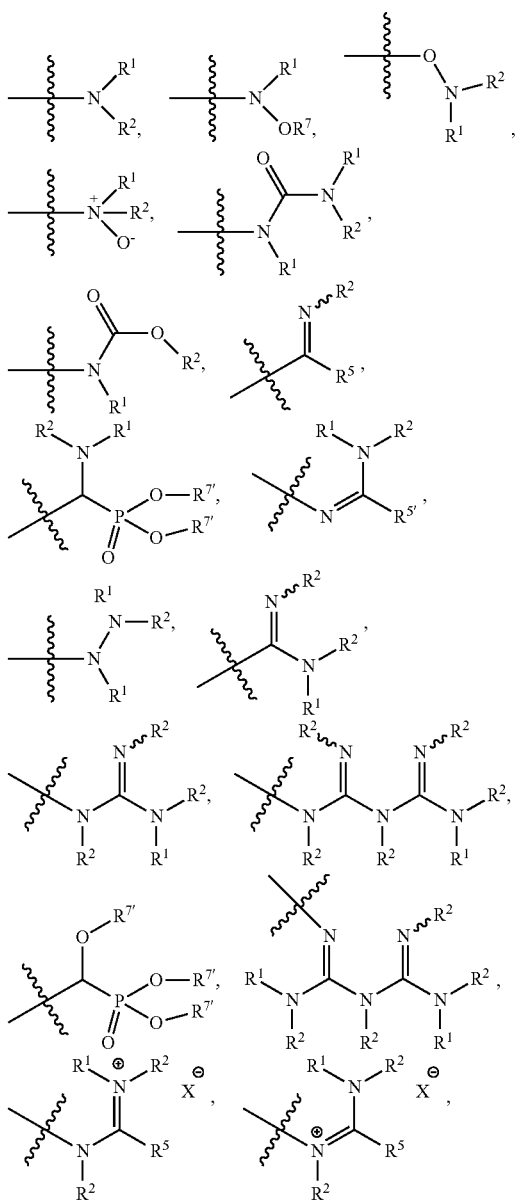

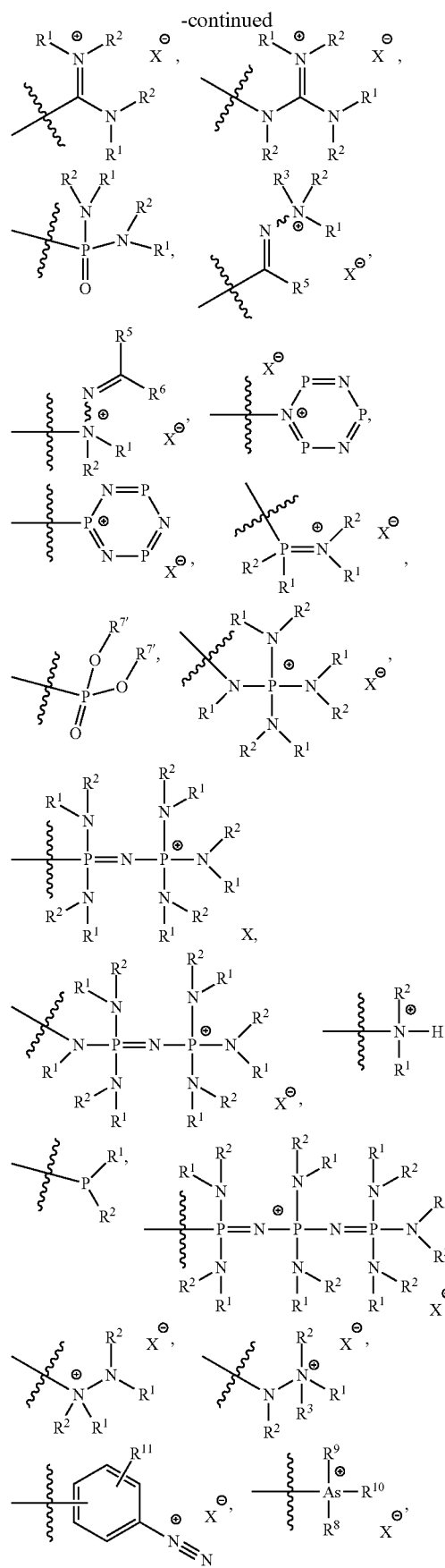
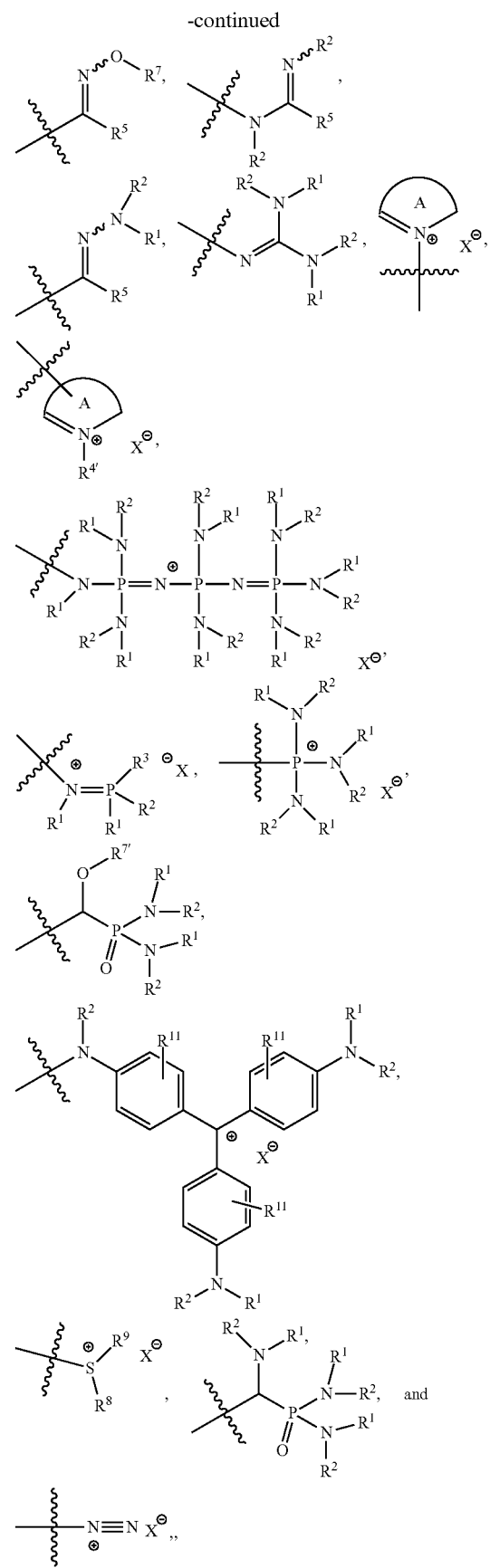

wherein: each occurrence of $R'$, $R^2$ and $R^3$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur; wherein two or more $R^1$, $R^2$ and $R^3$ groups can be taken together with intervening atoms to form one or more optionally substituted rings optionally containing one or more additional heteroatoms;

$R^{4'}$ is hydrogen or an optionally substituted radical selected from the group consisting of $C_{1-20}$ aliphatic; $C_{1-20}$ heteroaliphatic; phenyl; a 8- to 10-membered aryl; a 5- to 10-membered heteroaryl; 3- to 7-membered heterocyclic; oxide; and hydroxyl;

each occurrence of $R^5$ and $R^6$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur; wherein $R^5$ and $R^6$ can be taken together with intervening atoms to form one or more optionally substituted rings optionally containing one or more heteroatoms, and an $R^5$ or $R^6$ group can be taken with an $R^1$ or $R^2$ group to form one or more optionally substituted rings;

each occurrence of $R^7$ is independently hydrogen, a hydroxyl protecting group, or an optionally substituted radical selected from the group consisting of $C_{1-20}$ acyl; $C_{1-20}$ aliphatic; $C_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur, where an $R^7$ group can be taken with an $R^5$ group to form one or more optionally substituted rings optionally containing one or more heteroatoms;

each occurrence of $R^{7'}$, is independently hydrogen, a hydroxyl protecting group, or an optionally substituted radical selected from the group consisting of $C_{1-20}$ acyl; $C_{1-20}$ aliphatic; $C_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur; and where two $R^{7'}$ groups can be taken together with intervening atoms to form one or more optionally substituted rings optionally containing one or more heteroatoms, and an $R^{7'}$ group can be taken with an $R^1$ or $R^2$ group to form one or more optionally substituted rings optionally containing one or more heteroatoms;

each occurrence of $R^8$, $R^9$, and $R^{10}$ is independently hydrogen or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur; wherein any two or more $R^8$, $R^9$ and $R^{10}$ groups can be taken together with intervening atoms to form one or more optionally substituted rings;

each occurrence of $R^{11}$ is independently selected from the group consisting of: halogen, $-NO_2$, $-CN$, $-SR^y$, $-S(O)RR$, $-S(O)_2R^y$, $-NR^yC(O)R^y$, $-OC(O)R^y$, $-CO_2R^y$, $-NCO$, $-N_3$, $-OR^7$, $-OC(O)N(R^y)_2$, $-N(R^y)_2$, $-NR^yC(O)R^y$, $-NR^yC(O)OR^y$; and an optionally substituted radical selected from the group consisting of $C_{1-20}$ aliphatic; $C_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur, where each occurrence of $R^y$ is independently selected from the group consisting of hydrogen an optionally substituted $C_{1-6}$ aliphatic group, and an optionally substituted aryl group, where two or more adjacent $R^{11}$ groups can be taken together to form an optionally substituted saturated, partially unsaturated, or aromatic 5- to 12-membered ring containing 0 to 4 heteroatoms;

X is an anion; and ring A is an optionally substituted 5- to 10-membered heteroaryl group having 0 to 4 additional heteroatoms independently selected from nitrogen, oxygen, or sulfur.

10. The metal complex of claim 1, wherein at least one Z group is selected from the group consisting of amidine, guanidine, amidinium, and guanidinium.

11. The metal complex of claim 9, wherein at least one Z group is selected from the group consisting of

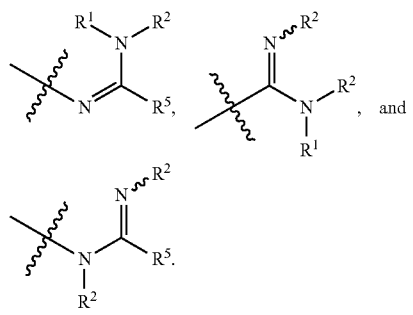

12. The metal complex of claim 11, wherein at least one Z group is selected from the group consisting of:

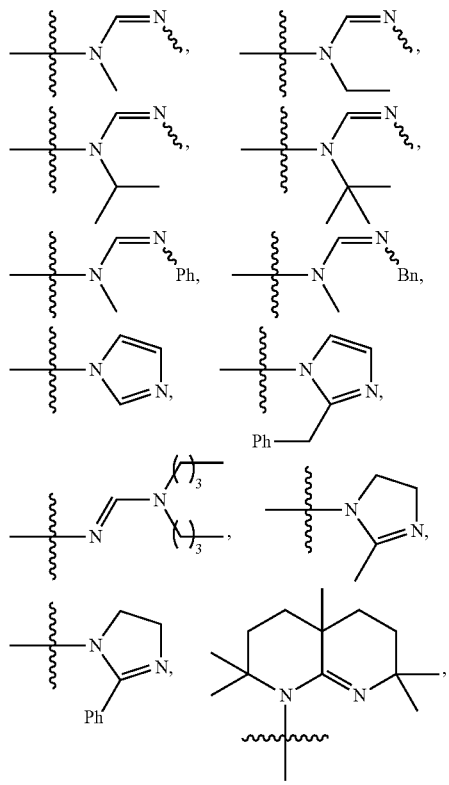

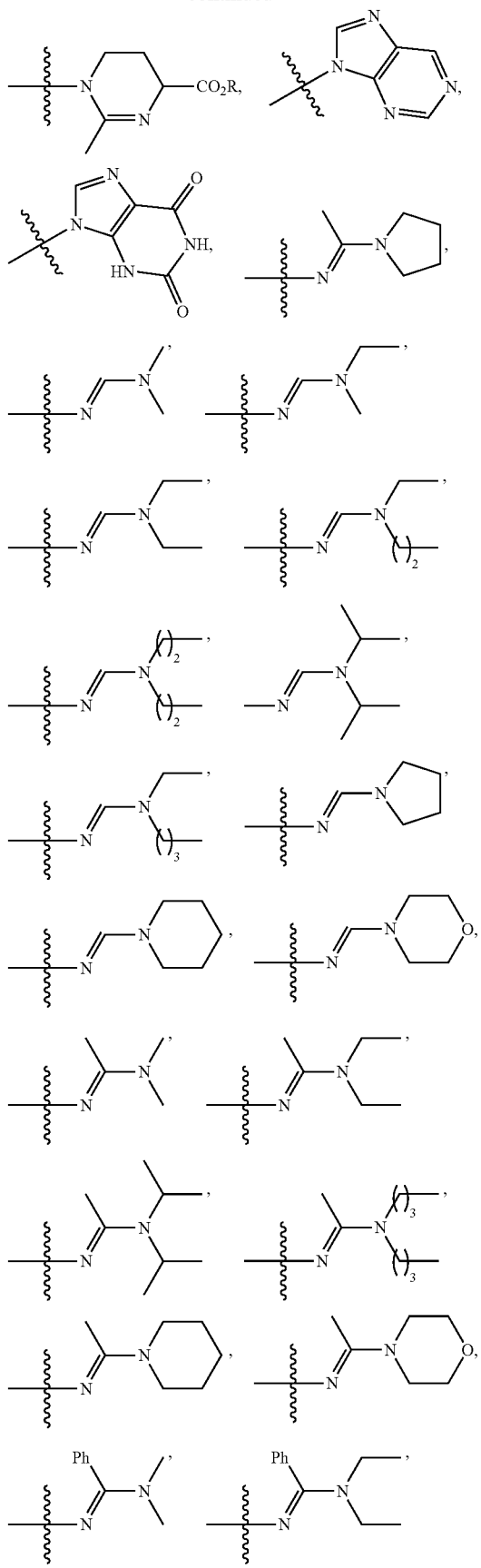

-continued
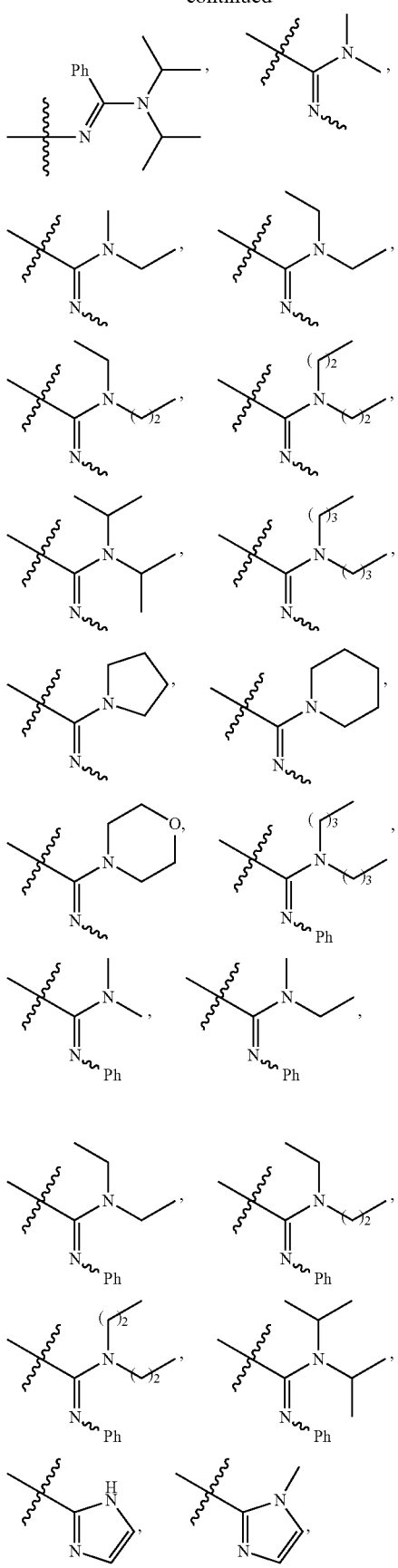
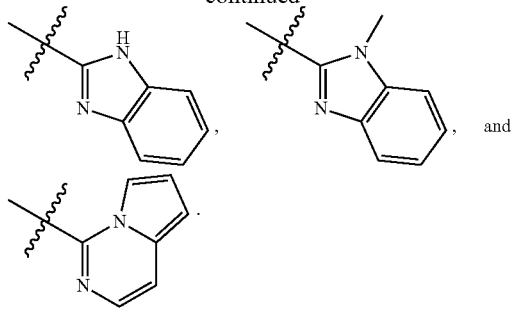
13. The metal complex of claim 9, wherein at least one Z group is selected from the group consisting of:
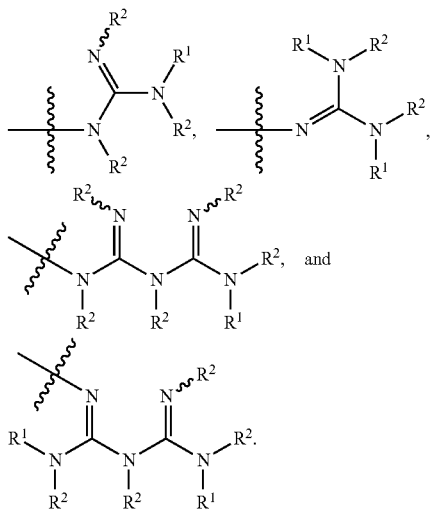
14. The metal complex of claim 13, wherein at least one Z group is selected from the group consisting of:
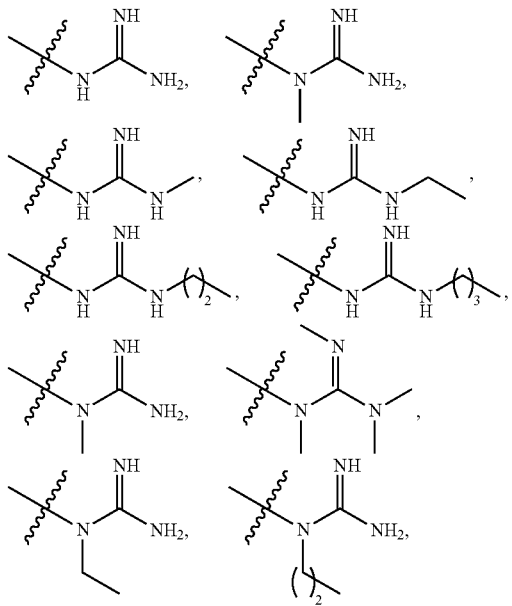

-continued
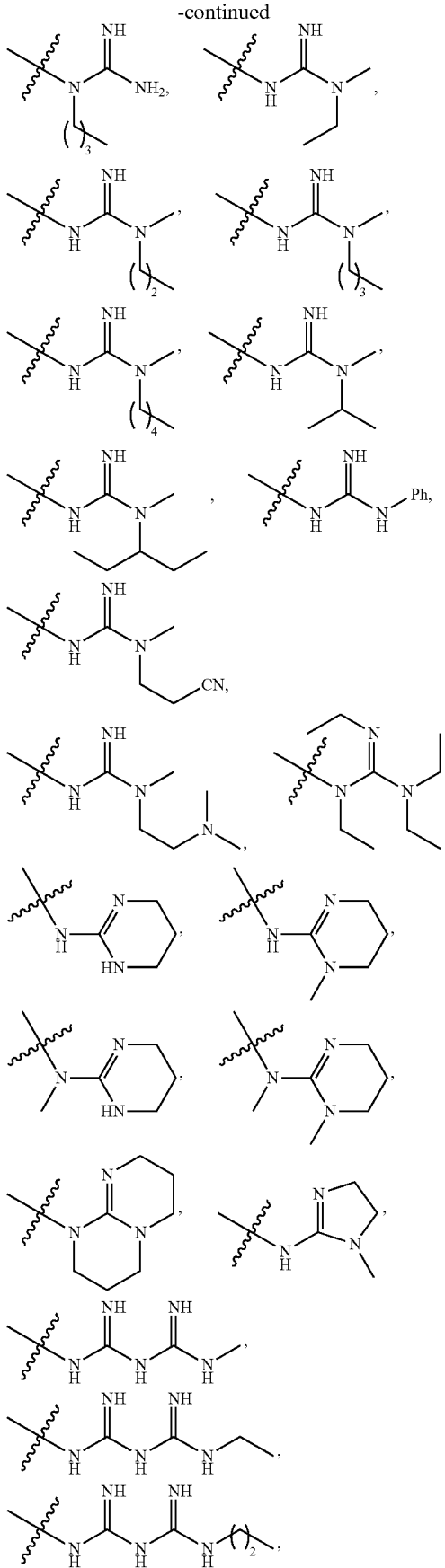
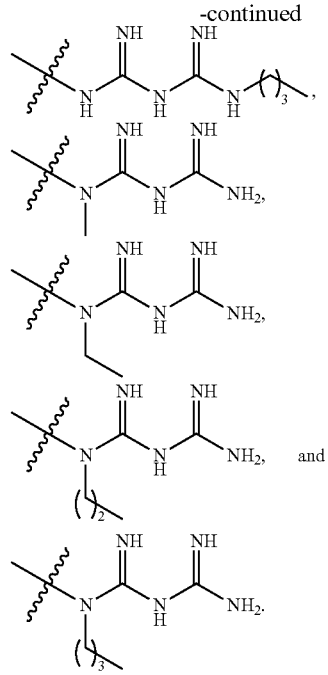
15. The metal complex of claim 9, wherein at least one Z group is selected from the group consisting of:
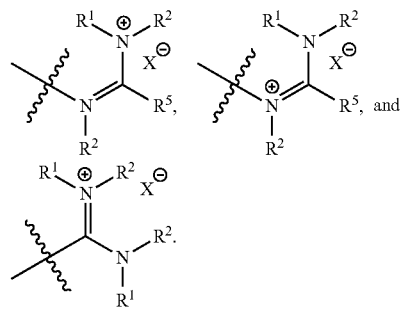
16. The metal complex of claim 9, wherein at least one Z group is
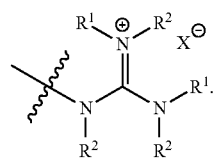
17. The metal complex of claim 1, wherein at least one Z group is selected from the group consisting of:
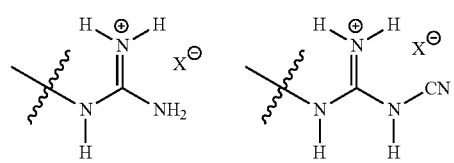

-continued
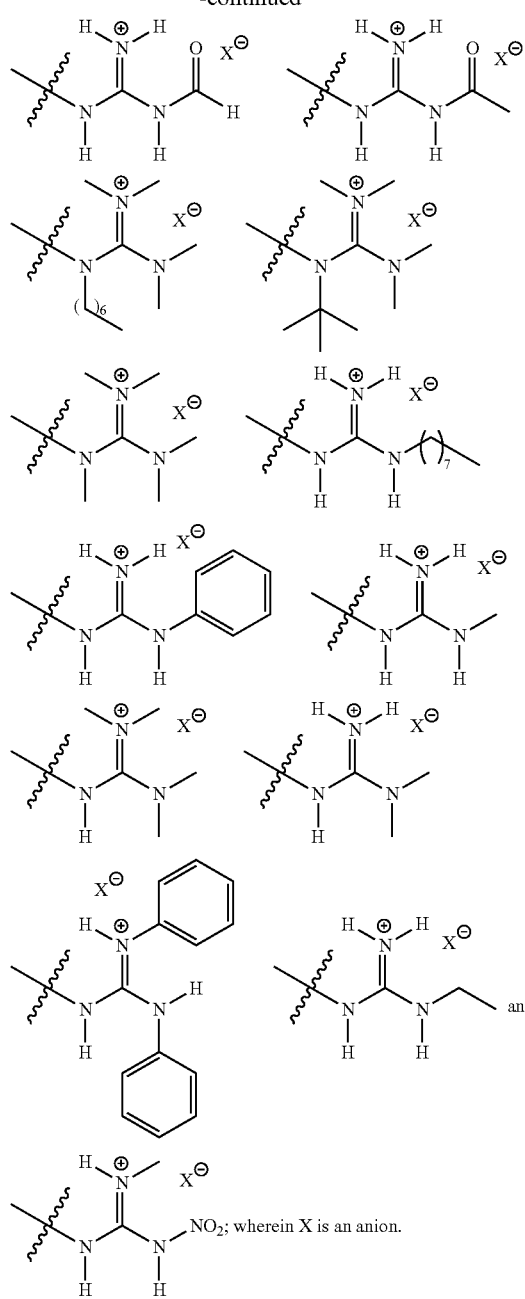
18. The metal complex of claim 9, wherein at least one Z group is selected from the group consisting of:
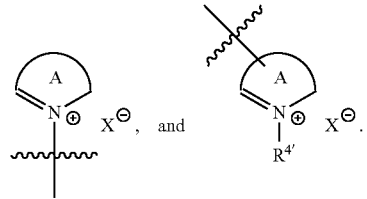
19. The metal complex of claim 1, wherein at least one Z group is selected from the group consisting of:
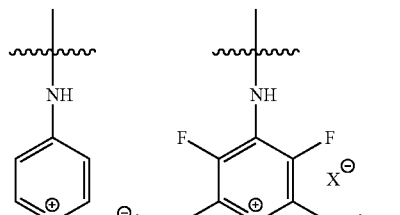
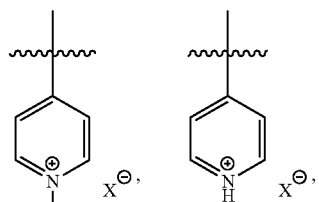
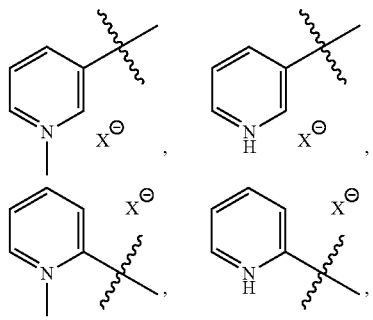
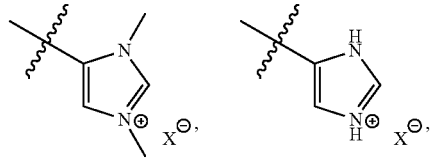
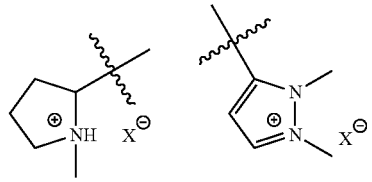
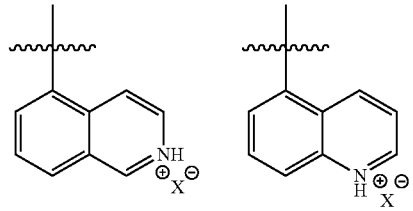
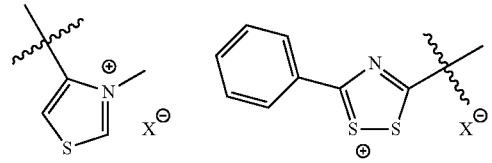
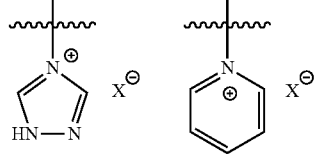
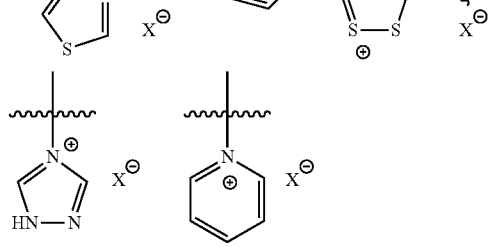

-continued
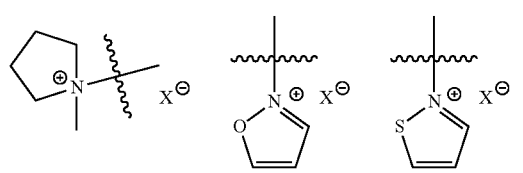
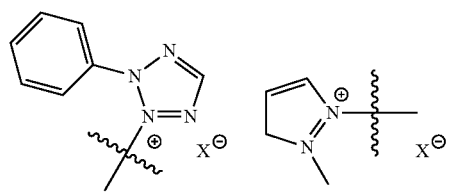
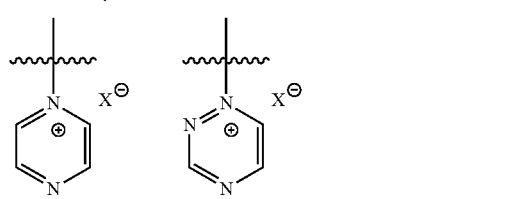
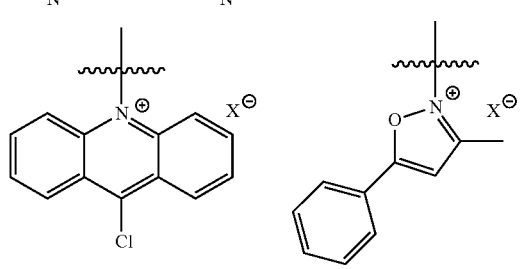
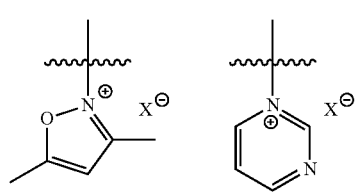
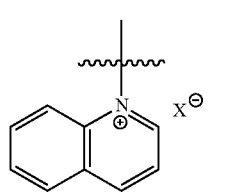
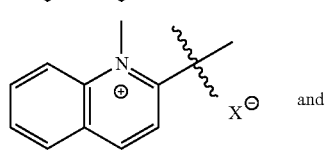
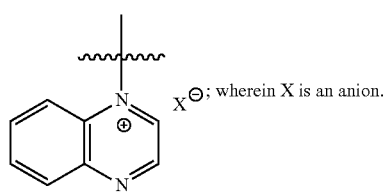; wherein X is an anion.
20. The metal complex of claim 1, wherein the compound is selected from the group consisting of:
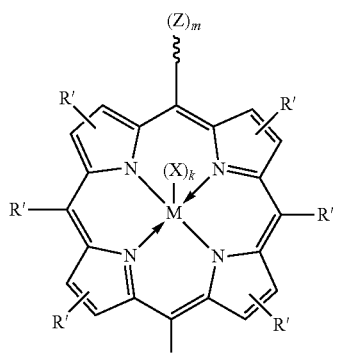
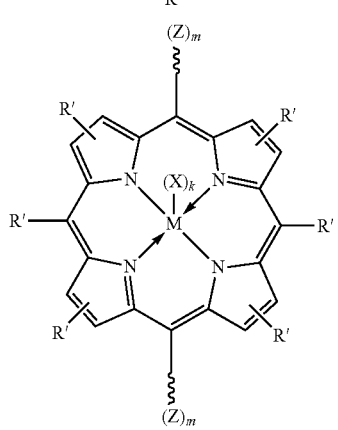
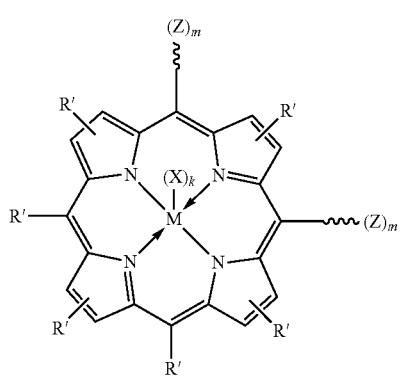
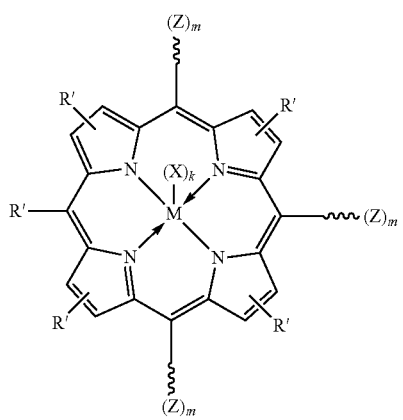

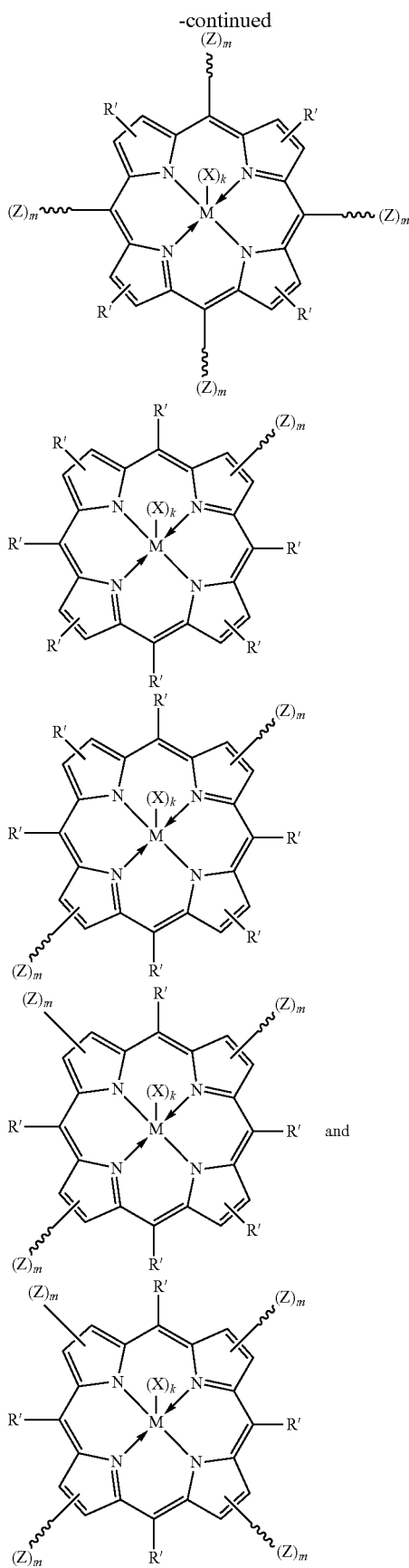

wherein
M is a metal atom;
X is nucleophile capable of ring opening an epoxide;
k is an integer from 0-2 inclusive;
R' represents one or more substituents optionally present and each R' is independently selected from the group consisting of: halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^7$, —OC(O)N(R$^y$)$_2$, —N(R$^y$)$_2$, —NR$^y$C(O)R$^y$, —NR$^y$C(O)OR$^y$; and an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur, where two or more adjacent R' groups can be taken together to form an optionally substituted saturated, partially unsaturated, or aromatic 5- to 12-membered ring containing 0 to 4 heteroatoms;
R$^y$ is —H, or an optionally substituted radical selected from the group consisting of C$_{1-6}$ aliphatic, 3- to 7-membered heterocyclic, phenyl, and 8- to 10-membered aryl; and
each occurrence of R$^7$ is independently hydrogen, a hydroxyl protecting group, or an optionally substituted radical selected from the group consisting of C$_{1-20}$ acyl; C$_{1-20}$ aliphatic; C$_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur, where an R$^7$ group can be taken with an R$^y$ group to form one or more optionally substituted rings optionally containing one or more heteroatoms.

21. The metal complex of claim 20, wherein M is selected from Cr, Co, or Al.

22. The metal complex of claim 20, wherein X is selected from the group consisting of: chlorine, bromine, an optionally substituted C$_{1-12}$ carboxylate, azide, an optionally substituted phenoxide, a sulfonate salt, and a combination of any two or more of these.

23. The metal complex of claim 20, wherein wherein X is selected from the group consisting of chloride, acetate, trifluoroacetate, azide, pentafluorobenzoate, and a nitrophenolate.

24. The metal complex of claim 1 selected from the group consisting of:
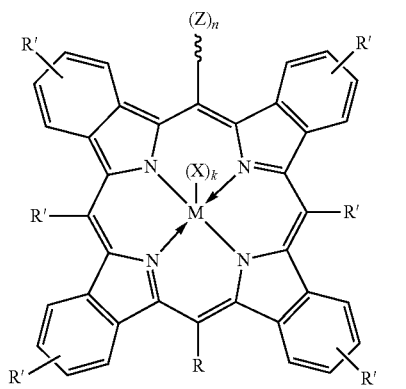
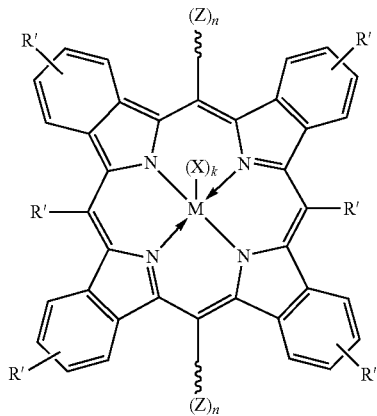
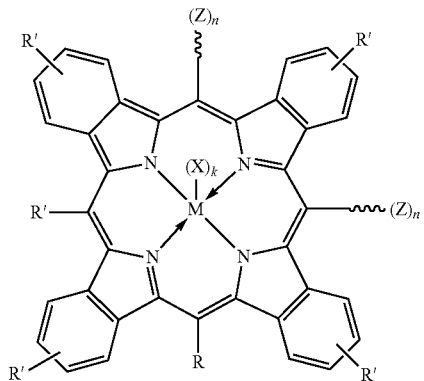
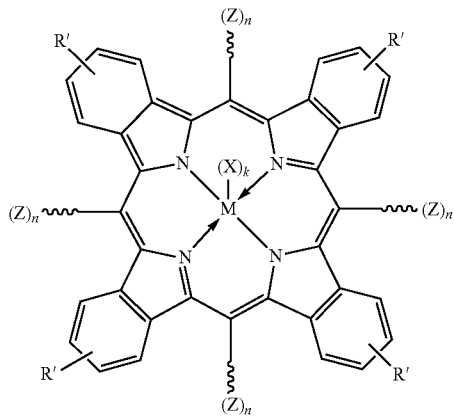
-continued
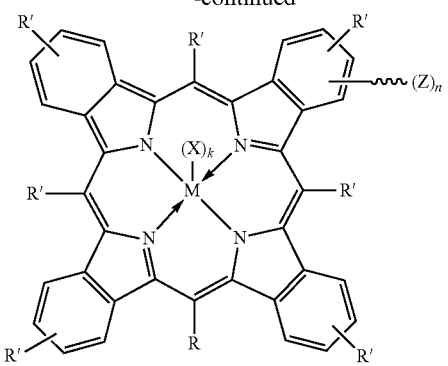
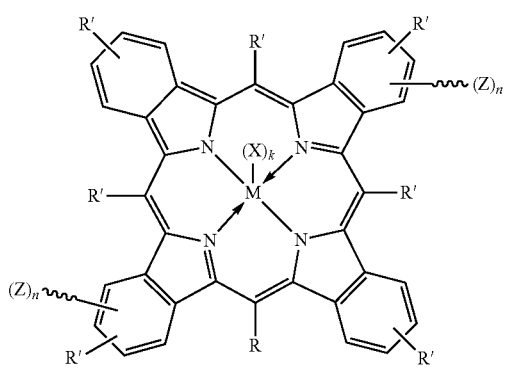
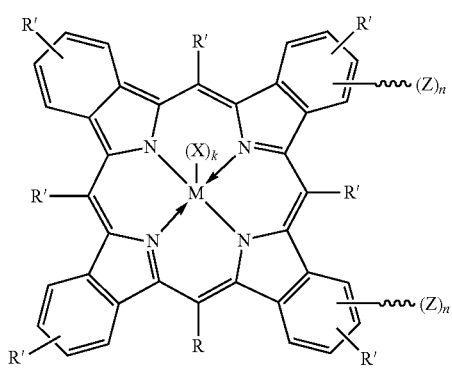
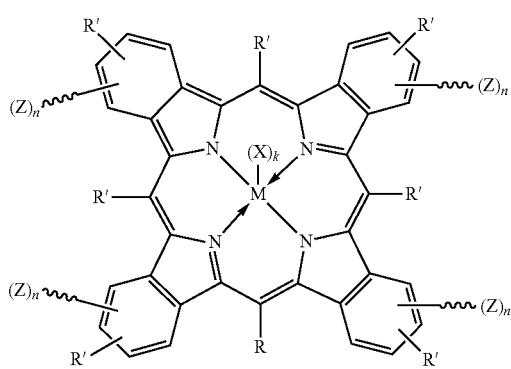
and wherein
M is a metal atom;

X is nucleophile capable of ring opening an epoxide;

k is an integer from 0-2 inclusive;

R' represents one or more substituents optionally present and each R' is independently selected from the group consisting of: halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^7$, —OC(O)N(R$^y$)$_2$, —N(R$^y$)$_2$, —NR$^y$C(O)R$^y$, —NR$^y$C(O)OR$^y$; and an optionally substituted radical selected from the group consisting of C$_{1-20}$ aliphatic; C$_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur, where two or more adjacent R' groups can be taken together to form an optionally substituted saturated, partially unsaturated, or aromatic 5- to 12-membered ring containing 0 to 4 heteroatoms;

R$^y$ is —H, or an optionally substituted radical selected from the group consisting of C$_{1-6}$ aliphatic, 3- to 7-membered heterocyclic, phenyl, and 8- to 10-membered 5 aryl; and each occurrence of R$^7$ is independently hydrogen, a hydroxyl protecting group, or an optionally substituted radical selected from the group consisting of C$_{1-20}$ acyl; C$_{1-20}$ aliphatic; C$_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur, where an R$^7$ group can be taken with an Ry group to form one or more optionally substituted rings optionally containing one or more heteroatoms.

25. The metal complex of claim 1 selected from

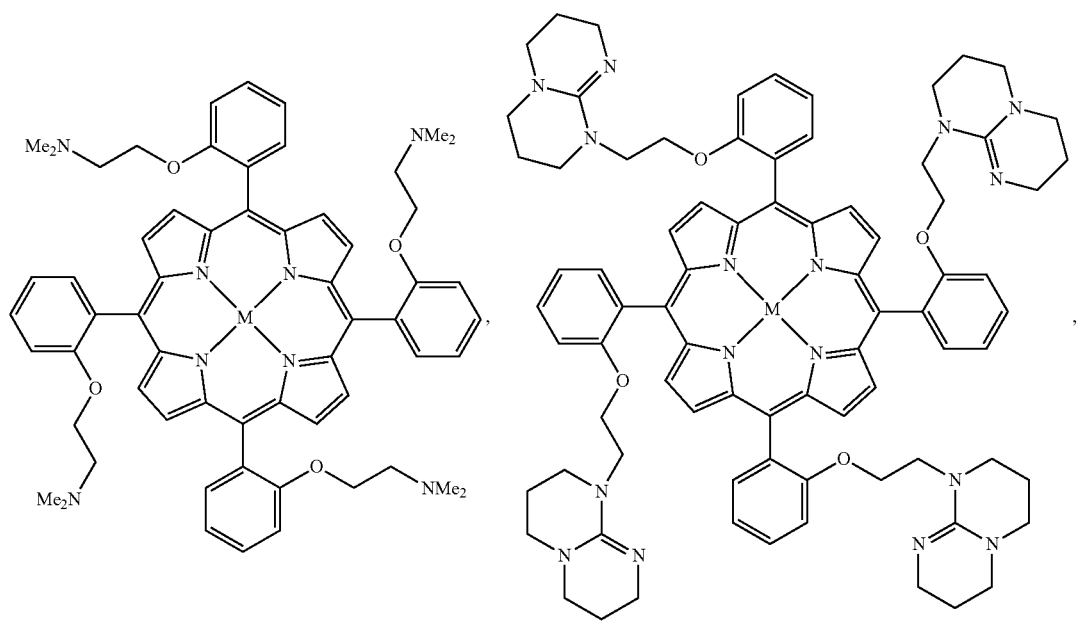

-continued
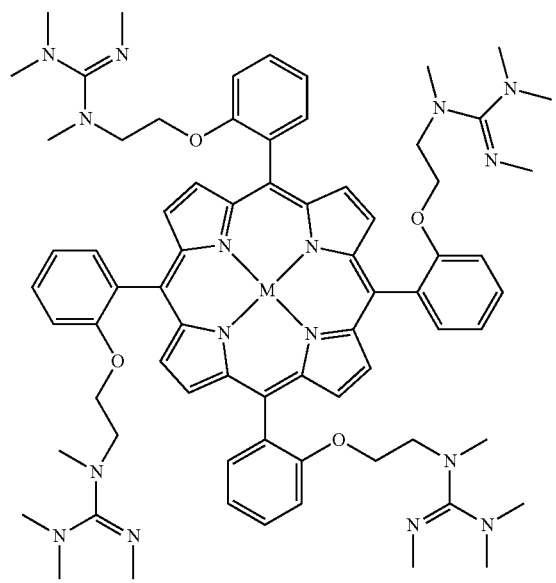
245
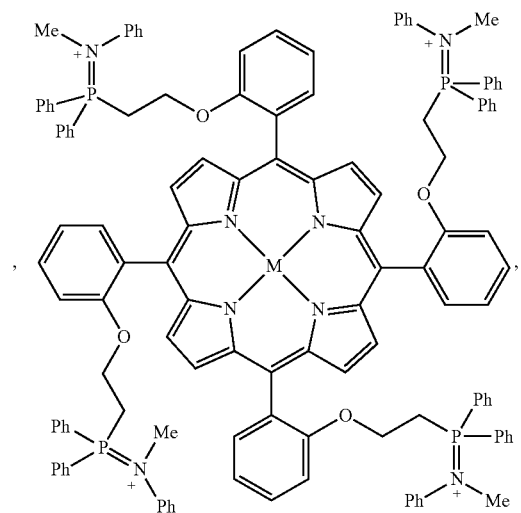
246
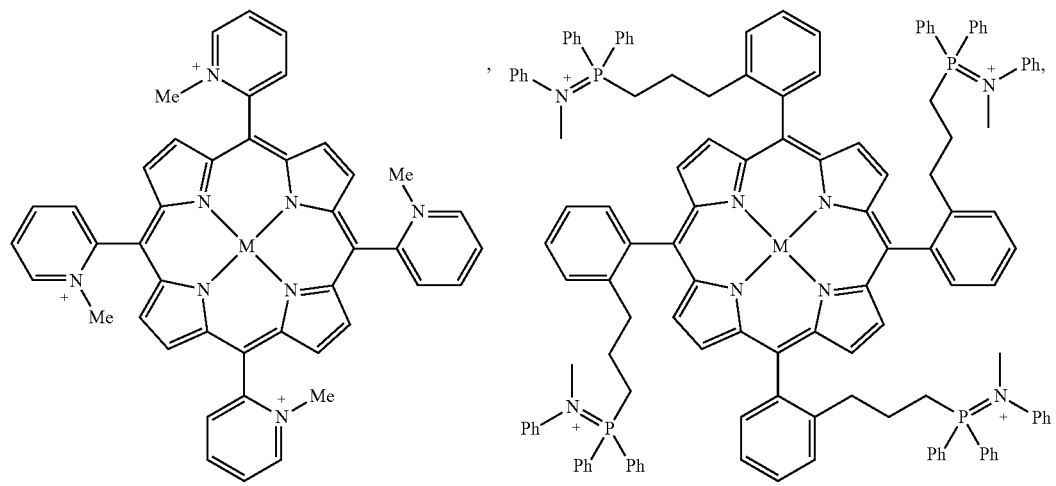
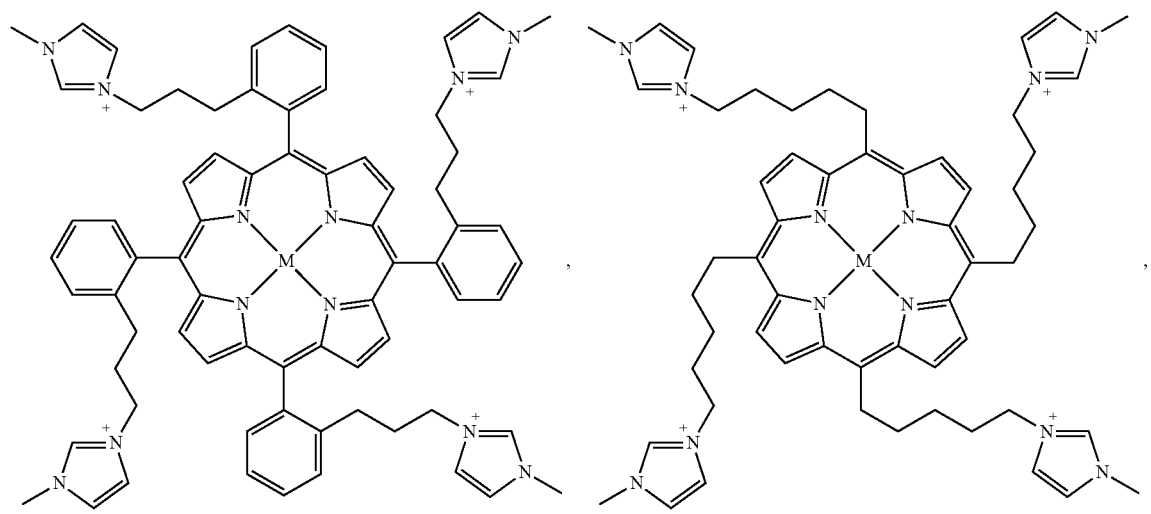

-continued
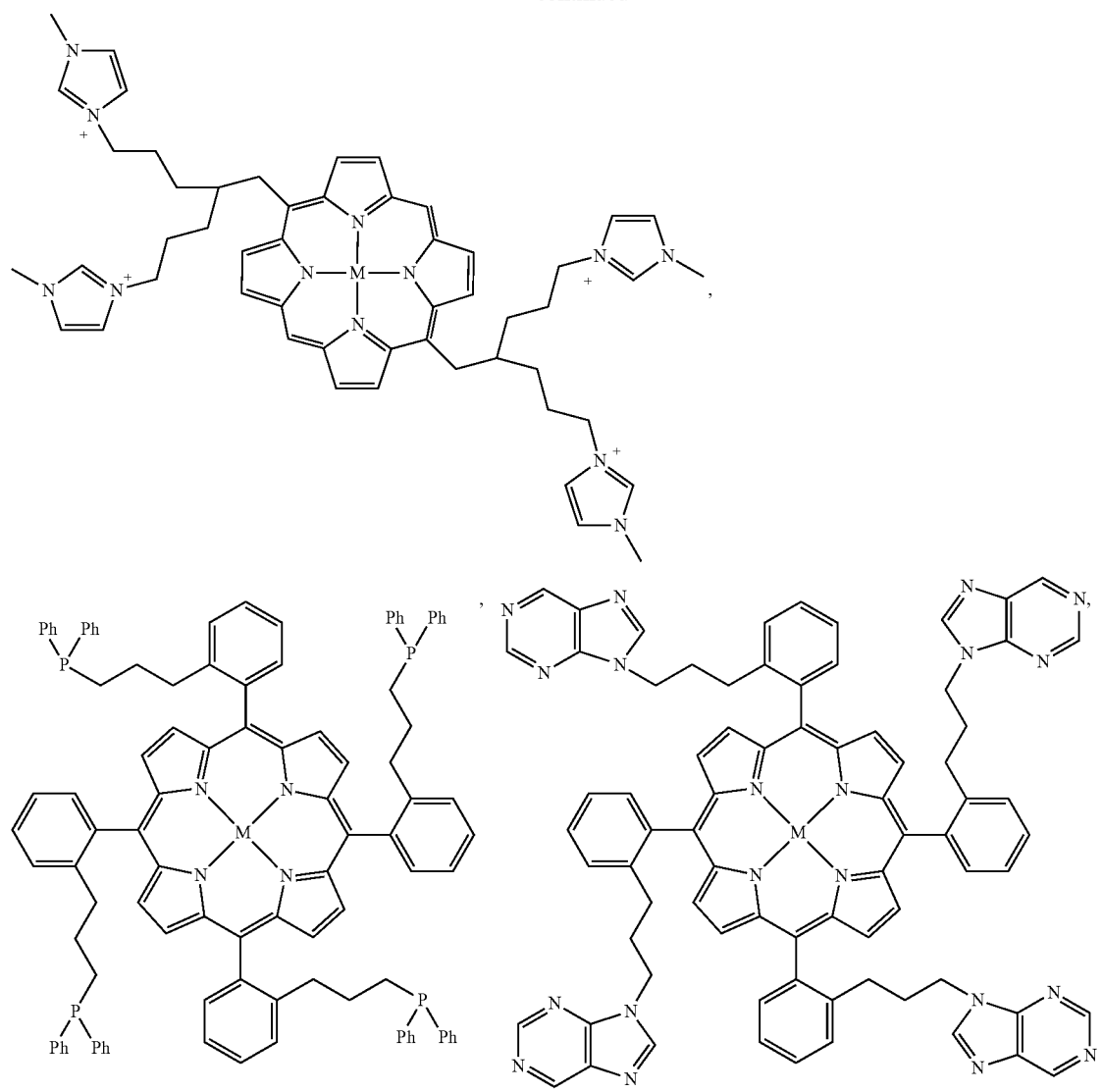
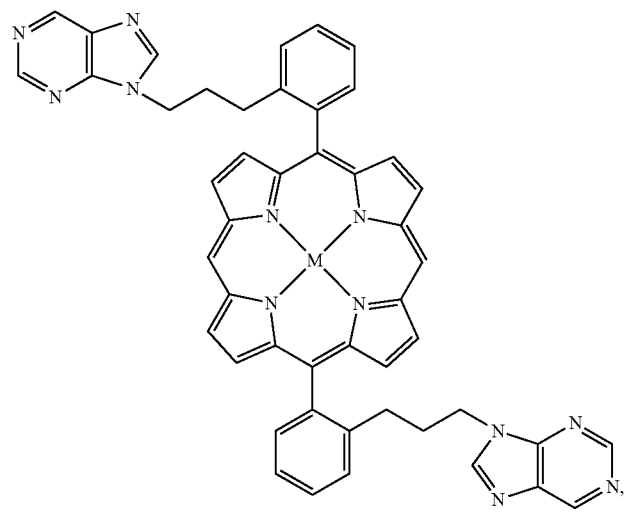

-continued
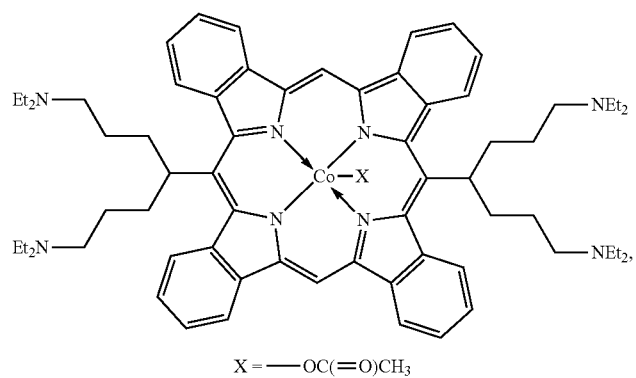
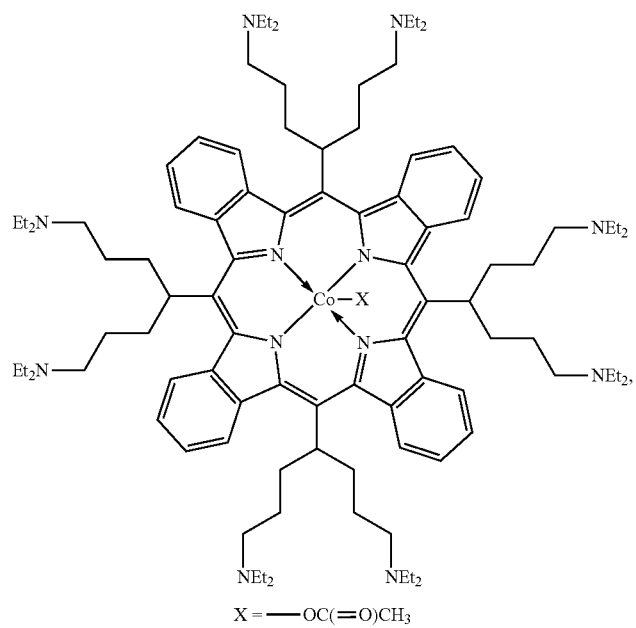
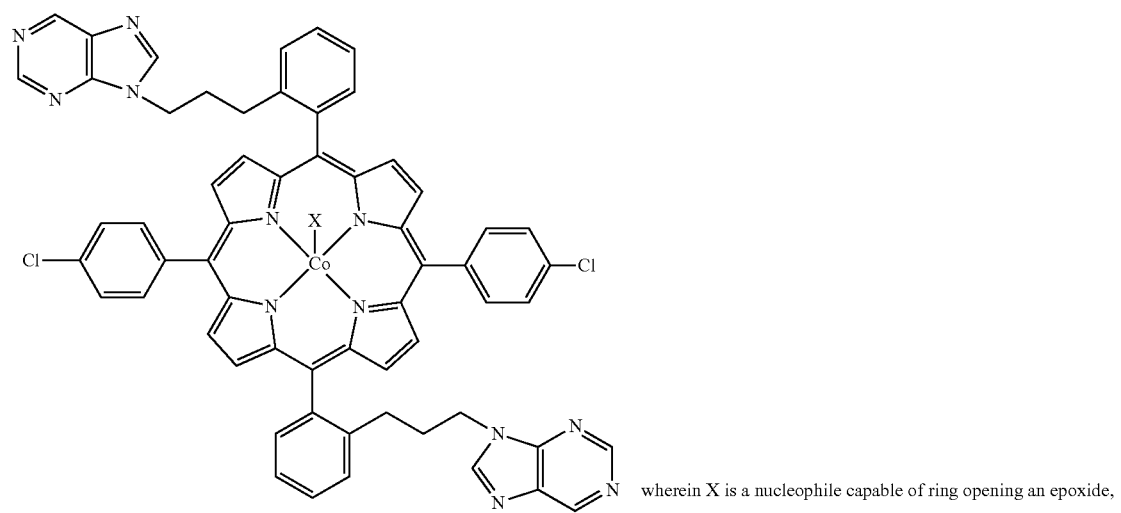
wherein X is a nucleophile capable of ring opening an epoxide, -continued

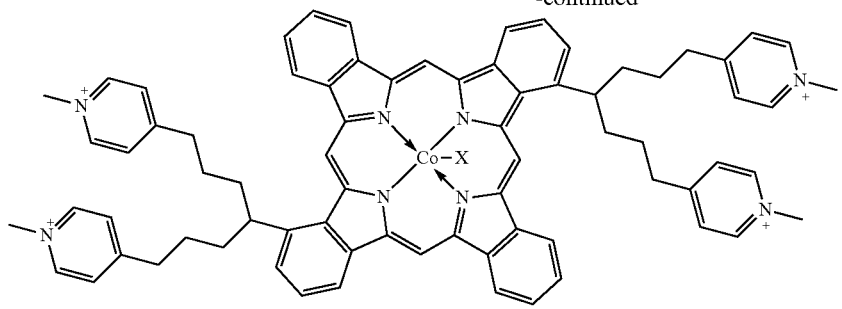

wherein X is a nucleophile capable of ring opening an epoxide,

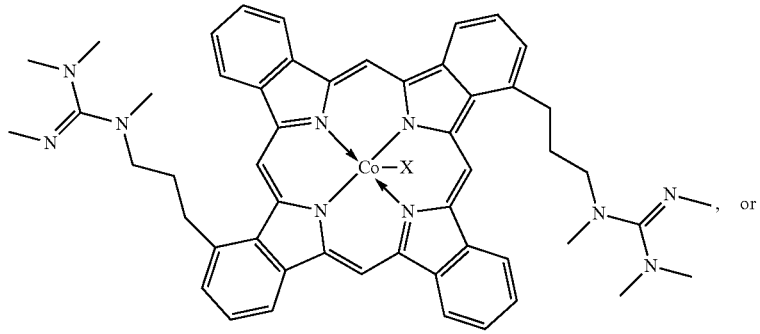

X = —OC(=O)CH₃

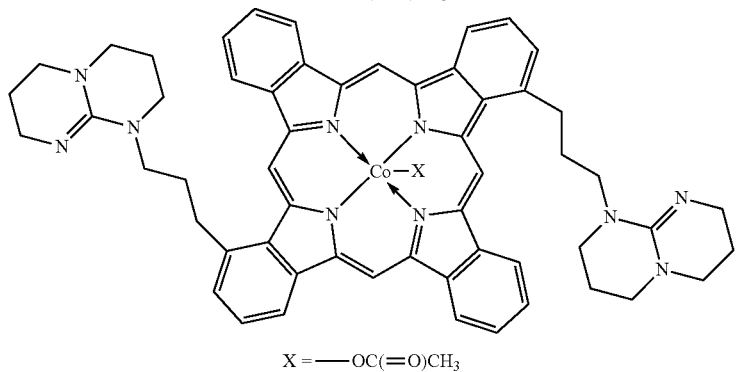

X = —OC(=O)CH₃

26. A method comprising the step of contacting an epoxide and carbon dioxide with a polymerization catalyst selected from the metal complex of claim 1.

27. A metal complex:

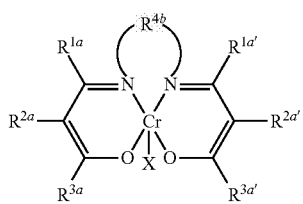

wherein:
$R^{2a}$ and $R^{2a'}$, are independently a —⋀⋀— $(Z)_m$ group, hydrogen, —OR, —NR₂, —SR, —CN, —NO₂, —SO₂R, —SOR, —SO₂NR₂; —CNO, —NRSO₂R, —NCO, —N₃, —SiR₃; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur;

$R^{1a}$, $R^{1a'}$, $R^{3a}$, and $R^{3a'}$ are independently a —⋀⋀— $(Z)_m$ group hydrogen, or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur, where any of [$R^{2a'}$ and $R^{3a'}$], [$R^{2a}$ and $R^{3a}$], [$R^{1a}$ and $R^{2a}$], and [$R^{1a'}$ and $R^{2a'}$] may optionally be taken together with intervening atoms to form one or more rings which may in turn be substituted with one or more $R^d$ groups;

$R^{4b}$ is selected from the group consisting of:

a)
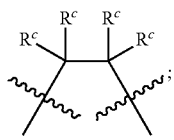

b)
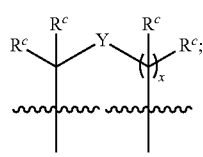

c)
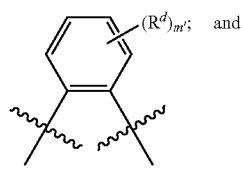 and d)
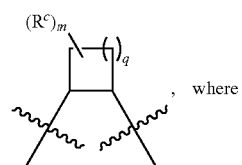, where $R^c$ at each occurrence is independently a $\text{---}\!\!\sim\!\!(Z)_m$ group, hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur; where two or more $l^e$ groups may be taken together with the carbon atoms to which they are attached and any intervening atoms to form one or more optionally substituted rings; when two $l^e$ groups are attached to the same carbon atom, they may optionally be taken together along with the carbon atom to which they are attached to form an optionally substituted moiety selected from the group consisting of: a 3- to 8-membered spirocyclic ring, a carbonyl, an oxime, a hydrazone, and an imine;

$R^d$ at each occurrence is independently a $\text{---}\!\!\sim\!\!(Z)_m$ group, hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; and an 8- to 10-membered bicyclic heteroaryl ring having 1-5 heteroatoms independently selected from nitrogen, oxygen, or sulfur; where two or more $R^d$ groups may be taken together with intervening atoms to form one or more optionally substituted rings optionally containing one or more heteroatoms, R at each occurrence is independently hydrogen or an optionally substituted radical selected the group consisting of acyl; $C_{1-6}$ aliphatic; $C_{1-6}$ heteroaliphatic; carbamoyl; arylalkyl; phenyl; a 3- to 8-membered saturated or partially unsaturated monocyclic carbocycle a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring, X is a nucleophile capable of ring opening an epoxide;

Y is a divalent linker selected from the group consisting of: —NR—, —N(R)C(O)—, —C(O)NR—, —O—, —C(O)—, —OC(O)—, —C(O)O—, —S—, —SO—, —SO$_2$—, —SiR$_2$—, —C(=S)—, —C(=NR)—, or —N=N—; a polyether; a $C_3$ to $C_8$ substituted or unsubstituted carbocycle; and a $C_1$ to $C_8$ substituted or unsubstituted heterocycle;

m' is 0 or an integer from 1 to 4, inclusive;

q is 0 or an integer from 1 to 4, inclusive;

x is 0, 1, or 2; and $\text{---}\!\!\sim\!\!(Z)_m$ represents one or more activating moieties tethered to the multidentate ligand, where $\text{---}\!\!\sim\!\!$ represents a linker moiety; m represents the number of Z groups present on a linker moiety and is an integer between 1 and 4 inclusive; and each (Z) represents an activating moiety.

* * * * *